(12) United States Patent
Chen et al.

(10) Patent No.: US 8,697,729 B2
(45) Date of Patent: Apr. 15, 2014

(54) SMALL MOLECULES MODULATOR OF EPIGENETIC REGULATION AND THEIR THERAPEUTIC APPLICATIONS

(75) Inventors: Lin Chen, La Canada, CA (US); Nimanthi Jayathilaka, Los Angeles, CA (US); Aidong Han, Los Angeles, CA (US); Nicos Petasis, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 286 days.

(21) Appl. No.: 12/613,521

(22) Filed: Nov. 5, 2009

(65) Prior Publication Data
US 2011/0275674 A1    Nov. 10, 2011

Related U.S. Application Data

(60) Provisional application No. 61/111,689, filed on Nov. 5, 2008, provisional application No. 61/246,934, filed on Sep. 29, 2009.

(51) Int. Cl.
*A01N 43/40*    (2006.01)

(52) U.S. Cl.
USPC .......... 514/332; 514/616; 564/157; 435/6.13; 435/375; 435/184; 435/320.1; 703/11; 436/501; 546/265

(58) Field of Classification Search
USPC .............. 541/332, 616; 435/184, 320.1, 6.13, 435/375; 514/332, 616; 564/157; 703/11; 436/501; 546/265
See application file for complete search history.

(56) References Cited

U.S. PATENT DOCUMENTS

2006/0160201 A1* 7/2006 Chen et al. .................... 435/196

FOREIGN PATENT DOCUMENTS

| WO | 2004094591 A2 | 11/2004 |
| WO | WO2007/058927 | * 5/2007 |

OTHER PUBLICATIONS

Zixu Mao, et al., "Neuronal Activity-Dependent Cell Survival Mediated by Transcription Factor MEF2", Science, vol. 286; (1999); pp. 785-790.
Chun Li Zhang, et al., "Class II Histone Deacetylases Act as Signal-Responsive Repressors of Cardiac Hypertrophy"; Cell, vol. 110, (2002); pp. 479-488.
Bin Li, et al.; "FOXP3 is a homo-oligomer and a component of a supramolecular regulatory complex disabled in the human XLAAD/IPEX autoimmune disease"; Int'l. Immunology, vol. 19, No. 7, pp. 825-835 (2007).
B.E. Morrison, et al., "Histone deacetylases: Focus on the nervous system"; Cell. Mol. Life Sci. (2007); vol. 64; pp. 2258-2269.
Matthew J. Potthoff, et al., "MEF2: a central regulator of diverse developmental program"; Development (2007); vol. 134: pp. 4131-4140.
Nimanthi Jayathilaka et al., "Inhibition of the function of class IIa HDACs by blocking their interaction with MEF2" Nucleic Acids Research, vol. 40, No. 12, pp. 5378-5388, Mar. 2012.
Jurate Savickiene et al., "The novel histone deacetylase inhibitor BML-210 exerts growth inhibitory, proapoptotic and differentiation stimulating effects on the human leukemia cell lines" European Journal of Pharmacology, vol. 549, pp. 9-18, Aug. 2006.
V.V. Borutinskaite et al., "Apoptotic effects of the novel histone deacetylase inhibitor BML-210 on HeLa cells" Biologija, vol. 54, No. 3, pp. 217-220, 2008.
Elizabeth Thomas et al., "The HDAC inhibitor 4b ameliorates the disease phenotype and transcriptional abnormalities in Huntington's disease transgenic mice" Proceedings of the National Academy of Sciences of the United States of America, vol. 105, No. 40, pp. 15564-15569, Oct. 2008.
Marielle Paris et al., "Histone Deacetylase Inhibitors: From Bench to Clinic" Journal of Medicinal Chemistry, vol. 51, No. 6, pp. 1505-1529, Mar. 2008.
European office action dated Apr. 9, 2013 issued in corresponding European application 09760375.7.

* cited by examiner

*Primary Examiner* — Jason M Sims
*Assistant Examiner* — Ibrahim D Bori
(74) *Attorney, Agent, or Firm* — DLA Piper LLP (US)

(57) ABSTRACT

Disclosed are methods and compositions for modulating the function of transcription factors, especially transcription factors that recruit epigenetic regulators (histone modifying enzymes) to specific DNA promoters. The targeted transcription factors include but are not limited to the myocyte enhancing factor (MEF2), the forkhead/winged helix transcription factor FOXP3 and the transcription factor GATA3. Also disclosed are small molecule modulators of MEF2 and its associated factors that include but not limited to histone deacetylases (HDACs), p300/CBP and Cabin1 and the therapeutic applications thereof.

11 Claims, 9 Drawing Sheets

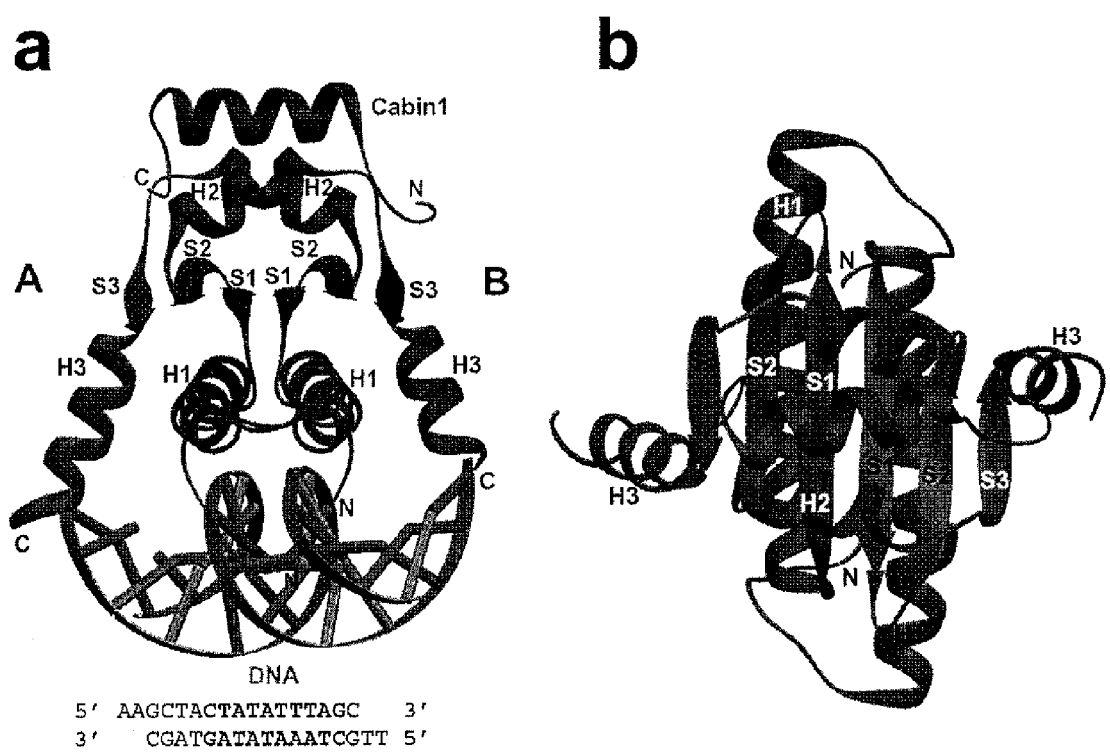
Figure 1 a – b

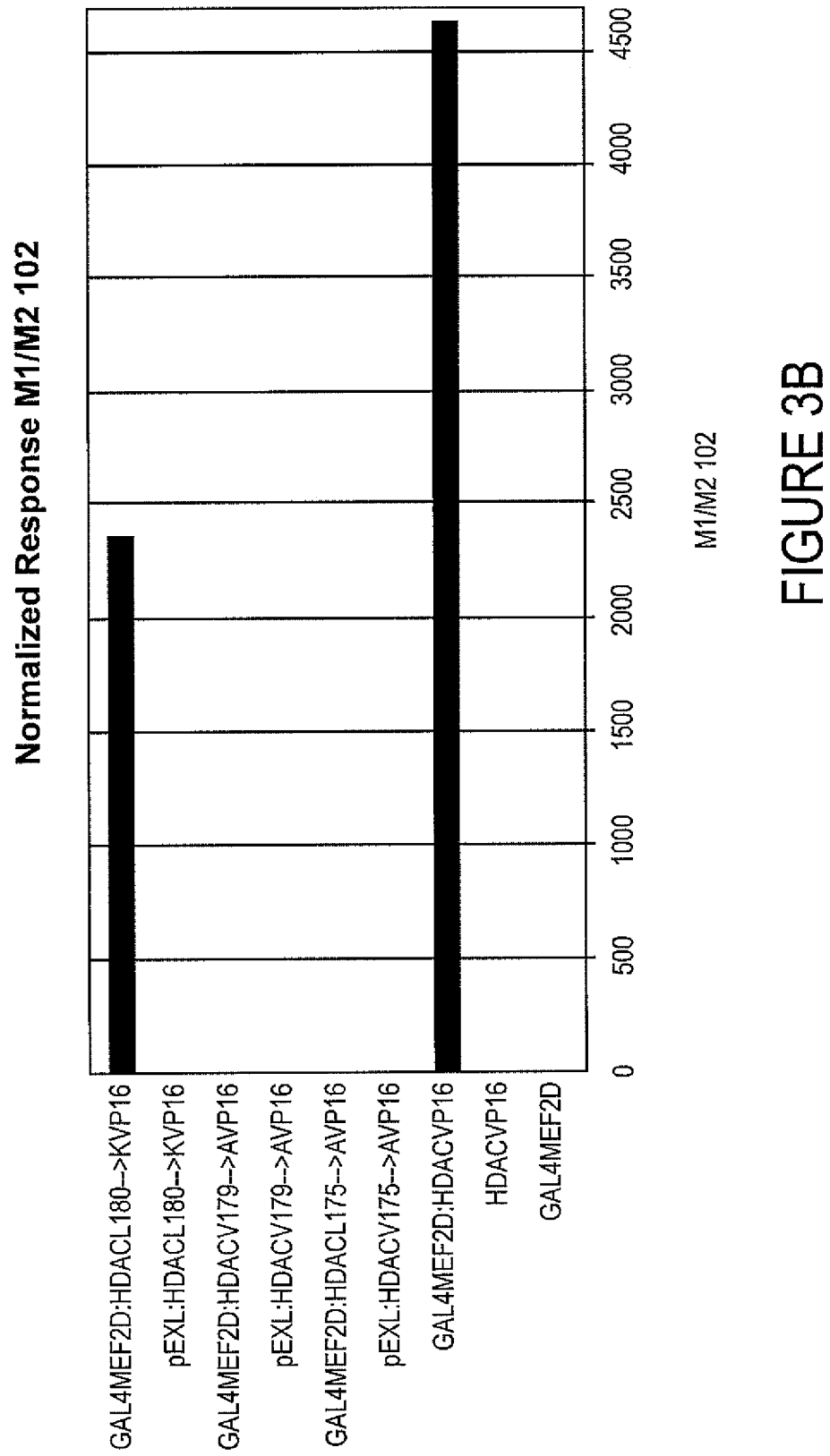

BML-210 inhibit the MEF2:HDAC reporter assay in a dosage dependent manner.

SEQUENCE LISTING

```
<160> NUMBER OF SEQ ID NOS: 7

<210> SEQ ID NO 1
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 1
aagctactat atttagc                                                   17

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
cgatgatata aatcgtt                                                   17

<210> SEQ ID NO 3
<211> LENGTH: 14
<212> TYPE: PRT
<213> ORGANISM: Artificial Sequence
<220> FEATURE:
<223> OTHER INFORMATION: Chemically synthesized peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: X at 3 can be either amino acid V or T
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
```

```
<221> NAME/KEY: MISC_FEATURE
<222> LOCATION: (11)..(11)
<223> OTHER INFORMATION: X at 11 can be either amino acid V, I, or L
<220> FEATURE:
<221> NAME/KEY: misc_feature
<222> LOCATION: (13)..(14)
<223> OTHER INFORMATION: Xaa can be any naturally occurring amino acid

<400> SEQUENCE: 3

Xaa Xaa Xaa Lys Xaa Tyr Leu Tyr Xaa Xaa Xaa Leu Xaa Xaa
1               5                   10

<210> SEQ ID NO 4
<211> LENGTH: 71
<212> TYPE: PRT
<213> ORGANISM: Artificial Sequence
<220> FEATURE:
<223> OTHER INFORMATION: peptide expressed in E. coli strain
      BL21(DE3)pLysS

<400> SEQUENCE: 4

Gly Arg Lys Lys Ile Gln Ile Thr Arg Ile Met Asp Glx Arg Asn Arg
1               5                   10                  15

Gln Val Thr Phe Thr Lys Arg Lys Phe Gly Leu Met Lys Lys Ala Tyr
            20                  25                  30

Glx Leu Ser Val Leu Cys Asp Cys Gly Ile Ala Leu Ile Ile Phe Asn
        35                  40                  45

Ser Ser Asn Lys Leu Phe Gln Tyr Ala Ser Thr Asp Met Asp Lys Val
    50                  55                  60

Leu Leu Lys Tyr Thr Glx Tyr
65                  70

<210> SEQ ID NO 5
<211> LENGTH: 72
<212> TYPE: PRT
<213> ORGANISM: Artificial Sequence
<220> FEATURE:
<223> OTHER INFORMATION: peptide expressed in E. coli strain
      BL21(DE3)pLysS

<400> SEQUENCE: 5

Gly Arg Lys Lys Ile Gln Ile Thr Arg Ile Met Asp Glx Arg Asn Arg
1               5                   10                  15

Gln Val Thr Phe Thr Lys Arg Lys Phe Gly Leu Met Lys Lys Ala Tyr
            20                  25                  30

Glx Leu Ser Val Leu Cys Asp Cys Gly Ile Ala Leu Ile Ile Phe Asn
        35                  40                  45

Ser Ser Asn Lys Leu Phe Gln Tyr Ala Ser Thr Asp Met Asp Lys Val
    50                  55                  60

Leu Leu Lys Tyr Thr Glx Tyr Asn
65                  70

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6
aaagctatta ttagctt                                                  17

<210> SEQ ID NO 7
<211> LENGTH: 17
```

```
<212> TYPE: DNA
<213> ORGANISM: Artificial Sequence
<220> FEATURE:
<223> OTHER INFORMATION: Synthetic oligonucleotide

<400> SEQUENCE: 7
taagctaata atagctt                                                  17
```

SMALL MOLECULES MODULATOR OF EPIGENETIC REGULATION AND THEIR THERAPEUTIC APPLICATIONS

CROSS-REFERENCE TO RELATED APPLICATIONS

This application claims the benefit of U.S. Provisional Application No. 61/111,689, filed on Nov. 5, 2008, and Provisional Application No. 61/246,934, filed on Sep. 29, 2009. The above provisional applications are hereby incorporated herein by reference.

STATEMENT REGARDING FEDERALLY SPONSORED RESEARCH AND DEVELOPMENT

This invention was made with support in part by the following grants from NIH R21AI49905, RO1HL076334, and RC1DA028790. Therefore, the U.S. government has certain rights.

FIELD OF THE INVENTION

The invention relates generally to the field of molecular medicine. In particular, the invention pertains to methods and compositions for modulating the function of transcription factors, especially transcription factors that recruit epigenetic regulators (histone modifying enzymes) to specific DNA promoters. The targeted transcription factors include but are not limited to the myocyte enhancing factor (MEF2), the forkhead/winged helix transcription factor FOXP3 and the transcription factor GATA3. More particularly, the invention pertains to small molecule modulators of MEF2 and its associated factors that include but not limited to histone deacetylases (HDACs), p300/CBP and Cabin1 and the therapeutic applications thereof.

BACKGROUND OF THE INVENTION

This invention relates to the use of small molecules for modulating the functions of transcription factors that are associated with certain diseases. Transcription factors are proteins that bind to specific DNA sequences and regulate gene expression either directly or through associated proteins such as co-activators and co-repressors, or by recruiting histone modifying enzymes such as histone acetyltransferases (HATs) and histone deacetylases (HDACs). Transcription factors play key roles in many biological processes by ensuring the appropriate level of gene expression. They can also be associated with certain disease states, if their ability to regulate transcription is aberrantly modified. The identification and development of small molecules that can selectively modulate the function of certain transcription factors, therefore, can lead to potentially new therapeutic applications. This invention is based on two basic ideas. One is to develop small molecules that bind a specific transcription factors such as MEF2, FOXP3 and GATA3 and modulate its interaction with transcription co-activators and co-repressors. The other is to develop small molecules to block the recruitment of HAT (such as p300 and CBP) and HDACs and other histone modifying enzymes (such as histone methyltransferases, and demethylases, DNA methyltransferases) and chromatin remodeling machineries to specific regions of chromatin.

In particular, this invention relates to the myocyte enhancer factor-2 (MEF2) which plays critical roles in the development and adaptive responses of the muscle, immune and nervous systems (Flavell et al., 2006; Kim et al., 2008; Mao et al., 1999; McKinsey et al., 2002; Pan et al., 2004; Potthoff and Olson, 2007; Youn and Liu, 2000; Youn et al., 1999). MEF2 has been implicated as a key regulator of hypertrophic responses in heart muscle cells. Heart hypertrophy induced by pathological stimuli can lead to heart failure in many forms of cardiovascular diseases.

MEF2 generally defines a family of transcription factors with four members: MEF2A, MEF2B, MEF2C and MEF2D. The importance of their function has been demonstrated in detail through the use of murine and *Drosophila* genetics (Potthoff and Olson, 2007). MEF2, in skeletal muscles where it was initially identified, together with myogenic basic helix-loop-helix transcription factors such as MyoD, promotes and maintains myogenesis (Molkentin and Olson, 1996). MEF2A, one member of the MEF2 family, has recently been coined as the "heart attack gene" because a mutation in this protein is linked to coronary artery disease (CAD) and myocardial infarction (MI) (Wang et al., 2003). These findings underlie a critical role of MEF2 in human heart diseases (Kim et al., 2008; Wei et al., 2008; Zhang et al., 2002).

MEF2 is now known to be a general transcriptional factor in many other cell types. For instance, MEF2 is one of the important transcriptional factors for mediating calcium signaling in lymph system development} (Pan et al., 2004; Youn and Liu, 2000; Youn et al., 1999). MEF2 regulates cytokine expression and immune responses. MEF2 also regulates transcription programs underlying neuronal survival and synaptic remodeling (Chen and Cepko, 2009; Flavell et al., 2006; Flavell and Greenberg, 2008; Flavell et al., 2008; Mao et al., 1999; Morrow et al., 2008; Shalizi et al., 2006; Shalizi and Bonni, 2005; Yang et al., 2009). These observations suggest that small molecules that modulate MEF2 function could have therapeutic effect in cardiac hypertrophy and heart failure, autoimmune diseases and transplant rejection, neurodegenerative diseases and pathological impairment of learning and memory (Fischer et al., 2007; Stefanko et al., 2009).

Inside cells, the action of MEF2 includes three distinct steps: (i) transcriptional repression; (ii) calcium-dependent de-repression; and (iii) transcription activation. Transcriptional repression by MEF2 depends on its association with a variety of transcriptional co-repressors with intrinsic or associated histone deacetylase (HDAC) activity. In T cells, MEF2 bind Cabin1, which in turn associate with class I HDACs such as HDAC1, HADC2 and HDAC3 (Youn and Liu, 2000). In muscle cells, MEF2 binds directly to class II HDACs such as HDAC4, HDAC5, and HDAC9 and inhibits the expression of specific genes involved in the development and adaptive responses of muscle (Chan et al., 2003; Gregoire et al., 2006; Gregoire and Yang, 2005; McKinsey et al., 2001, 2002; Miska et al., 1999; Sparrow et al., 1999). Mice whose HDAC5 or HDAC9 has been knocked out showed increased sensitivity to hypertrophic stimuli, suggesting important roles of class II HDACs in heart hypertrophy (Potthoff and Olson, 2007). These and other data indicate that MEF2 and Class II histone deacetylases (HDACs), and particularly HDAC5 and HDAC9, are key mediators of hypertrophic signals in cardiomyocytes. Ample data have suggested that the MEF2/class II HDAC pathway is potential therapeutic target for heart hypertrophy.

In response to specific calcium signals, Cabin1 and HDACs are removed from MEF2 (Potthoff and Olson, 2007). MEF2 then recruits co-activators such as p300 and CBP to turn on distinct programs by association with a variety of transcriptional activators and co-activators (McKinsey et al., 2001; Sartorelli et al., 1997; Slepak et al., 2001; Wei et al., 2008). A small increase of p300 has been shown to be necessary and sufficient to induce MEF2-dependent cardiac hypertrophy. MEF2 has a highly conserved N-terminal region (residues 2-93), consisting of the well-characterized MADS-box and a MEF2-specific domain (Shore and Sharrocks, 1995). The MADS-box/MEF2 domain is remarkably rich in function, mediating DNA binding, dimerization, and protein-protein interactions with a myriad of MEF2 transcription partners (McKinsey et al., 2001, 2002), including Cabin1, Class IIa HDACs and p300/CBP. It has been shown that the MADS-box/MEF2 domain in MEF2 is necessary and sufficient to bind with a small motif conserved in class II HDACs and Cabin1. The CH3 domain of p300 and CBP is also shown to bind the MADS-box/MEF2 domain.

Despite the extensive knowledge about MEF2's involvement in various cellular processes available in the art, it has heretofore been impossible to capitalize on the knowledge due the lack of suitable molecular tools. In particular, how to modulate the activity of MEF2 by small molecules has been a long standing challenge. This is because MEF2 is a relatively small transcription factor without any apparent enzymatic activity; its main function is to bind specific DNA and recruit transcription co-regulators such as Cabin1, class II HDACs and p300/CBP to specific promoters. This mode of function is generally considered not druggable or at least very difficult to target by small molecules. Discovery or creation of such molecules will facilitate further advances in this field and can lead to new mechanism-based and structure-based therapeutic applications for MEF2-associated diseases, including inflammation, autoimmune diseases, neurodegenerative diseases, cancer, and cardiovascular disease.

The invention described in this application can also be extended to modulating the activity of other transcription factors such as the forkhead/winged helix transcription factor FOXP3 (Bennett et al., 2001; Fontenot et al., 2003; Hori et al., 2003; Wu et al., 2006; Zheng and Rudensky, 2007). FOXP3 is a key transcription factor critical to the development and function of regulator T cells (Tregs). Tregs are a special population of T cells required for suppressing the excessive activation of the immune system. Loss of function of FOXP3 by mutations and other mechanisms lead to fetal autoimmune diseases such as IPEX whereas enhanced expression of FOXP3 or its activity can confer suppression function. Elevated FOXP3 function can be beneficial in treating autoimmune diseases and transplant rejection while strategic down regulation of FOXP3 activity can be used to develop immune-based anti-tumor therapies (Zuo et al., 2007a; Zuo et al., 2007b). Thus, small molecules that bind FOXP3 and modulate its interaction with co-repressors and co-activators could have therapeutic application in autoimmune diseases, transplant rejection and cancer therapy.

Similarly to MEF2, the function of FOXP3 is tightly regulated by transcription co-regulators that include HAT (such as TIP60) and HDACs (including class I and class II HDACs) (Li et al., 2007). Thus, small molecules could be developed by methods described in this invention that binds FOXP3 and blocks its interaction with co-regulators including epigenetic regulators such as histone modifying enzymes and chromatin remodeling machines.

Similarly, targeting transcription co-regulators has also met its share of challenges.

Among the transcription co-regulators of transcription factors such as MEF2, class II HDACs are the best studied group.

Histone deacetylases (HDACs) (EC number 3.5.1) are a class of enzymes that remove acetyl groups from an $\epsilon$-N-acetyl lysine amino acid on a histone. Its action is opposite to that of histone acetyltransferases (HATs). HDACs proteins are now also being referred to as lysine deacetylases (KDAC) to more precisely describe their activity rather than their target, which also includes numerous non-histone proteins.

As their name suggests, one of HDACs main functions is to remove acetyl groups from histone proteins. Histone proteins are the chief protein components of chromatin. They act as spools around which DNA winds and play an important role in gene regulation and DNA packaging. Histone proteins have tails that are normally positively charged due to the amine groups present on their lysine and arginine amino acids. These positive charges help the histone tails to interact with and bind to the negatively charged phosphate groups on the DNA backbone.

The association between DNA and histone acts as a vital control mechanism in regulating the ability of transcription factors to access DNA. Strong association between DNA and histones restricts access by transcription factors and therefore represses gene transcription (Morrison et al., 2007). Modification of histones or DNA can alter the strength of their association and thus modulate transcriptional activity (Morrison et al., 2007). Covalent addition of methyl, phosphate, or acetyl moieties has been shown to alter the nucleosome state and consequently affect transcription. Acetylation results from the addition of an acetyl group to the $\epsilon$-amino group of conserved N-terminal lysine residues on histones. Addition of acetyl groups to histones reduces the attractive force between positively charged histone proteins and the negatively charged DNA phosphate backbone, resulting in a more relaxed and accessible chromatin structure. HATs facilitate histone acetylation and are thus believed to be transcriptional activators. Conversely, HDACs serve to remove acetyl groups from histones and thereby repress transcription. Thus, it is the interplay between HATs and HDACs activity that primarily governs local chromatin structure and gene expression. HDACs alter global gene transcription through the deacetylation of chromatin. It should be noted that HDACs do not directly bind DNA sequence and require additional factors for target gene recognition (Morrison et al., 2007).

There are 4 recognized subtypes of HDAC proteins (class I-IV) based on function and DNA sequence similarities. The first two subtypes are considered "classical" HDACs whose activity are inhibited by trichostatin A (TSA). Class I HDACs includes HDACs 1, 2, 3 and 8, which are expressed ubiquitously (Zhang and Olsen, 2000). Class II HDACs has two subgroups, IIa that includes 4, 5, 7 and 9, and IIb that includes HDAC6 and HDAC10. Class IIa share a common structural organization, with carboxyl-terminal catalytic domain and an amino-terminal extension that mediates interactions with members of the myocyte enhancer factor 2 (MEF2) family of transcription factors. HDACs also differ in terms of their subcellular localization with class I generally found in the nucleus, class IIb are located mostly in the cytoplasm, while class IIa shuttle between the nucleus and the cytoplasm. Unlike class I HDACs, class IIa HDACs are tissue-restricted, with especially high levels of expression in heart, skeletal muscle, and brain (Zhang et al., 2002). Class III is a family of NAD$^+$-dependent proteins not affected by TSA and class IV is considered an atypical category of its own. HDAC11 is grouped in class V.

Given the important roles that HDACs play in cellular processes, the medical applications of HDAC inhibitors (HDACi) is an intense area of research. However, many uses of HDACi in medicine were discovered without knowledge of the underlying mechanism. For example, in psychiatry and neurology, there is a long history of using valproic acid as mood stabilizers and anti-epileptics. The anticonvulsant property of valproic acid was accidentally discovered when it was being used as a vehicle for a number of other compounds that were being investigated as anticonvulsant. It was not until later that valproic acid was identified as a HDACi. In recent years, HDACi are being actively studied as a mitigator or treatment for neurodegenerative diseases. There has also been extensive effort to develop HDACi for cancer therapy. For example, Vorinostat (SAHA) has recently been approved for treatment of cutaneous T-cell lymphoma (CTCL). An alternative agent under clinical evaluation for CTCL is the cyclic depsipeptide natural product FK228 (Romidepsin) which is a potent inhibitor of class I HDACs. In addition, a clinical trial is studying the effects of valproic acid on the latent pools of HIV in infected persons. Despite the growing interest in the medicinal applications of HDACi, the exact mechanisms by which these compounds work are still not well understood. Thus, these efforts are largely guided by guesswork and trial-and-error experiments.

One particular problem with the use of HDACi is that most of the known small molecules that inhibit HDAC activity are designed to function by targeting the catalytic activity of HDACs. However, since the active site is a conserved feature shared by a large number of different HDAC isoforms, it is inherently difficult to identify isoform-selective HDACi. Therefore, most HDACi have low specificity and are incapable of specific targeting of any particular species of HDAC. For example, trichostatin A (TSA) is among the most potent reversible HDACi currently known, with an $IC_{50}$ in low nanomolar range. TSA with its hydroxamic acid group and its five-carbon atom linker to the phenyl group, has the optimal conformation to fit into the active site of HDAC (de Ruijter et al., 2003; Somoza et al., 2004). All HDACs are thought to be approximately equally sensitive to inhibition by TSA (de Ruijter et al., 2003).

A major impediment, therefore, for the discovery of small molecules that inhibit the function of HDACs and thereby modulate the activity of related transcription factors, is that the current state of the art is focused on the discovery and optimization of HDACi that are identified and evaluated through their ability to bind to the active site of the HDAC enzymes. Typically, these HDACi have the general structure R-L-Z, where R is a protein surface recognition group connected via a short fatty linker L to a $Zn^{2+}$-chelating group Z that binds to the active site zinc atom. The most common chelating groups (Z) featured in the known HDACi are: hydroxamic acids (TSA, vorinostat, LAQ824, belinostat), thiol derivatives (FK228, largazole) or electrophilic ketones (trapoxin A). A potential drawback of such groups that bind tightly to metal cations like $Zn^{2+}$ is that they may lack sufficient selectivity for a particular protein, resulting in various side effects.

Another class of known HDACi are the benzamides that feature an ortho-aminoanilide (2-aminoanilide) moiety, including MS-725, MGCD0103, pimeloylanilide ortho-aminoanilide (PAOA) and compound 106 ($N^1$-(2-aminophenyl)-$N^7$-p-tolylheptanediamide) which was investigated as a potential therapeutic for neurodegenerative diseases including Friedreich's ataxia and Huntington disease (Chou et al., 2008; Herman et al., 2006; Paris et al., 2008; Rai et al., 2008; Thomas et al., 2008; Wong et al., 2003). Although the detailed molecular mechanism of action of this class of HDACi is not known, these molecules were postulated to involve binding of the o-aminoanilide group to the zinc atom of the HDAC active site, despite the lack of any direct evidence regarding such binding motif. Moreover, such molecules were found to exhibit biological activity implicating inhibition of HDAC function, even though other non-selective HDACi did not show similar activity. For example compound 106 was shown to be very active for the induction of frataxin, despite weak HDAC while closely related HDACi such as SAHA did not have this type of activity. Consequently, in light of the absence of a molecular mechanism for the actions of this class of compounds, the optimization of their therapeutic potential has been hampered.

Several additional factors resulting from the well-regulated biological roles of the various HDAC isoforms, impose further challenges for the conventional approaches to the design of HDACi. Experiments have shown that the amount of acetylated histones increases in the presence of HDACi. Yet, recruitment of HATs and HDACs by DNA-bound transcription factors results in the formation of multi-protein transcription regulatory complexes that confer cell type specificity and signal dependent regulation to arrays of subordinate genes. Using HDACi that inhibit HDACs indiscriminately is akin to throwing a monkey ranch into a complicated and delicately balanced machine. This explains the numerous undesirable side-effects observed in many of the trials involving HDACi.

The problems encountered in investigating medicinal uses of HDACi are also shared by researchers investigating epigenetic regulation. Epigenetic regulation is the establishment of inheritable gene expression patterns without permanently changing the DNA sequence. It has emerged as a key mechanism for regulating cellular function.

Alteration of epigenetic regulation is a hallmark of many diseases, especially cancer. Small molecules that are being developed as drugs in treating these diseases, typically found via phenotypic screening, act by modulating the epigenetic control of cellular process. As such, the fundamental mechanisms of epigenetic regulation is an area of intense interest. At the same time, the search for small molecule epigenetic regulators is becoming a very promising area for drug discovery.

Because epigenetic regulation is achieved largely through chemical modifications of chromatin structure by enzymes that act upon DNA (e.g. DNA cytosine methyltransferase) or proteins (e.g. HATs, HDACs, histone methylases, and histone demethylases), in this context, HDACs' role in regulating DNA transcription can be viewed as a component of epigenetic regulation. Similar to HDACi, the majority of current chemical modulators of epigenetic regulators inhibit these enzymes by binding to their catalytic site, which is often shared by multiple enzymes with distinct cellular roles.

Despite recent advances regarding the role of transcription factors such as MEF2, and its implication in several major diseases, it has not been possible to identify small molecules that are capable of modulating the function of MEF2. Such molecules would facilitate further advances in this field and can lead to new mechanism-based and structure-based therapeutic applications for MEF2-associated diseases, including inflammation, autoimmune diseases, neurodegenerative diseases, cancer, and cardiovascular disease.

Therefore, a general problem in this area of research has been the lack of small molecules that can target a specific epigenetic regulator enzyme or protein. A further problem has also been the lack of methods for the design, evaluation and optimization of such small molecules, in a manner that bestows the required selectivity without the associated drawbacks resulting from broad-spectrum activities across entire enzyme or protein classes. Such molecules will have important applications as molecular tools in studying the basic mechanism of epigenetic regulation as well as therapeutic agents for targeted therapeutic interventions.

SUMMARY OF THE INVENTION

Through extensive biochemical and structural studies (Guo et al., 2007; Han et al., 2005; Han et al., 2003), the inventors have unexpectedly discovered a unique structural feature of MEF2 that made it possible to modulate its activity using small molecules. This discovery lies at the core of the invention as it goes against conventional wisdom and opens up a new door of possibilities. Based on this unexpected discovery, inventors have devised a general strategy for modulating cellular processes by blocking the interactions between transcription factors and their co-factors via an interfacial inhibitor. Accordingly, this invention also provides methods for identifying, screening, assaying, and synthesizing small molecule modulators that are capable of binding to a site lying in the interfacial surface of the factor-cofactor complex, thereby, disrupting the formation of the complex.

Thus, this invention has solved the long standing problem of targeting the heretofore "undrugable" transcription factors such as MEF2.

With respect to the specificity problem faced by HDACi, this invention provides an alternative approach for the development of small molecule modulators of HDAC function. Rather than targeting the active site of a particular HDAC, the present invention targets the binding site of the HDAC with an associated transcription factor which is required for regulating transcription. Because different HDAC subtype will have different binding surface to different transcription factor, by targeting the interface of these protein-protein interactions, the specificity issue posed by the conservative active site is resolved.

In particular, the present invention targets the interaction between the transcription factor MEF2 and class IIa HDACs. The activity of MEF2 is controlled by class IIa HDACs that bind MEF2 on specific promoters to repress target gene expression (Potthoff and Olson, 2007). Some small molecule inhibitors of HDACs (HDACi) that are being developed for the treatment of a variety of cancers also show therapeutic potential in diseases where deregulation of MEF2 and HDACs activity is implicated, including cardiac hypertrophy, neurodegenerative disorders, and immune dysfunction (Morrison et al., 2007; Paris et al., 2008). These observations suggest that small molecules blocking class IIa HDAC:MEF2 interaction might offer similar clinical benefits as member-specific HDACi (Guo et al., 2007; Han et al., 2005; Han et al., 2003).

Class IIa HDACs function closely with MEF2 in muscle, neurons and T cells. Class IIa HDACs do not bind DNA but depend on its interaction with DNA-bound MEF2 for promoter targeting. This interaction is mediated by a short amphipathic helix conserved in class IIa HDACs but not other HDACs that binds to a hydrophobic groove on the MADS-box/MEF2 domain of MEF2 (Guo et al., 2007; Han et al., 2005; Han et al., 2003). Such a ligand/receptor like binding mechanism suggests that it might be possible to use small molecules to block the recruitment of class IIa HDACs to MEF2-specific promoters (Guo et al., 2007; Han et al., 2005; Han et al., 2003).

The invention is based on systematic structure and biochemical studies (Guo et al., 2007; Han et al., 2005; Han et al., 2003) suggesting that small molecules binding to MEF2 can modulate its activity in the recruitment of transcription co-regulator such as Cabin1, class IIa HADCS and p300/CBP. Most of the these co-regulators have intrinsic function to modify chromatin (e.g. HDACs, p300 and CBP) or the ability to recruit chromatin modifying enzymes and machinery (e.g. mSin3A that binds Cabin1, HP1, CtBP, 14-3-3 that binds class IIa HDACs). Thus, small molecules that bind MEF2 and modulate its interactions with other transcription co-regulators can serve as epigenetic modulators in tissues where MEF2 play key regulatory roles. These small molecules can therefore be used to treat diseases where the activity of MEF2-dependent gene expression is dysregulated. The dysregulation could result from genetic mutations of MEF2 and its associated factors, diminished or excessive signals leading to the reduced or overly activated MEF2 function, abnormal under- or over-expression of co-factors that bind and interact with MEF2. Potential clinical applications of the MEF2-binding small molecules include but not limited to diseases from the muscle, immune and nervous systems. In the muscle system are cardiac hypertrophy, muscle fiber type remodeling, and other muscle related diseases resulting from imbalanced MEF2 function. In the immune system are a variety of autoimmune diseases or immune deficiency that result from excessive or too little MEF2-dependent gene expression. MEF2-binding small molecules can also be used to manipulate the function of regulatory T cells and the overall immune response for preventing transplant rejection. Since MEF2-dependent gene expression is intimately linked to synapses remodeling and neuronal survival, MEF2-binding small molecules can also be used treat a variety of neurodegenerative diseases (e.g. Alzheimer's disease and Huntington disease etc), autism, psychiatric disorders, and impaired learning and memory that result from deregulated MEF2 function.

Because small molecule modulators of this invention operate by targeting binding sites located at the protein-protein interaction interface of the transcription factors and their co-factors, they are also referred to herein as interfacial inhibitors.

Having explained the basic principles of this invention, we now summarize the various aspects and embodiments of the invention below:

In a first aspect, the invention provides an assay for screening, identifying, or optimizing a candidate interfacial inhibitor. Assays in accordance with this aspect of the invention will generally include the steps of contacting the candidate interfacial inhibitor to an evaluating element comprising a molecular surface defined by a protein-protein interface, which includes beta strands S1, S2 and S3 and helix H2 of each MEF2 monomer and the short helix motif from Cabin1 and HDAC4 and HDAC 9. In some preferred embodiments, the evaluating element is operatively coupled with a reporting element that provides information about the candidate inhibitor. In a preferred embodiment, the assay is a cell-based luciferase assay that allow rapid and high throughput screen and optimization of small molecules that bind MEF2 and modulate its binding to transcription co-regulators. This assay is developed based on more than 10 years of structural and biochemical studies of MEF2 complexes by the inventor's laboratory. This invention claims that the protein-protein interface, first identified by crystallography studies, and further demonstrated by structure-guided mutation studies in the invention, could serve as the molecular basis for a highly specific and sensitive screen for MEF2-binding small molecules. In other embodiments, the evaluating element of the assay may be implemented with physical assays that include but are not limited to pull down, coimmunoprecipitation or fluorescence quenching and anisotropy or any in vitro binding assays and cell-based luciferase reporter assay, transgenic reporter assay that are based on the protein-protein interface indentified by this invention.

In a second aspect, this invention also provides compounds useful as epigenetic modulators of MEF2-dependent transcription in a variety of mammalian tissues that include but are not limited to muscle, immune and nervous systems. In some preferred embodiments, compounds in accordance with this aspect of the invention may include but are not limited to the previously published compounds (Chou et al., 2008; Herman et al., 2006; Paris et al., 2008; Rai et al., 2008; Thomas et al., 2008; Wong et al., 2003), pimeloylanilide orthoaminoanilide PAOA, and the commercially available homolog suberoylanilide orthoaminoanilide, or BML-210, as well as their structurally related derivatives.

In a third aspect, this invention also provides a molecular framework defined by the BML-210 binding site on MEF2 derived from the structural frame work established by the crystal structure of BML-210 bound to MEF2, as set forth in the crystal structure coordinates in Table 1. We co-crystallized BML-210 with a MEF2A (1-78) dimer bound to DNA. The crystals diffracted to 2.4 Å, and the structure was solved by molecular replacement using the MEF2A (1-78):DNA complex as the search model (Santelli and Richmond, 2000). BML-210 adopts an extended conformation to bind into the hydrophobic pocket of the MEF2 (FIG. 1d). One end of the molecule, the phenylamide group, is surrounded by a number of hydrophobic residues including Leu66, Leu67, Thr70, Leu66' (prime sign denote residues from the other monomer) and Thr70'. The amide group at this end is also in position to engage in hydrogen bonding interactions with Thr70 and Thr70', respectively. At the other end of the BML-210, the ring-link electron density is in a more hydrophilic environment surrounded by Asn73, Gln56', Asp61' and Asp63'. This region corresponds to the ortho-aminoanilide group. Here the ortho-aminoanilide moiety with its amide group make extensive van der waals contacts and potential hydrogen bonding interactions with residues of MEF2 (FIG. 1d). The methylene groups of the octanediamide fit snugly between helix H2 of the two MEF2 molecules, making numerous contacts to the main chain and side chain of MEF2 residues, mostly of hydrophobic nature (FIG. 1d). Based on the crystal structure of BML-210 bound to MEF2, we claim that the surface residues that contact or are close proximity to contact BML-210 and PAOA can be used to guide the design and screen of small molecules to MEF2 by experimental and computational based approaches. These residues include all the residues on strand S1, S2 and S3 and helix H2 of MEF2 that are exposed. This structural frame, coupled with the high throughput, specific and sensitive assay described in the present invention will allow rapid design and optimization MEF2-binding small molecules that include BML210 and PAOA derivatives and molecules based on novel molecular scaffolds. The crystal structure of BML-210 bound to MEF2 disclosed in this invention, in addition to defining the small molecule MEF2-binding site as described herein, it also reveals for the first time a likely binding site for the ortho-aminoanilide moiety present in BML-210 and in other benzamide-containing HDAC inhibitors. Notably, this binding site is different from the HDAC enzyme's active site as has been postulated previously for this class of HDAC inhibitors.

In a fourth aspect, the invention provides MEF2-binding small molecules useful for binding to the interfacial binding site defined by the molecular framework in the third aspect above. In one embodiment the provided molecules are MEF2-binding small molecules with a general structural formula derived from the identified binding site derived from the crystal structure of BML-210 bound to MEF2. The provided small molecules are designed to bind to the described structural fold and would potentially bind MEF2 with high affinity and selectivity. The compounds provided under this embodiment of the invention include compounds of the general formula $R^a$-L-$R^b$ that bind to the MEF2 binding site, wherein:

$R^a$ is a recognition group that binds to the hydrophobic region of the MEF2 binding site selected from a group that includes lower alkyl, alkenyl, alkynyl, aryl, heteroaryl, alkoxy, aryloxy, alkylthio, arylthio, or $R^cR^dNC(\!=\!\!O)\!-\!$, $R^cR^dN(SO_2)\!-\!$, wherein:
$R^c$ and $R^d$ are independently selected from a group consisting of hydrogen, alkyl, alkenyl, alkynyl, alkoxy, aryl, heteroaryl, alkylamino, dialkylamino, arylamino or heteroarylamino.

L is a linker consisting of a chain of up to 20 carbon atoms, provided that up to three carbon atoms can be replaced with an oxygen, nitrogen or sulfur atom, and further provided that it can include substituents selected from a group consisting of:
alkyl, alkenyl, alkynyl, aryl, heteroaryl, benzo, hydroxy, alkoxy, aryloxy, oxa, keto, amido, sulfonamido, or fluoro $R^b$ is a recognition group that binds to the hydrophilic region of the MEF2 binding site selected from a group that includes lower alkyl, alkenyl, alkynyl, aryl, heteroaryl, alkoxy, aryloxy, alkylthio, arylthio, or $R^cR^dNC(\!=\!\!O)\!-\!$, $R^cR^dN(SO_2)$, wherein:
$R^c$ and $R^d$ are independently selected from a group consisting of hydrogen, alkyl, alkenyl, alkynyl, alkoxy, aryl, heteroaryl, alkylamino, dialkylamino, arylamino or heteroarylamino.

In a preferred embodiment the provided compounds have the general structure $Ar^1$-$L^1$-$L^2$-$L^3$-$Ar^2$ wherein:
$Ar^1$ and $Ar^2$ are aromatic rings independently selected from a group consisting of benzene, naphthalene, pyridine, pyrimidine, pyrazine, quinoline, isoquinoline, pyrrole, furan, thiophene, imidazole, pyrazole, oxazole, thiazole, isoxazole, indole, benzimidazole, benzothiazole, benzoxazole, provided that the aromatic ring may contain up to seven substituents selected from a group consisting of: hydrogen, alkyl, alkenyl, alkynyl, alkoxy, aryl, heteroaryl, amino, alkylamino, dialkylamino, arylamino, heteroarylamino, hydroxy, or halo. The substituents can also join together to form a ring of up to 12 atoms,
$L^1$ and $L^3$ are linking groups independently selected from a group consisting of amino, alkylamino, arylamino, oxa, keto, NHC(=O), NR(C=O), S(=O) or —S(=O)$_2$—
$L^2$ is a linking group selected from a group consisting of a chain of up to 10 carbon atoms, provided that up to three atoms can be replaced with an oxygen, nitrogen or sulfur atom, and further provided that these atoms can contain substituents selected from a group consisting of:
alkyl, alkenyl, alkynyl, aryl, heteroaryl, benzo, hydroxy, alkoxy, aryloxy, oxa, keto, amido, sulfonamido, or fluoro In a further preferred embodiment, the provided compounds have the general formula:

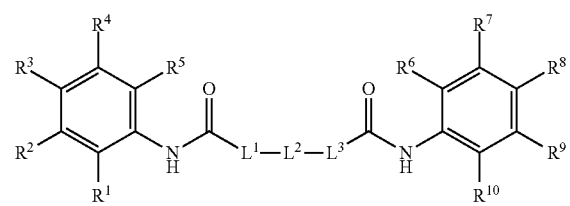

wherein:
$R^1$-$R^{10}$ are independently selected from a group consisting of hydrogen, alkyl, alkenyl, alkynyl, alkoxy, aryl, heteroaryl, amino, alkylamino, dialkylamino, arylamino, heteroarylamino, hydroxy, and halo;

L¹ and L³ are linkining groups independently selected from a group consisting of amino, alkylamino, arylamino, oxa, keto, NHC(=O), NR(C=O), S(=O) or —S(=O)2-

L² is a linking group selected from a group consisting of a chain of up to 10 carbon atoms, provided that up to three atoms can be replaced with an oxygen, nitrogen or sulfur atom, and further provided that these atoms can contain substituents selected from a group consisting of: alkyl, alkenyl, alkynyl, aryl, heteroaryl, benzo, hydroxyl, alkoxy, aryloxy, oxa, keto, amido, sulfonamide, or fluoro.

In a further preferred embodiment, the provided compounds are selected from the following list of compounds (FIG. 2)

These compounds showed a wide range of affinity in binding to MEF2 in vitro and in vivo, and could be used as lead to develop MEF2-based therapeutics in muscle, immune and nervous systems as mentioned above. The compounds indeed showed effect in promoting regulatory T cell functions in vitro and in mouse model, and are therefore potential drug leads for autoimmune diseases and preventing transplant rejection.

Methods for the preparation of the provided MEF2-binding molecules are also provided in this invention.

In a fifth aspect, the invention also provides compounds and compositions useful for treating diseases that result from deregulation of MEF2-dependent transcription. Compositions in accordance with this aspect of the invention will include one or more of a compound capable of blocking binding of MEF2 and its co-factors. The provided compounds and compositions can be used in therapeutic applications involving the modulation of epigenetic regulation associated with the interaction of transcription factors and their recruited histone-modifying enzymes. In particular, the provided MEF2-binding small molecules can be used to treat a variety of diseases resulting from deregulation of MEF2-dependent transcription, which include but not limited to cardiac hypertrophy, muscle fiber type remodeling, and other muscle-related diseases resulting from imbalanced MEF2 function; autoimmune diseases or immune deficiency that result from excessive or too little MEF2-dependent gene expression, and transplant rejection; a variety of neurodegenerative diseases (e.g. Alzheimer's disease and Huntington disease etc), autism, psychiatric disorders, and impaired learning and memory that result from deregulated MEF2 function. A further application of this embodiment of the invention involves small molecules that modulate the function of the FOXP3 transcription factor that can be used to treat a variety of diseases that result from deregulation of FOXP3-dependent transcription. These diseases include but not limited to autoimmune diseases, transplant rejection and cancer.

The sixth embodiment of this invention involves the preparation of the drug: MEF2 complex and its crystallization for structure determination. This protocol define the specific protein fragment of MEF2A (2-78) and the range of buffer conditions to obtain high quality of crystals of compounds bound to MEF2. This method of complex preparation and crystallization is essential for structural characterization of current and future small molecules bound to MEF2 and use the structure to guide the optimization of the lead compounds.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope Other aspects and advantages of the invention will be apparent from the following description and the appended claims.

DETAILED DESCRIPTION

Figure 1C:
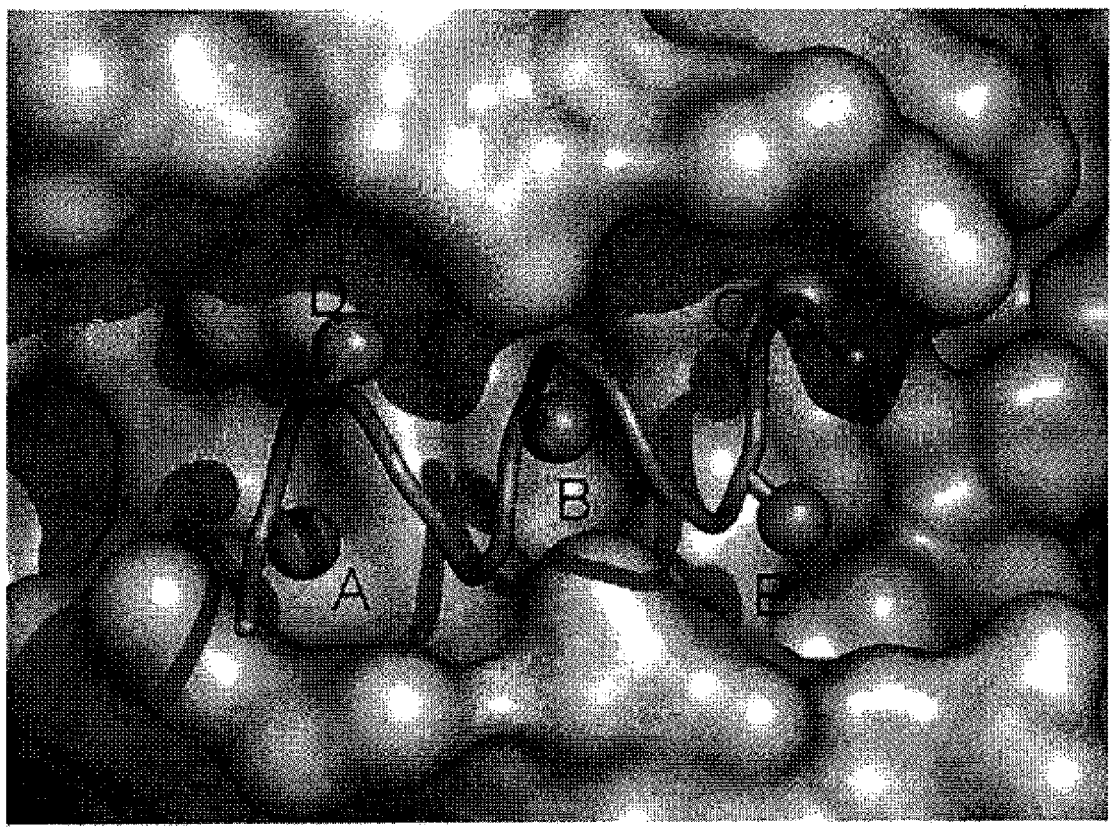
In FIG. 1c XX(V/T)KXY(L)YXX(V/I/L)(L)XX is SEQ ID NO:3.

Having summarized the various aspects of this invention, we now describe in detail the various exemplary embodiments to further illustrate the invention.

Specific Interfacial Inhibitors of HDACs and Uses Thereof.

As mentioned above, what makes the study of epigenetic regulators challenging is the fact that there are a large number of enzyme isoforms, many of which have distinct functions. For example, among the four HDAC enzyme super families, class I (HDAC 1, 2, 3, and 8) and class II (HDAC 4, 5, 6, 7, 9, and 10) are the two major classes implicated in cancer. Although the unique function of each individual member can be studies by molecular biology approaches such as knockout or knockdown, their roles in drug-based therapy cannot be assessed because most current HDAC inhibitors target the catalytic domain common to most HDACs (class I and II). In fact, it is often observed that a given HDAC inhibitor induces what appears to be opposing effects in different cellular conditions, presumably by affecting the activity of different HDAC isoforms. Thus, the lack of isoform specificity of current HDACi presents a major barrier to rational mechanistic studies of drug effects and the individual function of specific HDACs. Also, it is not clear if it is more pharmacologically beneficial to inhibit a large number of HDACs or a small subset or even a specific member. It is possible that certain clinical applications (e.g. cancer therapy) may require the former, whereas others (e.g. neurodegeneration and inflammation) may benefit from the latter.

Currently available inhibitors of class I and class II HDACs can be grouped into six categories based on the key features of their chemical structures: (1) hydroxamic acids; (2) thiol-containing molecules; (3) electrophilic ketones; (4) short-chain fatty acids; (5) benzamides (ortho-aminoanilides); and (6) cyclic depsipeptides. While it is well established that some of these molecules, including hydroxamic acids, thiols, and electrophilic ketones, work by binding to the zinc ion of the HDAC active site, the inhibitory mechanism of the other categories are not well defined. Different HDAC inhibitors have shown different activities on different classes of HDACs. For example, while members of the hydroxamic acids category, such as TSA and SAHA, are potent inhibitors across the entire class I and class II HDACs, some members of the benzamide family (e.g. pimeloylanilide ortho-aminoanilide (PAOA), MS-275, CI-994, MGCD-0103), and the cyclic peptide family (e.g. FK228), showed modest selectivity toward certain HDAC members or subclasses. However, because of the general lack of understanding of the molecular mechanisms of HDAC inhibitors, how this selectivity is achieved is not clear. Consequently, the empirical observations of selectivity in some HDAC inhibitors could not guide rational design of subtype-specific HDAC inhibitors. While crystal structures of the catalytic domain of several class I (HDAC8) and class II (HDAC4 and HDAC7) members and their complexes with different inhibitors have been solved, these structures and the structure-based sequence-alignments of class I and class II HDACs suggest that the active site is highly conserved and show only minor differences in the surrounding region. Therefore, they also fail to provide any insights with regard to potential mechanisms of selectivity. Given this background, rational design of subtype-specific inhibitors against the highly conserved catalytic domain is widely considered to be highly challenging.

Observing that HDACs often exist in large multi-protein complexes with specific co-regulators and other chromatin modifying enzymes, inventors of this invention postulated that a mechanism-based approach may offer a better pathway to identifying and optimizing novel HDAC-based small molecule epigenetic regulators. That is, instead of targeting the active site of the enzyme as dictated by conventional approaches of drug design, one would develop small-molecules targeting the protein-protein interactions between HDACs and their relevant functional partners.

Accordingly, in one aspect, this invention provides a method of modulating HDAC function by blocking the binding of HDAC to an associated transcription factor. In general, methods according to this aspect of the invention will have the steps of: contacting the transcription factor with interfacial inhibitor, wherein the interfacial inhibitor is capable of selectively binding to a site within the interfacial surface between the transcription factor and HDAC, thereby preventing this HDAC from performing its catalytic activity at protein sites that are located in the vicinity of the DNA-binding site of the transcription factor.

The HDAC may be any HDAC isoform from a classical HDAC or a subset thereof. Exemplary HDAC may include HDAC 4, 5, 6, 7, 9 and 10, or any subset thereof. In a preferred embodiment, the HDAC is a class IIa HDACs, and in a further preferred embodiment the HDAC is either HDAC4 or HDAC9.

The transcription factor may be any transcription factor known to bind to the HDAC. Exemplary transcription factors may include MEF2, FOXP3, GATA3, and Cabin1 but are not limited thereto. In a preferred embodiment, the transcription factor is MEF2.

The interfacial inhibitor may be a small molecule.

Methods described herein above may be used in a research setting for obtaining information regarding the function and mechanisms of a HDACs and the counterpart transcription factor in vivo or in vitro. They may also be used in a clinical setting for treating diseases.

Diseases that may be treated with methods of this invention are generally those involving cardiac hypertrophy, muscle fiber type remodeling, and other muscle-related diseases resulting from imbalanced MEF2 function; autoimmune diseases or immune deficiency that result from excessive or too little MEF2-dependent gene expression, and transplant rejection; a variety of neurodegenerative diseases (e.g. Friedrich's ataxia, Alzheimer's disease and Huntington disease etc), autism, psychiatric disorders, and impaired learning and memory that result from deregulated MEF2 function. Exemplary diseases may include neurodegenerative diseases, heart diseases, autoimmune diseases, inflammation, and cancer, but are not limited thereto.

When used in a clinical setting, methods in accordance with this aspect of the invention will include the general steps of: administering to a patient a pharmaceutically effective amount of a blocking agent, in which the blocking agent is capable of blocking the binding of a HDAC to a transcription factor.

When used in a different clinical setting, methods in accordance with this aspect of the invention will include the general steps of: administering to a patient a pharmaceutically effective amount of a blocking agent, in which the blocking agent is capable of blocking the binding of a Cabin1 to MEF2. Cabin1 is a transcription co-repressor of calcineurin-dependent transcription program. It is highly expressed in T cells and neuronal cells.

When used in yet a different clinical setting, methods in accordance with this aspect of the invention will include the general steps of: administering to a patient a pharmaceutically effective amount of a blocking agent, in which the blocking agent is capable of blocking the binding of a p300 to MEF2.

When used in yet a different clinical setting, methods in accordance with this aspect of the invention will include the general steps of: administering to a patient a pharmaceutically effective amount of a blocking agent, in which the blocking agent is capable of blocking the binding of a CBP to MEF2.

In a more general setting, methods in accordance with this aspect of the invention will include the general steps of: administering to a patient a pharmaceutically effective amount of a blocking agent, in which the blocking agent is capable of blocking the binding of any transcription co-regulators that bind MEF2.

As set forth above, the HDAC may be any classical HDAC or a subset thereof. The blocking agent may be a small molecule, a helical peptidomimetic, or a combination thereof, so long as the blocking agent is capable of selectively binding to a site located on the interfacial surface between the HDAC and the transcription factor. In a preferred embodiment, the transcription factor is MEF2.

Methods and Tools for Developing Interfacial Inhibitors

In another aspect, this invention also provides an assay for identifying an interfacial inhibitor capable of binding to an interfacial site between HDAC and a transcription factor so as to block the interactions thereof.

Assays in accordance with this aspect of the invention will generally have the steps of introducing a test compound to an evaluation element, wherein said evaluation element comprises an interfacial binding site on a MEF2 dimer defined by the interface between a first group of structural elements on the MEF2 dimer and a second group of structural elements. The first group of structural elements include the beta strands S1, S2, S3, and the helix H2 of each of the MEF2 monomer (The secondary structural elements and corresponding residue ranges are as described in Han et al., Nature 2003). The second group include the short helix, motif from Cabin1, HDAC4, HDAC9, HDAC5, HDAC7, p300 and CBF. The evaluation element may also be operatively coupled with a reporter element for reporting information related to the binding or non-binding of the test compound.

In a preferred embodiment, there is disclosed herein a two-hybrid system based assay includes a binding domain fused with a bait, an activating domain fused with a prey, and a reporter gene; and determining a reporter signal level. The binding domain comprises a MEF2D fused with GAL4 DNA (GAL4-MEF2); the activating domain comprises MEF2 binding motif of HDAC4 fused with VP-16 (HDAC4-VP16). The reporter gene is a GAL4-driven reporter plasmid (GAL4Luc), all hosted in a cell host.

This preferred embodiment of this invention is a cell-based luciferase assay that allows rapid and high throughput screening and optimization of small molecules that bind to a transcription factor such as MEF2 and modulate its binding to transcription co-regulators. The assay is developed based on more than 10 years of structural and biochemical studies of MEF2 complexes by the inventor's laboratory. This exemplary embodiment based that the protein-protein interface, first identified by crystallography studies, and further demonstrated by structure-guided mutation studies in the invention, could serve as the molecular basis for a highly specific and sensitive screen for MEF2-binding small molecules.

Any assay that based on this protein-protein interface, which include beta strands S1, S2 and S3 and helix H2 of each MEF2 monomer and the short helix motif from Cabin1 and HDAC4 and HDAC 9 are considered to be within the scope of this invention. Other exemplary assay implementations may include any physical assay techniques such as, but not limited to, pull-down, co-immunoprecipitation; fluorescence-based binding assays and functional assays including, but not limited to, luciferase reporter assay, and transgenic reporter assay that are based on the protein-protein interface indentified by this invention.

In particular, in order to establish if a provided compound can indeed disrupt the binding of class IIa HDAC inside cells, several types of assays can be used, including the Chromatin Immunoprecipitation (ChIP) assay. HDAC4 plasmid construct is transiently transfected into Hela Cells. HDAC4 occupation on MEF2 mediated promoters are detected by ChIP using appropriate specific antibodies and PCR primers in the presence of the tested compound and buffer control. A fluorescence imaging based method as an alternative approach to ChIP analysis can also be used. GFP-fused MEF2C and HDAC4 is transfected into HeLa or C2C12 cells to study their interaction. When expressed alone, GFP-HDAC4 localizes in the cytoplasm in a diffusive manner, whereas GFP-MEF2 localizes in the nucleus, also in a diffusive pattern. When co-expressed, HDAC4 and MEF2 form punctate bodies inside the nucleus. Although the nature of these punctate nuclear bodies is unknown, their formation is apparently dependent on MEF2:HDAC4 interaction, as a HDAC4 mutant lacking a functional MEF2-binding motif fails to target MEF2 to nuclear bodies. Finally, a genome-wide analysis of MEF2 target genes by mRNA profiling (microarray) and binding location (ChIP-on-chip) can further facilitate this method, by selecting well-known MEF2 target genes that show large responses to MEF2-dependent repression or activation in the resting or activated (e.g. with calcium signal turned on) state. Using this method it can be established if these genes are potentially regulated by class II HDACs or other MEF2 co-repressors (e.g. Cabin1) by detecting the promoter presence of class IIa HDAC using ChIP and by monitoring expression changes upon drug treatment or after siRNA knockdown of HDAC4, 5, 7 or 9 (expression changes due to siRNA are evaluated first). Overall this method can be used to evaluate a compound at a genome-wide level by analyzing gene expression using microarray and by detecting genome-wide binding of class IIa HDACs in the presence of various concentrations of the provided compound.

To facilitate performing the assay, this invention also provides a high throughput, highly sensitive and specific screen platform for searching MEF2-binding small molecules. This platform comprises stably transformed cell lines containing the GAL4-driven reporter plasmid (GAL4Luc), MEF2D fused with GAL4 DNA-binding domain (GAL4-MEF2), the MEF2-binding motif of HDAC4 fused with VP-16 (HDAC4-VP16), GAL4 DNA-binding domain fused with VP-16 (positive control) and various compounds as negative and positive controls. A kit consistent of the above stable cell lines, plasmids, and control compounds can be made for the screen by users searching for new MEF2-binding molecules and for optimizing existing leading compounds. By switching MEF2D to MEF2A, MEF2B and MEF2C, one can also use this method to search for compounds that bind selectively to an isoform of the MEF2 family. Such compounds can be used to study the function and involvement of specific MEF2 family members in diseases and can be employed in the development of diagnostic agents and for the identification of more specific therapeutic agents for MEF2-associated diseases.

In yet another aspect, the invention also provides a method for identifying a subtype-specific HDAC inhibitor/modulator by targeting their regulatory and functional complexes. Methods in accordance with this aspect of the invention generally includes the steps of: (1) solving the structure or substructure that contains functionally important interfaces; (2) applying docking analysis to the solved structures by computationally docking test molecules selected from existing or new potential HDAC inhibitors; (3) developing an assay for screening compounds that can disrupt the protein-protein interactions between the HDAC complex of interest; (4) characterizing the compound identified in step (3); (5) optimizing the compound computationally; and (6) synthesizing the optimized compound and validating the compound using the assay of step (3).

For step 1, the structure can be solved by molecular replacement using existing structure as the search model. If necessary, experimental phases can be obtained MAD or MIR. For step 2, docking can be performed using standard package such as AutoDock. Step 3 is as described above and will most be based on mammalian two-hybrid assay. The rest of the steps will depend on the nature of the compounds using methods known in the art.

In still another aspect, the invention also provides compounds useful as blocking agents for blocking the binding between a HDAC and a transcription factor. The HDAC may be any classical HDAC or a subset thereof. The transcription factor may be any transcription factor known to bind to HDAC, including but not limited to MEF2, FOXP3 and GATA3.

In a preferred embodiment, the transcription factor is MEF2.

Compounds according to this aspect of the invention include small organic molecules and helical peptidomimetics.

MEF2-binding small molecules can be identified using the method provided herein, by utilizing the disclosed MEF2 binding site as a guide. The provided small molecules have a general structural formula derived from the identified binding site revealed from the crystal structure of BML-210 bound to MEF2. The provided small molecules are designed to bind to the described structural fold and would potentially bind MEF2 with high affinity and selectivity. In order to identify more potent and selective compounds using this approach, methods known in the art can be utilized, including but not limited to: computer-aided structure-based design combined with in-silico screening, combinatorial library design combined with high-throughput screening, and fragment-based drug discovery for lead identification followed by lead optimization.

In a preferred embodiment, the compounds provided under this invention include compounds that bind to the MEF2 binding site with the general formula:

$R^a$-L-$R^b$, wherein:

$R^a$ is a recognition group that binds to the hydrophobic region of the MEF2 binding site selected from a group that includes lower alkyl, alkenyl, alkynyl, aryl, heteroaryl, alkoxy, aryloxy, alkylthio, arylthio, or $R^cR^dNC$(=O)—, $R^cR^dN(SO_2)$, wherein:
  $R^c$ and $R^d$ are independently selected from a group consisting of hydrogen, alkyl, alkenyl, alkynyl, alkoxy, aryl, heteroaryl, alkylamino, dialkylamino, arylamino or heteroarylamino.

L is a linker consisting of a chain of up to 20 carbon atoms, provided that up to three carbon atoms can be replaced with an oxygen, nitrogen or sulfur atom, and further provided that it can include substituents selected from a group consisting of:
  alkyl, alkenyl, alkynyl, aryl, heteroaryl, benzo, hydroxy, alkoxy, aryloxy, oxa, keto, amido, sulfonamido, or fluoro;

$R^b$ is a recognition group that binds to the hydrophilic region of the MEF2 binding site selected from a group that includes lower alkyl, alkenyl, alkynyl, aryl, heteroaryl, alkoxy, aryloxy, alkylthio, arylthio, or $R^cR^dNC$(=O)—, $R^CR^dN(SO_2)$, wherein:
  $R^c$ and $R^d$ are independently selected from a group consisting of hydrogen, alkyl, alkenyl, alkynyl, alkoxy, aryl, heteroaryl, alkylamino, dialkylamino, arylamino or heteroarylamino.

In a preferred embodiment the provided compounds have the general structure $Ar^1$-$L^1$-$L^2$-$L^3$-$Ar^2$ wherein:
  $Ar^1$ and $Ar^2$ are aromatic rings independently selected from a group consisting of benzene, naphthalene, pyridine, pyrimidine, pyrazine, quinoline, isoquinoline, pyrrole, furan, thiophene, imidazole, pyrazole, oxazole, thiazole, isoxazole, indole, benzimidazole, benzothiazole, benzoxazole, provided that the aromatic ring may contain up to seven substituents selected from a group consisting of: hydrogen, alkyl, alkenyl, alkynyl, alkoxy, aryl, heteroaryl, amino, alkylamino, dialkylamino, arylamino, heteroarylamino, hydroxy, or halo. The substituents can also join together to form a ring of up to 12 atoms,
  $L^1$ and $L^3$ are linking groups independently selected from a group consisting of amino, alkylamino, arylamino, oxa, keto, NHC(=O), NR(C=O), S(=O) or —S(=O)$_2$—
  $L^2$ is a linking group selected from a group consisting of a chain of up to 10 carbon atoms, provided that up to three atoms can be replaced with an oxygen, nitrogen or sulfur atom, and further provided that these atoms can contain substituents selected from a group consisting of:
    alkyl, alkenyl, alkynyl, aryl, heteroaryl, benzo, hydroxyl, alkoxy, aryloxy, oxa, keto, amido, sulfonamide, or fluoro In a further preferred embodiment, the provided compounds have the general formula:

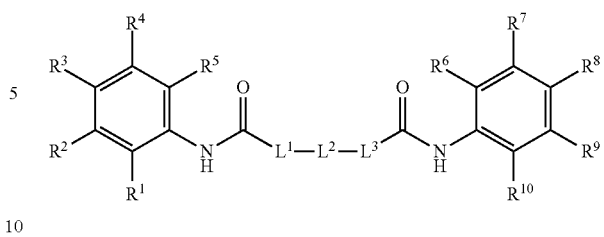

wherein:

$R^1$-$R^{10}$ are independently selected from a group consisting of hydrogen, alkyl, alkenyl, alkynyl, alkoxy, aryl, heteroaryl, amino, alkylamino, dialkylamino, arylamino, heteroarylamino, hydroxy, and halo;

$L^1$ and $L^3$ are linkining groups independently selected from a group consisting of amino, alkylamino, arylamino, oxa, keto, NHC(=O), NR(C=O), S(=O) or —S(=O) 2-

$L^2$ is a linking group selected from a group consisting of a chain of up to 10 carbon atoms, provided that up to three atoms can be replaced with an oxygen, nitrogen or sulfur atom, and further provided that these atoms can contain substituents selected from a group consisting of: alkyl, alkenyl, alkynyl, aryl, heteroaryl, benzo, hydroxyl, alkoxy, aryloxy, oxa, keto, amido, sulfonamide, or fluoro.

Figure 2:
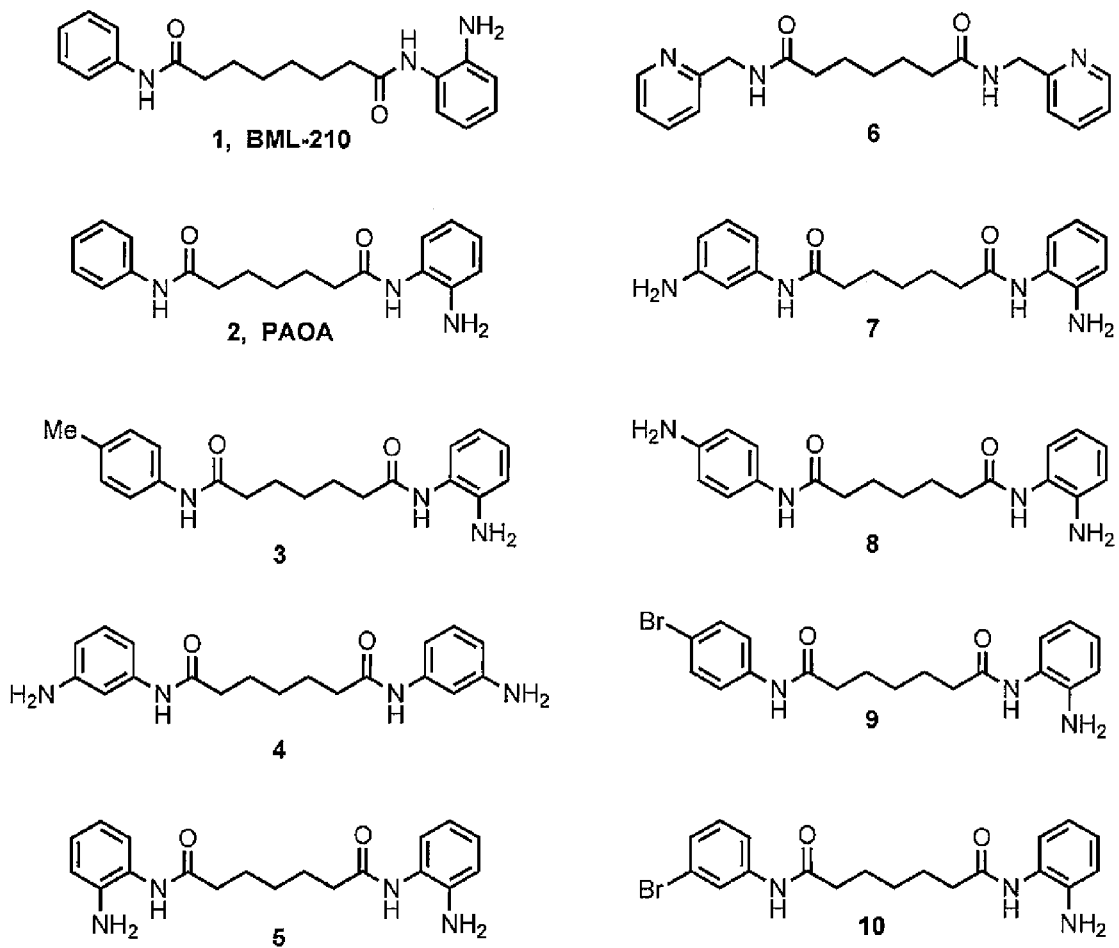
FIG. 2 shows the structures of BML-210, PAOA and related exemplary MEF2-binding molecules.

In a further preferred embodiment, the provided compounds are selected from the following list of compounds (FIG. 2)

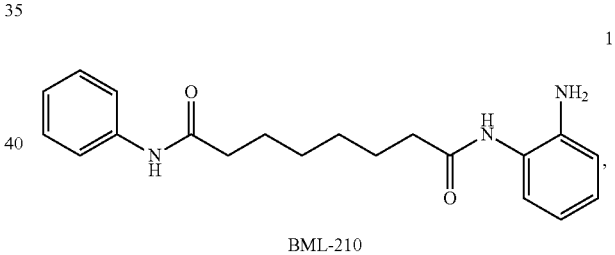

BML-210

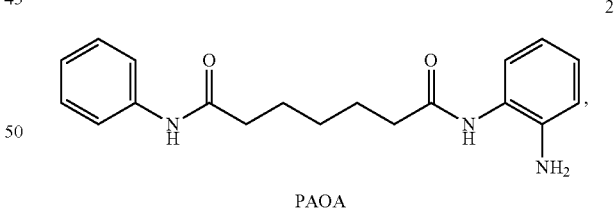

PAOA

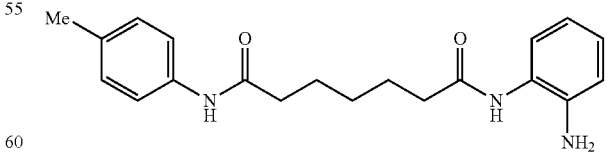

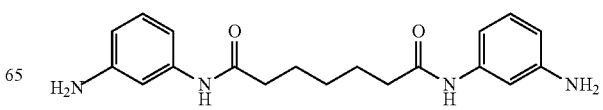

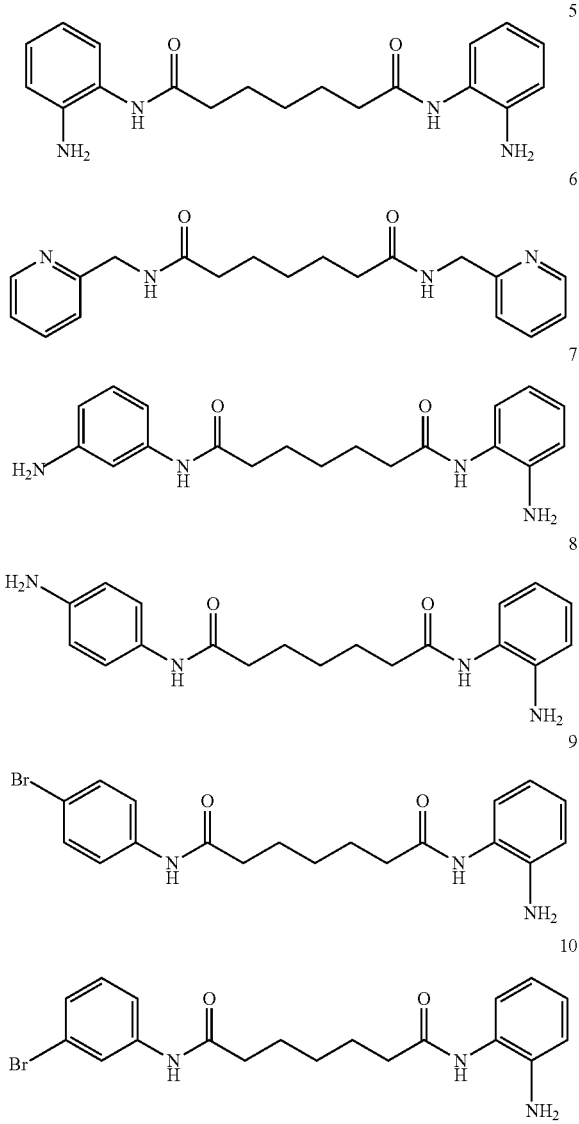

To further facilitate a complete understanding of the various aspects and ramifications of this invention, the following illustrative examples are provided.

EXAMPLES

Example 1

Strategy for Identifying Subtype-Specific HDAC Inhibitors/Modulators

This invention provides a novel strategy for identifying lead compounds that may act as subtype-specific HDAC inhibitor/modulators. The strategy consists of several iterative steps:

Step 1: for a given HDAC complex of interest, the structure or substructure of the HDAC bound to its associated regulatory protein is solved or its structure or substructure that contains functionally important interfaces is obtained.

Step 2: the structure is used for docking analysis of existing or new potential HDAC inhibitors that may bind the protein-protein interface. The virtual screen will be guided by functional data such as if the HDAC inhibitor showed effect in cellular processes involving the target HDAC complex and if the HDAC inhibitor seems to act through mechanisms other than active site inhibition.

Step 3: the structure and related biochemical information is also used to guide the development of assays that can be used to screen compounds that can disrupt the intended protein-protein interface.

Step 4: once such leads are found, their complexes with the protein target is characterized using the structural study system established in Step 1.

Step 5: the structural information, in combination with relevant chemistry methodologies is used to guide the design of analogs that can bind the target protein with higher affinity and specificity. The methods used are similar to that of Step 2.

Step 6: the designed analogs are synthesized and analyzed by assays established in Step 3. Finally, the optimized compounds are used for in vivo studies to test if they can mimic the effects of the parent compound but with higher potency and less non-specific/side effects.

Utilizing the above mechanism-based approach, inventors have demonstrated that a previous known HDAC inhibitor, PAOA, was identified as a lead compound that can specifically disrupt the function of class IIa HDACs by serving as a MEF2 inhibitor (MEF2I). Moreover, representative structural analogs of PAOA were also designed, synthesized and evaluated with the method described herein, and several more potent MEF2I were identified (FIG. 2), thereby demonstrating further aspects of this approach.

Example 2

Uses of Subtype-Specific HDAC Inhibitors in Therapeutic Applications

Class IIa HDACs play crucial roles in neuronal survival/synapse formation, T cell selection/activation, and muscle remodeling. Dysregulation of these activities are implicated in a number of diseases, including neurodegeneration, inflammation and cardiac hypertrophy. Some HDACi developed for cancer therapy showed beneficial effects against these disorders. Although the non-specific nature of these HDAC inhibitors prevent their clinical applications in these diseases, these observations raise an intriguing question whether the observed therapeutic effects were related to class IIa HDACs, and whether selected disruption of class IIa HDAC function could be a viable strategy for treating these diseases. To address these questions, small molecules that can specifically disrupt the function of class IIa HDACs are needed.

Based on the known cellular functions of MEF2 and class IIa HDACs and the effects of some HDAC inhibitors in muscle, immune and neuronal systems, we propose methods and compounds of this invention could be used to treat cardiac hypertrophy, muscle fiber type remodeling, and other muscle-related diseases resulting from imbalanced MEF2 function; autoimmune diseases or immune deficiency that result from excessive or too little MEF2-dependent gene expression, and transplant rejection; a variety of neurodegenerative diseases (e.g. Friedrich's ataxia, Alzheimer's disease and Huntington disease etc), autism, psychiatric disorders, and impaired learning and memory that result from deregulated MEF2 function.

The MEF2-binding molecules developed for treating various human diseases mentioned above could be administered orally, intramuscular, intraperitoneal, subcutaneous, intravenous injections. Other delivery methods are also possible, and the exact protocol will depend on the conditions that are being treated. The dose could also vary according to specific clinical applications. But the standard assays at which the compound shows effect in vitro is around 0.1-10 µM in vitro and 1-10 mg per KG of body mass in animal model studies.

Preferred compounds provided under this invention shown in FIG. 2 exhibited a wide range of affinity in binding to MEF2 in vitro and in vivo, and could serve as lead compounds to develop MEF2-based therapeutics in muscle, immune and nervous systems as mentioned above. The compounds indeed showed effect in promoting regulatory T cell functions in vitro and in mouse model, and are therefore potential drug leads for autoimmune diseases and preventing transplant rejection. For example, the MEF2-binding molecule NKL30 at 0.15 µM greatly enhanced regulatory T cell function as evident by the enhanced suppression activity in vivo. In an mouse model of homeostatic proliferation assay, the compound at 1 mg/KG body mass administered by intravenous injection also greatly enhanced the Treg function in vivo. These data strongly suggest that MEF2-binding molecules provided by this invention could be used to treat autoimmune diseases and for preventing transplant rejection.

Example 3

Targeting Class IIa HDACs for Functional Modulation

Compared with other HDACs, the class IIa family is unique in several aspects of function and regulation. First, class IIa HDACs are selectively expressed in muscle, brain and T cells, consistent with their functions in these tissues. Second, the activity of class IIa HDACs is tightly regulated by the calcium signal, a predominant second messenger in tissues where class IIa HDACs are expressed. Third, class II HDACs contain a large regulatory domain N-terminal to the catalytic domain, which confers unique properties to this subclass of HDACs. The N-terminal regulatory region contains domains and motifs that interact with a variety of proteins, including those regulating the calcium responsiveness of class II HDACs, such as CaM, CaMK and 14-3-3, and those targeting class II HDACs to specific promoters such as MEF2 and BCL-6, and other epigenetic regulators and effectors such as class I HDACs, CtBP and HP-1 that function cooperatively with class IIa HDACs. The structures of a number of these complexes are investigated as potential targets for specific disruption.

Among the many complexes involved in the regulation and function of class IIa HDACs, the best characterized is the MEF2 complex in terms of biochemistry and structure. MEF2 is a family of sequence-specific transcription factors (MEF2A-D) that has the same expression pattern as class IIa HDACs and is also implicated in neurodegeneration, inflammation and cardiac diseases. The MEF2 family of transcription factors share a highly conserved N-terminal region, referred to as the MADS-box/MEF2S domain, that mediates DNA binding, dimerization and protein-protein interactions with a variety of transcription factors and co-regulators. Class IIa HDACs do not bind DNA but depend on interaction with MEF2 to target specific chromatin regions for deacetylation. Blocking this interaction is selected as a potential way to disrupt the function of class IIa HDACs.

The interaction between class IIa HDACs and MEF2 has been the subject of extensive functional and biochemical analyses, which reveal that a short sequence motif (MEF2-binding motif) conserved in class IIa HDACs and the MADS-box/MEF2S domain of MEF2 are necessary and sufficient for their binding. Systematic structural and biophysical studies were conducted on the interaction between MEF2 and class IIa HDACs and a related transcription repression (Cabin1) that contain a similar MEF2-binding motif. The crystal structures reveal that the MEF2-binding motif adopts a short amphipathic helix structure to bind a hydrophobic groove on the MADS-box/MEF2 domain of MEF2. Such a ligand/receptor like binding mechanism suggests that it might be possible to use small molecules to block the recruitment of class IIa HDACs to MEF2-specific promoters (refs Han Nature and 2005).

Example 4

Development of a Sub-Class Specific HDAC Inhibition Assay

Figure 3A:
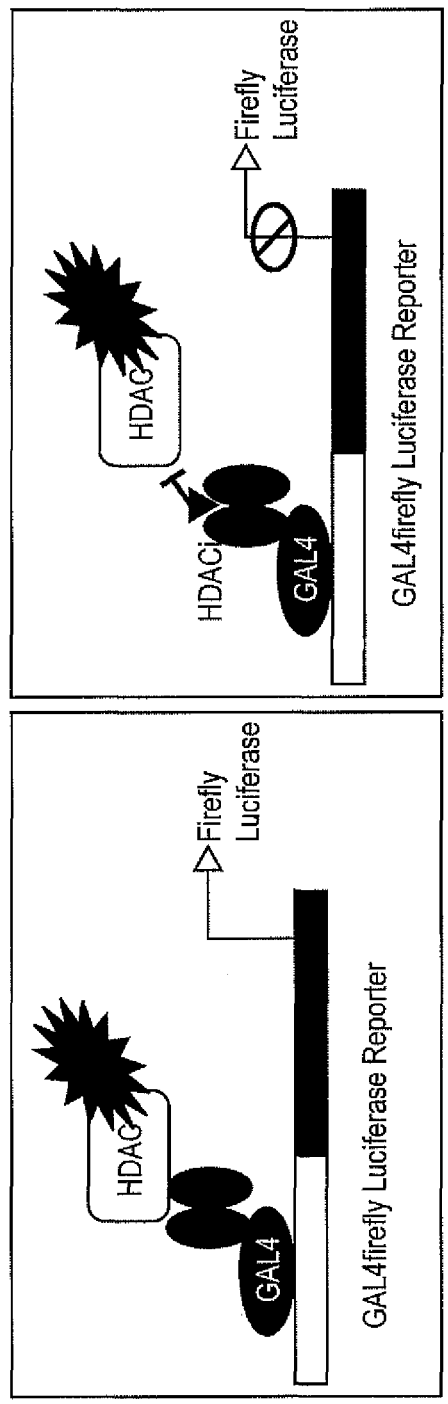
FIG. 3 shows a schematic diagram of MEF2-HDAC luciferase reporter assay for HDACi.

A series of MEF2-dependent luciferase reporter assays with transiently transfected MEF2D, HDAC4 and the co-activator p300 were used initially to screen various compounds. But these assays gave weak signal and high frequency of false positives, probably due to the complex transcription activation mechanisms of MEF2 and interference from endogenous factors. Through these observations, it was discovered that a highly sensitive and specific assay that can recapitulate the molecular interaction between HDAC4 and MEF2 inside cells is essential. To solve this problem, the inventors devised a mammalian two-hybrid system that is capable of detecting the interaction between HDAC4 and MEF2D with minimal interference from endogenous factors (FIG. 3).

In this assay system, MEF2D is fused with GAL4 DNA binding domain (GAL4-MEF2D) and the MEF2-binding motif of HDAC4 (aa 155-220) fused with VP-16 (HDAC4-VP16). Preliminary analysis showed that Hela Cells transiently transfected with both constructs and the GAL4-driven reporter plasmid (GAL4Luc) produced a strong signal comparable to that generated by the positive control of GAL4-VP16, whereas a MEF2D mutant Leu67Asp (L67D) that is previously shown to be defective in binding to HDAC4 failed to activate the reporter (data not shown). Protein expression levels in all luciferase reporter assays were confirmed by western blot.

Taking advantage of the structural insights, in addition to the MEF2D L67D mutant mentioned above, we introduced a number mutations in HDAC4 that had been previously shown to disrupt HDAC4:MEF2 interaction in vitro. These mutations also diminished the luciferase signal in the cell-based assay (FIG. 3b). Most interestingly, mutation of Val180Lys on HDCA4, which weakened the binding of MEF2 by ~60% in vitro (Kd of MEF2 binding by the wild type and the mutant HDAC4 are 0.47 µM and 0.81 µM, respectively), partially reduced the luciferase signal in the cell-based assay (FIG. 3b). These observations demonstrate that the signal from the mammalian two-hybrid assay correlates very well with the molecular interaction between HDAC4 and MEF2. These results not only provide further support for the structural model of the HDAC4:MEF2 interaction but also establish a sensitive and specific method for detecting the HADC4:MEF2 interaction inside the cells.

Example 5

Identifying Selective Inhibitors of the MEF2/HDAC Interaction

To reduce the complexity of the screening, the vast amount of functional data on existing HDAC inhibitors was utilized.

Although most of the these inhibitors target the catalytic domain, some of the compounds discovered through the cell based histone acetylation assays may affect other aspects of HDAC function, including the binding of class IIa HDACs to MEF2. With this in mind, we performed virtual screen (3D docking) against a small molecule database using a pharmacophore model derived from the crystal structure of the HDAC9:MEF2 complex. Although this search did not yield a novel target, it did show that the hydrophobic pocket of MEF2 prefers compounds with two aromatic rings connected by a linker of certain length. This result is consistent with crystallographic analysis showing that the MEF2 dimer contains two symmetry-related sites that can bind a phenylalanine from HDAC9 (refs Han et Nature and JMB). We therefore searched for known HDAC inhibitors that bear such structural features and tested their effect on HDAC4:MEF2 interaction using the mammalian two-hybrid assay.

Figure 4:
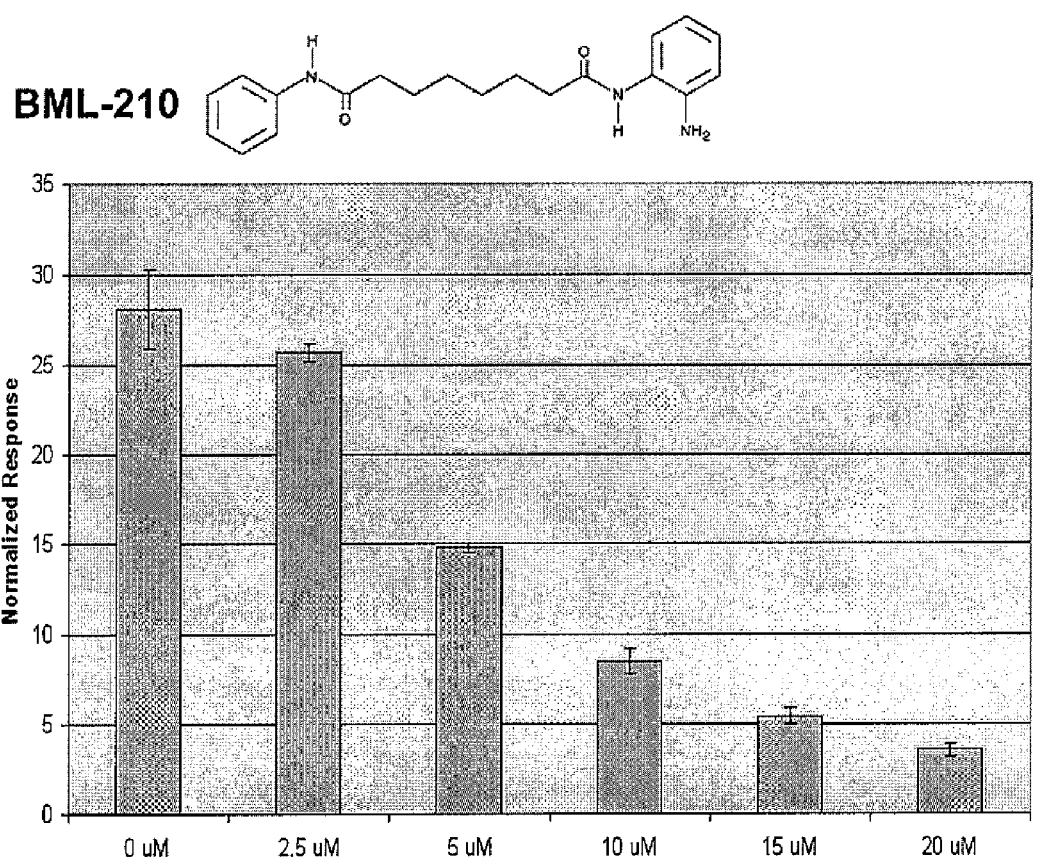
FIG. 4 shows normalized response for luciferase activity in MEF2-HDAC luciferase reporter assay 24 hrs after treatment with BML-210. The luciferase activity decreased in a dose dependent manner.

Screening a pool of selected HDAC inhibitors using the mammalian two-hybrid assay revealed that PAOA (FIG. 2), a previously studied compound inhibited the reporter signal in a dose dependent manner (FIG. 4). PAOA did not affect the expression of HDAC4-VP16 but reduced the reporter signal driven by GAL4-VP16 by 5.6 fold at 10 µM (data not shown), indicating non-specific inhibition by this compound on the expression of luciferase activity under our experimental conditions. However, the same concentration of PAOA decreased the reporter signal driven by GAL4-MEF2D and HDAC4-VP16 by about 26 fold, suggesting that PAOA have specific effect on disrupting the HDAC4:MEF2 interaction beyond its general inhibitory effect. By contrast, trichostatin A (TSA), a potent HDAC inhibitor that targets the zinc active site, showed similar inhibitory effect on the reporter signals driven by GAL4-VP16 and GAL4-MEF2D/HDAC4-VP16 (data not shown). These results suggest that PAOA but not TSA can disrupt the interaction between HDAC4 and MEF2D.

The IC50 of PAOA on HDAC4:MEF2 interaction is around 5 µM based on the mammalian two-hybrid assay, similar to that determined using histone acetylation inhibition assay. The Kd for HDAC4 binding to MEF2 was previously determined to be 0.47 µM. If we assume the equilibrium concentration of HDAC4 is ~0.5 µM under our assay condition, the Kd for the binding of PAOA to MEF2 is estimated to be 5 µM. However, the estimated Kd could be larger if the free HDAC4 concentration is lower in the cell-based assay.

Figure 5A:
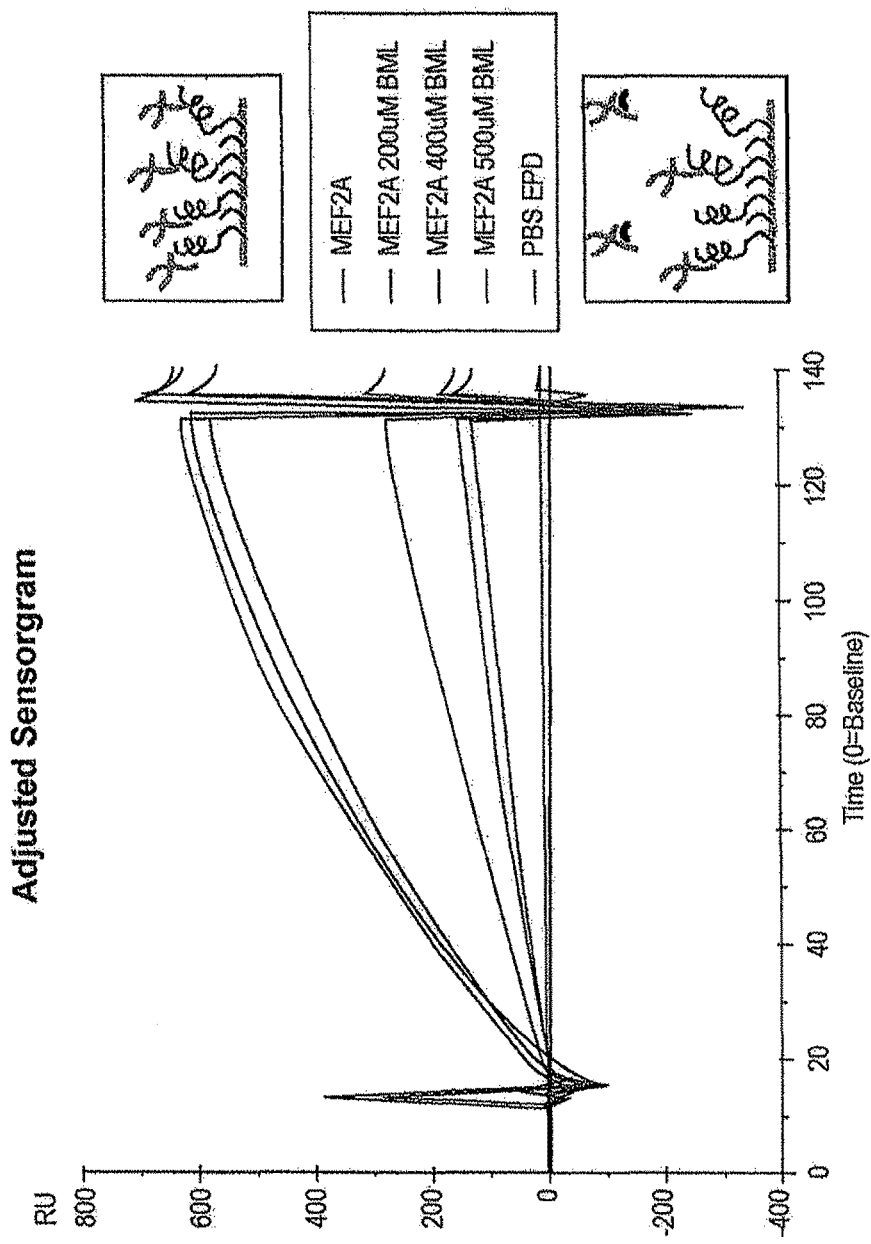
FIG. 5 (a) shows competitive inhibition of MEF2 binding to HDAC after incubation with BML-210 in Biacore assay; (b) Structural analysis showing that BML-210 and HDAC9 bind overlap regions on MEF2.
Figure 5B:
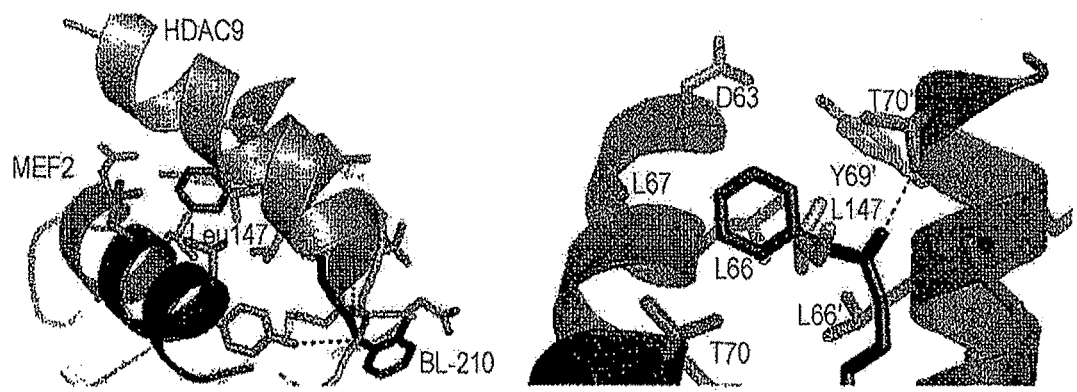

Whether PAOA binds MEF2 competitively with HDAC4 was also assessed in vitro using surface Plasmon resonance (SPR) on Biacore T-100. Here HDAC4 (aa 155-220) was immobilized on a CM5 sensor chip and purified MEF2A (1-95) was used as the analyte. The binding of MEF2A to HDAC4 at various concentrations generated a series of well-defined sensorgrams (data not shown). MEF2A incubated with increasing concentrations of PAOA showed dose dependent decrease of binding to the immobilized HDAC4 (FIG. 5). Analysis of the Biacore data indicates that the competitive binding reaction is complex, whereas direct binding of BML-210 to MEF2 was beyond the detection limit of the instrument. These technical limitations made it difficult to obtain a quantitative binding constant. Nevertheless, the preliminary data suggest that BML-210 indeed bind MEF2 competitively with HDAC4 in vitro.

PAOA was originally discovered as part of a group of compounds that selectively induce acetylation of histone but not tubulin, presumably through inhibition of HDACs other than HDAC6, a tubulin-specific HDAC. PAOA binds MEF2 competitively with HDAC4 in vitro. The inserts on the right illustrate the assay by Biacore. HDAC4: red helix; MEF2: green cross. deacetylase. Although the molecular basis of this selectivity is not known, it is noteworthy that HDAC6, which belongs to the class IIb subfamily, does not have the MEF2-binding motif conserved in class IIa and does seem to require MEF2 for function. PAOA and its derivatives have been recently shown to enhance the expression of frataxin in Friedreich's ataxia. Although the mechanism seems to involve induced histone acetylation, more potent but less specific HDAC inhibitors such as TSA and SAHA showed no effect on frataxin expression despite being able to induce higher level total histone acetylation in cells than PAOA. These observations suggest that PAOA and its derivatives possess a unique function to inhibit a specific HDAC or HDAC complex involved in frataxin silencing. Furthermore, the molecular basis for the action of PAOA can be further clarified with the crystal structure of BML-210 bound to MEF2 disclosed in this invention. In addition to defining the small molecule MEF2-binding site as described herein, this structure also reveals for the first time a likely binding site for the ortho-aminoanilide moiety present in BML-210, as well as PAOA and in other benzamide-containing HDAC inhibitors. Notably, this binding site is different from the HDAC enzyme's active site as has been postulated previously for this class of HDAC inhibitors.

Example 5

Preparation of Complexes of BML-210 Bound to MEF2 on DNA and the Crystals of the BML-210:MEF2:DNA Complex and the Atomic Details of the Complex Structure In order to characterize the detailed interaction of BML-210 bound to MEF2 and use the structural information to guide the design of more potent MEF2 binding molecules, we have determined the crystal structure of the BML-210 bound to MEF2 on DNA. The gene coding MEF2A1-78 was created by PCR amplification from MEF2AFL and cloning into the pET30b expression vector. Protein was expressed in *E. coli* strain BL21(DE3)pLysS, 25C, overnight and was purified by successive chromatographic steps on Sp-Sepharose, and gel filtration run at 4 C in 250 mM NaCl, 10 mM Hepes (pH7.6), 1 mM EDTA, 1 mM DTT to give a final yield of 0.6 mg/l. Oligonucleotides (Santelli and Richmond, 2000) were purchased from IDT DNA technologies, purified using MonoQ FPLC column followed by dialysis, lyophylization and annealing using thermal cycler.

$1/10^{th}$ protein sample volume of 10 mM BML 210 was added to the protein samples at 0.5 mg/ml and concentrated to approximately 17 mg/ml (0.9 mM). and DNA duplex was added at 1:1 ratio prior to setting trays (10% DMSO end concentration). Plate like crystals were obtained by hanging drop vapor diffusion conditions at 18C using 24% PEG4000, 140 mM NaCl, 5 mM $MgCl_2$, 10 mM $CaCl_2$, 0.004% $NaN_3$, 3.3% glycerol, 50 mM TrisHCl (pH 5.8-pH8.18). Crystals with drug density were obtained at pH 8.18. The crystal diffracted to 2.4 Å resolution and belongs to space group P1 (a=41.567 Å, b=61.622 Å c=61.478 Å α=114.12° β=89.99° γ=89.95°. The structure is solved by molecular replacement using 1TQE.pdb as search model (refs Richmond 2000). The final model has an Rfree of 26% and Rw of 23%. The coordinates are attached (11.1_001_nr_nh_bm1.pdb).

Example 6

Lead Optimization Using Structure-Guided Design and Chemical Methodologies

Most HDAC inhibitors discovered by functional screen have modest potency with IC50 in the micromolar or even millimolar range. Lead optimization is typically done by systematic modifications of the chemical structure and structure-activity relationships (SAR) studies. However, without knowing the target and the detailed binding interactions between the compound and its target, such an empirical approach is often labor intensive and of limited effectiveness. This is in fact the case for PAOA where a series of analogs were synthesized to search for more potent compounds that may be used for treating Friedreich's ataxia. Although some PAOA analogs did show higher activity than the parent compound, the effect was very modest and the mechanism of improvement was not clear.

Remarkably, the ability by which these PAOA derivatives activate frataxin expression did not correlate with their HDAC inhibition activity. For example, some of the derivatives were very weak in histone deacetylation inhibition assay and yet very active in frataxin induction. Our preliminary findings that PAOA binds MEF2 and block the recruitment of class IIa HDACs provide a potential molecular mechanism for these intriguing results. Class IIa HDAC can repress transcription independent of the deacetylase activity. For example, a naturally occurring splicing variant of HDAC9 that lacks the entire C-terminal catalytic domain, also known as MITR, is a potent transcription repressor of MEF2-dependent gene expression, presumably by recruiting other epigenetic effectors such as HP1 and CtBP. In this sense, small molecule inhibitors that target the catalytic domain of class IIa HDACs cannot eliminate the full epigenetic silencing potential of these proteins, which may explain the ineffectiveness of TSA and SAHA in reactivating frataxin expression. PAOA, on the other hand, can block the recruitment of HDAC activity and other transcription repressors together. Although MEF2 is also involved in gene activation by recruiting transcription activators such as CBP/p300, current data suggest that the main effect of PAOA on MEF2 dependent gene expression is alleviating the silencing effect of class IIa HDACs and other transcription repressors.

By relying on the above analysis and the disclosed structure of BML-210:MEF2:DNA, and by employing docking solutions of PAOA to MEF2A it is shown that this drug molecule can fit preferably into the experimentally observed electron density, demonstrating the relative effectiveness of the ICM-Docking protocol (Molsoft L.L.C) for the design of new PAOA-like compounds for MEF2 binding. This docking approach can be used to design and analyze new PAOA analogues with potentially greater affinity and selectivity. Some of the features of the structure are briefly described below to illustrate the principles to be used in designing new molecules that may bind MEF2 with higher affinity.

Figure 1D:
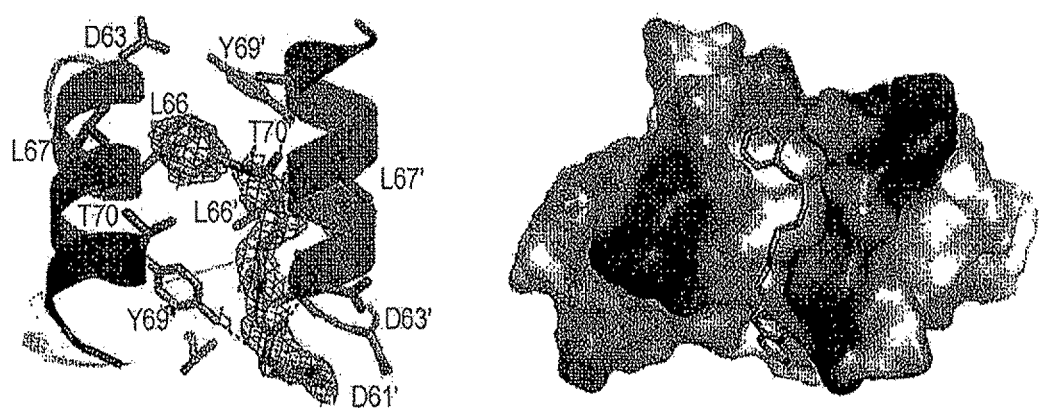
FIG. 1 shows three different depictions (a-c) of a crystal structure of MEF2 and the identified ligand binding site; (d) shown is BML-210 bound to MEF2A (1-78) at 2.4 Å resolution, including the amino acids involved in binding interactions with BML-210.
In FIG. 1a the top DNA sequence (i.e., AAGCTACTATATTTAGC) is SEQ ID NO:1 and the bottom DNA sequence (i.e., CGATGATATAAATCGTT) is SEQ ID NO:2.

BML-210 adopts an extended conformation to bind into the hydrophobic pocket of MEF2 (FIG. 1). This is also the binding site for the MEF2-binding motif conserved in class IIa HDACs and Cabin1. Since one end of the electron density resembles a simple aromatic ring and is surrounded by a number of hydrophobic residues including Leu66, Leu67, Thr70, Leu66', Leu67' and Thr70' (prime sign denote residues from the other monomer), we assigned this density to the phenyl group. The carbonyl group at this end is also in position to engage in hydrogen bonding interactions with Thr70' (FIG. 1).

The structure-based design of new and optimized MEF2-binding small molecules can be achieved using several known structures of MEF2. We have now solved the crystal structures of three MEF2 complexes. Two of them contain a peptide derived from the MEF2-binding motif of Cabin1 and HDAC9, respectively (Guo et al., 2007; Han et al., 2005; Han et al., 2003), whereas the third one is the BML-210 complex described herein, which is the first structure showing how a small molecule can bind to MEF2. In all three complexes, the small molecule ligand, whether naturally occurring peptide or synthetic molecule, binds to the deep groove on the surface of MEF2 dimer (FIG. 1). Our previous studies show that Cabin1 and HDAC9 bind MEF2 through similar as well as distinct protein-protein interactions (FIG. 1) Interestingly, BML-210 seems to mimic some aspects of natural ligands in binding to MEF2. For example, the binding of the phenyl ring of PAOA to the central hydrophobic pocket formed by Leu66, Leu67, Thr70, Leu66', Leu67' and Thr70' is reminiscent of that of Leu147 in HDAC9 (FIG. 1). Through detailed analyses of the three structures, we have identified a variety of structural features on the MEF2 groove that may be explored for small molecule binding, including a number of discrete hydrophobic pockets, hydrogen bond donors and acceptors, and several charged residues. We plan to utilize this structural information to design and optimize new series of small molecules that can bind selectively to MEF2.

Example 7

Structure-Guided Design of Small Molecule Inhibitors of the MEF2/HDAC Interaction Using the crystal structures as guide, a large number of PAOA analogs that can provide the basis for identifying new MEF2-active small molecules was designed. The first group of analogs were designed to explore two general elements of the PAOA structure. First is the length and rigidity of the linker. Second are the functional groups and their positions on the two aromatic binding units. The electron density of the linker indicates that it adopts multiple conformations, suggesting non-optimal binding between PAOA and MEF2 in this region. In HDAC9, on the other hand, the aliphatic side chain of Lys144 and Val143 fill up the groove of MEF2 nicely to establish extensive Van der Waals contact and a hydrogen bond. Functional groups introduced at the PAOA linker to mimic/improve these natural interactions may enhance the binding affinity. The designed compounds were subjected to docking analysis mentioned above to filter out energetically unfavorable ones. The remaining molecules were synthesized using standard techniques and subjected to in vitro and in vivo analysis as described previously.

A first series of potential inhibitors (FIG. 2) was synthesized, and already found that different compounds showed significantly different activity in their ability to inhibit the reporter signal in the mammalian two-hybrid assay. Most interestingly, one of these, compound 4, showed similar activity as PAOA but with no effect on the control signal driven by GAL-VP-16, suggesting that this new derivative is more specific than PAOA. The ortho-aminoanilide moiety in PAOA has previously been postulated to be a zinc chelating group that can bind to the active site of class I and class II HDACs, but direct evidence for this mode of action is yet to be obtained. In compound 4, this Zinc chelating group is eliminated by moving the amino group to the meta position. Yet this derivative is as active as PAOA with less nonspecific effect, suggesting that the observed effect of PAOA inside cells, under our assay condition, is mainly due to its ability to disrupt MEF2:HDAC4 interaction rather than inhibiting the catalytic activity.

Example 8

Synthesis of Compound 10

The provided compounds can be prepared by adaptation of methods known in the art. For example, the synthesis of compound 10:

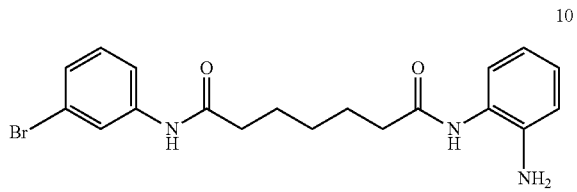

was prepared by the following steps:

Step 1: Pimelic acid (1 equiv) and 3-bromoaniline (1 equiv) were added to flask and stirred at 130° C. overnight. The reaction mixture was diluted in EtOAc and extracted with 10% potassium hydroxide. The aqueous layer was acidified to pH~2 with conc. HCl and extracted with ethyl acetate. The organic layer was reduced under vacuum and recrystallized with acetonitrile/water.

Step 2. To a solution of phenylenediamine in dichloromethane was added (Boc)$_2$O (1 equiv) at rt and the mixture was stirred overnight. The reaction was concentrated under vacuum, diluted with ethyl acetate, and was extracted with three times with water and brine. The organic la yer was reduced under vacuum and recrystallized chloroform/hexanes.

Step 3. The product of Step 1 (100 mg) was dissolved in DMSO (3 mL) and to this solution was added Hunig's base (1 equiv), HBTU (1 equiv), and the monoprotected phenylenediamine product of Step 2. The resulting solution was stirred overnight at rt. The solution was diluted with ethyl acetate and extracted with three times with brine. The organic layer was reduced under vacuum and purified by column chromatography (hexanes/ethyl acetate gradient). The isolated product was dissolved in dichloromethane, cooled to ° C. and treated with trifluoroacetic acid (1 mL). The solution was allowed to warm to rt and stirred overnight. The reaction was neutralized with sodium bicarbonate and concentrated under vacuum. The resulting solid was dissolved in ethyl acetate and extracted with a saturated sodium chloride solution. The organic layer was dried with magnesium sulfate, filtered, concentrated under vacuum, and purified by column chromatography (hexanes/ethyl acetate and dichloromethane/methanol gradient). Evaporation of the solvents under vacuum, provided the pure product 10, whose structure and purity was verified by NMR spectroscopy.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

The protein sequence Gly Arg Lys Lys Ile Gln Ile Thr Arg Ile Met Asp Glx Arg Asn Arg Gln Val Thr Phe Thr Lys Arg Lys Phe Gly Leu Met Lys Lys Ala Tyr Glx Leu Ser Val Leu Cys Asp Cys Gly Ile Ala Leu Ile Ile Phe Asn Ser Ser Asn Lys Leu Phe Gln Tyr Ala Ser Thr Asp Met Asp Lys Val Leu Leu Lys Tyr Thr Glx Tyr in Table 1 is SEQ ID NO:4. The protein sequence Gly Arg Lys Lys Ile Gln Ile Thr Arg Ile Met Asp Glx Arg Asn Arg Gln Val Thr Phe Thr Lys Arg Lys Phe Gly Leu Met Lys Lys Ala Tyr Glx Leu Ser Val Leu Cys Asp Cys Gly Ile Ala Leu Ile Ile Phe Asn Ser Ser Asn Lys Leu Phe Gln Tyr Ala Ser Thr Asp Met Asp Lys Val Leu Leu Lys Tyr Thr Glx Tyr Asn in Table 1 is SEQ ID NO:5. The DNA sequence AAAGCTATTATTAGCTT in Table 1 is SEQ ID NO:6. The DNA sequence TAAGCTAATAATAGCTT in Table 1 is SEQ ID NO:7.

TABLE 1

```
REMARK  Date 2009-01-07 Time 10:43:15 PST -0800 (1231353795.26 s)
REMARK  PHENIX refinement
REMARK
REMARK  ***************** INPUT FILES AND LABELS ******************************
REMARK  Reflections:
REMARK     file name:        3set-bm30-p1.mtz
REMARK     labels:           ['F__nat, SIGF__nat']
REMARK  R-free flags:
REMARK     file name:        3set-bm30-p1.mtz
REMARK     label:            FreeR__flag
REMARK     test__flag__value: 0
REMARK  Model file name(s):
REMARK     /Users/rajadey/bml30/phenix/11.1__001__nr__h__001.pdb__modified.pdb
REMARK
REMARK  ****************** REFINEMENT SUMMARY: QUICK FACTS ******************
REMARK  Start: r__work = 0.2261 r__free = 0.2662 bonds = 0.010 angles = 1.585
REMARK  Final: r__work = 0.2300 r__free = 0.2625 bonds = 0.004 angles = 0.999
REMARK  ***********************************************************************
REMARK
REMARK  ***************** REFINEMENT STATISTICS STEP BY STEP ******************
REMARK  leading digit, like 1__, means number of macro-cycle
REMARK  0:         statistics at the very beginning when nothing is done yet
REMARK  1__bss:    bulk solvent correction and/or (anisotropic) scaling
REMARK  1__xyz:    refinement of coordinates
REMARK  1__sar:    simulated annealing refinement of x, y, z
REMARK  1__gbr:    group B-factor refinement
REMARK  ----------------------------------------------------------------------
REMARK   R-factors, x-ray target values and norm of gradient of x-ray target
REMARK   stage          r-work   r-free    xray__target__w  xray__target__t
REMARK    0:            0.3724   0.4597    4.600657e+00     4.693864e+00
REMARK    1__bss:       0.2261   0.2662    4.353757e+00     4.511409e+00
REMARK    1__sar:       0.2304   0.2635    4.369227e+00     4.510175e+00
REMARK    1__xyz:       0.2300   0.2624    4.366691e+00     4.507881e+00
REMARK    1__adp:       0.2313   0.2633    4.364563e+00     4.506710e+00
REMARK    1__bss:       0.2300   0.2625    4.363161e+00     4.505319e+00
REMARK  ----------------------------------------------------------------------
REMARK   stage          k__sol   b__sol   b11    b22    b33    b12    b13    b23
```

TABLE 1-continued

```
REMARK      0:         0.000    0.000  0.000   0.000   0.000   0.000  0.000    0.000
REMARK      1__bss:    0.364   20.242 -6.805   6.192  -3.021  -0.487  0.775  -11.187
REMARK      1__sar:    0.364   20.242 -6.805   6.192  -3.021  -0.487  0.775  -11.187
REMARK      1__xyz:    0.364   20.242 -6.805   6.192  -3.021  -0.487  0.775  -11.187
REMARK      1__adp:    0.364   20.242 -6.805   6.192  -3.021  -0.487  0.775  -11.187
REMARK      1__bss:    0.365   21.349 -5.565   7.438  -1.873  -0.502  0.768  -11.282
REMARK    --------------------------------------------------------------
REMARK    stage       <pher>    fom    alpha    beta
REMARK      0:        38.723   0.6722  0.4429  3605.155
REMARK      1__bss:   29.255   0.7800  0.4779  1636.075
REMARK      1__sar:   29.008   0.7829  0.4789  1613.168
REMARK      1__xyz:   29.000   0.7829  0.4786  1605.471
REMARK      1__adp:   28.879   0.7844  0.4600  1604.065
REMARK      1__bss:   28.857   0.7846  0.4744  1600.058
REMARK    --------------------------------------------------------------
REMARK    stage       angl   bond   chir   dihe   plan   repu   geom_target
REMARK      0:        1.585  0.010  0.062  24.116  0.004  4.102  1.0603e-01
REMARK      1__bss:   1.585  0.010  0.062  24.116  0.004  4.102  1.0603e-01
REMARK      1__sar:   1.491  0.016  0.080  22.841  0.006  4.104  1.3573e-01
REMARK      1__xyz:   0.999  0.004  0.052  22.782  0.002  4.103  5.3401e-02
REMARK      1__adp:   0.999  0.004  0.052  22.782  0.002  4.103  5.3401e-02
REMARK      1__bss:   0.999  0.004  0.052  22.782  0.002  4.103  5.3401e-02
REMARK    --------------------------------------------------------------
REMARK               Maximal deviations:
REMARK    stage       angl    bond   chir   dihe    plan   repu    |grad|
REMARK      0:        19.277  0.072  0.199  87.514  0.017  2.477   7.1857e-02
REMARK      1__bss:   19.277  0.072  0.199  87.514  0.017  2.477   7.1857e-02
REMARK      1__sar:   13.759  0.149  0.349  82.939  0.024  2.483   2.0037e-01
REMARK      1__xyz:    5.840  0.026  0.193  83.107  0.009  2.480   2.2669e-02
REMARK      1__adp:    5.840  0.026  0.193  83.107  0.009  2.480   2.2669e-02
REMARK      1__bss:    5.840  0.026  0.193  83.107  0.009  2.480   2.2669e-02
REMARK    --------------------------------------------------------------
REMARK    stage       b_max   b_min   b_ave
REMARK      0:        98.49   10.66   34.81
REMARK      1__bss:   98.49   10.66   34.81
REMARK      1__sar:   98.49   10.66   34.81
REMARK      1__xyz:   98.49   10.66   34.81
REMARK      1__adp:   97.61    8.23   33.04
REMARK      1__bss:   97.70    8.32   33.12
REMARK    --------------------------------------------------------------
REMARK    stage       Deviation of refined
REMARK                model from start model
REMARK                 max     min    mean
REMARK      0:         0.000   0.000  0.000
REMARK      1__bss:    0.000   0.000  0.000
REMARK      1__sar:    0.779   0.002  0.073
REMARK      1__xyz:    0.781   0.003  0.069
REMARK      1__adp:    0.781   0.003  0.069
REMARK      1__bss:    0.781   0.003  0.069
REMARK    --------------------------------------------------------------
REMARK    MODEL CONTENT.
REMARK     ELEMENT          ATOM RECORD COUNT    OCCUPANCY SUM
REMARK     P                        64                  64.00
REMARK     C                      2188                2188.00
REMARK     S                        20                  20.00
REMARK     O                       824                 824.00
REMARK     N                       654                 654.00

REMARK    TOTAL                   3750                3750.00
REMARK    --------------------------------------------------------------
REMARK    r_free_flags.md5.hexdigest c7ab61ecd5d91bd96f477e00cb52bbd9
REMARK
REMARK    IF THIS FILE IS FOR PDB DEPOSITION: REMOVE ALL FROM THIS LINE UP.
REMARK     3
REMARK     3  REFINEMENT.
REMARK     3    PROGRAM     : PHENIX (phenix, refine)
REMARK     3    AUTHORS     : Paul Adams, Pavel Afonine, Vincent Chen, Ian
REMARK     3                : Davis, Kreshna Gopal, Ralf Grosse-Kunstleve,
REMARK     3                : Jeffrey Headd, Li-Wei Hung, Robert
REMARK     3                : Immormino, Tom Ioerger, Airlie McCoy, Erik
REMARK     3                : McKee, Nigel Moriarty, Reetal Pai, Randy
REMARK     3                : Read, Jane Richardson, David Richardson, Tod
REMARK     3                : Romo, Jim Sacchettini, Nicholas Sauter,
REMARK     3                : Jacob Smith, Laurent Storoni, Tom
REMARK     3                : Terwilliger, Peter Zwart
REMARK     3
REMARK     3  REFINEMENT TARGET: ML
REMARK     3
REMARK     3  DATA USED IN REFINEMENT.
REMARK     3    RESOLUTION RANGE HIGH    (ANGSTROMS): 2.434
```

TABLE 1-continued

```
REMARK   3   RESOLUTION RANGE LOW      (ANGSTROMS): 33.444
REMARK   3   MIN(FOBS/SIGMA_FOBS):                  2.00
REMARK   3   COMPLETENESS FOR RANGE          (%): 94.76
REMARK   3   NUMBER OF REFLECTIONS:               19820
REMARK   3
REMARK   3   FIT TO DATA USED IN REFINEMENT.
REMARK   3   R VALUE            (WORKING + TEST SET): 0.2318
REMARK   3   R VALUE                   (WORKING SET): 0.2300
REMARK   3   FREE R VALUE:                            0.2625
REMARK   3   FREE R VALUE TEST SET SIZE        (%): 5.18
REMARK   3   FREE R VALUE TEST SET COUNT:           1026
REMARK   3
REMARK   3   FIT TO DATA USED IN REFINEMENT (IN BINS).
REMARK   3   BIN  RESOLUTION RANGE   COMPL.   NWORK   NFREE   RWORK   RFREE
REMARK   3    1    33.4475-4.6528     0.98     2734     158    0.1822  0.2100
REMARK   3    2     4.6528-3.6946     0.96     2695     176    0.1877  0.2158
REMARK   3    3     3.6946-3.2280     0.96     2707     127    0.2008  0.2520
REMARK   3    4     3.2280-2.9331     0.95     2707     141    0.2463  0.2810
REMARK   3    5     2.9331-2.7229     0.95     2703     142    0.2703  0.3447
REMARK   3    6     2.7229-2.5624     0.95     2664     142    0.2602  0.2953
REMARK   3    7     2.5624-2.4342     0.89     2584     140    0.2774  0.3272
REMARK   3
REMARK   3   BULK SOLVENT MODELLING.
REMARK   3   METHOD USED:       FLAT BULK SOLVENT MODEL
REMARK   3   SOLVENT RADIUS:    1.11
REMARK   3   SHRINKAGE RADIUS:  0.90
REMARK   3   GRID STEP FACTOR:  4.00
REMARK   3   K_SOL:             0.365
REMARK   3   B_SOL:             21.349
REMARK   3
REMARK   3   ERROR ESTIMATES.
REMARK   3   COORDINATE ERROR (MAXIMUM-LIKELIHOOD BASED):      0.40
REMARK   3   PHASE ERROR (DEGREES, MAXIMUM-LIKELIHOOD BASED):  28.86
REMARK   3
REMARK   3   OVERALL SCALE FACTORS.
REMARK   3   SCALE = SUM(|F_OBS|*|F_MODEL|)/SUM(|F_MODEL|**2) : 0.5328
REMARK   3   ANISOTROPIC SCALE MATRIX ELEMENTS (IN CARTESIAN BASIS).
REMARK   3    B11:  -5.5649
REMARK   3    B22:   7.4379
REMARK   3    B33:  -1.8730
REMARK   3    B12:  -0.5019
REMARK   3    B13:   0.7684
REMARK   3    B23: -11.2823
REMARK   3
REMARK   3   R FACTOR FORMULA.
REMARK   3   R = SUM(||F_OBS|-SCALE*|F_MODEL||)/SUM(|F_OBS|)
REMARK   3
REMARK   3   TOTAL MODEL STRUCTURE FACTOR (F_MODEL).
REMARK   3   F_MODEL = FB_CART * (F_CALC_ATOMS + F_BULK)
REMARK   3   F_BULK = K_SOL * EXP(-B_SOL * S**2/4) * F_MASK
REMARK   3   F_CALC_ATOMS = ATOMIC MODEL STRUCTURE FACTORS
REMARK   3   FB_CART = EXP(-H(t) * A(-1) * B * A(-1t) * H)
REMARK   3     A = orthogonalization matrix, H = MILLER INDEX
REMARK   3     (t) = TRANSPOSE, (-1) = INVERSE
REMARK   3
REMARK   3   STRUCTURE FACTORS CALCULATION ALGORITHM: FFT
REMARK   3
REMARK   3   DEVIATIONS FROM IDEAL VALUES.
REMARK   3              RMSD     MAX      COUNT
REMARK   3   BOND:      0.004    0.026     3944
REMARK   3   ANGLE:     0.999    5.840     5574
REMARK   3   CHIRALITY: 0.052    0.193      630
REMARK   3   PLANARITY: 0.002    0.009      458
REMARK   3   DIHEDRAL: 22.782   83.107     1588
REMARK   3   MIN NONBONDED DISTANCE: 2.480
REMARK   3
REMARK   3   ATOMIC DISPLACEMENT PARAMETERS.
REMARK   3   WILSON B: 32.79
REMARK   3   RMS(B_ISO_OR_EQUIVALENT_BONDED): 5.16
REMARK   3   ATOMS             NUMBER OF ATOMS
REMARK   3                     ISO.       ANISO.
REMARK   3   ALL:              3750         0
REMARK   3   ALL (NO H):       3750         0
REMARK   3   SOLVENT:             0         0
REMARK   3   NON-SOLVENT:      3750         0
REMARK   3   HYDROGENS:           0         0
REMARK   3
CRYST1    41.567   61.622   61.478  114.12   89.99   89.95 P 1
SCALE1      0.024058 -0.000021 -0.000013    0.00000
SCALE2      0.000000  0.016228  0.007267    0.00000
```

TABLE 1-continued

| SCALE3 | | | 0.000000 | | 0.000000 | 0.017822 | 0.00000 | | | |
|---|---|---|---|---|---|---|---|---|---|---|
| ATOM | 1 | N | GLY | A | 2 | 5.558 | 9.665 | −0.148 | 1.00 | 40.48 A | N |
| ATOM | 2 | CA | GLY | A | 2 | 6.598 | 10.216 | 0.701 | 1.00 | 40.72 A | C |
| ATOM | 3 | C | GLY | A | 2 | 7.400 | 11.294 | −0.003 | 1.00 | 44.33 A | C |
| ATOM | 4 | O | GLY | A | 2 | 7.374 | 11.395 | −1.230 | 1.00 | 46.18 A | O |
| ATOM | 5 | N | ARG | A | 3 | 8.110 | 12.105 | 0.774 | 1.00 | 36.20 A | N |
| ATOM | 6 | CA | ARG | A | 3 | 8.920 | 13.177 | 0.212 | 1.00 | 36.54 A | C |
| ATOM | 7 | C | ARG | A | 3 | 9.915 | 12.608 | −0.791 | 1.00 | 39.57 A | C |
| ATOM | 8 | O | ARG | A | 3 | 10.208 | 13.222 | −1.818 | 1.00 | 41.96 A | O |
| ATOM | 9 | CB | ARG | A | 3 | 9.649 | 13.937 | 1.320 | 1.00 | 35.42 A | C |
| ATOM | 10 | CG | ARG | A | 3 | 8.729 | 14.765 | 2.204 | 1.00 | 35.12 A | C |
| ATOM | 11 | CD | ARG | A | 3 | 7.761 | 15.588 | 1.364 | 1.00 | 39.80 A | C |
| ATOM | 12 | NE | ARG | A | 3 | 6.939 | 16.479 | 2.177 | 1.00 | 35.64 A | N |
| ATOM | 13 | CZ | ARG | A | 3 | 7.340 | 17.668 | 2.620 | 1.00 | 40.68 A | C |
| ATOM | 14 | NH1 | ARG | A | 3 | 8.558 | 18.111 | 2.336 | 1.00 | 32.06 A | N |
| ATOM | 15 | NH2 | ARG | A | 3 | 6.522 | 18.412 | 3.353 | 1.00 | 37.63 A | N |
| ATOM | 16 | N | LYS | A | 4 | 10.426 | 11.423 | −0.481 | 1.00 | 34.29 A | N |
| ATOM | 17 | CA | LYS | A | 4 | 11.319 | 10.710 | −1.377 | 1.00 | 36.15 A | C |
| ATOM | 18 | C | LYS | A | 4 | 10.906 | 9.247 | −1.456 | 1.00 | 40.15 A | C |
| ATOM | 19 | O | LYS | A | 4 | 10.372 | 8.689 | −0.494 | 1.00 | 32.40 A | O |
| ATOM | 20 | CB | LYS | A | 4 | 12.772 | 10.822 | −0.901 | 1.00 | 37.35 A | C |
| ATOM | 21 | CG | LYS | A | 4 | 13.368 | 12.214 | −1.063 | 1.00 | 39.95 A | C |
| ATOM | 22 | CD | LYS | A | 4 | 13.177 | 12.709 | −2.489 | 1.00 | 40.70 A | C |
| ATOM | 23 | CE | LYS | A | 4 | 13.272 | 14.224 | −2.579 | 1.00 | 54.15 A | C |
| ATOM | 24 | NZ | LYS | A | 4 | 12.727 | 14.727 | −3.875 | 1.00 | 47.90 A | N |
| ATOM | 25 | N | LYS | A | 5 | 11.141 | 8.633 | −2.609 | 1.00 | 47.06 A | N |
| ATOM | 26 | CA | LYS | A | 5 | 10.950 | 7.199 | −2.740 | 1.00 | 44.41 A | C |
| ATOM | 27 | C | LYS | A | 5 | 12.022 | 6.496 | −1.927 | 1.00 | 46.84 A | C |
| ATOM | 28 | O | LYS | A | 5 | 13.159 | 6.963 | −1.860 | 1.00 | 51.80 A | O |
| ATOM | 29 | CB | LYS | A | 5 | 11.037 | 6.767 | −4.203 | 1.00 | 41.74 A | C |
| ATOM | 30 | CG | LYS | A | 5 | 11.031 | 5.260 | −4.387 | 1.00 | 49.22 A | C |
| ATOM | 31 | CD | LYS | A | 5 | 10.524 | 4.863 | −5.762 | 1.00 | 45.09 A | C |
| ATOM | 32 | CE | LYS | A | 5 | 10.369 | 3.358 | −5.865 | 1.00 | 49.10 A | C |
| ATOM | 33 | NZ | LYS | A | 5 | 9.791 | 2.946 | −7.171 | 1.00 | 54.49 A | N |
| ATOM | 34 | N | ILE | A | 6 | 11.661 | 5.385 | −1.296 | 1.00 | 40.65 A | N |
| ATOM | 35 | CA | ILE | A | 6 | 12.634 | 4.589 | −0.561 | 1.00 | 38.64 A | C |
| ATOM | 36 | C | ILE | A | 6 | 12.794 | 3.198 | −1.156 | 1.00 | 44.27 A | C |
| ATOM | 37 | O | ILE | A | 6 | 11.989 | 2.759 | −1.979 | 1.00 | 45.26 A | O |
| ATOM | 38 | CB | ILE | A | 6 | 12.258 | 4.448 | 0.920 | 1.00 | 41.86 A | C |
| ATOM | 39 | CG1 | ILE | A | 6 | 11.049 | 3.527 | 1.083 | 1.00 | 37.25 A | C |
| ATOM | 40 | CG2 | ILE | A | 6 | 11.993 | 5.811 | 1.527 | 1.00 | 44.72 A | C |
| ATOM | 41 | CD1 | ILE | A | 6 | 10.760 | 3.169 | 2.524 | 1.00 | 38.36 A | C |
| ATOM | 42 | N | GLN | A | 7 | 13.848 | 2.512 | −0.740 | 1.00 | 46.69 A | N |
| ATOM | 43 | CA | GLN | A | 7 | 14.063 | 1.137 | −1.149 | 1.00 | 45.95 A | C |
| ATOM | 44 | C | GLN | A | 7 | 13.629 | 0.232 | −0.017 | 1.00 | 44.14 A | C |
| ATOM | 45 | O | GLN | A | 7 | 13.755 | 0.587 | 1.154 | 1.00 | 43.70 A | O |
| ATOM | 46 | CB | GLN | A | 7 | 15.533 | 0.894 | −1.493 | 1.00 | 54.70 A | C |
| ATOM | 47 | CG | GLN | A | 7 | 15.980 | 1.567 | −2.781 | 1.00 | 56.91 A | C |
| ATOM | 48 | CD | GLN | A | 7 | 15.079 | 1.227 | −3.957 | 1.00 | 73.33 A | C |
| ATOM | 49 | OE1 | GLN | A | 7 | 14.583 | 0.104 | −4.071 | 1.00 | 77.38 A | O |
| ATOM | 50 | NE2 | GLN | A | 7 | 14.865 | 2.199 | −4.840 | 1.00 | 72.72 A | N |
| ATOM | 51 | N | ILE | A | 8 | 13.100 | −0.933 | −0.363 | 1.00 | 29.95 A | N |
| ATOM | 52 | CA | ILE | A | 8 | 12.650 | −1.870 | 0.650 | 1.00 | 22.66 A | C |
| ATOM | 53 | C | ILE | A | 8 | 13.831 | −2.654 | 1.210 | 1.00 | 25.91 A | C |
| ATOM | 54 | O | ILE | A | 8 | 14.156 | −3.748 | 0.749 | 1.00 | 26.66 A | O |
| ATOM | 55 | CB | ILE | A | 8 | 11.550 | −2.801 | 0.113 | 1.00 | 22.42 A | C |
| ATOM | 56 | CG1 | ILE | A | 8 | 10.316 | −1.972 | −0.262 | 1.00 | 28.59 A | C |
| ATOM | 57 | CG2 | ILE | A | 8 | 11.171 | −3.841 | 1.145 | 1.00 | 19.64 A | C |
| ATOM | 58 | CD1 | ILE | A | 8 | 9.862 | −1.025 | 0.835 | 1.00 | 23.12 A | C |
| ATOM | 59 | N | THR | A | 9 | 14.483 | −2.072 | 2.208 | 1.00 | 25.29 A | N |
| ATOM | 60 | CA | THR | A | 9 | 15.574 | −2.752 | 2.889 | 1.00 | 25.71 A | C |
| ATOM | 61 | C | THR | A | 9 | 15.621 | −2.310 | 4.343 | 1.00 | 23.18 A | C |
| ATOM | 62 | O | THR | A | 9 | 15.241 | −1.185 | 4.669 | 1.00 | 26.78 A | O |
| ATOM | 63 | CB | THR | A | 9 | 16.930 | −2.491 | 2.204 | 1.00 | 29.73 A | C |
| ATOM | 64 | OG1 | THR | A | 9 | 17.943 | −3.307 | 2.811 | 1.00 | 36.44 A | O |
| ATOM | 65 | CG2 | THR | A | 9 | 17.316 | −1.019 | 2.312 | 1.00 | 22.13 A | C |
| ATOM | 66 | N | ARG | A | 10 | 16.078 | −3.209 | 5.209 | 1.00 | 22.93 A | N |
| ATOM | 67 | CA | ARG | A | 10 | 16.159 | −2.950 | 6.642 | 1.00 | 28.37 A | C |
| ATOM | 68 | C | ARG | A | 10 | 16.693 | −1.557 | 6.955 | 1.00 | 26.68 A | C |
| ATOM | 69 | O | ARG | A | 10 | 17.735 | −1.148 | 6.443 | 1.00 | 27.49 A | O |
| ATOM | 70 | CB | ARG | A | 10 | 17.023 | −4.007 | 7.327 | 1.00 | 26.07 A | C |
| ATOM | 71 | CG | ARG | A | 10 | 16.937 | −3.984 | 8.836 | 1.00 | 25.73 A | C |
| ATOM | 72 | CD | ARG | A | 10 | 17.825 | −5.050 | 9.458 | 1.00 | 26.43 A | C |
| ATOM | 73 | NE | ARG | A | 10 | 17.850 | −4.937 | 10.912 | 1.00 | 42.58 A | N |
| ATOM | 74 | CZ | ARG | A | 10 | 18.617 | −4.080 | 11.579 | 1.00 | 36.16 A | C |
| ATOM | 75 | NH1 | ARG | A | 10 | 19.426 | −3.263 | 10.917 | 1.00 | 40.67 A | N |
| ATOM | 76 | NH2 | ARG | A | 10 | 18.578 | −4.039 | 12.906 | 1.00 | 33.57 A | N |
| ATOM | 77 | N | ILE | A | 11 | 15.952 | −0.833 | 7.785 | 1.00 | 16.41 A | N |
| ATOM | 78 | CA | ILE | A | 11 | 16.335 | 0.494 | 8.233 | 1.00 | 19.58 A | C |
| ATOM | 79 | C | ILE | A | 11 | 17.336 | 0.359 | 9.378 | 1.00 | 23.29 A | C |

TABLE 1-continued

| | | | | | | | | | | | |
|---|---|---|---|---|---|---|---|---|---|---|---|
| ATOM | 80 | O | ILE | A | 11 | 17.026 | −0.225 | 10.420 | 1.00 | 24.17 A | O |
| ATOM | 81 | CB | ILE | A | 11 | 15.093 | 1.288 | 8.695 | 1.00 | 24.31 A | C |
| ATOM | 82 | CG1 | ILE | A | 11 | 14.176 | 1.563 | 7.502 | 1.00 | 17.73 A | C |
| ATOM | 83 | CG2 | ILE | A | 11 | 15.493 | 2.592 | 9.378 | 1.00 | 17.50 A | C |
| ATOM | 84 | CD1 | ILE | A | 11 | 12.849 | 2.159 | 7.874 | 1.00 | 19.62 A | C |
| ATOM | 85 | N | MET | A | 12 | 18.540 | 0.887 | 9.176 | 1.00 | 25.66 A | N |
| ATOM | 86 | CA | MET | A | 12 | 19.642 | 0.655 | 10.103 | 1.00 | 32.46 A | C |
| ATOM | 87 | C | MET | A | 12 | 19.527 | 1.503 | 11.367 | 1.00 | 32.06 A | C |
| ATOM | 88 | O | MET | A | 12 | 20.041 | 1.130 | 12.419 | 1.00 | 31.35 A | O |
| ATOM | 89 | CB | MET | A | 12 | 20.989 | 0.904 | 9.414 | 1.00 | 27.61 A | C |
| ATOM | 90 | CG | MET | A | 12 | 21.231 | 0.039 | 8.175 | 1.00 | 32.68 A | C |
| ATOM | 91 | SD | MET | A | 12 | 21.173 | −1.741 | 8.497 | 1.00 | 34.64 A | S |
| ATOM | 92 | CE | MET | A | 12 | 22.666 | −1.967 | 9.473 | 1.00 | 28.81 A | C |
| ATOM | 93 | N | ASP | A | 13 | 18.851 | 2.643 | 11.249 | 1.00 | 53.42 A | N |
| ATOM | 94 | CA | ASP | A | 13 | 18.670 | 3.570 | 12.363 | 1.00 | 55.93 A | C |
| ATOM | 95 | C | ASP | A | 13 | 17.489 | 3.150 | 13.238 | 1.00 | 51.35 A | C |
| ATOM | 96 | O | ASP | A | 13 | 16.336 | 3.215 | 12.809 | 1.00 | 49.36 A | O |
| ATOM | 97 | CB | ASP | A | 13 | 18.460 | 4.991 | 11.826 | 1.00 | 56.02 A | C |
| ATOM | 98 | CG | ASP | A | 13 | 17.848 | 5.929 | 12.857 | 1.00 | 72.21 A | C |
| ATOM | 99 | OD1 | ASP | A | 13 | 18.235 | 5.856 | 14.043 | 1.00 | 78.94 A | O |
| ATOM | 100 | OD2 | ASP | A | 13 | 16.982 | 6.749 | 12.477 | 1.00 | 67.36 A | O |
| ATOM | 101 | N | GLU | A | 14 | 17.786 | 2.721 | 14.462 | 1.00 | 23.30 A | N |
| ATOM | 102 | CA | GLU | A | 14 | 16.768 | 2.257 | 15.407 | 1.00 | 28.94 A | C |
| ATOM | 103 | C | GLU | A | 14 | 15.663 | 3.287 | 15.636 | 1.00 | 34.28 A | C |
| ATOM | 104 | O | GLU | A | 14 | 14.500 | 2.934 | 15.842 | 1.00 | 26.54 A | O |
| ATOM | 105 | CB | GLU | A | 14 | 17.416 | 1.898 | 16.746 | 1.00 | 26.47 A | C |
| ATOM | 106 | CG | GLU | A | 14 | 16.449 | 1.557 | 17.868 | 1.00 | 28.84 A | C |
| ATOM | 107 | CD | GLU | A | 14 | 17.134 | 1.534 | 19.235 | 1.00 | 56.72 A | C |
| ATOM | 108 | OE1 | GLU | A | 14 | 17.945 | 2.448 | 19.516 | 1.00 | 62.38 A | O |
| ATOM | 109 | OE2 | GLU | A | 14 | 16.862 | 0.607 | 20.031 | 1.00 | 47.25 A | O |
| ATOM | 110 | N | ARG | A | 15 | 16.028 | 4.562 | 15.600 | 1.00 | 47.85 A | N |
| ATOM | 111 | CA | ARG | A | 15 | 15.056 | 5.624 | 15.804 | 1.00 | 40.56 A | C |
| ATOM | 112 | C | ARG | A | 15 | 14.036 | 5.672 | 14.670 | 1.00 | 36.17 A | C |
| ATOM | 113 | O | ARG | A | 15 | 12.834 | 5.592 | 14.914 | 1.00 | 32.41 A | O |
| ATOM | 114 | CB | ARG | A | 15 | 15.755 | 6.974 | 15.963 | 1.00 | 49.45 A | C |
| ATOM | 115 | CG | ARG | A | 15 | 14.860 | 8.051 | 16.537 | 1.00 | 54.99 A | C |
| ATOM | 116 | CD | ARG | A | 15 | 15.619 | 8.954 | 17.492 | 1.00 | 65.98 A | C |
| ATOM | 117 | NE | ARG | A | 15 | 14.821 | 9.226 | 18.684 | 1.00 | 72.44 A | N |
| ATOM | 118 | CZ | ARG | A | 15 | 14.831 | 8.464 | 19.774 | 1.00 | 68.90 A | C |
| ATOM | 119 | NH1 | ARG | A | 15 | 15.607 | 7.387 | 19.827 | 1.00 | 77.09 A | N |
| ATOM | 120 | NH2 | ARG | A | 15 | 14.067 | 8.778 | 20.813 | 1.00 | 50.97 A | N |
| ATOM | 121 | N | ASN | A | 16 | 14.511 | 5.798 | 13.433 | 1.00 | 34.37 A | N |
| ATOM | 122 | CA | ASN | A | 16 | 13.610 | 5.821 | 12.282 | 1.00 | 30.83 A | C |
| ATOM | 123 | C | ASN | A | 16 | 12.915 | 4.478 | 12.068 | 1.00 | 26.73 A | C |
| ATOM | 124 | O | ASN | A | 16 | 11.836 | 4.417 | 11.485 | 1.00 | 25.88 A | O |
| ATOM | 125 | CB | ASN | A | 16 | 14.340 | 6.245 | 11.000 | 1.00 | 36.12 A | C |
| ATOM | 126 | CG | ASN | A | 16 | 13.409 | 6.283 | 9.777 | 1.00 | 44.40 A | C |
| ATOM | 127 | OD1 | ASN | A | 16 | 12.378 | 6.962 | 9.784 | 1.00 | 34.71 A | O |
| ATOM | 128 | ND2 | ASN | A | 16 | 13.776 | 5.552 | 8.725 | 1.00 | 30.96 A | N |
| ATOM | 129 | N | ARG | A | 17 | 13.530 | 3.399 | 12.535 | 1.00 | 19.72 A | N |
| ATOM | 130 | CA | ARG | A | 17 | 12.931 | 2.088 | 12.349 | 1.00 | 22.57 A | C |
| ATOM | 131 | C | ARG | A | 17 | 11.716 | 1.960 | 13.253 | 1.00 | 23.83 A | C |
| ATOM | 132 | O | ARG | A | 17 | 10.688 | 1.407 | 12.862 | 1.00 | 22.36 A | O |
| ATOM | 133 | CB | ARG | A | 17 | 13.935 | 0.969 | 12.626 | 1.00 | 19.23 A | C |
| ATOM | 134 | CG | ARG | A | 17 | 13.410 | −0.412 | 12.279 | 1.00 | 19.82 A | C |
| ATOM | 135 | CD | ARG | A | 17 | 14.508 | −1.472 | 12.340 | 1.00 | 23.69 A | C |
| ATOM | 136 | NE | ARG | A | 17 | 15.061 | −1.590 | 13.683 | 1.00 | 27.46 A | N |
| ATOM | 137 | CZ | ARG | A | 17 | 16.306 | −1.263 | 14.017 | 1.00 | 30.61 A | C |
| ATOM | 138 | NH1 | ARG | A | 17 | 17.159 | −0.816 | 13.097 | 1.00 | 23.50 A | N |
| ATOM | 139 | NH2 | ARG | A | 17 | 16.701 | −1.399 | 15.276 | 1.00 | 31.20 A | N |
| ATOM | 140 | N | GLN | A | 18 | 11.842 | 2.487 | 14.465 | 1.00 | 28.12 A | N |
| ATOM | 141 | CA | GLN | A | 18 | 10.745 | 2.492 | 15.423 | 1.00 | 29.50 A | C |
| ATOM | 142 | C | GLN | A | 18 | 9.583 | 3.356 | 14.921 | 1.00 | 25.82 A | C |
| ATOM | 143 | O | GLN | A | 18 | 8.423 | 2.952 | 14.994 | 1.00 | 21.13 A | O |
| ATOM | 144 | CB | GLN | A | 18 | 11.245 | 2.984 | 16.787 | 1.00 | 25.64 A | C |
| ATOM | 145 | CG | GLN | A | 18 | 10.148 | 3.365 | 17.764 | 1.00 | 26.78 A | C |
| ATOM | 146 | CD | GLN | A | 18 | 9.184 | 2.227 | 18.041 | 1.00 | 41.07 A | C |
| ATOM | 147 | OE1 | GLN | A | 18 | 9.474 | 1.063 | 17.760 | 1.00 | 49.03 A | O |
| ATOM | 148 | NE2 | GLN | A | 18 | 8.024 | 2.562 | 18.601 | 1.00 | 51.07 A | N |
| ATOM | 149 | N | VAL | A | 19 | 9.910 | 4.541 | 14.410 | 1.00 | 27.77 A | N |
| ATOM | 150 | CA | VAL | A | 19 | 8.916 | 5.456 | 13.861 | 1.00 | 26.66 A | C |
| ATOM | 151 | C | VAL | A | 19 | 8.195 | 4.853 | 12.660 | 1.00 | 30.61 A | C |
| ATOM | 152 | O | VAL | A | 19 | 6.964 | 4.827 | 12.610 | 1.00 | 30.39 A | O |
| ATOM | 153 | CB | VAL | A | 19 | 9.561 | 6.781 | 13.424 | 1.00 | 29.19 A | C |
| ATOM | 154 | CG1 | VAL | A | 19 | 8.619 | 7.558 | 12.511 | 1.00 | 27.30 A | C |
| ATOM | 155 | CG2 | VAL | A | 19 | 9.944 | 7.606 | 14.640 | 1.00 | 27.00 A | C |
| ATOM | 156 | N | THR | A | 20 | 8.965 | 4.376 | 11.689 | 1.00 | 24.75 A | N |
| ATOM | 157 | CA | THR | A | 20 | 8.387 | 3.772 | 10.501 | 1.00 | 25.94 A | C |
| ATOM | 158 | C | THR | A | 20 | 7.502 | 2.592 | 10.884 | 1.00 | 25.46 A | C |
| ATOM | 159 | O | THR | A | 20 | 6.453 | 2.356 | 10.277 | 1.00 | 23.02 A | O |

TABLE 1-continued

| | | | | | | | | | | | |
|---|---|---|---|---|---|---|---|---|---|---|---|
| ATOM | 160 | CB | THR | A | 20 | 9.473 | 3.280 | 9.537 | 1.00 | 28.24 A | C |
| ATOM | 161 | OG1 | THR | A | 20 | 10.148 | 4.405 | 8.961 | 1.00 | 26.89 A | O |
| ATOM | 162 | CG2 | THR | A | 20 | 8.850 | 2.434 | 8.430 | 1.00 | 23.49 A | C |
| ATOM | 163 | N | PHE | A | 21 | 7.930 | 1.853 | 11.898 | 1.00 | 22.67 A | N |
| ATOM | 164 | CA | PHE | A | 21 | 7.191 | 0.675 | 12.326 | 1.00 | 25.01 A | C |
| ATOM | 165 | C | PHE | A | 21 | 5.824 | 1.033 | 12.904 | 1.00 | 23.93 A | C |
| ATOM | 166 | O | PHE | A | 21 | 4.838 | 0.345 | 12.645 | 1.00 | 23.30 A | O |
| ATOM | 167 | CB | PHE | A | 21 | 7.996 | −0.136 | 13.339 | 1.00 | 20.65 A | C |
| ATOM | 168 | CG | PHE | A | 21 | 7.201 | −1.214 | 14.011 | 1.00 | 22.59 A | C |
| ATOM | 169 | CD1 | PHE | A | 21 | 7.028 | −2.448 | 13.400 | 1.00 | 17.85 A | C |
| ATOM | 170 | CD2 | PHE | A | 21 | 6.616 | −0.993 | 15.249 | 1.00 | 22.78 A | C |
| ATOM | 171 | CE1 | PHE | A | 21 | 6.300 | −3.446 | 14.014 | 1.00 | 20.66 A | C |
| ATOM | 172 | CE2 | PHE | A | 21 | 5.876 | −1.989 | 15.872 | 1.00 | 23.04 A | C |
| ATOM | 173 | CZ | PHE | A | 21 | 5.720 | −3.218 | 15.255 | 1.00 | 27.67 A | C |
| ATOM | 174 | N | THR | A | 22 | 5.767 | 2.102 | 13.690 | 1.00 | 17.65 A | N |
| ATOM | 175 | CA | THR | A | 22 | 4.503 | 2.537 | 14.271 | 1.00 | 18.23 A | C |
| ATOM | 176 | C | THR | A | 22 | 3.548 | 3.066 | 13.196 | 1.00 | 16.79 A | C |
| ATOM | 177 | O | THR | A | 22 | 2.354 | 2.772 | 13.221 | 1.00 | 17.70 A | O |
| ATOM | 178 | CB | THR | A | 22 | 4.703 | 3.611 | 15.378 | 1.00 | 19.42 A | C |
| ATOM | 179 | OG1 | THR | A | 22 | 5.340 | 3.023 | 16.521 | 1.00 | 16.50 A | O |
| ATOM | 180 | CG2 | THR | A | 22 | 3.365 | 4.185 | 15.803 | 1.00 | 13.05 A | C |
| ATOM | 181 | N | LYS | A | 23 | 4.070 | 3.850 | 12.258 | 1.00 | 21.15 A | N |
| ATOM | 182 | CA | LYS | A | 23 | 3.245 | 4.375 | 11.177 | 1.00 | 22.13 A | C |
| ATOM | 183 | C | LYS | A | 23 | 2.692 | 3.252 | 10.312 | 1.00 | 21.52 A | C |
| ATOM | 184 | O | LYS | A | 23 | 1.487 | 3.165 | 10.100 | 1.00 | 22.00 A | O |
| ATOM | 185 | CB | LYS | A | 23 | 4.032 | 5.350 | 10.300 | 1.00 | 25.46 A | C |
| ATOM | 186 | CG | LYS | A | 23 | 4.247 | 6.727 | 10.908 | 1.00 | 31.78 A | C |
| ATOM | 187 | CD | LYS | A | 23 | 5.175 | 7.556 | 10.019 | 1.00 | 35.00 A | C |
| ATOM | 188 | CE | LYS | A | 23 | 5.361 | 8.963 | 10.558 | 1.00 | 38.42 A | C |
| ATOM | 189 | NZ | LYS | A | 23 | 6.455 | 9.677 | 9.844 | 1.00 | 36.46 A | N |
| ATOM | 190 | N | ARG | A | 24 | 3.578 | 2.393 | 9.818 | 1.00 | 18.04 A | N |
| ATOM | 191 | CA | ARG | A | 24 | 3.181 | 1.335 | 8.887 | 1.00 | 17.50 A | C |
| ATOM | 192 | C | ARG | A | 24 | 2.380 | 0.210 | 9.547 | 1.00 | 19.35 A | C |
| ATOM | 193 | O | ARG | A | 24 | 1.571 | −0.436 | 8.878 | 1.00 | 18.00 A | O |
| ATOM | 194 | CB | ARG | A | 24 | 4.395 | 0.765 | 8.149 | 1.00 | 14.94 A | C |
| ATOM | 195 | CG | ARG | A | 24 | 4.892 | 1.624 | 6.987 | 1.00 | 16.36 A | C |
| ATOM | 196 | CD | ARG | A | 24 | 6.120 | 0.999 | 6.313 | 1.00 | 15.51 A | C |
| ATOM | 197 | NE | ARG | A | 24 | 6.453 | 1.675 | 5.062 | 1.00 | 17.77 A | N |
| ATOM | 198 | CZ | ARG | A | 24 | 6.091 | 1.244 | 3.855 | 1.00 | 19.55 A | C |
| ATOM | 199 | NH1 | ARG | A | 24 | 5.388 | 0.122 | 3.722 | 1.00 | 19.36 A | N |
| ATOM | 200 | NH2 | ARG | A | 24 | 6.430 | 1.934 | 2.778 | 1.00 | 14.87 A | N |
| ATOM | 201 | N | LYS | A | 25 | 2.600 | −0.029 | 10.843 | 1.00 | 19.64 A | N |
| ATOM | 202 | CA | LYS | A | 25 | 1.820 | −1.041 | 11.560 | 1.00 | 20.34 A | C |
| ATOM | 203 | C | LYS | A | 25 | 0.370 | −0.608 | 11.601 | 1.00 | 20.24 A | C |
| ATOM | 204 | O | LYS | A | 25 | −0.537 | −1.397 | 11.351 | 1.00 | 20.44 A | O |
| ATOM | 205 | CB | LYS | A | 25 | 2.326 | −1.257 | 12.987 | 1.00 | 26.21 A | C |
| ATOM | 206 | CG | LYS | A | 25 | 1.347 | −2.046 | 13.867 | 1.00 | 22.43 A | C |
| ATOM | 207 | CD | LYS | A | 25 | 2.031 | −2.639 | 15.101 | 1.00 | 28.10 A | C |
| ATOM | 208 | CE | LYS | A | 25 | 2.524 | −1.564 | 16.083 | 1.00 | 24.12 A | C |
| ATOM | 209 | NZ | LYS | A | 25 | 1.411 | −0.839 | 16.761 | 1.00 | 21.37 A | N |
| ATOM | 210 | N | PHE | A | 26 | 0.160 | 0.661 | 11.917 | 1.00 | 16.23 A | N |
| ATOM | 211 | CA | PHE | A | 26 | −1.165 | 1.248 | 11.835 | 1.00 | 18.62 A | C |
| ATOM | 212 | C | PHE | A | 26 | −1.732 | 1.076 | 10.415 | 1.00 | 18.38 A | C |
| ATOM | 213 | O | PHE | A | 26 | −2.837 | 0.573 | 10.234 | 1.00 | 19.75 A | O |
| ATOM | 214 | CB | PHE | A | 26 | −1.101 | 2.727 | 12.213 | 1.00 | 15.46 A | C |
| ATOM | 215 | CG | PHE | A | 26 | −2.443 | 3.384 | 12.314 | 1.00 | 19.64 A | C |
| ATOM | 216 | CD1 | PHE | A | 26 | −3.053 | 3.558 | 13.548 | 1.00 | 22.13 A | C |
| ATOM | 217 | CD2 | PHE | A | 26 | −3.095 | 3.834 | 11.177 | 1.00 | 17.94 A | C |
| ATOM | 218 | CE1 | PHE | A | 26 | −4.290 | 4.168 | 13.645 | 1.00 | 23.01 A | C |
| ATOM | 219 | CE2 | PHE | A | 26 | −4.329 | 4.440 | 11.266 | 1.00 | 21.01 A | C |
| ATOM | 220 | CZ | PHE | A | 26 | −4.929 | 4.609 | 12.505 | 1.00 | 27.60 A | C |
| ATOM | 221 | N | GLY | A | 27 | −0.962 | 1.487 | 9.413 | 1.00 | 27.12 A | N |
| ATOM | 222 | CA | GLY | A | 27 | −1.369 | 1.366 | 8.024 | 1.00 | 25.34 A | C |
| ATOM | 223 | C | GLY | A | 27 | −1.735 | −0.049 | 7.618 | 1.00 | 23.53 A | C |
| ATOM | 224 | O | GLY | A | 27 | −2.658 | −0.250 | 6.832 | 1.00 | 25.30 A | O |
| ATOM | 225 | N | LEU | A | 28 | −1.017 | −1.032 | 8.154 | 1.00 | 20.30 A | N |
| ATOM | 226 | CA | LEU | A | 28 | −1.255 | −2.431 | 7.800 | 1.00 | 20.79 A | C |
| ATOM | 227 | C | LEU | A | 28 | −2.542 | −2.957 | 8.432 | 1.00 | 19.85 A | C |
| ATOM | 228 | O | LEU | A | 28 | −3.313 | −3.672 | 7.790 | 1.00 | 17.99 A | O |
| ATOM | 229 | CB | LEU | A | 28 | −0.070 | −3.310 | 8.210 | 1.00 | 23.59 A | C |
| ATOM | 230 | CG | LEU | A | 28 | −0.132 | −4.788 | 7.794 | 1.00 | 20.17 A | C |
| ATOM | 231 | CD1 | LEU | A | 28 | −0.146 | −4.926 | 6.293 | 1.00 | 16.98 A | C |
| ATOM | 232 | CD2 | LEU | A | 28 | 1.026 | −5.582 | 8.385 | 1.00 | 17.88 A | C |
| ATOM | 233 | N | MET | A | 29 | −2.774 | −2.585 | 9.690 | 1.00 | 23.01 A | N |
| ATOM | 234 | CA | MET | A | 29 | −3.980 | −3.002 | 10.395 | 1.00 | 20.12 A | C |
| ATOM | 235 | C | MET | A | 29 | −5.208 | −2.346 | 9.777 | 1.00 | 18.22 A | C |
| ATOM | 236 | O | MET | A | 29 | −6.250 | −2.976 | 9.629 | 1.00 | 16.78 A | O |
| ATOM | 237 | CB | MET | A | 29 | −3.889 | −2.672 | 11.887 | 1.00 | 20.50 A | C |
| ATOM | 238 | CG | MET | A | 29 | −2.792 | −3.423 | 12.641 | 1.00 | 20.16 A | C |
| ATOM | 239 | SD | MET | A | 29 | −3.158 | −3.552 | 14.417 | 1.00 | 22.93 A | S |

TABLE 1-continued

| | | | | | | | | | | | |
|---|---|---|---|---|---|---|---|---|---|---|---|
| ATOM | 240 | CE | MET | A | 29 | −1.718 | −4.473 | 14.963 | 1.00 | 25.26 A | C |
| ATOM | 241 | N | LYS | A | 30 | −5.082 | −1.079 | 9.406 | 1.00 | 21.44 A | N |
| ATOM | 242 | CA | LYS | A | 30 | −6.195 | −0.385 | 8.770 | 1.00 | 22.10 A | C |
| ATOM | 243 | C | LYS | A | 30 | −6.676 | −1.145 | 7.529 | 1.00 | 21.81 A | C |
| ATOM | 244 | O | LYS | A | 30 | −7.861 | −1.459 | 7.403 | 1.00 | 24.17 A | O |
| ATOM | 245 | CB | LYS | A | 30 | −5.813 | 1.053 | 8.416 | 1.00 | 20.87 A | C |
| ATOM | 246 | CG | LYS | A | 30 | −6.980 | 1.885 | 7.914 | 1.00 | 29.30 A | C |
| ATOM | 247 | CD | LYS | A | 30 | −6.576 | 3.329 | 7.647 | 1.00 | 29.06 A | C |
| ATOM | 248 | CE | LYS | A | 30 | −7.756 | 4.132 | 7.118 | 1.00 | 35.72 A | C |
| ATOM | 249 | NZ | LYS | A | 30 | −7.340 | 5.436 | 6.528 | 1.00 | 30.83 A | N |
| ATOM | 250 | N | LYS | A | 31 | −5.756 | −1.460 | 6.623 | 1.00 | 18.84 A | N |
| ATOM | 251 | CA | LYS | A | 31 | −6.119 | −2.177 | 5.399 | 1.00 | 22.05 A | C |
| ATOM | 252 | C | LYS | A | 31 | −6.644 | −3.592 | 5.653 | 1.00 | 17.61 A | C |
| ATOM | 253 | O | LYS | A | 31 | −7.568 | −4.043 | 4.985 | 1.00 | 21.05 A | O |
| ATOM | 254 | CB | LYS | A | 31 | −4.951 | −2.188 | 4.412 | 1.00 | 18.86 A | C |
| ATOM | 255 | CG | LYS | A | 31 | −4.954 | −0.991 | 3.476 | 1.00 | 20.01 A | C |
| ATOM | 256 | CD | LYS | A | 31 | −3.568 | −0.685 | 2.946 | 1.00 | 22.22 A | C |
| ATOM | 257 | CE | LYS | A | 31 | −3.641 | 0.064 | 1.623 | 1.00 | 21.55 A | C |
| ATOM | 258 | NZ | LYS | A | 31 | −4.901 | 0.856 | 1.487 | 1.00 | 21.23 A | N |
| ATOM | 259 | N | ALA | A | 32 | −6.069 | −4.283 | 6.630 | 1.00 | 13.45 A | N |
| ATOM | 260 | CA | ALA | A | 32 | −6.528 | −5.624 | 6.967 | 1.00 | 13.40 A | C |
| ATOM | 261 | C | ALA | A | 32 | −7.983 | −5.576 | 7.417 | 1.00 | 17.70 A | C |
| ATOM | 262 | O | ALA | A | 32 | −8.813 | −6.346 | 6.928 | 1.00 | 17.45 A | O |
| ATOM | 263 | CB | ALA | A | 32 | −5.645 | −6.244 | 8.043 | 1.00 | 12.68 A | C |
| ATOM | 264 | N | TYR | A | 33 | −8.285 | −4.664 | 8.343 | 1.00 | 22.08 A | N |
| ATOM | 265 | CA | TYR | A | 33 | −9.655 | −4.417 | 8.791 | 1.00 | 21.79 A | C |
| ATOM | 266 | C | TYR | A | 33 | −10.596 | −4.066 | 7.633 | 1.00 | 24.76 A | C |
| ATOM | 267 | O | TYR | A | 33 | −11.714 | −4.577 | 7.554 | 1.00 | 25.28 A | O |
| ATOM | 268 | CB | TYR | A | 33 | −9.682 | −3.303 | 9.848 | 1.00 | 26.33 A | C |
| ATOM | 269 | CG | TYR | A | 33 | −11.001 | −2.557 | 9.934 | 1.00 | 24.65 A | C |
| ATOM | 270 | CD1 | TYR | A | 33 | −12.060 | −3.060 | 10.676 | 1.00 | 28.98 A | C |
| ATOM | 271 | CD2 | TYR | A | 33 | −11.184 | −1.349 | 9.271 | 1.00 | 26.32 A | C |
| ATOM | 272 | CE1 | TYR | A | 33 | −13.266 | −2.382 | 10.757 | 1.00 | 30.58 A | C |
| ATOM | 273 | CE2 | TYR | A | 33 | −12.389 | −0.664 | 9.341 | 1.00 | 25.98 A | C |
| ATOM | 274 | CZ | TYR | A | 33 | −13.424 | −1.185 | 10.087 | 1.00 | 31.84 A | C |
| ATOM | 275 | OH | TYR | A | 33 | −14.621 | −0.509 | 10.165 | 1.00 | 30.84 A | O |
| ATOM | 276 | N | GLU | A | 34 | −10.146 | −3.187 | 6.744 | 1.00 | 23.16 A | N |
| ATOM | 277 | CA | GLU | A | 34 | −10.947 | −2.799 | 5.589 | 1.00 | 21.92 A | C |
| ATOM | 278 | C | GLU | A | 34 | −11.227 | −3.986 | 4.675 | 1.00 | 22.46 A | C |
| ATOM | 279 | O | GLU | A | 34 | −12.328 | −4.113 | 4.129 | 1.00 | 22.16 A | O |
| ATOM | 280 | CB | GLU | A | 34 | −10.266 | −1.673 | 4.810 | 1.00 | 21.12 A | C |
| ATOM | 281 | CG | GLU | A | 34 | −10.229 | −0.344 | 5.557 | 1.00 | 20.36 A | C |
| ATOM | 282 | CD | GLU | A | 34 | −9.648 | 0.778 | 4.718 | 1.00 | 21.90 A | C |
| ATOM | 283 | OE1 | GLU | A | 34 | −9.002 | 0.483 | 3.690 | 1.00 | 23.00 A | O |
| ATOM | 284 | OE2 | GLU | A | 34 | −9.836 | 1.956 | 5.081 | 1.00 | 19.62 A | O |
| ATOM | 285 | N | LEU | A | 35 | −10.244 | −4.867 | 4.520 | 1.00 | 19.11 A | N |
| ATOM | 286 | CA | LEU | A | 35 | −10.450 | −6.059 | 3.696 | 1.00 | 19.55 A | C |
| ATOM | 287 | C | LEU | A | 35 | −11.446 | −7.026 | 4.342 | 1.00 | 20.70 A | C |
| ATOM | 288 | O | LEU | A | 35 | −12.263 | −7.643 | 3.652 | 1.00 | 22.13 A | O |
| ATOM | 289 | CB | LEU | A | 35 | −9.129 | −6.769 | 3.392 | 1.00 | 16.66 A | C |
| ATOM | 290 | CG | LEU | A | 35 | −9.271 | −8.010 | 2.511 | 1.00 | 19.14 A | C |
| ATOM | 291 | CD1 | LEU | A | 35 | −9.903 | −7.645 | 1.173 | 1.00 | 17.50 A | C |
| ATOM | 292 | CD2 | LEU | A | 35 | −7.933 | −8.701 | 2.306 | 1.00 | 18.21 A | C |
| ATOM | 293 | N | SER | A | 36 | −11.379 | −7.157 | 5.662 | 1.00 | 22.42 A | N |
| ATOM | 294 | CA | SER | A | 36 | −12.327 | −8.001 | 6.379 | 1.00 | 27.64 A | C |
| ATOM | 295 | C | SER | A | 36 | −13.764 | −7.538 | 6.134 | 1.00 | 24.59 A | C |
| ATOM | 296 | O | SER | A | 36 | −14.650 | −8.346 | 5.866 | 1.00 | 26.35 A | O |
| ATOM | 297 | CB | SER | A | 36 | −12.026 | −8.000 | 7.879 | 1.00 | 29.01 A | C |
| ATOM | 298 | OG | SER | A | 36 | −12.983 | −8.771 | 8.588 | 1.00 | 28.51 A | O |
| ATOM | 299 | N | VAL | A | 37 | −13.983 | −6.230 | 6.217 | 1.00 | 20.31 A | N |
| ATOM | 300 | CA | VAL | A | 37 | −15.321 | −5.664 | 6.084 | 1.00 | 19.68 A | C |
| ATOM | 301 | C | VAL | A | 37 | −15.815 | −5.656 | 4.637 | 1.00 | 21.49 A | C |
| ATOM | 302 | O | VAL | A | 37 | −16.905 | −6.141 | 4.344 | 1.00 | 21.28 A | O |
| ATOM | 303 | CB | VAL | A | 37 | −15.382 | −4.229 | 6.643 | 1.00 | 20.47 A | C |
| ATOM | 304 | CG1 | VAL | A | 37 | −16.750 | −3.610 | 6.387 | 1.00 | 17.32 A | C |
| ATOM | 305 | CG2 | VAL | A | 37 | −15.060 | −4.228 | 8.124 | 1.00 | 21.67 A | C |
| ATOM | 306 | N | LEU | A | 38 | −15.016 | −5.093 | 3.738 | 1.00 | 24.67 A | N |
| ATOM | 307 | CA | LEU | A | 38 | −15.401 | −4.971 | 2.338 | 1.00 | 20.97 A | C |
| ATOM | 308 | C | LEU | A | 38 | −15.745 | −6.319 | 1.717 | 1.00 | 22.62 A | C |
| ATOM | 309 | O | LEU | A | 38 | −16.724 | −6.438 | 0.975 | 1.00 | 24.77 A | O |
| ATOM | 310 | CB | LEU | A | 38 | −14.274 | −4.327 | 1.527 | 1.00 | 20.39 A | C |
| ATOM | 311 | CG | LEU | A | 38 | −13.936 | −2.859 | 1.771 | 1.00 | 18.81 A | C |
| ATOM | 312 | CD1 | LEU | A | 38 | −12.570 | −2.532 | 1.177 | 1.00 | 16.96 A | C |
| ATOM | 313 | CD2 | LEU | A | 38 | −15.017 | −1.951 | 1.204 | 1.00 | 19.42 A | C |
| ATOM | 314 | N | CYS | A | 39 | −14.937 | −7.331 | 2.013 | 1.00 | 21.00 A | N |
| ATOM | 315 | CA | CYS | A | 39 | −15.071 | −8.615 | 1.330 | 1.00 | 22.90 A | C |
| ATOM | 316 | C | CYS | A | 39 | −15.531 | −9.750 | 2.239 | 1.00 | 24.81 A | C |
| ATOM | 317 | O | CYS | A | 39 | −15.504 | −10.915 | 1.847 | 1.00 | 28.63 A | O |
| ATOM | 318 | CB | CYS | A | 39 | −13.757 | −8.989 | 0.640 | 1.00 | 18.48 A | C |
| ATOM | 319 | SG | CYS | A | 39 | −13.163 | −7.706 | −0.472 | 1.00 | 18.20 A | S |

TABLE 1-continued

| ATOM | 320 | N | ASP | A | 40 | −15.944 | −9.413 | 3.455 | 1.00 | 28.63 A | N |
|---|---|---|---|---|---|---|---|---|---|---|---|
| ATOM | 321 | CA | ASP | A | 40 | −16.503 | −10.417 | 4.351 | 1.00 | 30.28 A | C |
| ATOM | 322 | C | ASP | A | 40 | −15.583 | −11.631 | 4.483 | 1.00 | 31.00 A | C |
| ATOM | 323 | O | ASP | A | 40 | −15.878 | −12.695 | 3.944 | 1.00 | 30.22 A | O |
| ATOM | 324 | CB | ASP | A | 40 | −17.876 | −10.858 | 3.831 | 1.00 | 27.25 A | C |
| ATOM | 325 | CG | ASP | A | 40 | −18.585 | −11.821 | 4.770 | 1.00 | 31.14 A | C |
| ATOM | 326 | OD1 | ASP | A | 40 | −18.189 | −11.932 | 5.948 | 1.00 | 32.84 A | O |
| ATOM | 327 | OD2 | ASP | A | 40 | −19.552 | −12.472 | 4.318 | 1.00 | 47.25 A | O |
| ATOM | 328 | N | CYS | A | 41 | −14.469 | −11.472 | 5.192 | 1.00 | 28.67 A | N |
| ATOM | 329 | CA | CYS | A | 41 | −13.600 | −12.611 | 5.476 | 1.00 | 34.11 A | C |
| ATOM | 330 | C | CYS | A | 41 | −12.962 | −12.566 | 6.867 | 1.00 | 33.64 A | C |
| ATOM | 331 | O | CYS | A | 41 | −12.839 | −11.500 | 7.470 | 1.00 | 32.01 A | O |
| ATOM | 332 | CB | CYS | A | 41 | −12.530 | −12.771 | 4.390 | 1.00 | 34.49 A | C |
| ATOM | 333 | SG | CYS | A | 41 | −11.901 | −11.242 | 3.695 | 1.00 | 42.38 A | S |
| ATOM | 334 | N | GLU | A | 42 | −12.589 | −13.739 | 7.377 | 1.00 | 35.13 A | N |
| ATOM | 335 | CA | GLU | A | 42 | −11.835 | −13.837 | 8.617 | 1.00 | 31.41 A | C |
| ATOM | 336 | C | GLU | A | 42 | −10.393 | −13.499 | 8.312 | 1.00 | 31.12 A | C |
| ATOM | 337 | O | GLU | A | 42 | −9.852 | −13.934 | 7.299 | 1.00 | 34.59 A | O |
| ATOM | 338 | CB | GLU | A | 42 | −11.864 | −15.258 | 9.177 | 1.00 | 36.09 A | C |
| ATOM | 339 | CG | GLU | A | 42 | −13.223 | −15.801 | 9.546 | 1.00 | 50.30 A | C |
| ATOM | 340 | CD | GLU | A | 42 | −13.107 | −17.105 | 10.310 | 1.00 | 48.91 A | C |
| ATOM | 341 | OE1 | GLU | A | 42 | −13.992 | −17.973 | 10.160 | 1.00 | 69.71 A | O |
| ATOM | 342 | OE2 | GLU | A | 42 | −12.118 | −17.264 | 11.053 | 1.00 | 39.96 A | O |
| ATOM | 343 | N | ILE | A | 43 | −9.760 | −12.740 | 9.196 | 1.00 | 22.52 A | N |
| ATOM | 344 | CA | ILE | A | 43 | −8.359 | −12.401 | 9.012 | 1.00 | 18.82 A | C |
| ATOM | 345 | C | ILE | A | 43 | −7.604 | −12.413 | 10.333 | 1.00 | 18.26 A | C |
| ATOM | 346 | O | ILE | A | 43 | −8.152 | −12.074 | 11.378 | 1.00 | 19.33 A | O |
| ATOM | 347 | CB | ILE | A | 43 | −8.204 | −11.046 | 8.308 | 1.00 | 18.81 A | C |
| ATOM | 348 | CG1 | ILE | A | 43 | −8.579 | −11.199 | 6.828 | 1.00 | 19.26 A | C |
| ATOM | 349 | CG2 | ILE | A | 43 | −6.774 | −10.523 | 8.471 | 1.00 | 14.71 A | C |
| ATOM | 350 | CD1 | ILE | A | 43 | −8.902 | −9.910 | 6.115 | 1.00 | 17.63 A | C |
| ATOM | 351 | N | ALA | A | 44 | −6.347 | −12.832 | 10.282 | 1.00 | 20.70 A | N |
| ATOM | 352 | CA | ALA | A | 44 | −5.490 | −12.809 | 11.456 | 1.00 | 22.51 A | C |
| ATOM | 353 | C | ALA | A | 44 | −4.138 | −12.232 | 11.077 | 1.00 | 21.54 A | C |
| ATOM | 354 | O | ALA | A | 44 | −3.557 | −12.601 | 10.061 | 1.00 | 24.49 A | O |
| ATOM | 355 | CB | ALA | A | 44 | −5.335 | −14.210 | 12.044 | 1.00 | 20.18 A | C |
| ATOM | 356 | N | LEU | A | 45 | −3.645 | −11.321 | 11.902 | 1.00 | 17.20 A | N |
| ATOM | 357 | CA | LEU | A | 45 | −2.373 | −10.673 | 11.656 | 1.00 | 15.17 A | C |
| ATOM | 358 | C | LEU | A | 45 | −1.574 | −10.679 | 12.949 | 1.00 | 18.70 A | C |
| ATOM | 359 | O | LEU | A | 45 | −1.992 | −10.088 | 13.944 | 1.00 | 18.56 A | O |
| ATOM | 360 | CB | LEU | A | 45 | −2.605 | −9.233 | 11.184 | 1.00 | 17.70 A | C |
| ATOM | 361 | CG | LEU | A | 45 | −1.376 | −8.343 | 10.969 | 1.00 | 18.97 A | C |
| ATOM | 362 | CD1 | LEU | A | 45 | −0.350 | −9.045 | 10.095 | 1.00 | 13.61 A | C |
| ATOM | 363 | CD2 | LEU | A | 45 | −1.769 | −6.995 | 10.371 | 1.00 | 15.25 A | C |
| ATOM | 364 | N | ILE | A | 46 | −0.435 | −11.361 | 12.938 | 1.00 | 26.22 A | N |
| ATOM | 365 | CA | ILE | A | 46 | 0.447 | −11.399 | 14.100 | 1.00 | 28.53 A | C |
| ATOM | 366 | C | ILE | A | 46 | 1.785 | −10.754 | 13.769 | 1.00 | 28.91 A | C |
| ATOM | 367 | O | ILE | A | 46 | 2.450 | −11.141 | 12.804 | 1.00 | 26.44 A | O |
| ATOM | 368 | CB | ILE | A | 46 | 0.683 | −12.842 | 14.585 | 1.00 | 31.11 A | C |
| ATOM | 369 | CG1 | ILE | A | 46 | −0.604 | −13.416 | 15.186 | 1.00 | 29.74 A | C |
| ATOM | 370 | CG2 | ILE | A | 46 | 1.810 | −12.883 | 15.600 | 1.00 | 27.36 A | C |
| ATOM | 371 | CD1 | ILE | A | 46 | −0.564 | −14.908 | 15.418 | 1.00 | 29.20 A | C |
| ATOM | 372 | N | ILE | A | 47 | 2.179 | −9.771 | 14.572 | 1.00 | 23.77 A | N |
| ATOM | 373 | CA | ILE | A | 47 | 3.412 | −9.032 | 14.328 | 1.00 | 24.05 A | C |
| ATOM | 374 | C | ILE | A | 47 | 4.284 | −8.942 | 15.572 | 1.00 | 24.16 A | C |
| ATOM | 375 | O | ILE | A | 47 | 3.843 | −8.444 | 16.608 | 1.00 | 27.34 A | O |
| ATOM | 376 | CB | ILE | A | 47 | 3.118 | −7.585 | 13.884 | 1.00 | 24.61 A | C |
| ATOM | 377 | CG1 | ILE | A | 47 | 2.161 | −7.561 | 12.691 | 1.00 | 22.79 A | C |
| ATOM | 378 | CG2 | ILE | A | 47 | 4.420 | −6.847 | 13.569 | 1.00 | 25.34 A | C |
| ATOM | 379 | CD1 | ILE | A | 47 | 1.725 | −6.168 | 12.318 | 1.00 | 20.83 A | C |
| ATOM | 380 | N | PHE | A | 48 | 5.521 | −9.410 | 15.467 | 1.00 | 22.85 A | N |
| ATOM | 381 | CA | PHE | A | 48 | 6.512 | −9.211 | 16.518 | 1.00 | 22.42 A | C |
| ATOM | 382 | C | PHE | A | 48 | 7.548 | −8.240 | 15.990 | 1.00 | 25.30 A | C |
| ATOM | 383 | O | PHE | A | 48 | 8.218 | −8.543 | 15.007 | 1.00 | 29.18 A | O |
| ATOM | 384 | CB | PHE | A | 48 | 7.226 | −10.522 | 16.859 | 1.00 | 25.20 A | C |
| ATOM | 385 | CG | PHE | A | 48 | 6.317 | −11.609 | 17.348 | 1.00 | 23.66 A | C |
| ATOM | 386 | CD1 | PHE | A | 48 | 5.817 | −12.556 | 16.471 | 1.00 | 22.65 A | C |
| ATOM | 387 | CD2 | PHE | A | 48 | 5.979 | −11.699 | 18.688 | 1.00 | 27.45 A | C |
| ATOM | 388 | CE1 | PHE | A | 48 | 4.982 | −13.567 | 16.920 | 1.00 | 23.46 A | C |
| ATOM | 389 | CE2 | PHE | A | 48 | 5.147 | −12.709 | 19.142 | 1.00 | 29.13 A | C |
| ATOM | 390 | CZ | PHE | A | 48 | 4.649 | −13.645 | 18.251 | 1.00 | 24.78 A | C |
| ATOM | 391 | N | ASN | A | 49 | 7.701 | −7.086 | 16.631 | 1.00 | 25.18 A | N |
| ATOM | 392 | CA | ASN | A | 49 | 8.713 | −6.132 | 16.184 | 1.00 | 24.60 A | C |
| ATOM | 393 | C | ASN | A | 49 | 10.116 | −6.668 | 16.455 | 1.00 | 25.56 A | C |
| ATOM | 394 | O | ASN | A | 49 | 10.268 | −7.771 | 16.984 | 1.00 | 25.60 A | O |
| ATOM | 395 | CB | ASN | A | 49 | 8.504 | −4.745 | 16.807 | 1.00 | 22.23 A | C |
| ATOM | 396 | CG | ASN | A | 49 | 8.835 | −4.702 | 18.290 | 1.00 | 28.49 A | C |
| ATOM | 397 | OD1 | ASN | A | 49 | 9.250 | −5.702 | 18.884 | 1.00 | 28.05 A | O |
| ATOM | 398 | ND2 | ASN | A | 49 | 8.654 | −3.532 | 18.895 | 1.00 | 25.55 A | N |
| ATOM | 399 | N | SER | A | 50 | 11.135 | −5.899 | 16.081 | 1.00 | 25.43 A | N |

TABLE 1-continued

| | | | | | | | | | | | |
|---|---|---|---|---|---|---|---|---|---|---|---|
| ATOM | 400 | CA | SER | A | 50 | 12.519 | −6.333 | 16.254 | 1.00 | 31.36 A | C |
| ATOM | 401 | C | SER | A | 50 | 12.881 | −6.563 | 17.719 | 1.00 | 35.94 A | C |
| ATOM | 402 | O | SER | A | 50 | 13.703 | −7.423 | 18.026 | 1.00 | 40.93 A | O |
| ATOM | 403 | CB | SER | A | 50 | 13.492 | −5.338 | 15.610 | 1.00 | 31.21 A | C |
| ATOM | 404 | OG | SER | A | 50 | 13.188 | −4.003 | 15.972 | 1.00 | 36.34 A | O |
| ATOM | 405 | N | SER | A | 51 | 12.263 | −5.801 | 18.618 | 1.00 | 40.78 A | N |
| ATOM | 406 | CA | SER | A | 51 | 12.503 | −5.959 | 20.055 | 1.00 | 40.97 A | C |
| ATOM | 407 | C | SER | A | 51 | 11.650 | −7.080 | 20.648 | 1.00 | 44.26 A | C |
| ATOM | 408 | O | SER | A | 51 | 11.588 | −7.245 | 21.867 | 1.00 | 37.55 A | O |
| ATOM | 409 | CB | SER | A | 51 | 12.231 | −4.650 | 20.801 | 1.00 | 35.21 A | C |
| ATOM | 410 | OG | SER | A | 51 | 12.982 | −3.582 | 20.252 | 1.00 | 42.54 A | O |
| ATOM | 411 | N | ASN | A | 52 | 10.978 | −7.827 | 19.775 | 1.00 | 42.32 A | N |
| ATOM | 412 | CA | ASN | A | 52 | 10.240 | −9.032 | 20.156 | 1.00 | 39.65 A | C |
| ATOM | 413 | C | ASN | A | 52 | 8.901 | −8.797 | 20.870 | 1.00 | 39.57 A | C |
| ATOM | 414 | O | ASN | A | 52 | 8.307 | −9.735 | 21.406 | 1.00 | 40.20 A | O |
| ATOM | 415 | CB | ASN | A | 52 | 11.123 | −9.962 | 20.990 | 1.00 | 40.53 A | C |
| ATOM | 416 | CG | ASN | A | 52 | 11.150 | −11.379 | 20.449 | 1.00 | 54.19 A | C |
| ATOM | 417 | OD1 | ASN | A | 52 | 11.503 | −11.606 | 19.288 | 1.00 | 47.98 A | O |
| ATOM | 418 | ND2 | ASN | A | 52 | 10.787 | −12.343 | 21.290 | 1.00 | 54.16 A | N |
| ATOM | 419 | N | LYS | A | 53 | 8.420 | −7.558 | 20.880 | 1.00 | 28.18 A | N |
| ATOM | 420 | CA | LYS | A | 53 | 7.092 | −7.297 | 21.431 | 1.00 | 31.87 A | C |
| ATOM | 421 | C | LYS | A | 53 | 5.992 | −7.674 | 20.436 | 1.00 | 29.62 A | C |
| ATOM | 422 | O | LYS | A | 53 | 6.091 | −7.392 | 19.242 | 1.00 | 24.49 A | O |
| ATOM | 423 | CB | LYS | A | 53 | 6.927 | −5.841 | 21.878 | 1.00 | 29.10 A | C |
| ATOM | 424 | CG | LYS | A | 53 | 5.561 | −5.579 | 22.522 | 1.00 | 36.89 A | C |
| ATOM | 425 | CD | LYS | A | 53 | 5.352 | −4.114 | 22.898 | 1.00 | 32.62 A | C |
| ATOM | 426 | CE | LYS | A | 53 | 3.962 | −3.900 | 23.489 | 1.00 | 35.52 A | C |
| ATOM | 427 | NZ | LYS | A | 53 | 3.638 | −2.459 | 23.700 | 1.00 | 34.56 A | N |
| ATOM | 428 | N | LEU | A | 54 | 4.941 | −8.303 | 20.951 | 1.00 | 30.84 A | N |
| ATOM | 429 | CA | LEU | A | 54 | 3.848 | −8.811 | 20.135 | 1.00 | 25.96 A | C |
| ATOM | 430 | C | LEU | A | 54 | 2.779 | −7.753 | 19.832 | 1.00 | 24.55 A | C |
| ATOM | 431 | O | LEU | A | 54 | 2.358 | −7.010 | 20.711 | 1.00 | 32.55 A | O |
| ATOM | 432 | CB | LEU | A | 54 | 3.212 | −10.008 | 20.844 | 1.00 | 30.00 A | C |
| ATOM | 433 | CG | LEU | A | 54 | 1.897 | −10.574 | 20.308 | 1.00 | 33.18 A | C |
| ATOM | 434 | CD1 | LEU | A | 54 | 2.067 | −11.111 | 18.891 | 1.00 | 23.66 A | C |
| ATOM | 435 | CD2 | LEU | A | 54 | 1.372 | −11.655 | 21.245 | 1.00 | 28.80 A | C |
| ATOM | 436 | N | PHE | A | 55 | 2.358 | −7.687 | 18.574 | 1.00 | 25.64 A | N |
| ATOM | 437 | CA | PHE | A | 55 | 1.218 | −6.867 | 18.175 | 1.00 | 25.15 A | C |
| ATOM | 438 | C | PHE | A | 55 | 0.298 | −7.729 | 17.324 | 1.00 | 23.57 A | C |
| ATOM | 439 | O | PHE | A | 55 | 0.767 | −8.560 | 16.554 | 1.00 | 29.95 A | O |
| ATOM | 440 | CB | PHE | A | 55 | 1.673 | −5.645 | 17.378 | 1.00 | 25.44 A | C |
| ATOM | 441 | CG | PHE | A | 55 | 2.542 | −4.702 | 18.157 | 1.00 | 20.82 A | C |
| ATOM | 442 | CD1 | PHE | A | 55 | 3.918 | −4.851 | 18.163 | 1.00 | 23.48 A | C |
| ATOM | 443 | CD2 | PHE | A | 55 | 1.980 | −3.663 | 18.880 | 1.00 | 24.05 A | C |
| ATOM | 444 | CE1 | PHE | A | 55 | 4.723 | −3.984 | 18.881 | 1.00 | 28.55 A | C |
| ATOM | 445 | CE2 | PHE | A | 55 | 2.776 | −2.786 | 19.602 | 1.00 | 27.58 A | C |
| ATOM | 446 | CZ | PHE | A | 55 | 4.152 | −2.945 | 19.601 | 1.00 | 31.46 A | C |
| ATOM | 447 | N | GLN | A | 56 | −1.008 | −7.542 | 17.456 | 1.00 | 24.49 A | N |
| ATOM | 448 | CA | GLN | A | 56 | −1.934 | −8.428 | 16.774 | 1.00 | 25.21 A | C |
| ATOM | 449 | C | GLN | A | 56 | −3.247 | −7.778 | 16.369 | 1.00 | 27.21 A | C |
| ATOM | 450 | O | GLN | A | 56 | −3.723 | −6.842 | 17.009 | 1.00 | 29.58 A | O |
| ATOM | 451 | CB | GLN | A | 56 | −2.216 | −9.658 | 17.641 | 1.00 | 31.95 A | C |
| ATOM | 452 | CG | GLN | A | 56 | −2.730 | −9.336 | 19.035 | 1.00 | 28.95 A | C |
| ATOM | 453 | CD | GLN | A | 56 | −2.850 | −10.574 | 19.914 | 1.00 | 40.70 A | C |
| ATOM | 454 | OE1 | GLN | A | 56 | −3.506 | −11.554 | 19.547 | 1.00 | 35.84 A | O |
| ATOM | 455 | NE2 | GLN | A | 56 | −2.216 | −10.532 | 21.084 | 1.00 | 38.27 A | N |
| ATOM | 456 | N | TYR | A | 57 | −3.819 | −8.294 | 15.287 | 1.00 | 24.23 A | N |
| ATOM | 457 | CA | TYR | A | 57 | −5.164 | −7.950 | 14.866 | 1.00 | 23.97 A | C |
| ATOM | 458 | C | TYR | A | 57 | −5.876 | −9.216 | 14.415 | 1.00 | 25.38 A | C |
| ATOM | 459 | O | TYR | A | 57 | −5.253 | −10.121 | 13.855 | 1.00 | 29.08 A | O |
| ATOM | 460 | CB | TYR | A | 57 | −5.164 | −6.947 | 13.708 | 1.00 | 28.41 A | C |
| ATOM | 461 | CG | TYR | A | 57 | −6.492 | −6.947 | 12.975 | 1.00 | 26.05 A | C |
| ATOM | 462 | CD1 | TYR | A | 57 | −7.586 | −6.260 | 13.483 | 1.00 | 25.02 A | C |
| ATOM | 463 | CD2 | TYR | A | 57 | −6.665 | −7.675 | 11.806 | 1.00 | 22.16 A | C |
| ATOM | 464 | CE1 | TYR | A | 57 | −8.809 | −6.279 | 12.836 | 1.00 | 23.65 A | C |
| ATOM | 465 | CE2 | TYR | A | 57 | −7.883 | −7.699 | 11.150 | 1.00 | 21.67 A | C |
| ATOM | 466 | CZ | TYR | A | 57 | −8.952 | −7.002 | 11.669 | 1.00 | 25.56 A | C |
| ATOM | 467 | OH | TYR | A | 57 | −10.168 | −7.017 | 11.021 | 1.00 | 25.78 A | O |
| ATOM | 468 | N | ALA | A | 58 | −7.183 | −9.270 | 14.645 | 1.00 | 13.45 A | N |
| ATOM | 469 | CA | ALA | A | 58 | −8.001 | −10.369 | 14.156 | 1.00 | 18.60 A | C |
| ATOM | 470 | C | ALA | A | 58 | −9.446 | −9.907 | 13.982 | 1.00 | 17.25 A | C |
| ATOM | 471 | O | ALA | A | 58 | −9.962 | −9.165 | 14.810 | 1.00 | 18.31 A | O |
| ATOM | 472 | CB | ALA | A | 58 | −7.918 | −11.548 | 15.100 | 1.00 | 19.29 A | C |
| ATOM | 473 | N | SER | A | 59 | −10.092 | −10.341 | 12.902 | 1.00 | 19.89 A | N |
| ATOM | 474 | CA | SER | A | 59 | −11.471 | −9.942 | 12.632 | 1.00 | 23.73 A | C |
| ATOM | 475 | C | SER | A | 59 | −12.451 | −10.641 | 13.572 | 1.00 | 25.80 A | C |
| ATOM | 476 | O | SER | A | 59 | −13.630 | −10.306 | 13.605 | 1.00 | 26.75 A | O |
| ATOM | 477 | CB | SER | A | 59 | −11.849 | −10.200 | 11.170 | 1.00 | 21.23 A | C |
| ATOM | 478 | OG | SER | A | 59 | −11.812 | −11.582 | 10.859 | 1.00 | 20.25 A | O |
| ATOM | 479 | N | THR | A | 60 | −11.952 | −11.625 | 14.318 | 1.00 | 40.12 A | N |

TABLE 1-continued

| | | | | | | | | | | | |
|---|---|---|---|---|---|---|---|---|---|---|---|
| ATOM | 480 | CA | THR | A | 60 | −12.699 | −12.265 | 15.398 | 1.00 | 40.61 A | C |
| ATOM | 481 | C | THR | A | 60 | −11.684 | −12.718 | 16.431 | 1.00 | 43.22 A | C |
| ATOM | 482 | O | THR | A | 60 | −10.506 | −12.388 | 16.322 | 1.00 | 43.35 A | O |
| ATOM | 483 | CB | THR | A | 60 | −13.469 | −13.508 | 14.926 | 1.00 | 49.84 A | C |
| ATOM | 484 | OG1 | THR | A | 60 | −12.545 | −14.580 | 14.689 | 1.00 | 54.22 A | O |
| ATOM | 485 | CG2 | THR | A | 60 | −14.257 | −13.220 | 13.655 | 1.00 | 57.35 A | C |
| ATOM | 486 | N | ASP | A | 61 | −12.126 | −13.481 | 17.426 | 1.00 | 31.10 A | N |
| ATOM | 487 | CA | ASP | A | 61 | −11.191 | −14.035 | 18.405 | 1.00 | 35.26 A | C |
| ATOM | 488 | C | ASP | A | 61 | −10.038 | −14.736 | 17.691 | 1.00 | 35.75 A | C |
| ATOM | 489 | O | ASP | A | 61 | −10.254 | −15.609 | 16.839 | 1.00 | 32.83 A | O |
| ATOM | 490 | CB | ASP | A | 61 | −11.891 | −15.008 | 19.363 | 1.00 | 37.37 A | C |
| ATOM | 491 | CG | ASP | A | 61 | −12.676 | −14.296 | 20.454 | 1.00 | 40.45 A | C |
| ATOM | 492 | OD1 | ASP | A | 61 | −13.084 | −13.137 | 20.237 | 1.00 | 42.00 A | O |
| ATOM | 493 | OD2 | ASP | A | 61 | −12.883 | −14.895 | 21.530 | 1.00 | 47.45 A | O |
| ATOM | 494 | N | MET | A | 62 | −8.817 | −14.343 | 18.038 | 1.00 | 45.71 A | N |
| ATOM | 495 | CA | MET | A | 62 | −7.619 | −14.912 | 17.430 | 1.00 | 39.27 A | C |
| ATOM | 496 | C | MET | A | 62 | −7.597 | −16.434 | 17.508 | 1.00 | 42.49 A | C |
| ATOM | 497 | O | MET | A | 62 | −7.261 | −17.105 | 16.534 | 1.00 | 45.64 A | O |
| ATOM | 498 | CB | MET | A | 62 | −6.363 | −14.350 | 18.092 | 1.00 | 31.62 A | C |
| ATOM | 499 | CG | MET | A | 62 | −5.077 | −14.872 | 17.479 | 1.00 | 41.13 A | C |
| ATOM | 500 | SD | MET | A | 62 | −4.955 | −14.470 | 15.724 | 1.00 | 33.45 A | S |
| ATOM | 501 | CE | MET | A | 62 | −4.563 | −12.724 | 15.799 | 1.00 | 30.51 A | C |
| ATOM | 502 | N | ASP | A | 63 | −7.956 | −16.971 | 18.670 | 1.00 | 50.73 A | N |
| ATOM | 503 | CA | ASP | A | 63 | −7.911 | −18.411 | 18.898 | 1.00 | 51.32 A | C |
| ATOM | 504 | C | ASP | A | 63 | −8.782 | −19.163 | 17.898 | 1.00 | 45.54 A | C |
| ATOM | 505 | O | ASP | A | 63 | −8.557 | −20.342 | 17.631 | 1.00 | 52.73 A | O |
| ATOM | 506 | CB | ASP | A | 63 | −8.338 | −18.744 | 20.334 | 1.00 | 56.83 A | C |
| ATOM | 507 | CG | ASP | A | 63 | −9.849 | −18.803 | 20.499 | 1.00 | 68.01 A | C |
| ATOM | 508 | OD1 | ASP | A | 63 | −10.443 | −19.866 | 20.207 | 1.00 | 61.02 A | O |
| ATOM | 509 | OD2 | ASP | A | 63 | −10.442 | −17.792 | 20.934 | 1.00 | 68.32 A | O |
| ATOM | 510 | N | LYS | A | 64 | −9.775 | −18.478 | 17.344 | 1.00 | 35.97 A | N |
| ATOM | 511 | CA | LYS | A | 64 | −10.681 | −19.107 | 16.389 | 1.00 | 37.94 A | C |
| ATOM | 512 | C | LYS | A | 64 | −10.058 | −19.207 | 14.997 | 1.00 | 40.31 A | C |
| ATOM | 513 | O | LYS | A | 64 | −10.062 | −20.276 | 14.385 | 1.00 | 29.12 A | O |
| ATOM | 514 | CB | LYS | A | 64 | −12.016 | −18.358 | 16.331 | 1.00 | 36.49 A | C |
| ATOM | 515 | CG | LYS | A | 64 | −12.829 | −18.456 | 17.611 | 1.00 | 43.90 A | C |
| ATOM | 516 | CD | LYS | A | 64 | −14.061 | −17.571 | 17.552 | 1.00 | 45.07 A | C |
| ATOM | 517 | CE | LYS | A | 64 | −14.886 | −17.686 | 18.824 | 1.00 | 46.12 A | C |
| ATOM | 518 | NZ | LYS | A | 64 | −15.996 | −16.690 | 18.845 | 1.00 | 53.34 A | N |
| ATOM | 519 | N | VAL | A | 65 | −9.524 | −18.091 | 14.504 | 1.00 | 37.32 A | N |
| ATOM | 520 | CA | VAL | A | 65 | −8.883 | −18.071 | 13.194 | 1.00 | 34.82 A | C |
| ATOM | 521 | C | VAL | A | 65 | −7.770 | −19.110 | 13.153 | 1.00 | 34.94 A | C |
| ATOM | 522 | O | VAL | A | 65 | −7.611 | −19.830 | 12.163 | 1.00 | 32.76 A | O |
| ATOM | 523 | CB | VAL | A | 65 | −8.287 | −16.687 | 12.863 | 1.00 | 33.26 A | C |
| ATOM | 524 | CG1 | VAL | A | 65 | −7.703 | −16.687 | 11.461 | 1.00 | 25.32 A | C |
| ATOM | 525 | CG2 | VAL | A | 65 | −9.337 | −15.602 | 13.000 | 1.00 | 31.07 A | C |
| ATOM | 526 | N | LEU | A | 66 | −7.013 | −19.191 | 14.245 | 1.00 | 33.50 A | N |
| ATOM | 527 | CA | LEU | A | 66 | −5.907 | −20.131 | 14.346 | 1.00 | 34.39 A | C |
| ATOM | 528 | C | LEU | A | 66 | −6.369 | −21.582 | 14.224 | 1.00 | 43.02 A | C |
| ATOM | 529 | O | LEU | A | 66 | −5.812 | −22.356 | 13.437 | 1.00 | 40.25 A | O |
| ATOM | 530 | CB | LEU | A | 66 | −5.142 | −19.924 | 15.653 | 1.00 | 37.57 A | C |
| ATOM | 531 | CG | LEU | A | 66 | −4.360 | −18.614 | 15.753 | 1.00 | 41.06 A | C |
| ATOM | 532 | CD1 | LEU | A | 66 | −3.493 | −18.610 | 16.994 | 1.00 | 40.01 A | C |
| ATOM | 533 | CD2 | LEU | A | 66 | −3.513 | −18.409 | 14.508 | 1.00 | 34.50 A | C |
| ATOM | 534 | N | LEU | A | 67 | −7.385 | −21.950 | 14.998 | 1.00 | 44.58 A | N |
| ATOM | 535 | CA | LEU | A | 67 | −7.897 | −23.315 | 14.961 | 1.00 | 45.52 A | C |
| ATOM | 536 | C | LEU | A | 67 | −8.462 | −23.658 | 13.590 | 1.00 | 44.52 A | C |
| ATOM | 537 | O | LEU | A | 67 | −8.327 | −24.782 | 13.122 | 1.00 | 46.24 A | O |
| ATOM | 538 | CB | LEU | A | 67 | −8.947 | −23.542 | 16.051 | 1.00 | 49.95 A | C |
| ATOM | 539 | CG | LEU | A | 67 | −8.367 | −23.854 | 17.434 | 1.00 | 58.40 A | C |
| ATOM | 540 | CD1 | LEU | A | 67 | −9.474 | −24.163 | 18.430 | 1.00 | 62.44 A | C |
| ATOM | 541 | CD2 | LEU | A | 67 | −7.373 | −25.009 | 17.354 | 1.00 | 52.35 A | C |
| ATOM | 542 | N | LYS | A | 68 | −9.087 | −22.677 | 12.951 | 1.00 | 28.77 A | N |
| ATOM | 543 | CA | LYS | A | 68 | −9.634 | −22.855 | 11.616 | 1.00 | 30.29 A | C |
| ATOM | 544 | C | LYS | A | 68 | −8.490 | −23.109 | 10.637 | 1.00 | 33.93 A | C |
| ATOM | 545 | O | LYS | A | 68 | −8.659 | −23.794 | 9.624 | 1.00 | 33.71 A | O |
| ATOM | 546 | CB | LYS | A | 68 | −10.441 | −21.616 | 11.218 | 1.00 | 32.94 A | C |
| ATOM | 547 | CG | LYS | A | 68 | −11.349 | −21.788 | 10.010 | 1.00 | 35.71 A | C |
| ATOM | 548 | CD | LYS | A | 68 | −12.588 | −20.911 | 10.149 | 1.00 | 33.52 A | C |
| ATOM | 549 | CE | LYS | A | 68 | −13.498 | −21.001 | 8.930 | 1.00 | 31.15 A | C |
| ATOM | 550 | NZ | LYS | A | 68 | −13.079 | −20.050 | 7.866 | 1.00 | 35.48 A | N |
| ATOM | 551 | N | TYR | A | 69 | −7.321 | −22.563 | 10.959 | 1.00 | 40.79 A | N |
| ATOM | 552 | CA | TYR | A | 69 | −6.119 | −22.772 | 10.155 | 1.00 | 42.75 A | C |
| ATOM | 553 | C | TYR | A | 69 | −5.551 | −24.177 | 10.350 | 1.00 | 43.67 A | C |
| ATOM | 554 | O | TYR | A | 69 | −5.195 | −24.849 | 9.381 | 1.00 | 39.63 A | O |
| ATOM | 555 | CB | TYR | A | 69 | −5.049 | −21.726 | 10.495 | 1.00 | 35.20 A | C |
| ATOM | 556 | CG | TYR | A | 69 | −3.719 | −21.966 | 9.812 | 1.00 | 29.77 A | C |
| ATOM | 557 | CD1 | TYR | A | 69 | −3.504 | −21.552 | 8.504 | 1.00 | 30.89 A | C |
| ATOM | 558 | CD2 | TYR | A | 69 | −2.682 | −22.608 | 10.472 | 1.00 | 31.32 A | C |
| ATOM | 559 | CE1 | TYR | A | 69 | −2.295 | −21.768 | 7.875 | 1.00 | 27.04 A | C |

TABLE 1-continued

| | | | | | | | | | | | |
|---|---|---|---|---|---|---|---|---|---|---|---|
| ATOM | 560 | CE2 | TYR | A | 69 | −1.465 | −22.831 | 9.848 | 1.00 | 28.93 A | C |
| ATOM | 561 | CZ | TYR | A | 69 | −1.280 | −22.409 | 8.550 | 1.00 | 29.92 A | C |
| ATOM | 562 | OH | TYR | A | 69 | −0.075 | −22.628 | 7.922 | 1.00 | 31.31 A | O |
| ATOM | 563 | N | THR | A | 70 | −5.459 | −24.613 | 11.605 | 1.00 | 36.69 A | N |
| ATOM | 564 | CA | THR | A | 70 | −4.898 | −25.928 | 11.906 | 1.00 | 43.59 A | C |
| ATOM | 565 | C | THR | A | 70 | −5.838 | −27.048 | 11.470 | 1.00 | 45.00 A | C |
| ATOM | 566 | O | THR | A | 70 | −5.397 | −28.043 | 10.894 | 1.00 | 48.92 A | O |
| ATOM | 567 | CB | THR | A | 70 | −4.529 | −26.084 | 13.403 | 1.00 | 41.16 A | C |
| ATOM | 568 | OG1 | THR | A | 70 | −5.627 | −25.665 | 14.221 | 1.00 | 56.03 A | O |
| ATOM | 569 | CG2 | THR | A | 70 | −3.305 | −25.240 | 13.741 | 1.00 | 41.46 A | C |
| ATOM | 570 | N | GLU | A | 71 | −7.130 | −26.877 | 11.732 | 1.00 | 71.37 A | N |
| ATOM | 571 | CA | GLU | A | 71 | −8.130 | −27.853 | 11.308 | 1.00 | 82.63 A | C |
| ATOM | 572 | C | GLU | A | 71 | −8.173 | −27.949 | 9.786 | 1.00 | 76.61 A | C |
| ATOM | 573 | O | GLU | A | 71 | −8.610 | −28.954 | 9.229 | 1.00 | 81.40 A | O |
| ATOM | 574 | CB | GLU | A | 71 | −9.521 | −27.478 | 11.838 | 1.00 | 78.47 A | C |
| ATOM | 575 | CG | GLU | A | 71 | −9.607 | −27.275 | 13.348 | 1.00 | 86.35 A | C |
| ATOM | 576 | CD | GLU | A | 71 | −9.479 | −28.566 | 14.132 | 1.00 | 90.69 A | C |
| ATOM | 577 | OE1 | GLU | A | 71 | −9.615 | −29.650 | 13.525 | 1.00 | 97.70 A | O |
| ATOM | 578 | OE2 | GLU | A | 71 | −9.249 | −28.494 | 15.359 | 1.00 | 83.58 A | O |
| ATOM | 579 | N | TYR | A | 72 | −7.713 | −26.894 | 9.120 | 1.00 | 49.20 A | N |
| ATOM | 580 | CA | TYR | A | 72 | −7.800 | −26.799 | 7.667 | 1.00 | 47.92 A | C |
| ATOM | 581 | C | TYR | A | 72 | −7.085 | −27.958 | 6.983 | 1.00 | 45.30 A | C |
| ATOM | 582 | O | TYR | A | 72 | −7.519 | −28.423 | 5.930 | 1.00 | 42.68 A | O |
| ATOM | 583 | CB | TYR | A | 72 | −7.225 | −25.464 | 7.187 | 1.00 | 44.29 A | C |
| ATOM | 584 | CG | TYR | A | 72 | −7.659 | −25.054 | 5.794 | 1.00 | 41.13 A | C |
| ATOM | 585 | CD1 | TYR | A | 72 | −8.875 | −24.416 | 5.586 | 1.00 | 35.47 A | C |
| ATOM | 586 | CD2 | TYR | A | 72 | −6.845 | −25.291 | 4.689 | 1.00 | 43.90 A | C |
| ATOM | 587 | CE1 | TYR | A | 72 | −9.277 | −24.030 | 4.316 | 1.00 | 34.32 A | C |
| ATOM | 588 | CE2 | TYR | A | 72 | −7.235 | −24.906 | 3.414 | 1.00 | 38.74 A | C |
| ATOM | 589 | CZ | TYR | A | 72 | −8.453 | −24.275 | 3.234 | 1.00 | 42.36 A | C |
| ATOM | 590 | OH | TYR | A | 72 | −8.852 | −23.888 | 1.972 | 1.00 | 38.66 A | O |
| TER | | | | | | | | | | | |
| ATOM | 591 | N | GLY | B | 2 | −9.188 | 5.872 | −5.539 | 1.00 | 35.93 B | N |
| ATOM | 592 | CA | GLY | B | 2 | −9.888 | 5.453 | −6.741 | 1.00 | 41.50 B | C |
| ATOM | 593 | C | GLY | B | 2 | −10.704 | 6.574 | −7.356 | 1.00 | 43.98 B | C |
| ATOM | 594 | O | GLY | B | 2 | −10.628 | 7.722 | −6.907 | 1.00 | 39.60 B | O |
| ATOM | 595 | N | ARG | B | 3 | −11.484 | 6.244 | −8.384 | 1.00 | 34.91 B | N |
| ATOM | 596 | CA | ARG | B | 3 | −12.303 | 7.235 | −9.080 | 1.00 | 36.90 B | C |
| ATOM | 597 | C | ARG | B | 3 | −13.303 | 7.899 | −8.138 | 1.00 | 39.43 B | C |
| ATOM | 598 | O | ARG | B | 3 | −13.661 | 9.065 | −8.311 | 1.00 | 43.98 B | O |
| ATOM | 599 | CB | ARG | B | 3 | −13.029 | 6.601 | −10.267 | 1.00 | 37.34 B | C |
| ATOM | 600 | CG | ARG | B | 3 | −12.101 | 6.102 | −11.369 | 1.00 | 39.68 B | C |
| ATOM | 601 | CD | ARG | B | 3 | −11.130 | 7.187 | −11.823 | 1.00 | 42.23 B | C |
| ATOM | 602 | NE | ARG | B | 3 | −10.365 | 6.783 | −13.000 | 1.00 | 38.79 B | N |
| ATOM | 603 | CZ | ARG | B | 3 | −10.840 | 6.808 | −14.242 | 1.00 | 44.35 B | C |
| ATOM | 604 | NH1 | ARG | B | 3 | −12.084 | 7.212 | −14.474 | 1.00 | 33.55 B | N |
| ATOM | 605 | NH2 | ARG | B | 3 | −10.073 | 6.423 | −15.253 | 1.00 | 43.80 B | N |
| ATOM | 606 | N | LYS | B | 4 | −13.753 | 7.144 | −7.143 | 1.00 | 32.66 B | N |
| ATOM | 607 | CA | LYS | B | 4 | −14.606 | 7.679 | −6.094 | 1.00 | 32.76 B | C |
| ATOM | 608 | C | LYS | B | 4 | −14.195 | 7.094 | −4.752 | 1.00 | 36.67 B | C |
| ATOM | 609 | O | LYS | B | 4 | −13.841 | 5.915 | −4.658 | 1.00 | 31.80 B | O |
| ATOM | 610 | CB | LYS | B | 4 | −16.075 | 7.341 | −6.357 | 1.00 | 35.54 B | C |
| ATOM | 611 | CG | LYS | B | 4 | −16.670 | 7.976 | −7.605 | 1.00 | 39.71 B | C |
| ATOM | 612 | CD | LYS | B | 4 | −18.000 | 7.320 | −7.949 | 1.00 | 35.56 B | C |
| ATOM | 613 | CE | LYS | B | 4 | −18.425 | 7.630 | −9.371 | 1.00 | 47.36 B | C |
| ATOM | 614 | NZ | LYS | B | 4 | −19.420 | 6.635 | −9.876 | 1.00 | 51.32 B | N |
| ATOM | 615 | N | LYS | B | 5 | −14.235 | 7.922 | −3.716 | 1.00 | 40.04 B | N |
| ATOM | 616 | CA | LYS | B | 5 | −14.081 | 7.426 | −2.362 | 1.00 | 37.87 B | C |
| ATOM | 617 | C | LYS | B | 5 | −15.249 | 6.499 | −2.081 | 1.00 | 39.79 B | C |
| ATOM | 618 | O | LYS | B | 5 | −16.384 | 6.802 | −2.449 | 1.00 | 40.95 B | O |
| ATOM | 619 | CB | LYS | B | 5 | −14.082 | 8.583 | −1.359 | 1.00 | 35.44 B | C |
| ATOM | 620 | CG | LYS | B | 5 | −14.292 | 8.145 | 0.087 | 1.00 | 40.32 B | C |
| ATOM | 621 | CD | LYS | B | 5 | −13.906 | 9.244 | 1.069 | 1.00 | 36.82 B | C |
| ATOM | 622 | CE | LYS | B | 5 | −13.884 | 8.717 | 2.494 | 1.00 | 46.24 B | C |
| ATOM | 623 | NZ | LYS | B | 5 | −13.497 | 9.771 | 3.476 | 1.00 | 52.66 B | N |
| ATOM | 624 | N | ILE | B | 6 | −14.972 | 5.363 | −1.449 | 1.00 | 39.51 B | N |
| ATOM | 625 | CA | ILE | B | 6 | −16.037 | 4.465 | −1.020 | 1.00 | 39.10 B | C |
| ATOM | 626 | C | ILE | B | 6 | −16.194 | 4.479 | 0.495 | 1.00 | 44.95 B | C |
| ATOM | 627 | O | ILE | B | 6 | −15.428 | 5.129 | 1.207 | 1.00 | 43.30 B | O |
| ATOM | 628 | CB | ILE | B | 6 | −15.795 | 3.017 | −1.473 | 1.00 | 43.66 B | C |
| ATOM | 629 | CG1 | ILE | B | 6 | −14.604 | 2.411 | −0.728 | 1.00 | 41.77 B | C |
| ATOM | 630 | CG2 | ILE | B | 6 | −15.606 | 2.954 | −2.982 | 1.00 | 47.69 B | C |
| ATOM | 631 | CD1 | ILE | B | 6 | −14.433 | 0.923 | −0.970 | 1.00 | 39.73 B | C |
| ATOM | 632 | N | GLN | B | 7 | −17.203 | 3.765 | 0.977 | 1.00 | 36.28 B | N |
| ATOM | 633 | CA | GLN | B | 7 | −17.422 | 3.616 | 2.405 | 1.00 | 37.59 B | C |
| ATOM | 634 | C | GLN | B | 7 | −17.066 | 2.196 | 2.786 | 1.00 | 33.90 B | C |
| ATOM | 635 | O | GLN | B | 7 | −17.264 | 1.269 | 2.000 | 1.00 | 33.84 B | O |
| ATOM | 636 | CB | GLN | B | 7 | −18.880 | 3.911 | 2.765 | 1.00 | 47.49 B | C |
| ATOM | 637 | CG | GLN | B | 7 | −19.228 | 5.391 | 2.796 | 1.00 | 45.21 B | C |
| ATOM | 638 | CD | GLN | B | 7 | −18.721 | 6.085 | 4.048 | 1.00 | 62.62 B | C |

TABLE 1-continued

| | | | | | | | | | | | |
|---|---|---|---|---|---|---|---|---|---|---|---|
| ATOM | 639 | OE1 | GLN | B | 7 | −19.133 | 5.760 | 5.164 | 1.00 | 65.96 B | O |
| ATOM | 640 | NE2 | GLN | B | 7 | −17.829 | 7.054 | 3.866 | 1.00 | 64.78 B | N |
| ATOM | 641 | N | ILE | B | 8 | −16.534 | 2.025 | 3.990 | 1.00 | 28.89 B | N |
| ATOM | 642 | CA | ILE | B | 8 | −16.087 | 0.712 | 4.435 | 1.00 | 24.06 B | C |
| ATOM | 643 | C | ILE | B | 8 | −17.257 | −0.135 | 4.929 | 1.00 | 26.92 B | C |
| ATOM | 644 | O | ILE | B | 8 | −17.536 | −0.209 | 6.128 | 1.00 | 26.19 B | O |
| ATOM | 645 | CB | ILE | B | 8 | −14.965 | 0.823 | 5.495 | 1.00 | 20.79 B | C |
| ATOM | 646 | CG1 | ILE | B | 8 | −13.755 | 1.528 | 4.882 | 1.00 | 20.90 B | C |
| ATOM | 647 | CG2 | ILE | B | 8 | −14.556 | −0.546 | 6.017 | 1.00 | 18.34 B | C |
| ATOM | 648 | CD1 | ILE | B | 8 | −13.387 | 1.003 | 3.506 | 1.00 | 20.40 B | C |
| ATOM | 649 | N | THR | B | 9 | −17.947 | −0.767 | 3.984 | 1.00 | 28.04 B | N |
| ATOM | 650 | CA | THR | B | 9 | −19.038 | −1.677 | 4.313 | 1.00 | 28.46 B | C |
| ATOM | 651 | C | THR | B | 9 | −19.055 | −2.860 | 3.344 | 1.00 | 24.67 B | C |
| ATOM | 652 | O | THR | B | 9 | −18.658 | −2.724 | 2.186 | 1.00 | 28.00 B | O |
| ATOM | 653 | CB | THR | B | 9 | −20.399 | −0.949 | 4.311 | 1.00 | 34.72 B | C |
| ATOM | 654 | OG1 | THR | B | 9 | −21.408 | −1.809 | 4.860 | 1.00 | 36.57 B | O |
| ATOM | 655 | CG2 | THR | B | 9 | −20.784 | −0.520 | 2.894 | 1.00 | 26.37 B | C |
| ATOM | 656 | N | ARG | B | 10 | −19.502 | −4.015 | 3.830 | 1.00 | 23.22 B | N |
| ATOM | 657 | CA | ARG | B | 10 | −19.521 | −5.249 | 3.041 | 1.00 | 27.96 B | C |
| ATOM | 658 | C | ARG | B | 10 | −20.109 | −5.073 | 1.644 | 1.00 | 27.22 B | C |
| ATOM | 659 | O | ARG | B | 10 | −21.267 | −4.682 | 1.491 | 1.00 | 29.90 B | O |
| ATOM | 660 | CB | ARG | B | 10 | −20.283 | −6.353 | 3.777 | 1.00 | 27.06 B | C |
| ATOM | 661 | CG | ARG | B | 10 | −20.326 | −7.678 | 3.024 | 1.00 | 27.66 B | C |
| ATOM | 662 | CD | ARG | B | 10 | −21.227 | −8.687 | 3.728 | 1.00 | 30.60 B | C |
| ATOM | 663 | NE | ARG | B | 10 | −21.283 | −9.974 | 3.035 | 1.00 | 44.23 B | N |
| ATOM | 664 | CZ | ARG | B | 10 | −22.086 | −10.242 | 2.007 | 1.00 | 41.38 B | C |
| ATOM | 665 | NH1 | ARG | B | 10 | −22.905 | −9.309 | 1.539 | 1.00 | 42.70 B | N |
| ATOM | 666 | NH2 | ARG | B | 10 | −22.070 | −11.443 | 1.442 | 1.00 | 34.97 B | N |
| ATOM | 667 | N | ILE | B | 11 | −19.299 | −5.367 | 0.632 | 1.00 | 18.77 B | N |
| ATOM | 668 | CA | ILE | B | 11 | −19.735 | −5.298 | −0.756 | 1.00 | 19.25 B | C |
| ATOM | 669 | C | ILE | B | 11 | −20.735 | −6.417 | −1.041 | 1.00 | 25.50 B | C |
| ATOM | 670 | O | ILE | B | 11 | −20.462 | −7.592 | −0.773 | 1.00 | 23.75 B | O |
| ATOM | 671 | CB | ILE | B | 11 | −18.539 | −5.406 | −1.714 | 1.00 | 20.42 B | C |
| ATOM | 672 | CG1 | ILE | B | 11 | −17.639 | −4.181 | −1.565 | 1.00 | 15.67 B | C |
| ATOM | 673 | CG2 | ILE | B | 11 | −19.009 | −5.539 | −3.154 | 1.00 | 18.62 B | C |
| ATOM | 674 | CD1 | ILE | B | 11 | −16.254 | −4.380 | −2.103 | 1.00 | 17.71 B | C |
| ATOM | 675 | N | MET | B | 12 | −21.893 | −6.047 | −1.579 | 1.00 | 22.51 B | N |
| ATOM | 676 | CA | MET | B | 12 | −23.000 | −6.985 | −1.720 | 1.00 | 24.87 B | C |
| ATOM | 677 | C | MET | B | 12 | −22.909 | −7.816 | −2.996 | 1.00 | 31.08 B | C |
| ATOM | 678 | O | MET | B | 12 | −23.373 | −8.955 | −3.032 | 1.00 | 25.68 B | O |
| ATOM | 679 | CB | MET | B | 12 | −24.341 | −6.246 | −1.657 | 1.00 | 25.38 B | C |
| ATOM | 680 | CG | MET | B | 12 | −24.564 | −5.470 | −0.358 | 1.00 | 30.39 B | C |
| ATOM | 681 | SD | MET | B | 12 | −24.573 | −6.517 | 1.118 | 1.00 | 35.66 B | S |
| ATOM | 682 | CE | MET | B | 12 | −26.117 | −7.406 | 0.874 | 1.00 | 22.73 B | C |
| ATOM | 683 | N | ASP | B | 13 | −22.315 | −7.242 | −4.039 | 1.00 | 38.07 B | N |
| ATOM | 684 | CA | ASP | B | 13 | −22.152 | −7.942 | −5.311 | 1.00 | 39.19 B | C |
| ATOM | 685 | C | ASP | B | 13 | −20.988 | −8.931 | −5.246 | 1.00 | 41.47 B | C |
| ATOM | 686 | O | ASP | B | 13 | −19.841 | −8.536 | −5.025 | 1.00 | 36.72 B | O |
| ATOM | 687 | CB | ASP | B | 13 | −21.925 | −6.939 | −6.448 | 1.00 | 39.47 B | C |
| ATOM | 688 | CG | ASP | B | 13 | −21.667 | −7.617 | −7.790 | 1.00 | 59.19 B | C |
| ATOM | 689 | OD1 | ASP | B | 13 | −22.367 | −8.603 | −8.109 | 1.00 | 58.53 B | O |
| ATOM | 690 | OD2 | ASP | B | 13 | −20.767 | −7.158 | −8.530 | 1.00 | 56.17 B | O |
| ATOM | 691 | N | GLU | B | 14 | −21.290 | −10.212 | −5.433 | 1.00 | 29.13 B | N |
| ATOM | 692 | CA | GLU | B | 14 | −20.272 | −11.262 | −5.425 | 1.00 | 30.70 B | C |
| ATOM | 693 | C | GLU | B | 14 | −19.154 | −10.996 | −6.431 | 1.00 | 35.92 B | C |
| ATOM | 694 | O | GLU | B | 14 | −17.984 | −11.262 | −6.157 | 1.00 | 32.47 B | O |
| ATOM | 695 | CB | GLU | B | 14 | −20.906 | −12.622 | −5.718 | 1.00 | 29.50 B | C |
| ATOM | 696 | CG | GLU | B | 14 | −19.928 | −13.785 | −5.799 | 1.00 | 35.92 B | C |
| ATOM | 697 | CD | GLU | B | 14 | −20.584 | −15.052 | −6.339 | 1.00 | 61.30 B | C |
| ATOM | 698 | OE1 | GLU | B | 14 | −21.212 | −14.986 | −7.421 | 1.00 | 65.75 B | O |
| ATOM | 699 | OE2 | GLU | B | 14 | −20.475 | −16.112 | −5.683 | 1.00 | 53.89 B | O |
| ATOM | 700 | N | ARG | B | 15 | −19.511 | −10.473 | −7.597 | 1.00 | 46.25 B | N |
| ATOM | 701 | CA | ARG | B | 15 | −18.516 | −10.214 | −8.631 | 1.00 | 39.81 B | C |
| ATOM | 702 | C | ARG | B | 15 | −17.541 | −9.116 | −8.215 | 1.00 | 34.94 B | C |
| ATOM | 703 | O | ARG | B | 15 | −16.337 | −9.348 | −8.165 | 1.00 | 30.98 B | O |
| ATOM | 704 | CB | ARG | B | 15 | −19.184 | −9.880 | −9.965 | 1.00 | 47.87 B | C |
| ATOM | 705 | CG | ARG | B | 15 | −18.255 | −9.253 | −10.988 | 1.00 | 53.75 B | C |
| ATOM | 706 | CD | ARG | B | 15 | −18.624 | −9.678 | −12.403 | 1.00 | 61.36 B | C |
| ATOM | 707 | NE | ARG | B | 15 | −18.159 | −11.032 | −12.697 | 1.00 | 67.24 B | N |
| ATOM | 708 | CZ | ARG | B | 15 | −18.907 | −12.127 | −12.584 | 1.00 | 69.40 B | C |
| ATOM | 709 | NH1 | ARG | B | 15 | −20.170 | −12.036 | −12.188 | 1.00 | 74.25 B | N |
| ATOM | 710 | NH2 | ARG | B | 15 | −18.389 | −13.317 | −12.873 | 1.00 | 47.80 B | N |
| ATOM | 711 | N | ASN | B | 16 | −18.057 | −7.927 | −7.916 | 1.00 | 38.39 B | N |
| ATOM | 712 | CA | ASN | B | 16 | −17.201 | −6.832 | −7.467 | 1.00 | 33.29 B | C |
| ATOM | 713 | C | ASN | B | 16 | −16.510 | −7.157 | −6.144 | 1.00 | 30.20 B | C |
| ATOM | 714 | O | ASN | B | 16 | −15.475 | −6.580 | −5.820 | 1.00 | 31.16 B | O |
| ATOM | 715 | CB | ASN | B | 16 | −17.980 | −5.514 | −7.344 | 1.00 | 38.21 B | C |
| ATOM | 716 | CG | ASN | B | 16 | −17.124 | −4.371 | −6.764 | 1.00 | 48.55 B | C |
| ATOM | 717 | OD1 | ASN | B | 16 | −15.983 | −4.145 | −7.190 | 1.00 | 31.35 B | O |
| ATOM | 718 | ND2 | ASN | B | 16 | −17.681 | −3.646 | −5.790 | 1.00 | 34.92 B | N |

TABLE 1-continued

| | | | | | | | | | | | |
|---|---|---|---|---|---|---|---|---|---|---|---|
| ATOM | 719 | N | ARG | B | 17 | −17.079 | −8.077 | −5.374 | 1.00 | 21.31 B | N |
| ATOM | 720 | CA | ARG | B | 17 | −16.484 | −8.412 | −4.091 | 1.00 | 25.28 B | C |
| ATOM | 721 | C | ARG | B | 17 | −15.244 | −9.251 | −4.316 | 1.00 | 27.07 B | C |
| ATOM | 722 | O | ARG | B | 17 | −14.212 | −9.041 | −3.675 | 1.00 | 27.84 B | O |
| ATOM | 723 | CB | ARG | B | 17 | −17.464 | −9.151 | −3.184 | 1.00 | 24.01 B | C |
| ATOM | 724 | CG | ARG | B | 17 | −16.867 | −9.515 | −1.834 | 1.00 | 23.82 B | C |
| ATOM | 725 | CD | ARG | B | 17 | −17.926 | −9.981 | −0.842 | 1.00 | 26.00 B | C |
| ATOM | 726 | NE | ARG | B | 17 | −18.536 | −11.237 | −1.258 | 1.00 | 32.53 B | N |
| ATOM | 727 | CZ | ARG | B | 17 | −19.797 | −11.363 | −1.661 | 1.00 | 33.84 B | C |
| ATOM | 728 | NH1 | ARG | B | 17 | −20.604 | −10.306 | −1.687 | 1.00 | 26.61 B | N |
| ATOM | 729 | NH2 | ARG | B | 17 | −20.251 | −12.553 | −2.031 | 1.00 | 33.93 B | N |
| ATOM | 730 | N | GLN | B | 18 | −15.350 | −10.202 | −5.236 | 1.00 | 29.00 B | N |
| ATOM | 731 | CA | GLN | B | 18 | −14.225 | −11.058 | −5.573 | 1.00 | 30.09 B | C |
| ATOM | 732 | C | GLN | B | 18 | −13.091 | −10.247 | −6.192 | 1.00 | 25.53 B | C |
| ATOM | 733 | O | GLN | B | 18 | −11.921 | −10.457 | −5.868 | 1.00 | 22.89 B | O |
| ATOM | 734 | CB | GLN | B | 18 | −14.669 | −12.182 | −6.513 | 1.00 | 28.95 B | C |
| ATOM | 735 | CG | GLN | B | 18 | −13.522 | −12.988 | −7.104 | 1.00 | 29.28 B | C |
| ATOM | 736 | CD | GLN | B | 18 | −12.610 | −13.585 | −6.048 | 1.00 | 33.30 B | C |
| ATOM | 737 | OE1 | GLN | B | 18 | −12.886 | −13.510 | −4.850 | 1.00 | 38.50 B | O |
| ATOM | 738 | NE2 | GLN | B | 18 | −11.508 | −14.184 | −6.492 | 1.00 | 42.99 B | N |
| ATOM | 739 | N | VAL | B | 19 | −13.448 | −9.313 | −7.070 | 1.00 | 25.06 B | N |
| ATOM | 740 | CA | VAL | B | 19 | −12.472 | −8.442 | −7.718 | 1.00 | 28.61 B | C |
| ATOM | 741 | C | VAL | B | 19 | −11.723 | −7.571 | −6.710 | 1.00 | 29.35 B | C |
| ATOM | 742 | O | VAL | B | 19 | −10.495 | −7.502 | −6.728 | 1.00 | 30.32 B | O |
| ATOM | 743 | CB | VAL | B | 19 | −13.136 | −7.529 | −8.765 | 1.00 | 27.95 B | C |
| ATOM | 744 | CG1 | VAL | B | 19 | −12.285 | −6.291 | −9.013 | 1.00 | 28.44 B | C |
| ATOM | 745 | CG2 | VAL | B | 19 | −13.361 | −8.288 | −10.053 | 1.00 | 31.41 B | C |
| ATOM | 746 | N | THR | B | 20 | −12.469 | −6.905 | −5.836 | 1.00 | 28.91 B | N |
| ATOM | 747 | CA | THR | B | 20 | −11.866 | −6.061 | −4.815 | 1.00 | 26.07 B | C |
| ATOM | 748 | C | THR | B | 20 | −11.017 | −6.903 | −3.875 | 1.00 | 27.75 B | C |
| ATOM | 749 | O | THR | B | 20 | −9.937 | −6.488 | −3.453 | 1.00 | 24.01 B | O |
| ATOM | 750 | CB | THR | B | 20 | −12.928 | −5.306 | −4.012 | 1.00 | 27.80 B | C |
| ATOM | 751 | OG1 | THR | B | 20 | −13.454 | −4.244 | −4.814 | 1.00 | 29.96 B | O |
| ATOM | 752 | CG2 | THR | B | 20 | −12.324 | −4.722 | −2.735 | 1.00 | 24.77 B | C |
| ATOM | 753 | N | PHE | B | 21 | −11.503 | −8.096 | −3.556 | 1.00 | 22.15 B | N |
| ATOM | 754 | CA | PHE | B | 21 | −10.746 | −8.998 | −2.698 | 1.00 | 21.89 B | C |
| ATOM | 755 | C | PHE | B | 21 | −9.365 | −9.324 | −3.272 | 1.00 | 18.93 B | C |
| ATOM | 756 | O | PHE | B | 21 | −8.367 | −9.306 | −2.553 | 1.00 | 19.66 B | O |
| ATOM | 757 | CB | PHE | B | 21 | −11.523 | −10.287 | −2.446 | 1.00 | 19.40 B | C |
| ATOM | 758 | CG | PHE | B | 21 | −10.707 | −11.361 | −1.796 | 1.00 | 19.58 B | C |
| ATOM | 759 | CD1 | PHE | B | 21 | −10.525 | −11.374 | −0.424 | 1.00 | 17.26 B | C |
| ATOM | 760 | CD2 | PHE | B | 21 | −10.116 | −12.353 | −2.557 | 1.00 | 19.84 B | C |
| ATOM | 761 | CE1 | PHE | B | 21 | −9.774 | −12.358 | 0.180 | 1.00 | 20.45 B | C |
| ATOM | 762 | CE2 | PHE | B | 21 | −9.360 | −13.343 | −1.960 | 1.00 | 22.00 B | C |
| ATOM | 763 | CZ | PHE | B | 21 | −9.190 | −13.348 | −0.589 | 1.00 | 28.35 B | C |
| ATOM | 764 | N | THR | B | 22 | −9.312 | −9.628 | −4.563 | 1.00 | 21.88 B | N |
| ATOM | 765 | CA | THR | B | 22 | −8.054 | −9.996 | −5.202 | 1.00 | 20.53 B | C |
| ATOM | 766 | C | THR | B | 22 | −7.093 | −8.808 | −5.230 | 1.00 | 19.42 B | C |
| ATOM | 767 | O | THR | B | 22 | −5.899 | −8.960 | −4.967 | 1.00 | 20.21 B | O |
| ATOM | 768 | CB | THR | B | 22 | −8.267 | −10.561 | −6.640 | 1.00 | 24.17 B | C |
| ATOM | 769 | OG1 | THR | B | 22 | −8.869 | −11.862 | −6.570 | 1.00 | 23.68 B | O |
| ATOM | 770 | CG2 | THR | B | 22 | −6.945 | −10.675 | −7.377 | 1.00 | 15.72 B | C |
| ATOM | 771 | N | LYS | B | 23 | −7.607 | −7.622 | −5.542 | 1.00 | 17.48 B | N |
| ATOM | 772 | CA | LYS | B | 23 | −6.756 | −6.437 | −5.542 | 1.00 | 19.24 B | C |
| ATOM | 773 | C | LYS | B | 23 | −6.181 | −6.175 | −4.149 | 1.00 | 18.39 B | C |
| ATOM | 774 | O | LYS | B | 23 | −4.962 | −6.144 | −3.971 | 1.00 | 18.07 B | O |
| ATOM | 775 | CB | LYS | B | 23 | −7.511 | −5.203 | −6.050 | 1.00 | 20.59 B | C |
| ATOM | 776 | CG | LYS | B | 23 | −7.846 | −5.236 | −7.535 | 1.00 | 26.67 B | C |
| ATOM | 777 | CD | LYS | B | 23 | −8.583 | −3.964 | −7.961 | 1.00 | 28.62 B | C |
| ATOM | 778 | CE | LYS | B | 23 | −8.978 | −4.026 | −9.431 | 1.00 | 28.02 B | C |
| ATOM | 779 | NZ | LYS | B | 23 | −9.916 | −2.935 | −9.814 | 1.00 | 32.81 B | N |
| ATOM | 780 | N | ARG | B | 24 | −7.061 | −6.009 | −3.165 | 1.00 | 16.09 B | N |
| ATOM | 781 | CA | ARG | B | 24 | −6.640 | −5.635 | −1.812 | 1.00 | 16.07 B | C |
| ATOM | 782 | C | ARG | B | 24 | −5.836 | −6.711 | −1.072 | 1.00 | 18.15 B | C |
| ATOM | 783 | O | ARG | B | 24 | −5.008 | −6.378 | −0.218 | 1.00 | 15.59 B | O |
| ATOM | 784 | CB | ARG | B | 24 | −7.832 | −5.174 | −0.969 | 1.00 | 13.10 B | C |
| ATOM | 785 | CG | ARG | B | 24 | −8.234 | −3.717 | −1.203 | 1.00 | 14.76 B | C |
| ATOM | 786 | CD | ARG | B | 24 | −9.495 | −3.357 | −0.424 | 1.00 | 14.27 B | C |
| ATOM | 787 | NE | ARG | B | 24 | −9.879 | −1.954 | −0.584 | 1.00 | 15.73 B | N |
| ATOM | 788 | CZ | ARG | B | 24 | −9.536 | −0.980 | 0.258 | 1.00 | 18.12 B | C |
| ATOM | 789 | NH1 | ARG | B | 24 | −8.797 | −1.247 | 1.331 | 1.00 | 16.01 B | N |
| ATOM | 790 | NH2 | ARG | B | 24 | −9.933 | 0.263 | 0.028 | 1.00 | 16.88 B | N |
| ATOM | 791 | N | LYS | B | 25 | −6.064 | −7.987 | −1.394 | 1.00 | 19.04 B | N |
| ATOM | 792 | CA | LYS | B | 25 | −5.278 | −9.061 | −0.779 | 1.00 | 19.08 B | C |
| ATOM | 793 | C | LYS | B | 25 | −3.822 | −8.901 | −1.164 | 1.00 | 18.45 B | C |
| ATOM | 794 | O | LY5 | B | 25 | −2.930 | −8.970 | −0.328 | 1.00 | 19.20 B | O |
| ATOM | 795 | CB | LYS | B | 25 | −5.762 | −10.447 | −1.214 | 1.00 | 23.30 B | C |
| ATOM | 796 | CG | LYS | B | 25 | −4.782 | −11.570 | −0.853 | 1.00 | 19.47 B | C |
| ATOM | 797 | CD | LYS | B | 25 | −5.469 | −12.936 | −0.772 | 1.00 | 22.91 B | C |
| ATOM | 798 | CE | LYS | B | 25 | −5.988 | −13.411 | −2.138 | 1.00 | 26.31 B | C |

TABLE 1-continued

| | | | | | | | | | | | |
|---|---|---|---|---|---|---|---|---|---|---|---|
| ATOM | 799 | NZ | LYS | B | 25 | −4.897 | −13.779 | −3.087 | 1.00 | 20.74 B | N |
| ATOM | 800 | N | PHE | B | 26 | −3.594 | −8.692 | −2.451 | 1.00 | 16.72 B | N |
| ATOM | 801 | CA | PHE | B | 26 | −2.260 | −8.430 | −2.954 | 1.00 | 17.53 B | C |
| ATOM | 802 | C | PHE | B | 26 | −1.655 | −7.216 | −2.226 | 1.00 | 19.47 B | C |
| ATOM | 803 | O | PHE | B | 26 | −0.552 | −7.285 | −1.684 | 1.00 | 20.99 B | O |
| ATOM | 804 | CB | PHE | B | 26 | −2.336 | −8.184 | −4.460 | 1.00 | 17.86 B | C |
| ATOM | 805 | CG | PHE | B | 26 | −1.008 | −8.004 | −5.109 | 1.00 | 21.69 B | C |
| ATOM | 806 | CD1 | PHE | B | 26 | −0.379 | −9.073 | −5.732 | 1.00 | 25.97 B | C |
| ATOM | 807 | CD2 | PHE | B | 26 | −0.386 | −6.768 | −5.110 | 1.00 | 18.89 B | C |
| ATOM | 808 | CE1 | PHE | B | 26 | 0.853 | −8.913 | −6.342 | 1.00 | 25.80 B | C |
| ATOM | 809 | CE2 | PHE | B | 26 | 0.848 | −6.602 | −5.718 | 1.00 | 25.93 B | C |
| ATOM | 810 | CZ | PHE | B | 26 | 1.467 | −7.676 | −6.333 | 1.00 | 23.95 B | C |
| ATOM | 811 | N | GLY | B | 27 | −2.395 | −6.111 | −2.213 | 1.00 | 19.53 B | N |
| ATOM | 812 | CA | GLY | B | 27 | −1.966 | −4.896 | −1.548 | 1.00 | 18.26 B | C |
| ATOM | 813 | C | GLY | B | 27 | −1.679 | −5.073 | −0.069 | 1.00 | 17.11 B | C |
| ATOM | 814 | O | GLY | B | 27 | −0.796 | −4.415 | 0.474 | 1.00 | 15.96 B | O |
| ATOM | 815 | N | LEU | B | 28 | −2.423 | −5.959 | 0.589 | 1.00 | 18.00 B | N |
| ATOM | 816 | CA | LEU | B | 28 | −2.214 | −6.213 | 2.016 | 1.00 | 18.51 B | C |
| ATOM | 817 | C | LEU | B | 28 | −0.923 | −6.999 | 2.259 | 1.00 | 18.19 B | C |
| ATOM | 818 | O | LEU | B | 28 | −0.141 | −6.670 | 3.156 | 1.00 | 15.92 B | O |
| ATOM | 819 | CB | LEU | B | 28 | −3.406 | −6.962 | 2.619 | 1.00 | 18.03 B | C |
| ATOM | 820 | CG | LEU | B | 28 | −3.321 | −7.263 | 4.123 | 1.00 | 17.44 B | C |
| ATOM | 821 | CD1 | LEU | B | 28 | −3.250 | −5.981 | 4.924 | 1.00 | 15.32 B | C |
| ATOM | 822 | CD2 | LEU | B | 28 | −4.506 | −8.112 | 4.579 | 1.00 | 16.82 B | C |
| ATOM | 823 | N | MET | B | 29 | −0.710 | −8.034 | 1.450 | 1.00 | 20.23 B | N |
| ATOM | 824 | CA | MET | B | 29 | 0.502 | −8.845 | 1.525 | 1.00 | 19.85 B | C |
| ATOM | 825 | C | MET | B | 29 | 1.733 | −8.013 | 1.190 | 1.00 | 17.85 B | C |
| ATOM | 826 | O | MET | B | 29 | 2.770 | −8.150 | 1.823 | 1.00 | 17.90 B | O |
| ATOM | 827 | CB | MET | B | 29 | 0.410 | −10.050 | 0.585 | 1.00 | 21.04 B | C |
| ATOM | 828 | CG | MET | B | 29 | −0.699 | −11.045 | 0.936 | 1.00 | 20.57 B | C |
| ATOM | 829 | SD | MET | B | 29 | −0.410 | −12.688 | 0.227 | 1.00 | 25.22 B | S |
| ATOM | 830 | CE | MET | B | 29 | −1.808 | −13.585 | 0.911 | 1.00 | 25.68 B | C |
| ATOM | 831 | N | LYS | B | 30 | 1.612 | −7.141 | 0.198 | 1.00 | 21.15 B | N |
| ATOM | 832 | CA | LYS | B | 30 | 2.733 | −6.297 | −0.199 | 1.00 | 23.46 B | C |
| ATOM | 833 | C | LYS | B | 30 | 3.208 | −5.420 | 0.963 | 1.00 | 22.21 B | C |
| ATOM | 834 | O | LYS | B | 30 | 4.409 | −5.327 | 1.230 | 1.00 | 22.98 B | O |
| ATOM | 835 | CB | LYS | B | 30 | 2.380 | −5.439 | −1.418 | 1.00 | 22.85 B | C |
| ATOM | 836 | CG | LYS | B | 30 | 3.597 | −4.786 | −2.066 | 1.00 | 31.19 B | C |
| ATOM | 837 | CD | LYS | B | 30 | 3.233 | −3.940 | −3.284 | 1.00 | 30.28 B | C |
| ATOM | 838 | CE | LYS | B | 30 | 4.410 | −3.069 | −3.708 | 1.00 | 32.21 B | C |
| ATOM | 839 | NZ | LYS | B | 30 | 3.999 | −1.884 | −4.515 | 1.00 | 32.92 B | N |
| ATOM | 840 | N | LYS | B | 31 | 2.269 | −4.785 | 1.661 | 1.00 | 18.51 B | N |
| ATOM | 841 | CA | LYS | B | 31 | 2.629 | −3.953 | 2.810 | 1.00 | 19.94 B | C |
| ATOM | 842 | C | LYS | B | 31 | 3.135 | −4.774 | 4.002 | 1.00 | 17.10 B | C |
| ATOM | 843 | O | LYS | B | 31 | 4.045 | −4.354 | 4.707 | 1.00 | 19.53 B | O |
| ATOM | 844 | CB | LYS | B | 31 | 1.474 | −3.025 | 3.202 | 1.00 | 16.96 B | C |
| ATOM | 845 | CG | LYS | B | 31 | 1.285 | −1.885 | 2.214 | 1.00 | 16.08 B | C |
| ATOM | 846 | CD | LYS | B | 31 | 0.282 | −0.855 | 2.704 | 1.00 | 22.23 B | C |
| ATOM | 847 | CE | LYS | B | 31 | 0.246 | 0.355 | 1.779 | 1.00 | 22.27 B | C |
| ATOM | 848 | NZ | LYS | B | 31 | 1.595 | 0.974 | 1.641 | 1.00 | 23.12 B | N |
| ATOM | 849 | N | ALA | B | 32 | 2.560 | −5.953 | 4.206 | 1.00 | 11.50 B | N |
| ATOM | 850 | CA | ALA | B | 32 | 3.033 | −6.860 | 5.242 | 1.00 | 12.27 B | C |
| ATOM | 851 | C | ALA | B | 32 | 4.503 | −7.208 | 4.998 | 1.00 | 15.88 B | C |
| ATOM | 852 | O | ALA | B | 32 | 5.327 | −7.137 | 5.913 | 1.00 | 13.80 B | O |
| ATOM | 853 | CB | ALA | B | 32 | 2.182 | −8.123 | 5.269 | 1.00 | 11.97 B | C |
| ATOM | 854 | N | TYR | B | 33 | 4.819 | −7.581 | 3.757 | 1.00 | 22.53 B | N |
| ATOM | 855 | CA | TYR | B | 33 | 6.189 | −7.880 | 3.346 | 1.00 | 21.55 B | C |
| ATOM | 856 | C | TYR | B | 33 | 7.141 | −6.692 | 3.554 | 1.00 | 23.48 B | C |
| ATOM | 857 | O | TYR | B | 33 | 8.224 | −6.843 | 4.124 | 1.00 | 24.87 B | O |
| ATOM | 858 | CB | TYR | B | 33 | 6.214 | −8.336 | 1.880 | 1.00 | 26.95 B | C |
| ATOM | 859 | CG | TYR | B | 33 | 7.560 | −8.179 | 1.202 | 1.00 | 25.09 B | C |
| ATOM | 860 | CD1 | TYR | B | 33 | 8.596 | −9.064 | 1.460 | 1.00 | 27.42 B | C |
| ATOM | 861 | CD2 | TYR | B | 33 | 7.794 | −7.140 | 0.306 | 1.00 | 25.48 B | C |
| ATOM | 862 | CE1 | TYR | B | 33 | 9.831 | −8.922 | 0.848 | 1.00 | 29.33 B | C |
| ATOM | 863 | CE2 | TYR | B | 33 | 9.027 | −6.986 | −0.308 | 1.00 | 25.23 B | C |
| ATOM | 864 | CZ | TYR | B | 33 | 10.040 | −7.881 | −0.033 | 1.00 | 29.66 B | C |
| ATOM | 865 | OH | TYR | B | 33 | 11.269 | −7.743 | −0.642 | 1.00 | 32.89 B | O |
| ATOM | 866 | N | GLU | B | 34 | 6.735 | −5.517 | 3.086 | 1.00 | 17.81 B | N |
| ATOM | 867 | CA | GLU | B | 34 | 7.539 | −4.308 | 3.231 | 1.00 | 19.60 B | C |
| ATOM | 868 | C | GLU | B | 34 | 7.810 | −3.965 | 4.696 | 1.00 | 20.91 B | C |
| ATOM | 869 | O | GLU | B | 34 | 8.931 | −3.579 | 5.054 | 1.00 | 17.67 B | O |
| ATOM | 870 | CB | GLU | B | 34 | 6.876 | −3.126 | 2.518 | 1.00 | 18.42 B | C |
| ATOM | 871 | CG | GLU | B | 34 | 6.846 | −3.262 | 0.997 | 1.00 | 19.82 B | C |
| ATOM | 872 | CD | GLU | B | 34 | 6.199 | −2.067 | 0.310 | 1.00 | 25.58 B | C |
| ATOM | 873 | OE1 | GLU | B | 34 | 5.545 | −1.255 | 1.004 | 1.00 | 22.87 B | O |
| ATOM | 874 | OE2 | GLU | B | 34 | 6.345 | −1.939 | −0.926 | 1.00 | 21.30 B | O |
| ATOM | 875 | N | LEU | B | 35 | 6.793 | −4.115 | 5.544 | 1.00 | 16.91 B | N |
| ATOM | 876 | CA | LEU | B | 35 | 6.966 | −3.847 | 6.972 | 1.00 | 16.29 B | C |
| ATOM | 877 | C | LEU | B | 35 | 7.932 | −4.845 | 7.619 | 1.00 | 16.61 B | C |
| ATOM | 878 | O | LEU | B | 35 | 8.731 | −4.482 | 8.487 | 1.00 | 18.25 B | O |

TABLE 1-continued

| | | | | | | | | | | | |
|---|---|---|---|---|---|---|---|---|---|---|---|
| ATOM | 879 | CB | LEU | B | 35 | 5.626 | −3.850 | 7.708 | 1.00 | 13.34 B | C |
| ATOM | 880 | CG | LEU | B | 35 | 5.763 | −3.654 | 9.219 | 1.00 | 14.59 B | C |
| ATOM | 881 | CD1 | LEU | B | 35 | 6.310 | −2.272 | 9.516 | 1.00 | 14.93 B | C |
| ATOM | 882 | CD2 | LEU | B | 35 | 4.451 | −3.882 | 9.940 | 1.00 | 14.02 B | C |
| ATOM | 883 | N | SER | B | 36 | 7.860 | −6.102 | 7.204 | 1.00 | 17.19 B | N |
| ATOM | 884 | CA | SER | B | 36 | 8.792 | −7.102 | 7.716 | 1.00 | 26.25 B | C |
| ATOM | 885 | C | SER | B | 36 | 10.251 | −6.770 | 7.364 | 1.00 | 21.13 B | C |
| ATOM | 886 | O | SER | B | 36 | 11.153 | −6.935 | 8.183 | 1.00 | 23.34 B | O |
| ATOM | 887 | CB | SER | B | 36 | 8.431 | −8.494 | 7.199 | 1.00 | 23.09 B | C |
| ATOM | 888 | OG | SER | B | 36 | 9.402 | −9.438 | 7.616 | 1.00 | 27.07 B | O |
| ATOM | 889 | N | VAL | B | 37 | 10.473 | −6.299 | 6.143 | 1.00 | 20.97 B | N |
| ATOM | 890 | CA | VAL | B | 37 | 11.820 | −5.988 | 5.678 | 1.00 | 21.94 B | C |
| ATOM | 891 | C | VAL | B | 37 | 12.328 | −4.665 | 6.247 | 1.00 | 22.41 B | C |
| ATOM | 892 | O | VAL | B | 37 | 13.440 | −4.588 | 6.769 | 1.00 | 22.46 B | O |
| ATOM | 893 | CB | VAL | B | 37 | 11.877 | −5.935 | 4.139 | 1.00 | 21.78 B | C |
| ATOM | 894 | CG1 | VAL | B | 37 | 13.164 | −5.273 | 3.667 | 1.00 | 17.34 B | C |
| ATOM | 895 | CG2 | VAL | B | 37 | 11.742 | −7.336 | 3.562 | 1.00 | 22.73 B | C |
| ATOM | 896 | N | LEU | B | 38 | 11.509 | −3.625 | 6.139 | 1.00 | 29.65 B | N |
| ATOM | 897 | CA | LEU | B | 38 | 11.895 | −2.302 | 6.606 | 1.00 | 29.22 B | C |
| ATOM | 898 | C | LEU | B | 38 | 12.222 | −2.292 | 8.095 | 1.00 | 29.43 B | C |
| ATOM | 899 | O | LEU | B | 38 | 13.176 | −1.639 | 8.527 | 1.00 | 29.26 B | O |
| ATOM | 900 | CB | LEU | B | 38 | 10.781 | −1.294 | 6.326 | 1.00 | 27.68 B | C |
| ATOM | 901 | CG | LEU | B | 38 | 10.564 | −0.877 | 4.875 | 1.00 | 27.08 B | C |
| ATOM | 902 | CD1 | LEU | B | 38 | 9.277 | −0.077 | 4.758 | 1.00 | 23.22 B | C |
| ATOM | 903 | CD2 | LEU | B | 38 | 11.756 | −0.083 | 4.363 | 1.00 | 24.95 B | C |
| ATOM | 904 | N | CYS | B | 39 | 11.432 | −3.015 | 8.880 | 1.00 | 17.61 B | N |
| ATOM | 905 | CA | CYS | B | 39 | 11.579 | −2.941 | 10.330 | 1.00 | 22.07 B | C |
| ATOM | 906 | C | CYS | B | 39 | 12.059 | −4.238 | 10.992 | 1.00 | 21.34 B | C |
| ATOM | 907 | O | CYS | B | 39 | 12.094 | −4.338 | 12.216 | 1.00 | 24.49 B | O |
| ATOM | 908 | CB | CYS | B | 39 | 10.276 | −2.448 | 10.968 | 1.00 | 15.92 B | C |
| ATOM | 909 | SG | CYS | B | 39 | 9.701 | −0.901 | 10.239 | 1.00 | 19.75 B | S |
| ATOM | 910 | N | ASP | B | 40 | 12.433 | −5.226 | 10.191 | 1.00 | 31.69 B | N |
| ATOM | 911 | CA | ASP | B | 40 | 12.981 | −6.454 | 10.754 | 1.00 | 37.68 B | C |
| ATOM | 912 | C | ASP | B | 40 | 12.040 | −7.040 | 11.810 | 1.00 | 37.06 B | C |
| ATOM | 913 | O | ASP | B | 40 | 12.325 | −6.975 | 13.006 | 1.00 | 34.46 B | O |
| ATOM | 914 | CB | ASP | B | 40 | 14.351 | −6.169 | 11.382 | 1.00 | 33.34 B | C |
| ATOM | 915 | CG | ASP | B | 40 | 15.076 | −7.432 | 11.824 | 1.00 | 41.25 B | C |
| ATOM | 916 | OD1 | ASP | B | 40 | 14.704 | −8.540 | 11.380 | 1.00 | 43.90 B | O |
| ATOM | 917 | OD2 | ASP | B | 40 | 16.031 | −7.312 | 12.621 | 1.00 | 52.43 B | O |
| ATOM | 918 | N | CYS | B | 41 | 10.919 | −7.603 | 11.370 | 1.00 | 28.73 B | N |
| ATOM | 919 | CA | CYS | B | 41 | 9.996 | −8.257 | 12.289 | 1.00 | 33.22 B | C |
| ATOM | 920 | C | CYS | B | 41 | 9.336 | −9.506 | 11.693 | 1.00 | 31.42 B | C |
| ATOM | 921 | O | CYS | B | 41 | 9.191 | −9.620 | 10.477 | 1.00 | 31.49 B | O |
| ATOM | 922 | CB | CYS | B | 41 | 8.943 | −7.266 | 12.798 | 1.00 | 30.60 B | C |
| ATOM | 923 | SG | CYS | B | 41 | 8.329 | −6.093 | 11.583 | 1.00 | 39.58 B | S |
| ATOM | 924 | N | GLU | B | 42 | 8.966 | −10.446 | 12.561 | 1.00 | 32.53 B | N |
| ATOM | 925 | CA | GLU | B | 42 | 8.232 | −11.638 | 12.153 | 1.00 | 34.28 B | C |
| ATOM | 926 | C | GLU | B | 42 | 6.772 | −11.284 | 11.955 | 1.00 | 31.82 B | C |
| ATOM | 927 | O | GLU | B | 42 | 6.133 | −10.739 | 12.853 | 1.00 | 32.57 B | O |
| ATOM | 928 | CB | GLU | B | 42 | 8.303 | −12.725 | 13.225 | 1.00 | 36.20 B | C |
| ATOM | 929 | CG | GLU | B | 42 | 9.646 | −13.393 | 13.405 | 1.00 | 46.15 B | C |
| ATOM | 930 | CD | GLU | B | 42 | 9.568 | −14.549 | 14.382 | 1.00 | 47.22 B | C |
| ATOM | 931 | OE1 | GLU | B | 42 | 10.523 | −14.734 | 15.167 | 1.00 | 64.02 B | O |
| ATOM | 932 | OE2 | GLU | B | 42 | 8.542 | −15.265 | 14.372 | 1.00 | 37.09 B | O |
| ATOM | 933 | N | ILE | B | 43 | 6.232 | −11.615 | 10.792 | 1.00 | 20.98 B | N |
| ATOM | 934 | CA | ILE | B | 43 | 4.832 | −11.335 | 10.524 | 1.00 | 20.90 B | C |
| ATOM | 935 | C | ILE | B | 43 | 4.116 | −12.561 | 9.975 | 1.00 | 20.19 B | C |
| ATOM | 936 | O | ILE | B | 43 | 4.693 | −13.344 | 9.223 | 1.00 | 21.90 B | O |
| ATOM | 937 | CB | ILE | B | 43 | 4.678 | −10.128 | 9.578 | 1.00 | 21.58 B | C |
| ATOM | 938 | CG1 | ILE | B | 43 | 5.102 | −8.848 | 10.310 | 1.00 | 18.84 B | C |
| ATOM | 939 | CG2 | ILE | B | 43 | 3.244 | −10.033 | 9.056 | 1.00 | 14.53 B | C |
| ATOM | 940 | CD1 | ILE | B | 43 | 5.145 | −7.608 | 9.446 | 1.00 | 16.56 B | C |
| ATOM | 941 | N | ALA | B | 44 | 2.865 | −12.735 | 10.381 | 1.00 | 22.30 B | N |
| ATOM | 942 | CA | ALA | B | 44 | 2.028 | −13.807 | 9.861 | 1.00 | 22.53 B | C |
| ATOM | 943 | C | ALA | B | 44 | 0.660 | −13.234 | 9.523 | 1.00 | 20.25 B | C |
| ATOM | 944 | O | ALA | B | 44 | 0.123 | −12.420 | 10.266 | 1.00 | 22.18 B | O |
| ATOM | 945 | CB | ALA | B | 44 | 1.907 | −14.946 | 10.878 | 1.00 | 20.13 B | C |
| ATOM | 946 | N | LEU | B | 45 | 0.102 | −13.660 | 8.398 | 1.00 | 21.92 B | N |
| ATOM | 947 | CA | LEU | B | 45 | −1.165 | −13.124 | 7.928 | 1.00 | 18.74 B | C |
| ATOM | 948 | C | LEU | B | 45 | −2.013 | −14.241 | 7.342 | 1.00 | 22.81 B | C |
| ATOM | 949 | O | LEU | B | 45 | −1.791 | −14.662 | 6.210 | 1.00 | 25.91 B | O |
| ATOM | 950 | CB | LEU | B | 45 | −0.908 | −12.046 | 6.869 | 1.00 | 21.14 B | C |
| ATOM | 951 | CG | LEU | B | 45 | −2.098 | −11.413 | 6.139 | 1.00 | 21.33 B | C |
| ATOM | 952 | CD1 | LEU | B | 45 | −3.034 | −10.714 | 7.115 | 1.00 | 18.73 B | C |
| ATOM | 953 | CD2 | LEU | B | 45 | −1.623 | −10.441 | 5.059 | 1.00 | 15.76 B | C |
| ATOM | 954 | N | ILE | B | 46 | −2.980 | −14.726 | 8.112 | 1.00 | 28.56 B | N |
| ATOM | 955 | CA | ILE | B | 46 | −3.894 | −15.759 | 7.627 | 1.00 | 28.46 B | C |
| ATOM | 956 | C | ILE | B | 46 | −5.221 | −15.148 | 7.187 | 1.00 | 27.91 B | C |
| ATOM | 957 | O | ILE | B | 46 | −5.828 | −14.367 | 7.922 | 1.00 | 28.37 B | O |
| ATOM | 958 | CB | ILE | B | 46 | −4.152 | −16.829 | 8.704 | 1.00 | 29.75 B | C |

TABLE 1-continued

| | | | | | | | | | | | |
|---|---|---|---|---|---|---|---|---|---|---|---|
| ATOM | 959 | CG1 | ILE | B | 46 | −2.865 | −17.601 | 8.999 | 1.00 | 27.86 B | C |
| ATOM | 960 | CG2 | ILE | B | 46 | −5.243 | −17.774 | 8.258 | 1.00 | 29.11 B | C |
| ATOM | 961 | CD1 | ILE | B | 46 | −2.877 | −18.332 | 10.321 | 1.00 | 30.75 B | C |
| ATOM | 962 | N | ILE | B | 47 | −5.668 | −15.509 | 5.988 | 1.00 | 24.78 B | N |
| ATOM | 963 | CA | ILE | B | 47 | −6.883 | −14.943 | 5.405 | 1.00 | 22.12 B | C |
| ATOM | 964 | C | ILE | B | 47 | −7.777 | −16.006 | 4.768 | 1.00 | 25.06 B | C |
| ATOM | 965 | O | ILE | B | 47 | −7.330 | −16.774 | 3.914 | 1.00 | 26.66 B | O |
| ATOM | 966 | CB | ILE | B | 47 | −6.544 | −13.927 | 4.299 | 1.00 | 25.90 B | C |
| ATOM | 967 | CG1 | ILE | B | 47 | −5.569 | −12.864 | 4.805 | 1.00 | 25.54 B | C |
| ATOM | 968 | CG2 | ILE | B | 47 | −7.815 | −13.286 | 3.747 | 1.00 | 28.25 B | C |
| ATOM | 969 | CD1 | ILE | B | 47 | −5.081 | −11.952 | 3.706 | 1.00 | 22.33 B | C |
| ATOM | 970 | N | PHE | B | 48 | −9.044 | −16.035 | 5.172 | 1.00 | 23.95 B | N |
| ATOM | 971 | CA | PHE | B | 48 | −10.031 | −16.927 | 4.574 | 1.00 | 25.54 B | C |
| ATOM | 972 | C | PHE | B | 48 | −11.088 | −16.077 | 3.887 | 1.00 | 30.58 B | C |
| ATOM | 973 | O | PHE | B | 48 | −11.813 | −15.347 | 4.556 | 1.00 | 29.00 B | O |
| ATOM | 974 | CB | PHE | B | 48 | −10.725 | −17.782 | 5.646 | 1.00 | 25.36 B | C |
| ATOM | 975 | CG | PHE | B | 48 | −9.798 | −18.674 | 6.429 | 1.00 | 26.77 B | C |
| ATOM | 976 | CD1 | PHE | B | 48 | −9.260 | −18.251 | 7.636 | 1.00 | 24.64 B | C |
| ATOM | 977 | CD2 | PHE | B | 48 | −9.487 | −19.946 | 5.974 | 1.00 | 28.62 B | C |
| ATOM | 978 | CE1 | PHE | B | 48 | −8.412 | −19.074 | 8.366 | 1.00 | 23.95 B | C |
| ATOM | 979 | CE2 | PHE | B | 48 | −8.645 | −20.775 | 6.700 | 1.00 | 28.73 B | C |
| ATOM | 980 | CZ | PHE | B | 48 | −8.107 | −20.335 | 7.898 | 1.00 | 25.90 B | C |
| ATOM | 981 | N | ASN | B | 49 | −11.197 | −16.170 | 2.565 | 1.00 | 23.38 B | N |
| ATOM | 982 | CA | ASN | B | 49 | −12.209 | −15.384 | 1.863 | 1.00 | 27.57 B | C |
| ATOM | 983 | C | ASN | B | 49 | −13.626 | −15.824 | 2.242 | 1.00 | 27.92 B | C |
| ATOM | 984 | O | ASN | B | 49 | −13.801 | −16.750 | 3.038 | 1.00 | 28.71 B | O |
| ATOM | 985 | CB | ASN | B | 49 | −11.995 | −15.419 | 0.346 | 1.00 | 22.94 B | C |
| ATOM | 986 | CG | ASN | B | 49 | −12.275 | −16.780 | −0.257 | 1.00 | 32.75 B | C |
| ATOM | 987 | OD1 | ASN | B | 49 | −12.822 | −17.671 | 0.403 | 1.00 | 30.86 B | O |
| ATOM | 988 | ND2 | ASN | B | 49 | −11.902 | −16.949 | −1.523 | 1.00 | 25.20 B | N |
| ATOM | 989 | N | SER | B | 50 | −14.631 | −15.158 | 1.683 | 1.00 | 33.24 B | N |
| ATOM | 990 | CA | SER | B | 50 | −16.019 | −15.449 | 2.039 | 1.00 | 40.75 B | C |
| ATOM | 991 | C | SER | B | 50 | −16.472 | −16.818 | 1.540 | 1.00 | 40.36 B | C |
| ATOM | 992 | O | SER | B | 50 | −17.562 | −17.272 | 1.877 | 1.00 | 41.94 B | O |
| ATOM | 993 | CB | SER | B | 50 | −16.960 | −14.355 | 1.524 | 1.00 | 38.64 B | C |
| ATOM | 994 | OG | SER | B | 50 | −16.843 | −14.194 | 0.122 | 1.00 | 41.82 B | O |
| ATOM | 995 | N | SER | B | 51 | −15.632 | −17.468 | 0.738 | 1.00 | 49.72 B | N |
| ATOM | 996 | CA | SER | B | 51 | −15.915 | −18.819 | 0.251 | 1.00 | 48.33 B | C |
| ATOM | 997 | C | SER | B | 51 | −15.090 | −19.846 | 1.015 | 1.00 | 48.30 B | C |
| ATOM | 998 | O | SER | B | 51 | −14.964 | −20.992 | 0.587 | 1.00 | 39.41 B | O |
| ATOM | 999 | CB | SER | B | 51 | −15.619 | −18.938 | −1.247 | 1.00 | 44.33 B | C |
| ATOM | 1000 | OG | SER | B | 51 | −16.500 | −18.134 | −2.010 | 1.00 | 55.02 B | O |
| ATOM | 1001 | N | ASN | B | 52 | −14.514 | −19.416 | 2.135 | 1.00 | 47.00 B | N |
| ATOM | 1002 | CA | ASN | B | 52 | −13.750 | −20.302 | 3.013 | 1.00 | 42.12 B | C |
| ATOM | 1003 | C | ASN | B | 52 | −12.414 | −20.795 | 2.464 | 1.00 | 41.08 B | C |
| ATOM | 1004 | O | ASN | B | 52 | −11.768 | −21.645 | 3.080 | 1.00 | 42.93 B | O |
| ATOM | 1005 | CB | ASN | B | 52 | −14.604 | −21.489 | 3.462 | 1.00 | 49.34 B | C |
| ATOM | 1006 | CG | ASN | B | 52 | −15.199 | −21.287 | 4.840 | 1.00 | 56.21 B | C |
| ATOM | 1007 | OD1 | ASN | B | 52 | −16.408 | −21.114 | 4.993 | 1.00 | 46.14 B | O |
| ATOM | 1008 | ND2 | ASN | B | 52 | −14.344 | −21.299 | 5.854 | 1.00 | 54.50 B | N |
| ATOM | 1009 | N | LYS | B | 53 | −11.996 | −20.273 | 1.315 | 1.00 | 31.71 B | N |
| ATOM | 1010 | CA | LYS | B | 53 | −10.663 | −20.590 | 0.811 | 1.00 | 33.29 B | C |
| ATOM | 1011 | C | LYS | B | 53 | −9.585 | −19.861 | 1.621 | 1.00 | 33.31 B | C |
| ATOM | 1012 | O | LYS | B | 53 | −9.771 | −18.720 | 2.044 | 1.00 | 27.43 B | O |
| ATOM | 1013 | CB | LYS | B | 53 | −10.517 | −20.266 | −0.679 | 1.00 | 27.59 B | C |
| ATOM | 1014 | CG | LYS | B | 53 | −9.121 | −20.606 | −1.208 | 1.00 | 36.54 B | C |
| ATOM | 1015 | CD | LYS | B | 53 | −9.032 | −20.560 | −2.730 | 1.00 | 42.26 B | C |
| ATOM | 1016 | CE | LYS | B | 53 | −7.659 | −21.035 | −3.201 | 1.00 | 35.17 B | C |
| ATOM | 1017 | NZ | LYS | B | 53 | −7.479 | −20.908 | −4.672 | 1.00 | 35.78 B | N |
| ATOM | 1018 | N | LEU | B | 54 | −8.461 | −20.537 | 1.829 | 1.00 | 33.51 B | N |
| ATOM | 1019 | CA | LEU | B | 54 | −7.380 | −20.017 | 2.652 | 1.00 | 27.32 B | C |
| ATOM | 1020 | C | LEU | B | 54 | −6.290 | −19.334 | 1.820 | 1.00 | 29.53 B | C |
| ATOM | 1021 | O | LEU | B | 54 | −5.893 | −19.830 | 0.767 | 1.00 | 36.19 B | O |
| ATOM | 1022 | CB | LEU | B | 54 | −6.781 | −21.156 | 3.480 | 1.00 | 31.38 B | C |
| ATOM | 1023 | CG | LEU | B | 54 | −5.476 | −20.910 | 4.237 | 1.00 | 33.67 B | C |
| ATOM | 1024 | CD1 | LEU | B | 54 | −5.650 | −19.818 | 5.278 | 1.00 | 27.50 B | C |
| ATOM | 1025 | CD2 | LEU | B | 54 | −4.986 | −22.199 | 4.882 | 1.00 | 32.84 B | C |
| ATOM | 1026 | N | PHE | B | 55 | −5.824 | −18.185 | 2.297 | 1.00 | 28.75 B | N |
| ATOM | 1027 | CA | PHE | B | 55 | −4.682 | −17.494 | 1.708 | 1.00 | 27.50 B | C |
| ATOM | 1028 | C | PHE | B | 55 | −3.775 | −17.062 | 2.846 | 1.00 | 25.87 B | C |
| ATOM | 1029 | O | PHE | B | 55 | −4.255 | −16.629 | 3.884 | 1.00 | 32.23 B | O |
| ATOM | 1030 | CB | PHE | B | 55 | −5.131 | −16.261 | 0.921 | 1.00 | 27.64 B | C |
| ATOM | 1031 | CG | PHE | B | 55 | −6.026 | −16.572 | −0.244 | 1.00 | 22.94 B | C |
| ATOM | 1032 | CD1 | PHE | B | 55 | −7.399 | −16.567 | −0.096 | 1.00 | 22.20 B | C |
| ATOM | 1033 | CD2 | PHE | B | 55 | −5.488 | −16.854 | −1.491 | 1.00 | 27.54 B | C |
| ATOM | 1034 | CE1 | PHE | B | 55 | −8.226 | −16.847 | −1.165 | 1.00 | 30.38 B | C |
| ATOM | 1035 | CE2 | PHE | B | 55 | −6.306 | −17.135 | −2.572 | 1.00 | 26.44 B | C |
| ATOM | 1036 | CZ | PHE | B | 55 | −7.681 | −17.130 | −2.408 | 1.00 | 32.90 B | C |
| ATOM | 1037 | N | GLN | B | 56 | −2.467 | −17.172 | 2.668 | 1.00 | 28.02 B | N |
| ATOM | 1038 | CA | GLN | B | 56 | −1.576 | −16.878 | 3.773 | 1.00 | 27.44 B | C |

TABLE 1-continued

| | | | | | | | | | | | |
|---|---|---|---|---|---|---|---|---|---|---|---|
| ATOM | 1039 | C | GLN | B | 56 | −0.267 | −16.221 | 3.363 | 1.00 | 31.46 B | C |
| ATOM | 1040 | O | GLN | B | 56 | 0.192 | −16.362 | 2.231 | 1.00 | 37.98 B | O |
| ATOM | 1041 | CB | GLN | B | 56 | −1.301 | −18.151 | 4.576 | 1.00 | 33.26 B | C |
| ATOM | 1042 | CG | GLN | B | 56 | −0.939 | −19.360 | 3.730 | 1.00 | 32.44 B | C |
| ATOM | 1043 | CD | GLN | B | 56 | −0.622 | −20.589 | 4.571 | 1.00 | 41.26 B | C |
| ATOM | 1044 | OE1 | GLN | B | 56 | 0.246 | −20.552 | 5.445 | 1.00 | 40.41 B | O |
| ATOM | 1045 | NE2 | GLN | B | 56 | −1.325 | −21.687 | 4.305 | 1.00 | 39.56 B | N |
| ATOM | 1046 | N | TYR | B | 57 | 0.317 | −15.487 | 4.302 | 1.00 | 21.88 B | N |
| ATOM | 1047 | CA | TYR | B | 57 | 1.658 | −14.946 | 4.150 | 1.00 | 22.42 B | C |
| ATOM | 1048 | C | TYR | B | 57 | 2.390 | −15.047 | 5.480 | 1.00 | 22.08 B | C |
| ATOM | 1049 | O | TYR | B | 57 | 1.793 | −14.877 | 6.539 | 1.00 | 23.51 B | O |
| ATOM | 1050 | CB | TYR | B | 57 | 1.638 | −13.479 | 3.701 | 1.00 | 24.62 B | C |
| ATOM | 1051 | CG | TYR | B | 57 | 2.957 | −12.787 | 3.985 | 1.00 | 23.21 B | C |
| ATOM | 1052 | CD1 | TYR | B | 57 | 4.037 | −12.924 | 3.120 | 1.00 | 24.26 B | C |
| ATOM | 1053 | CD2 | TYR | B | 57 | 3.137 | −12.036 | 5.140 | 1.00 | 21.52 B | C |
| ATOM | 1054 | CE1 | TYR | B | 57 | 5.252 | −12.318 | 3.387 | 1.00 | 22.38 B | C |
| ATOM | 1055 | CE2 | TYR | B | 57 | 4.348 | −11.422 | 5.416 | 1.00 | 20.47 B | C |
| ATOM | 1056 | CZ | TYR | B | 57 | 5.402 | −11.565 | 4.537 | 1.00 | 25.24 B | C |
| ATOM | 1057 | OH | TYR | B | 57 | 6.609 | −10.950 | 4.805 | 1.00 | 20.23 B | O |
| ATOM | 1058 | N | ALA | B | 58 | 3.689 | −15.308 | 5.424 | 1.00 | 21.77 B | N |
| ATOM | 1059 | CA | ALA | B | 58 | 4.499 | −15.335 | 6.631 | 1.00 | 24.55 B | C |
| ATOM | 1060 | C | ALA | B | 58 | 5.950 | −14.993 | 6.308 | 1.00 | 20.16 B | C |
| ATOM | 1061 | O | ALA | B | 58 | 6.479 | −15.431 | 5.294 | 1.00 | 20.99 B | O |
| ATOM | 1062 | CB | ALA | B | 58 | 4.393 | −16.689 | 7.302 | 1.00 | 27.40 B | C |
| ATOM | 1063 | N | SER | B | 59 | 6.585 | −14.199 | 7.168 | 1.00 | 24.98 B | N |
| ATOM | 1064 | CA | SER | B | 59 | 7.967 | −13.781 | 6.941 | 1.00 | 26.54 B | C |
| ATOM | 1065 | C | SER | B | 59 | 8.948 | −14.926 | 7.182 | 1.00 | 30.03 B | C |
| ATOM | 1066 | O | SER | B | 59 | 10.132 | −14.809 | 6.877 | 1.00 | 21.34 B | O |
| ATOM | 1067 | CB | SER | B | 59 | 8.327 | −12.559 | 7.794 | 1.00 | 22.90 B | C |
| ATOM | 1068 | OG | SER | B | 59 | 8.172 | −12.824 | 9.179 | 1.00 | 25.51 B | O |
| ATOM | 1069 | N | THR | B | 60 | 8.439 | −16.020 | 7.748 | 1.00 | 48.65 B | N |
| ATOM | 1070 | CA | THR | B | 60 | 9.151 | −17.296 | 7.827 | 1.00 | 46.35 B | C |
| ATOM | 1071 | C | THR | B | 60 | 8.101 | −18.397 | 7.770 | 1.00 | 52.29 B | C |
| ATOM | 1072 | O | THR | B | 60 | 6.948 | −18.134 | 7.434 | 1.00 | 49.50 B | O |
| ATOM | 1073 | CB | THR | B | 60 | 9.948 | −17.458 | 9.134 | 1.00 | 54.49 B | C |
| ATOM | 1074 | OG1 | THR | B | 60 | 9.042 | −17.536 | 10.243 | 1.00 | 57.06 B | O |
| ATOM | 1075 | CG2 | THR | B | 60 | 10.910 | −16.295 | 9.340 | 1.00 | 65.06 B | C |
| ATOM | 1076 | N | ASP | B | 61 | 8.486 | −19.625 | 8.104 | 1.00 | 37.07 B | N |
| ATOM | 1077 | CA | ASP | B | 61 | 7.527 | −20.726 | 8.124 | 1.00 | 35.62 B | C |
| ATOM | 1078 | C | ASP | B | 61 | 6.343 | −20.347 | 9.009 | 1.00 | 40.19 B | C |
| ATOM | 1079 | O | ASP | B | 61 | 6.513 | −19.998 | 10.183 | 1.00 | 36.11 B | O |
| ATOM | 1080 | CB | ASP | B | 61 | 8.173 | −22.024 | 8.623 | 1.00 | 41.27 B | C |
| ATOM | 1081 | CG | ASP | B | 61 | 9.378 | −22.440 | 7.792 | 1.00 | 49.43 B | C |
| ATOM | 1082 | OD1 | ASP | B | 61 | 10.392 | −21.707 | 7.787 | 1.00 | 53.39 B | O |
| ATOM | 1083 | OD2 | ASP | B | 61 | 9.320 | −23.512 | 7.156 | 1.00 | 44.21 B | O |
| ATOM | 1084 | N | MET | B | 62 | 5.146 | −20.409 | 8.432 | 1.00 | 43.31 B | N |
| ATOM | 1085 | CA | MET | B | 62 | 3.926 | −20.014 | 9.128 | 1.00 | 38.52 B | C |
| ATOM | 1086 | C | MET | B | 62 | 3.808 | −20.643 | 10.511 | 1.00 | 42.96 B | C |
| ATOM | 1087 | O | MET | B | 62 | 3.315 | −20.015 | 11.451 | 1.00 | 41.37 B | O |
| ATOM | 1088 | CB | MET | B | 62 | 2.696 | −20.381 | 8.301 | 1.00 | 31.75 B | C |
| ATOM | 1089 | CG | MET | B | 62 | 1.390 | −20.116 | 9.027 | 1.00 | 37.30 B | C |
| ATOM | 1090 | SD | MET | B | 62 | 1.265 | −18.411 | 9.606 | 1.00 | 31.33 B | S |
| ATOM | 1091 | CE | MET | B | 62 | 0.980 | −17.545 | 8.070 | 1.00 | 24.54 B | C |
| ATOM | 1092 | N | ASP | B | 63 | 4.265 | −21.884 | 10.629 | 1.00 | 49.42 B | N |
| ATOM | 1093 | CA | ASP | B | 63 | 4.104 | −22.643 | 11.862 | 1.00 | 47.63 B | C |
| ATOM | 1094 | C | ASP | B | 63 | 5.076 | −22.198 | 12.950 | 1.00 | 44.15 B | C |
| ATOM | 1095 | O | ASP | B | 63 | 4.859 | −22.462 | 14.127 | 1.00 | 46.49 B | O |
| ATOM | 1096 | CB | ASP | B | 63 | 4.250 | −24.140 | 11.587 | 1.00 | 59.12 B | C |
| ATOM | 1097 | CG | ASP | B | 63 | 3.201 | −24.656 | 10.616 | 1.00 | 66.90 B | C |
| ATOM | 1098 | OD1 | ASP | B | 63 | 2.006 | −24.684 | 10.985 | 1.00 | 59.57 B | O |
| ATOM | 1099 | OD2 | ASP | B | 63 | 3.576 | −25.034 | 9.483 | 1.00 | 67.57 B | O |
| ATOM | 1100 | N | LYS | B | 64 | 6.147 | −21.520 | 12.558 | 1.00 | 41.21 B | N |
| ATOM | 1101 | CA | LYS | B | 64 | 7.111 | −21.032 | 13.536 | 1.00 | 39.98 B | C |
| ATOM | 1102 | C | LYS | B | 64 | 6.595 | −19.774 | 14.237 | 1.00 | 39.97 B | C |
| ATOM | 1103 | O | LYS | B | 64 | 6.717 | −19.639 | 15.454 | 1.00 | 33.04 B | O |
| ATOM | 1104 | CB | LYS | B | 64 | 8.471 | −20.785 | 12.880 | 1.00 | 44.04 B | C |
| ATOM | 1105 | CG | LYS | B | 64 | 9.091 | −22.046 | 12.290 | 1.00 | 54.30 B | C |
| ATOM | 1106 | CD | LYS | B | 64 | 10.492 | −21.798 | 11.749 | 1.00 | 57.87 B | C |
| ATOM | 1107 | CE | LYS | B | 64 | 11.106 | −23.085 | 11.213 | 1.00 | 56.54 B | C |
| ATOM | 1108 | NZ | LYS | B | 64 | 12.416 | −22.845 | 10.554 | 1.00 | 57.68 B | N |
| ATOM | 1109 | N | VAL | B | 65 | 6.011 | −18.862 | 13.464 | 1.00 | 35.84 B | N |
| ATOM | 1110 | CA | VAL | B | 65 | 5.418 | −17.651 | 14.022 | 1.00 | 32.80 B | C |
| ATOM | 1111 | C | VAL | B | 65 | 4.295 | −18.006 | 14.994 | 1.00 | 32.81 B | C |
| ATOM | 1112 | O | VAL | B | 65 | 4.166 | −17.406 | 16.067 | 1.00 | 29.45 B | O |
| ATOM | 1113 | CB | VAL | B | 65 | 4.836 | −16.746 | 12.919 | 1.00 | 30.22 B | C |
| ATOM | 1114 | CG1 | VAL | B | 65 | 4.343 | −15.435 | 13.517 | 1.00 | 25.45 B | C |
| ATOM | 1115 | CG2 | VAL | B | 65 | 5.868 | −16.493 | 11.835 | 1.00 | 34.33 B | C |
| ATOM | 1116 | N | LEU | B | 66 | 3.488 | −18.990 | 14.610 | 1.00 | 29.80 B | N |
| ATOM | 1117 | CA | LEU | B | 66 | 2.369 | −19.424 | 15.430 | 1.00 | 34.20 B | C |
| ATOM | 1118 | C | LEU | B | 66 | 2.828 | −19.990 | 16.773 | 1.00 | 41.26 B | C |

TABLE 1-continued

| | | | | | | | | | | | |
|---|---|---|---|---|---|---|---|---|---|---|---|
| ATOM | 1119 | O | LEU | B | 66 | 2.331 | −19.586 | 17.827 | 1.00 | 39.01 B | O |
| ATOM | 1120 | CB | LEU | B | 66 | 1.517 | −20.443 | 14.673 | 1.00 | 35.53 B | C |
| ATOM | 1121 | CG | LEU | B | 66 | 0.792 | −19.857 | 13.460 | 1.00 | 36.37 B | C |
| ATOM | 1122 | CD1 | LEU | B | 66 | −0.167 | −20.870 | 12.864 | 1.00 | 31.71 B | C |
| ATOM | 1123 | CD2 | LEU | B | 66 | 0.056 | −18.584 | 13.861 | 1.00 | 31.61 B | C |
| ATOM | 1124 | N | LEU | B | 67 | 3.779 | −20.917 | 16.737 | 1.00 | 41.41 B | N |
| ATOM | 1125 | CA | LEU | B | 67 | 4.285 | −21.510 | 17.967 | 1.00 | 41.65 B | C |
| ATOM | 1126 | C | LEU | B | 67 | 4.886 | −20.442 | 18.870 | 1.00 | 41.31 B | C |
| ATOM | 1127 | O | LEU | B | 67 | 4.796 | −20.532 | 20.093 | 1.00 | 44.99 B | O |
| ATOM | 1128 | CB | LEU | B | 67 | 5.309 | −22.611 | 17.672 | 1.00 | 44.98 B | C |
| ATOM | 1129 | CG | LEU | B | 67 | 4.740 | −24.028 | 17.518 | 1.00 | 46.47 B | C |
| ATOM | 1130 | CD1 | LEU | B | 67 | 3.909 | −24.399 | 18.741 | 1.00 | 51.36 B | C |
| ATOM | 1131 | CD2 | LEU | B | 67 | 3.910 | −24.170 | 16.247 | 1.00 | 47.13 B | C |
| ATOM | 1132 | N | LYS | B | 68 | 5.490 | −19.429 | 18.260 | 1.00 | 30.15 B | N |
| ATOM | 1133 | CA | LYS | B | 68 | 6.064 | −18.321 | 19.007 | 1.00 | 28.49 B | C |
| ATOM | 1134 | C | LYS | B | 68 | 4.952 | −17.512 | 19.664 | 1.00 | 36.89 B | C |
| ATOM | 1135 | O | LYS | B | 68 | 5.133 | −16.932 | 20.736 | 1.00 | 38.72 B | O |
| ATOM | 1136 | CB | LYS | B | 68 | 6.905 | −17.433 | 18.087 | 1.00 | 31.22 B | C |
| ATOM | 1137 | CG | LYS | B | 68 | 7.590 | −16.276 | 18.794 | 1.00 | 36.27 B | C |
| ATOM | 1138 | CD | LYS | B | 68 | 8.714 | −15.695 | 17.952 | 1.00 | 41.13 B | C |
| ATOM | 1139 | CE | LYS | B | 68 | 9.450 | −14.598 | 18.705 | 1.00 | 38.43 B | C |
| ATOM | 1140 | NZ | LYS | B | 68 | 10.588 | −14.050 | 17.922 | 1.00 | 37.80 B | N |
| ATOM | 1141 | N | TYR | B | 69 | 3.794 | −17.486 | 19.013 | 1.00 | 39.71 B | N |
| ATOM | 1142 | CA | TYR | B | 69 | 2.631 | −16.793 | 19.547 | 1.00 | 41.49 B | C |
| ATOM | 1143 | C | TYR | B | 69 | 2.057 | −17.534 | 20.750 | 1.00 | 40.39 B | C |
| ATOM | 1144 | O | TYR | B | 69 | 1.821 | −16.941 | 21.803 | 1.00 | 39.82 B | O |
| ATOM | 1145 | CB | TYR | B | 69 | 1.561 | −16.645 | 18.464 | 1.00 | 36.39 B | C |
| ATOM | 1146 | CG | TYR | B | 69 | 0.250 | −16.092 | 18.968 | 1.00 | 31.52 B | C |
| ATOM | 1147 | CD1 | TYR | B | 69 | 0.068 | −14.727 | 19.125 | 1.00 | 28.35 B | C |
| ATOM | 1148 | CD2 | TYR | B | 69 | −0.805 | −16.935 | 19.284 | 1.00 | 32.82 B | C |
| ATOM | 1149 | CE1 | TYR | B | 69 | −1.126 | −14.217 | 19.581 | 1.00 | 26.39 B | C |
| ATOM | 1150 | CE2 | TYR | B | 69 | −2.006 | −16.432 | 19.744 | 1.00 | 26.38 B | C |
| ATOM | 1151 | CZ | TYR | B | 69 | −2.160 | −15.072 | 19.889 | 1.00 | 27.61 B | C |
| ATOM | 1152 | OH | TYR | B | 69 | −3.352 | −14.558 | 20.349 | 1.00 | 30.19 B | O |
| ATOM | 1153 | N | THR | B | 70 | 1.828 | −18.832 | 20.586 | 1.00 | 34.49 B | N |
| ATOM | 1154 | CA | THR | B | 70 | 1.244 | −19.635 | 21.652 | 1.00 | 40.30 B | C |
| ATOM | 1155 | C | THR | B | 70 | 2.209 | −19.763 | 22.824 | 1.00 | 43.81 B | C |
| ATOM | 1156 | O | THR | B | 70 | 1.792 | −19.786 | 23.982 | 1.00 | 52.58 B | O |
| ATOM | 1157 | CB | THR | B | 70 | 0.812 | −21.030 | 21.152 | 1.00 | 41.92 B | C |
| ATOM | 1158 | OG1 | THR | B | 70 | 1.903 | −21.656 | 20.466 | 1.00 | 51.10 B | O |
| ATOM | 1159 | CG2 | THR | B | 70 | −0.368 | −20.909 | 20.198 | 1.00 | 38.12 B | C |
| ATOM | 1160 | N | GLU | B | 71 | 3.501 | −19.835 | 22.521 | 1.00 | 44.26 B | N |
| ATOM | 1161 | CA | GLU | B | 71 | 4.524 | −19.856 | 23.561 | 1.00 | 52.17 B | C |
| ATOM | 1162 | C | GLU | B | 71 | 4.573 | −18.509 | 24.278 | 1.00 | 47.45 B | C |
| ATOM | 1163 | O | GLU | B | 71 | 4.934 | −18.430 | 25.452 | 1.00 | 51.35 B | O |
| ATOM | 1164 | CB | GLU | B | 71 | 5.899 | −20.193 | 22.970 | 1.00 | 41.33 B | C |
| ATOM | 1165 | N | TYR | B | 72 | 4.206 | −17.453 | 23.557 | 1.00 | 47.78 B | N |
| ATOM | 1166 | CA | TYR | B | 72 | 4.186 | −16.103 | 24.107 | 1.00 | 49.37 B | C |
| ATOM | 1167 | C | TYR | B | 72 | 3.136 | −16.007 | 25.205 | 1.00 | 57.87 B | C |
| ATOM | 1168 | O | TYR | B | 72 | 3.440 | −15.631 | 26.340 | 1.00 | 57.55 B | O |
| ATOM | 1169 | CB | TYR | B | 72 | 3.871 | −15.097 | 22.997 | 1.00 | 50.17 B | C |
| ATOM | 1170 | CG | TYR | B | 72 | 4.235 | −13.657 | 23.302 | 1.00 | 46.16 B | C |
| ATOM | 1171 | CD1 | TYR | B | 72 | 5.430 | −13.114 | 22.846 | 1.00 | 41.62 B | C |
| ATOM | 1172 | CD2 | TYR | B | 72 | 3.374 | −12.833 | 24.024 | 1.00 | 47.37 B | C |
| ATOM | 1173 | CE1 | TYR | B | 72 | 5.768 | −11.798 | 23.107 | 1.00 | 38.98 B | C |
| ATOM | 1174 | CE2 | TYR | B | 72 | 3.702 | −11.509 | 24.291 | 1.00 | 41.15 B | C |
| ATOM | 1175 | CZ | TYR | B | 72 | 4.903 | −11.000 | 23.828 | 1.00 | 46.34 B | C |
| ATOM | 1176 | OH | TYR | B | 72 | 5.246 | −9.691 | 24.081 | 1.00 | 48.06 B | O |
| ATOM | 1177 | N | ASN | B | 73 | 1.900 | −16.354 | 24.854 | 1.00 | 73.31 B | N |
| ATOM | 1178 | CA | ASN | B | 73 | 0.776 | −16.302 | 25.784 | 1.00 | 74.49 B | C |
| ATOM | 1179 | C | ASN | B | 73 | 0.903 | −17.343 | 26.894 | 1.00 | 82.99 B | C |
| ATOM | 1180 | O | ASN | B | 73 | 0.162 | −18.328 | 26.926 | 1.00 | 80.74 B | O |
| ATOM | 1181 | CB | ASN | B | 73 | −0.557 | −16.487 | 25.042 | 1.00 | 71.38 B | C |
| ATOM | 1182 | CG | ASN | B | 73 | −0.860 | −15.349 | 24.071 | 1.00 | 61.49 B | C |
| ATOM | 1183 | OD1 | ASN | B | 73 | −1.840 | −14.621 | 24.237 | 1.00 | 64.97 B | O |
| ATOM | 1184 | ND2 | ASN | B | 73 | −0.023 | −15.198 | 23.053 | 1.00 | 53.52 B | N |
| TER | | | | | | | | | | | |
| ATOM | 1185 | O5' | ADE | E | 1 | −18.730 | −9.736 | −18.656 | 1.00 | 29.47 E | O |
| ATOM | 1186 | C5' | ADE | E | 1 | −18.988 | −11.075 | −19.073 | 1.00 | 30.92 E | C |
| ATOM | 1187 | C4' | ADE | E | 1 | −17.709 | −11.792 | −19.477 | 1.00 | 31.56 E | C |
| ATOM | 1188 | O4' | ADE | E | 1 | −17.094 | −11.116 | −20.606 | 1.00 | 28.61 E | O |
| ATOM | 1189 | C3' | ADE | E | 1 | −16.621 | −11.853 | −18.406 | 1.00 | 35.77 E | C |
| ATOM | 1190 | O3' | ADE | E | 1 | −15.887 | −13.057 | −18.533 | 1.00 | 31.63 E | O |
| ATOM | 1191 | C2' | ADE | E | 1 | −15.739 | −10.670 | −18.779 | 1.00 | 36.34 E | C |
| ATOM | 1192 | C1' | ADE | E | 1 | −15.738 | −10.885 | −20.284 | 1.00 | 30.42 E | C |
| ATOM | 1193 | N9 | ADE | E | 1 | −15.256 | −9.747 | −21.050 | 1.00 | 30.35 E | N |
| ATOM | 1194 | C8 | ADE | E | 1 | −14.044 | −9.644 | −21.669 | 1.00 | 31.25 E | C |
| ATOM | 1195 | N7 | ADE | E | 1 | −13.867 | −8.508 | −22.293 | 1.00 | 29.12 E | N |
| ATOM | 1196 | C5 | ADE | E | 1 | −15.041 | −7.823 | −22.062 | 1.00 | 24.57 E | C |
| ATOM | 1197 | C6 | ADE | E | 1 | −15.465 | −6.552 | −22.461 | 1.00 | 26.42 E | C |

TABLE 1-continued

| | | | | | | | | | | | |
|---|---|---|---|---|---|---|---|---|---|---|---|
| ATOM | 1198 | N6 | ADE | E | 1 | −14.705 | −5.753 | −23.207 | 1.00 | 29.08 E | N |
| ATOM | 1199 | N1 | ADE | E | 1 | −16.693 | −6.147 | −22.069 | 1.00 | 32.94 E | N |
| ATOM | 1200 | C2 | ADE | E | 1 | −17.434 | −6.980 | −21.321 | 1.00 | 32.52 E | C |
| ATOM | 1201 | N3 | ADE | E | 1 | −17.138 | −8.206 | −20.882 | 1.00 | 29.17 E | N |
| ATOM | 1202 | C4 | ADE | E | 1 | −15.913 | −8.567 | −21.297 | 1.00 | 28.60 E | C |
| ATOM | 1203 | P | ADE | E | 2 | −14.960 | −13.540 | −17.328 | 1.00 | 39.32 E | P |
| ATOM | 1204 | OP1 | ADE | E | 2 | −14.609 | −14.955 | −17.546 | 1.00 | 40.48 E | O |
| ATOM | 1205 | OP2 | ADE | E | 2 | −15.600 | −13.127 | −16.063 | 1.00 | 34.58 E | O |
| ATOM | 1206 | O5' | ADE | E | 2 | −13.642 | −12.657 | −17.522 | 1.00 | 46.72 E | O |
| ATOM | 1207 | C5' | ADE | E | 2 | −12.623 | −13.009 | −18.459 | 1.00 | 35.44 E | C |
| ATOM | 1208 | C4' | ADE | E | 2 | −11.485 | −12.005 | −18.354 | 1.00 | 37.56 E | C |
| ATOM | 1209 | O4' | ADE | E | 2 | −11.957 | −10.700 | −18.795 | 1.00 | 40.64 E | O |
| ATOM | 1210 | C3' | ADE | E | 2 | −10.967 | −11.762 | −16.938 | 1.00 | 35.93 E | C |
| ATOM | 1211 | O3' | ADE | E | 2 | −9.635 | −11.291 | −16.984 | 1.00 | 43.80 E | O |
| ATOM | 1212 | C2' | ADE | E | 2 | −11.869 | −10.630 | −16.474 | 1.00 | 37.03 E | C |
| ATOM | 1213 | C1' | ADE | E | 2 | −11.769 | −9.786 | −17.734 | 1.00 | 32.46 E | C |
| ATOM | 1214 | N9 | ADE | E | 2 | −12.739 | −8.703 | −17.801 | 1.00 | 30.38 E | N |
| ATOM | 1215 | C8 | ADE | E | 2 | −13.795 | −8.479 | −16.959 | 1.00 | 33.19 E | C |
| ATOM | 1216 | N7 | ADE | E | 2 | −14.493 | −7.404 | −17.259 | 1.00 | 31.00 E | N |
| ATOM | 1217 | C5 | ADE | E | 2 | −13.843 | −6.893 | −18.372 | 1.00 | 30.47 E | C |
| ATOM | 1218 | C6 | ADE | E | 2 | −14.084 | −5.764 | −19.174 | 1.00 | 29.69 E | C |
| ATOM | 1219 | N6 | ADE | E | 2 | −15.097 | −4.919 | −18.959 | 1.00 | 30.34 E | N |
| ATOM | 1220 | N1 | ADE | E | 2 | −13.242 | −5.537 | −20.202 | 1.00 | 27.90 E | N |
| ATOM | 1221 | C2 | ADE | E | 2 | −12.230 | −6.383 | −20.416 | 1.00 | 27.22 E | C |
| ATOM | 1222 | N3 | ADE | E | 2 | −11.905 | −7.479 | −19.735 | 1.00 | 27.95 E | N |
| ATOM | 1223 | C4 | ADE | E | 2 | −12.760 | −7.679 | −18.718 | 1.00 | 29.70 E | C |
| ATOM | 1224 | P | ADE | E | 3 | −8.398 | −12.239 | −16.627 | 1.00 | 42.48 E | P |
| ATOM | 1225 | OP1 | ADE | E | 3 | −8.627 | −13.552 | −17.273 | 1.00 | 38.14 E | O |
| ATOM | 1226 | OP2 | ADE | E | 3 | −8.173 | −12.152 | −15.165 | 1.00 | 39.30 E | O |
| ATOM | 1227 | O5' | ADE | E | 3 | −7.186 | −11.486 | −17.357 | 1.00 | 35.22 E | O |
| ATOM | 1228 | C5' | ADE | E | 3 | −7.251 | −11.226 | −18.752 | 1.00 | 29.83 E | C |
| ATOM | 1229 | C4' | ADE | E | 3 | −6.680 | −9.856 | −19.079 | 1.00 | 33.29 E | C |
| ATOM | 1230 | O4' | ADE | E | 3 | −7.724 | −8.849 | −19.015 | 1.00 | 30.41 E | O |
| ATOM | 1231 | C3' | ADE | E | 3 | −5.559 | −9.369 | −18.163 | 1.00 | 40.46 E | C |
| ATOM | 1232 | O3' | ADE | E | 3 | −4.525 | −8.798 | −18.955 | 1.00 | 37.31 E | O |
| ATOM | 1233 | C2' | ADE | E | 3 | −6.237 | −8.316 | −17.280 | 1.00 | 34.29 E | C |
| ATOM | 1234 | C1' | ADE | E | 3 | −7.283 | −7.751 | −18.235 | 1.00 | 37.00 E | C |
| ATOM | 1235 | N9 | ADE | E | 3 | −8.454 | −7.181 | −17.576 | 1.00 | 31.30 E | N |
| ATOM | 1236 | C8 | ADE | E | 3 | −9.136 | −7.698 | −16.508 | 1.00 | 30.32 E | C |
| ATOM | 1237 | N7 | ADE | E | 3 | −10.162 | −6.971 | −16.133 | 1.00 | 31.10 E | N |
| ATOM | 1238 | C5 | ADE | E | 3 | −10.153 | −5.905 | −17.019 | 1.00 | 29.56 E | C |
| ATOM | 1239 | C6 | ADE | E | 3 | −10.988 | −4.779 | −17.159 | 1.00 | 28.07 E | C |
| ATOM | 1240 | N6 | ADE | E | 3 | −12.036 | −4.540 | −16.363 | 1.00 | 32.00 E | N |
| ATOM | 1241 | N1 | ADE | E | 3 | −10.700 | −3.905 | −18.150 | 1.00 | 32.19 E | N |
| ATOM | 1242 | C2 | ADE | E | 3 | −9.650 | −4.146 | −18.946 | 1.00 | 29.48 E | C |
| ATOM | 1243 | N3 | ADE | E | 3 | −8.799 | −5.172 | −18.911 | 1.00 | 29.41 E | N |
| ATOM | 1244 | C4 | ADE | E | 3 | −9.108 | −6.019 | −17.917 | 1.00 | 28.05 E | C |
| ATOM | 1245 | P | GUA | E | 4 | −3.192 | −8.251 | −18.255 | 1.00 | 44.81 E | P |
| ATOM | 1246 | OP1 | GUA | E | 4 | −2.061 | −8.508 | −19.174 | 1.00 | 26.47 E | O |
| ATOM | 1247 | OP2 | GUA | E | 4 | −3.173 | −8.771 | −16.867 | 1.00 | 42.97 E | O |
| ATOM | 1248 | O5' | GUA | E | 4 | −3.445 | −6.670 | −18.204 | 1.00 | 41.54 E | O |
| ATOM | 1249 | C5' | GUA | E | 4 | −3.525 | −5.970 | −19.443 | 1.00 | 41.38 E | C |
| ATOM | 1250 | C4' | GUA | E | 4 | −4.139 | −4.590 | −19.282 | 1.00 | 40.49 E | C |
| ATOM | 1251 | O4' | GUA | E | 4 | −5.362 | −4.659 | −18.507 | 1.00 | 41.29 E | O |
| ATOM | 1252 | C3' | GUA | E | 4 | −3.273 | −3.548 | −18.579 | 1.00 | 49.70 E | C |
| ATOM | 1253 | O3' | GUA | E | 4 | −3.057 | −2.496 | −19.513 | 1.00 | 51.54 E | O |
| ATOM | 1254 | C2' | GUA | E | 4 | −4.099 | −3.111 | −17.362 | 1.00 | 40.72 E | C |
| ATOM | 1255 | C1' | GUA | E | 4 | −5.513 | −3.432 | −17.833 | 1.00 | 35.99 E | C |
| ATOM | 1256 | N9 | GUA | E | 4 | −6.536 | −3.626 | −16.805 | 1.00 | 35.36 E | N |
| ATOM | 1257 | C8 | GUA | E | 4 | −6.606 | −4.633 | −15.869 | 1.00 | 31.20 E | C |
| ATOM | 1258 | N7 | GUA | E | 4 | −7.657 | −4.550 | −15.094 | 1.00 | 30.27 E | N |
| ATOM | 1259 | C5 | GUA | E | 4 | −8.334 | −3.418 | −15.544 | 1.00 | 31.07 E | C |
| ATOM | 1260 | C6 | GUA | E | 4 | −9.545 | −2.824 | −15.091 | 1.00 | 29.65 E | C |
| ATOM | 1261 | O6 | GUA | E | 4 | −10.299 | −3.183 | −14.166 | 1.00 | 25.90 E | O |
| ATOM | 1262 | N1 | GUA | E | 4 | −9.863 | −1.693 | −15.837 | 1.00 | 27.69 E | N |
| ATOM | 1263 | C2 | GUA | E | 4 | −9.114 | −1.197 | −16.878 | 1.00 | 32.22 E | C |
| ATOM | 1264 | N2 | GUA | E | 4 | −9.586 | −0.090 | −17.471 | 1.00 | 36.73 E | N |
| ATOM | 1265 | N3 | GUA | E | 4 | −7.981 | −1.739 | −17.312 | 1.00 | 30.68 E | N |
| ATOM | 1266 | C4 | GUA | E | 4 | −7.655 | −2.844 | −16.601 | 1.00 | 32.71 E | C |
| ATOM | 1267 | P | CYT | E | 5 | −2.178 | −1.210 | −19.151 | 1.00 | 55.63 E | P |
| ATOM | 1268 | OP1 | CYT | E | 5 | −1.471 | −0.815 | −20.393 | 1.00 | 38.22 E | O |
| ATOM | 1269 | OP2 | CYT | E | 5 | −1.446 | −1.473 | −17.889 | 1.00 | 40.16 E | O |
| ATOM | 1270 | O5' | CYT | E | 5 | −3.303 | −0.112 | −18.855 | 1.00 | 37.38 E | O |
| ATOM | 1271 | C5' | CYT | E | 5 | −4.265 | 0.131 | −19.866 | 1.00 | 33.01 E | C |
| ATOM | 1272 | C4' | CYT | E | 5 | −5.032 | 1.402 | −19.579 | 1.00 | 33.11 E | C |
| ATOM | 1273 | O4' | CYT | E | 5 | −6.050 | 1.157 | −18.576 | 1.00 | 30.77 E | O |
| ATOM | 1274 | C3' | CYT | E | 5 | −4.180 | 2.557 | −19.075 | 1.00 | 34.24 E | C |
| ATOM | 1275 | O3' | CYT | E | 5 | −4.639 | 3.713 | −19.760 | 1.00 | 39.20 E | O |
| ATOM | 1276 | C2' | CYT | E | 5 | −4.446 | 2.561 | −17.565 | 1.00 | 31.20 E | C |
| ATOM | 1277 | C1' | CYT | E | 5 | −5.863 | 2.000 | −17.463 | 1.00 | 28.63 E | C |

TABLE 1-continued

| | | | | | | | | | | |
|---|---|---|---|---|---|---|---|---|---|---|
| ATOM | 1278 | N1 | CYT | E | 5 | −6.146 | 1.145 | −16.274 | 1.00 | 29.46 E | N |
| ATOM | 1279 | C2 | CYT | E | 5 | −7.212 | 1.483 | −15.439 | 1.00 | 26.08 E | C |
| ATOM | 1280 | O2 | CYT | E | 5 | −7.885 | 2.490 | −15.698 | 1.00 | 28.38 E | O |
| ATOM | 1281 | N3 | CYT | E | 5 | −7.479 | 0.700 | −14.367 | 1.00 | 26.72 E | N |
| ATOM | 1282 | C4 | CYT | E | 5 | −6.735 | −0.378 | −14.115 | 1.00 | 25.28 E | C |
| ATOM | 1283 | N4 | CYT | E | 5 | −7.053 | −1.106 | −13.036 | 1.00 | 22.58 E | N |
| ATOM | 1284 | C5 | CYT | E | 5 | −5.642 | −0.745 | −14.956 | 1.00 | 25.38 E | C |
| ATOM | 1285 | C6 | CYT | E | 5 | −5.390 | 0.038 | −16.014 | 1.00 | 30.65 E | C |
| ATOM | 1286 | P | THY | E | 6 | −4.170 | 5.191 | −19.383 | 1.00 | 60.37 E | P |
| ATOM | 1287 | OP1 | THY | E | 6 | −4.538 | 6.060 | −20.525 | 1.00 | 54.22 E | O |
| ATOM | 1288 | OP2 | THY | E | 6 | −2.773 | 5.142 | −18.892 | 1.00 | 49.93 E | O |
| ATOM | 1289 | O5' | THY | E | 6 | −5.109 | 5.566 | −18.140 | 1.00 | 47.68 E | O |
| ATOM | 1290 | C5' | THY | E | 6 | −6.386 | 6.162 | −18.345 | 1.00 | 46.46 E | C |
| ATOM | 1291 | C4' | THY | E | 6 | −6.806 | 6.961 | −17.125 | 1.00 | 38.37 E | C |
| ATOM | 1292 | O4' | THY | E | 6 | −7.109 | 6.050 | −16.035 | 1.00 | 39.69 E | O |
| ATOM | 1293 | C3' | THY | E | 6 | −5.735 | 7.892 | −16.572 | 1.00 | 43.33 E | C |
| ATOM | 1294 | O3' | THY | E | 6 | −6.340 | 8.950 | −15.857 | 1.00 | 49.28 E | O |
| ATOM | 1295 | C2' | THY | E | 6 | −5.027 | 6.982 | −15.582 | 1.00 | 39.84 E | C |
| ATOM | 1296 | C1' | THY | E | 6 | −6.267 | 6.372 | −14.942 | 1.00 | 44.31 E | C |
| ATOM | 1297 | N1 | THY | E | 6 | −5.997 | 5.155 | −14.132 | 1.00 | 36.55 E | N |
| ATOM | 1298 | C2 | THY | E | 6 | −6.920 | 4.771 | −13.188 | 1.00 | 34.38 E | C |
| ATOM | 1299 | O2 | THY | E | 6 | −7.955 | 5.381 | −12.988 | 1.00 | 33.38 E | O |
| ATOM | 1300 | N3 | THY | E | 6 | −6.584 | 3.638 | −12.489 | 1.00 | 29.23 E | N |
| ATOM | 1301 | C4 | THY | E | 6 | −5.440 | 2.878 | −12.640 | 1.00 | 30.85 E | C |
| ATOM | 1302 | O4 | THY | E | 6 | −5.220 | 1.878 | −11.967 | 1.00 | 34.06 E | O |
| ATOM | 1303 | C5 | THY | E | 6 | −4.515 | 3.343 | −13.642 | 1.00 | 32.80 E | C |
| ATOM | 1304 | C7 | THY | E | 6 | −3.238 | 2.592 | −13.883 | 1.00 | 27.26 E | C |
| ATOM | 1305 | C6 | THY | E | 6 | −4.831 | 4.446 | −14.332 | 1.00 | 30.87 E | C |
| ATOM | 1306 | P | ADE | E | 7 | −6.618 | 10.359 | −16.554 | 1.00 | 45.58 E | P |
| ATOM | 1307 | OP1 | ADE | E | 7 | −7.118 | 10.099 | −17.923 | 1.00 | 48.75 E | O |
| ATOM | 1308 | OP2 | ADE | E | 7 | −5.421 | 11.205 | −16.345 | 1.00 | 50.29 E | O |
| ATOM | 1309 | O5' | ADE | E | 7 | −7.804 | 10.955 | −15.662 | 1.00 | 37.42 E | O |
| ATOM | 1310 | C5' | ADE | E | 7 | −9.051 | 10.284 | −15.612 | 1.00 | 40.53 E | C |
| ATOM | 1311 | C4' | ADE | E | 7 | −9.601 | 10.242 | −14.196 | 1.00 | 40.88 E | C |
| ATOM | 1312 | O4' | ADE | E | 7 | −8.962 | 9.183 | −13.434 | 1.00 | 42.29 E | O |
| ATOM | 1313 | C3' | ADE | E | 7 | −9.423 | 11.515 | −13.380 | 1.00 | 43.86 E | C |
| ATOM | 1314 | O3' | ADE | E | 7 | −10.618 | 11.704 | −12.623 | 1.00 | 46.18 E | O |
| ATOM | 1315 | C2' | ADE | E | 7 | −8.191 | 11.211 | −12.518 | 1.00 | 38.63 E | C |
| ATOM | 1316 | C1' | ADE | E | 7 | −8.329 | 9.708 | −12.280 | 1.00 | 40.37 E | C |
| ATOM | 1317 | N9 | ADE | E | 7 | −7.083 | 8.955 | −12.110 | 1.00 | 35.39 E | N |
| ATOM | 1318 | C8 | ADE | E | 7 | −5.878 | 9.165 | −12.724 | 1.00 | 38.43 E | C |
| ATOM | 1319 | N7 | ADE | E | 7 | −4.946 | 8.303 | −12.375 | 1.00 | 38.83 E | N |
| ATOM | 1320 | C5 | ADE | E | 7 | −5.583 | 7.461 | −11.475 | 1.00 | 32.45 E | C |
| ATOM | 1321 | C6 | ADE | E | 7 | −5.153 | 6.335 | −10.738 | 1.00 | 28.45 E | C |
| ATOM | 1322 | N6 | ADE | E | 7 | −3.917 | 5.831 | −10.788 | 1.00 | 23.96 E | N |
| ATOM | 1323 | N1 | ADE | E | 7 | −6.052 | 5.733 | −9.930 | 1.00 | 28.10 E | N |
| ATOM | 1324 | C2 | ADE | E | 7 | −7.293 | 6.222 | −9.866 | 1.00 | 28.25 E | C |
| ATOM | 1325 | N3 | ADE | E | 7 | −7.814 | 7.266 | −10.509 | 1.00 | 34.76 E | N |
| ATOM | 1326 | C4 | ADE | E | 7 | −6.901 | 7.849 | −11.306 | 1.00 | 35.01 E | C |
| ATOM | 1327 | P | THY | E | 8 | −10.849 | 13.012 | −11.730 | 1.00 | 56.64 E | P |
| ATOM | 1328 | OP1 | THY | E | 8 | −12.282 | 13.371 | −11.831 | 1.00 | 50.90 E | O |
| ATOM | 1329 | OP2 | THY | E | 8 | −9.782 | 13.995 | −12.048 | 1.00 | 41.51 E | O |
| ATOM | 1330 | O5' | THY | E | 8 | −10.591 | 12.465 | −10.254 | 1.00 | 37.60 E | O |
| ATOM | 1331 | C5' | THY | E | 8 | −11.256 | 11.287 | −9.857 | 1.00 | 37.93 E | C |
| ATOM | 1332 | C4' | THY | E | 8 | −10.552 | 10.694 | −8.657 | 1.00 | 38.57 E | C |
| ATOM | 1333 | O4' | THY | E | 8 | −9.292 | 10.106 | −9.047 | 1.00 | 40.12 E | O |
| ATOM | 1334 | C3' | THY | E | 8 | −10.174 | 11.692 | −7.570 | 1.00 | 30.77 E | C |
| ATOM | 1335 | O3' | THY | E | 8 | −11.212 | 11.693 | −6.602 | 1.00 | 31.18 E | O |
| ATOM | 1336 | C2' | THY | E | 8 | −8.839 | 11.161 | −7.031 | 1.00 | 28.75 E | C |
| ATOM | 1337 | C1' | THY | E | 8 | −8.637 | 9.870 | −7.823 | 1.00 | 31.57 E | C |
| ATOM | 1338 | N1 | THY | E | 8 | −7.211 | 9.446 | −8.069 | 1.00 | 30.96 E | N |
| ATOM | 1339 | C2 | THY | E | 8 | −6.738 | 8.325 | −7.418 | 1.00 | 29.46 E | C |
| ATOM | 1340 | O2 | THY | E | 8 | −7.411 | 7.658 | −6.647 | 1.00 | 28.41 E | O |
| ATOM | 1341 | N3 | THY | E | 8 | −5.434 | 8.008 | −7.696 | 1.00 | 25.51 E | N |
| ATOM | 1342 | C4 | THY | E | 8 | −4.573 | 8.678 | −8.543 | 1.00 | 28.41 E | C |
| ATOM | 1343 | O4 | THY | E | 8 | −3.414 | 8.304 | −8.725 | 1.00 | 24.27 E | O |
| ATOM | 1344 | C5 | THY | E | 8 | −5.133 | 9.838 | −9.195 | 1.00 | 28.63 E | C |
| ATOM | 1345 | C7 | THY | E | 8 | −4.291 | 10.650 | −10.138 | 1.00 | 36.79 E | C |
| ATOM | 1346 | C6 | THY | E | 8 | −6.405 | 10.163 | −8.930 | 1.00 | 26.96 E | C |
| ATOM | 1347 | P | THY | E | 9 | −11.056 | 12.419 | −5.183 | 1.00 | 42.41 E | P |
| ATOM | 1348 | OP1 | THY | E | 9 | −12.415 | 12.694 | −4.663 | 1.00 | 31.14 E | O |
| ATOM | 1349 | OP2 | THY | E | 9 | −10.054 | 13.502 | −5.314 | 1.00 | 35.31 E | O |
| ATOM | 1350 | O5' | THY | E | 9 | −10.434 | 11.264 | −4.279 | 1.00 | 37.55 E | O |
| ATOM | 1351 | C5' | THY | E | 9 | −11.266 | 10.160 | −3.990 | 1.00 | 35.57 E | C |
| ATOM | 1352 | C4' | THY | E | 9 | −10.478 | 9.121 | −3.227 | 1.00 | 33.83 E | C |
| ATOM | 1353 | O4' | THY | E | 9 | −9.220 | 8.899 | −3.906 | 1.00 | 29.86 E | O |
| ATOM | 1354 | C3' | THY | E | 9 | −10.144 | 9.494 | −1.786 | 1.00 | 28.03 E | C |
| ATOM | 1355 | O3' | THY | E | 9 | −10.370 | 8.323 | −1.022 | 1.00 | 31.20 E | O |
| ATOM | 1356 | C2' | THY | E | 9 | −8.675 | 9.907 | −1.859 | 1.00 | 27.45 E | C |
| ATOM | 1357 | C1' | THY | E | 9 | −8.172 | 8.985 | −2.967 | 1.00 | 31.01 E | C |

TABLE 1-continued

| | | | | | | | | | | | |
|---|---|---|---|---|---|---|---|---|---|---|---|
| ATOM | 1358 | N1 | THY | E | 9 | −6.962 | 9.450 | −3.704 | 1.00 | 28.12 E | N |
| ATOM | 1359 | C2 | THY | E | 9 | −5.909 | 8.582 | −3.811 | 1.00 | 25.18 E | C |
| ATOM | 1360 | O2 | THY | E | 9 | −5.927 | 7.464 | −3.328 | 1.00 | 26.89 E | O |
| ATOM | 1361 | N3 | THY | E | 9 | −4.838 | 9.074 | −4.507 | 1.00 | 26.79 E | N |
| ATOM | 1362 | C4 | THY | E | 9 | −4.717 | 10.316 | −5.095 | 1.00 | 24.43 E | C |
| ATOM | 1363 | O4 | THY | E | 9 | −3.708 | 10.664 | −5.700 | 1.00 | 27.08 E | O |
| ATOM | 1364 | C5 | THY | E | 9 | −5.853 | 11.178 | −4.945 | 1.00 | 26.20 E | C |
| ATOM | 1365 | C7 | THY | E | 9 | −5.819 | 12.553 | −5.545 | 1.00 | 26.68 E | C |
| ATOM | 1366 | C6 | THY | E | 9 | −6.911 | 10.711 | −4.266 | 1.00 | 30.99 E | C |
| ATOM | 1367 | P | ADE | E | 10 | −10.116 | 8.233 | 0.551 | 1.00 | 27.69 E | P |
| ATOM | 1368 | OP1 | ADE | E | 10 | −10.999 | 7.180 | 1.102 | 1.00 | 25.31 E | O |
| ATOM | 1369 | OP2 | ADE | E | 10 | −10.161 | 9.594 | 1.123 | 1.00 | 31.49 E | O |
| ATOM | 1370 | O5' | ADE | E | 10 | −8.616 | 7.674 | 0.595 | 1.00 | 37.35 E | O |
| ATOM | 1371 | C5' | ADE | E | 10 | −8.361 | 6.335 | 0.171 | 1.00 | 23.82 E | C |
| ATOM | 1372 | C4' | ADE | E | 10 | −6.969 | 5.856 | 0.564 | 1.00 | 22.72 E | C |
| ATOM | 1373 | O4' | ADE | E | 10 | −5.977 | 6.502 | −0.266 | 1.00 | 23.11 E | O |
| ATOM | 1374 | C3' | ADE | E | 10 | −6.531 | 6.128 | 2.002 | 1.00 | 25.58 E | C |
| ATOM | 1375 | O3' | ADE | E | 10 | −5.853 | 4.975 | 2.479 | 1.00 | 22.92 E | O |
| ATOM | 1376 | C2' | ADE | E | 10 | −5.596 | 7.330 | 1.881 | 1.00 | 19.12 E | C |
| ATOM | 1377 | C1' | ADE | E | 10 | −4.945 | 7.047 | 0.533 | 1.00 | 23.66 E | C |
| ATOM | 1378 | N9 | ADE | E | 10 | −4.450 | 8.219 | −0.185 | 1.00 | 23.63 E | N |
| ATOM | 1379 | C8 | ADE | E | 10 | −5.137 | 9.377 | −0.427 | 1.00 | 20.43 E | C |
| ATOM | 1380 | N7 | ADE | E | 10 | −4.449 | 10.259 | −1.116 | 1.00 | 21.56 E | N |
| ATOM | 1381 | C5 | ADE | E | 10 | −3.232 | 9.637 | −1.348 | 1.00 | 20.27 E | C |
| ATOM | 1382 | C6 | ADE | E | 10 | −2.065 | 10.050 | −2.026 | 1.00 | 23.27 E | C |
| ATOM | 1383 | N6 | ADE | E | 10 | −1.935 | 11.243 | −2.621 | 1.00 | 22.55 E | N |
| ATOM | 1384 | N1 | ADE | E | 10 | −1.028 | 9.186 | −2.072 | 1.00 | 21.68 E | N |
| ATOM | 1385 | C2 | ADE | E | 10 | −1.159 | 7.995 | −1.473 | 1.00 | 20.08 E | C |
| ATOM | 1386 | N3 | ADE | E | 10 | −2.204 | 7.498 | −0.811 | 1.00 | 21.84 E | N |
| ATOM | 1387 | C4 | ADE | E | 10 | −3.218 | 8.376 | −0.783 | 1.00 | 20.33 E | C |
| ATOM | 1388 | P | THY | E | 11 | −5.251 | 4.906 | 3.959 | 1.00 | 30.15 E | P |
| ATOM | 1389 | OP1 | THY | E | 11 | −5.489 | 3.533 | 4.453 | 1.00 | 30.86 E | O |
| ATOM | 1390 | OP2 | THY | E | 11 | −5.725 | 6.061 | 4.753 | 1.00 | 22.38 E | O |
| ATOM | 1391 | O5' | THY | E | 11 | −3.686 | 5.080 | 3.667 | 1.00 | 31.02 E | O |
| ATOM | 1392 | C5' | THY | E | 11 | −3.054 | 4.141 | 2.808 | 1.00 | 24.15 E | C |
| ATOM | 1393 | C4' | THY | E | 11 | −1.576 | 4.434 | 2.624 | 1.00 | 27.89 E | C |
| ATOM | 1394 | O4' | THY | E | 11 | −1.390 | 5.685 | 1.914 | 1.00 | 25.80 E | O |
| ATOM | 1395 | C3' | THY | E | 11 | −0.762 | 4.531 | 3.910 | 1.00 | 29.91 E | C |
| ATOM | 1396 | O3' | THY | E | 11 | 0.381 | 3.686 | 3.729 | 1.00 | 26.16 E | O |
| ATOM | 1397 | C2' | THY | E | 11 | −0.441 | 6.029 | 4.018 | 1.00 | 26.53 E | C |
| ATOM | 1398 | C1' | THY | E | 11 | −0.387 | 6.444 | 2.547 | 1.00 | 25.90 E | C |
| ATOM | 1399 | N1 | THY | E | 11 | −0.686 | 7.873 | 2.192 | 1.00 | 23.31 E | N |
| ATOM | 1400 | C2 | THY | E | 11 | 0.223 | 8.558 | 1.409 | 1.00 | 24.11 E | C |
| ATOM | 1401 | O2 | THY | E | 11 | 1.270 | 8.088 | 1.011 | 1.00 | 29.11 E | O |
| ATOM | 1402 | N3 | THY | E | 11 | −0.121 | 9.841 | 1.100 | 1.00 | 22.87 E | N |
| ATOM | 1403 | C4 | THY | E | 11 | −1.265 | 10.498 | 1.485 | 1.00 | 28.65 E | C |
| ATOM | 1404 | O4 | THY | E | 11 | −1.474 | 11.662 | 1.151 | 1.00 | 36.71 E | O |
| ATOM | 1405 | C5 | THY | E | 11 | −2.185 | 9.732 | 2.295 | 1.00 | 24.77 E | C |
| ATOM | 1406 | C7 | THY | E | 11 | −3.464 | 10.372 | 2.759 | 1.00 | 24.15 E | C |
| ATOM | 1407 | C6 | THY | E | 11 | −1.862 | 8.466 | 2.606 | 1.00 | 22.01 E | C |
| ATOM | 1408 | P | THY | E | 12 | 1.421 | 3.356 | 4.904 | 1.00 | 25.44 E | P |
| ATOM | 1409 | OP1 | THY | E | 12 | 2.065 | 2.075 | 4.536 | 1.00 | 24.55 E | O |
| ATOM | 1410 | OP2 | THY | E | 12 | 0.765 | 3.505 | 6.222 | 1.00 | 32.62 E | O |
| ATOM | 1411 | O5' | THY | E | 12 | 2.496 | 4.537 | 4.755 | 1.00 | 26.81 E | O |
| ATOM | 1412 | C5' | THY | E | 12 | 3.296 | 4.563 | 3.566 | 1.00 | 21.48 E | C |
| ATOM | 1413 | C4' | THY | E | 12 | 4.129 | 5.825 | 3.493 | 1.00 | 23.82 E | C |
| ATOM | 1414 | O4' | THY | E | 12 | 3.290 | 6.969 | 3.188 | 1.00 | 23.67 E | O |
| ATOM | 1415 | C3' | THY | E | 12 | 4.867 | 6.182 | 4.783 | 1.00 | 24.81 E | C |
| ATOM | 1416 | O3' | THY | E | 12 | 6.206 | 6.506 | 4.466 | 1.00 | 25.36 E | O |
| ATOM | 1417 | C2' | THY | E | 12 | 4.120 | 7.416 | 5.290 | 1.00 | 18.68 E | C |
| ATOM | 1418 | C1' | THY | E | 12 | 3.788 | 8.050 | 3.948 | 1.00 | 20.51 E | C |
| ATOM | 1419 | N1 | THY | E | 12 | 2.771 | 9.121 | 3.988 | 1.00 | 21.40 E | N |
| ATOM | 1420 | C2 | THY | E | 12 | 2.955 | 10.241 | 3.198 | 1.00 | 22.05 E | C |
| ATOM | 1421 | O2 | THY | E | 12 | 3.910 | 10.394 | 2.460 | 1.00 | 21.47 E | O |
| ATOM | 1422 | N3 | THY | E | 12 | 1.967 | 11.186 | 3.304 | 1.00 | 18.78 E | N |
| ATOM | 1423 | C4 | THY | E | 12 | 0.843 | 11.109 | 4.096 | 1.00 | 19.13 E | C |
| ATOM | 1424 | O4 | THY | E | 12 | 0.012 | 12.009 | 4.111 | 1.00 | 26.75 E | O |
| ATOM | 1425 | C5 | THY | E | 12 | 0.713 | 9.915 | 4.898 | 1.00 | 18.25 E | C |
| ATOM | 1426 | C7 | THY | E | 12 | −0.472 | 9.735 | 5.805 | 1.00 | 19.51 E | C |
| ATOM | 1427 | C6 | THY | E | 12 | 1.670 | 8.989 | 4.811 | 1.00 | 19.46 E | C |
| ATOM | 1428 | P | ADE | E | 13 | 7.377 | 5.414 | 4.483 | 1.00 | 30.98 E | P |
| ATOM | 1429 | OP1 | ADE | E | 13 | 7.071 | 4.389 | 3.460 | 1.00 | 28.50 E | O |
| ATOM | 1430 | OP2 | ADE | E | 13 | 7.606 | 5.022 | 5.896 | 1.00 | 23.43 E | O |
| ATOM | 1431 | O5' | ADE | E | 13 | 8.623 | 6.284 | 3.975 | 1.00 | 29.72 E | O |
| ATOM | 1432 | C5' | ADE | E | 13 | 8.538 | 6.922 | 2.706 | 1.00 | 26.78 E | C |
| ATOM | 1433 | C4' | ADE | E | 13 | 9.483 | 8.111 | 2.612 | 1.00 | 31.36 E | C |
| ATOM | 1434 | O4' | ADE | E | 13 | 8.780 | 9.358 | 2.850 | 1.00 | 26.91 E | O |
| ATOM | 1435 | C3' | ADE | E | 13 | 10.671 | 8.113 | 3.567 | 1.00 | 24.84 E | C |
| ATOM | 1436 | O3' | ADE | E | 13 | 11.755 | 8.715 | 2.871 | 1.00 | 25.02 E | O |
| ATOM | 1437 | C2' | ADE | E | 13 | 10.168 | 8.953 | 4.739 | 1.00 | 24.93 E | C |

TABLE 1-continued

| | | | | | | | | | | | |
|---|---|---|---|---|---|---|---|---|---|---|---|
| ATOM | 1438 | C1' | ADE | E | 13 | 9.149 | 9.897 | 4.101 | 1.00 | 28.31 E | C |
| ATOM | 1439 | N9 | ADE | E | 13 | 7.913 | 10.036 | 4.860 | 1.00 | 22.96 E | N |
| ATOM | 1440 | C8 | ADE | E | 13 | 7.461 | 9.213 | 5.849 | 1.00 | 20.48 E | C |
| ATOM | 1441 | N7 | ADE | E | 13 | 6.310 | 9.588 | 6.352 | 1.00 | 21.80 E | N |
| ATOM | 1442 | C5 | ADE | E | 13 | 5.977 | 10.724 | 5.631 | 1.00 | 19.63 E | C |
| ATOM | 1443 | C6 | ADE | E | 13 | 4.867 | 11.590 | 5.680 | 1.00 | 20.30 E | C |
| ATOM | 1444 | N6 | ADE | E | 13 | 3.845 | 11.428 | 6.529 | 1.00 | 19.00 E | N |
| ATOM | 1445 | N1 | ADE | E | 13 | 4.852 | 12.631 | 4.819 | 1.00 | 21.87 E | N |
| ATOM | 1446 | C2 | ADE | E | 13 | 5.879 | 12.785 | 3.971 | 1.00 | 21.40 E | C |
| ATOM | 1447 | N3 | ADE | E | 13 | 6.973 | 12.039 | 3.838 | 1.00 | 20.80 E | N |
| ATOM | 1448 | C4 | ADE | E | 13 | 6.958 | 11.014 | 4.703 | 1.00 | 21.32 E | C |
| ATOM | 1449 | P | GUA | E | 14 | 13.159 | 9.030 | 3.570 | 1.00 | 31.66 E | P |
| ATOM | 1450 | OP1 | GUA | E | 14 | 14.216 | 8.918 | 2.535 | 1.00 | 31.34 E | O |
| ATOM | 1451 | OP2 | GUA | E | 14 | 13.251 | 8.231 | 4.813 | 1.00 | 22.94 E | O |
| ATOM | 1452 | O5' | GUA | E | 14 | 13.004 | 10.579 | 3.943 | 1.00 | 25.42 E | O |
| ATOM | 1453 | C5' | GUA | E | 14 | 12.824 | 11.512 | 2.891 | 1.00 | 25.99 E | C |
| ATOM | 1454 | C4' | GUA | E | 14 | 12.492 | 12.896 | 3.415 | 1.00 | 34.31 E | C |
| ATOM | 1455 | O4' | GUA | E | 14 | 11.188 | 12.895 | 4.055 | 1.00 | 34.27 E | O |
| ATOM | 1456 | C3' | GUA | E | 14 | 13.485 | 13.460 | 4.429 | 1.00 | 37.50 E | C |
| ATOM | 1457 | O3' | GUA | E | 14 | 13.899 | 14.742 | 3.973 | 1.00 | 41.76 E | O |
| ATOM | 1458 | C2' | GUA | E | 14 | 12.698 | 13.526 | 5.738 | 1.00 | 34.47 E | C |
| ATOM | 1459 | C1' | GUA | E | 14 | 11.253 | 13.627 | 5.258 | 1.00 | 31.30 E | C |
| ATOM | 1460 | N9 | GUA | E | 14 | 10.291 | 13.055 | 6.194 | 1.00 | 29.91 E | N |
| ATOM | 1461 | C8 | GUA | E | 14 | 10.424 | 11.900 | 6.934 | 1.00 | 30.46 E | C |
| ATOM | 1462 | N7 | GUA | E | 14 | 9.388 | 11.644 | 7.689 | 1.00 | 28.53 E | N |
| ATOM | 1463 | C5 | GUA | E | 14 | 8.513 | 12.695 | 7.432 | 1.00 | 24.42 E | C |
| ATOM | 1464 | C6 | GUA | E | 14 | 7.230 | 12.965 | 7.955 | 1.00 | 24.43 E | C |
| ATOM | 1465 | O6 | GUA | E | 14 | 6.586 | 12.305 | 8.777 | 1.00 | 28.12 E | O |
| ATOM | 1466 | N1 | GUA | E | 14 | 6.687 | 14.137 | 7.435 | 1.00 | 24.65 E | N |
| ATOM | 1467 | C2 | GUA | E | 14 | 7.309 | 14.949 | 6.517 | 1.00 | 28.51 E | C |
| ATOM | 1468 | N2 | GUA | E | 14 | 6.629 | 16.039 | 6.125 | 1.00 | 28.83 E | N |
| ATOM | 1469 | N3 | GUA | E | 14 | 8.513 | 14.708 | 6.013 | 1.00 | 30.78 E | N |
| ATOM | 1470 | C4 | GUA | E | 14 | 9.053 | 13.570 | 6.515 | 1.00 | 29.53 E | C |
| ATOM | 1471 | P | CYT | E | 15 | 14.736 | 15.739 | 4.898 | 1.00 | 56.84 E | P |
| ATOM | 1472 | OP1 | CYT | E | 15 | 15.666 | 16.475 | 4.014 | 1.00 | 65.29 E | O |
| ATOM | 1473 | OP2 | CYT | E | 15 | 15.262 | 14.989 | 6.062 | 1.00 | 49.85 E | O |
| ATOM | 1474 | O5' | CYT | E | 15 | 13.603 | 16.748 | 5.406 | 1.00 | 55.19 E | O |
| ATOM | 1475 | C5' | CYT | E | 15 | 12.708 | 17.324 | 4.454 | 1.00 | 56.18 E | C |
| ATOM | 1476 | C4' | CYT | E | 15 | 11.642 | 18.176 | 5.128 | 1.00 | 61.42 E | C |
| ATOM | 1477 | O4' | CYT | E | 15 | 10.704 | 17.348 | 5.868 | 1.00 | 54.03 E | O |
| ATOM | 1478 | C3' | CYT | E | 15 | 12.169 | 19.200 | 6.129 | 1.00 | 63.66 E | C |
| ATOM | 1479 | O3' | CYT | E | 15 | 11.386 | 20.389 | 6.042 | 1.00 | 69.99 E | O |
| ATOM | 1480 | C2' | CYT | E | 15 | 11.981 | 18.488 | 7.465 | 1.00 | 52.85 E | C |
| ATOM | 1481 | C1' | CYT | E | 15 | 10.653 | 17.784 | 7.212 | 1.00 | 49.35 E | C |
| ATOM | 1482 | N1 | CYT | E | 15 | 10.426 | 16.603 | 8.090 | 1.00 | 42.67 E | N |
| ATOM | 1483 | C2 | CYT | E | 15 | 9.266 | 16.548 | 8.872 | 1.00 | 37.19 E | C |
| ATOM | 1484 | O2 | CYT | E | 15 | 8.458 | 17.484 | 8.812 | 1.00 | 38.83 E | O |
| ATOM | 1485 | N3 | CYT | E | 15 | 9.062 | 15.470 | 9.671 | 1.00 | 31.91 E | N |
| ATOM | 1486 | C4 | CYT | E | 15 | 9.963 | 14.484 | 9.704 | 1.00 | 35.66 E | C |
| ATOM | 1487 | N4 | CYT | E | 15 | 9.715 | 13.443 | 10.508 | 1.00 | 33.17 E | N |
| ATOM | 1488 | C5 | CYT | E | 15 | 11.156 | 14.526 | 8.915 | 1.00 | 37.46 E | C |
| ATOM | 1489 | C6 | CYT | E | 15 | 11.346 | 15.593 | 8.129 | 1.00 | 38.60 E | C |
| ATOM | 1490 | P | THY | E | 16 | 11.995 | 21.808 | 6.469 | 1.00 | 78.44 E | P |
| ATOM | 1491 | OP1 | THY | E | 16 | 11.959 | 22.665 | 5.264 | 1.00 | 50.40 E | O |
| ATOM | 1492 | OP2 | THY | E | 16 | 13.261 | 21.586 | 7.212 | 1.00 | 63.19 E | O |
| ATOM | 1493 | O5' | THY | E | 16 | 10.923 | 22.349 | 7.524 | 1.00 | 70.06 E | O |
| ATOM | 1494 | C5' | THY | E | 16 | 9.533 | 22.263 | 7.241 | 1.00 | 65.61 E | C |
| ATOM | 1495 | C4' | THY | E | 16 | 8.750 | 22.391 | 8.533 | 1.00 | 64.41 E | C |
| ATOM | 1496 | O4' | THY | E | 16 | 8.692 | 21.120 | 9.230 | 1.00 | 56.65 E | O |
| ATOM | 1497 | C3' | THY | E | 16 | 9.346 | 23.382 | 9.527 | 1.00 | 64.90 E | C |
| ATOM | 1498 | O3' | THY | E | 16 | 8.281 | 24.127 | 10.092 | 1.00 | 70.01 E | O |
| ATOM | 1499 | C2' | THY | E | 16 | 10.035 | 22.482 | 10.552 | 1.00 | 55.44 E | C |
| ATOM | 1500 | C1' | THY | E | 16 | 9.040 | 21.330 | 10.583 | 1.00 | 49.98 E | C |
| ATOM | 1501 | N1 | THY | E | 16 | 9.550 | 20.043 | 11.132 | 1.00 | 46.89 E | N |
| ATOM | 1502 | C2 | THY | E | 16 | 8.698 | 19.308 | 11.926 | 1.00 | 41.72 E | C |
| ATOM | 1503 | O2 | THY | E | 16 | 7.565 | 19.677 | 12.194 | 1.00 | 36.25 E | O |
| ATOM | 1504 | N3 | THY | E | 16 | 9.225 | 18.128 | 12.392 | 1.00 | 36.45 E | N |
| ATOM | 1505 | C4 | THY | E | 16 | 10.491 | 17.628 | 12.146 | 1.00 | 38.15 E | C |
| ATOM | 1506 | O4 | THY | E | 16 | 10.882 | 16.559 | 12.606 | 1.00 | 36.21 E | O |
| ATOM | 1507 | C5 | THY | E | 16 | 11.327 | 18.448 | 11.309 | 1.00 | 39.53 E | C |
| ATOM | 1508 | C7 | THY | E | 16 | 12.717 | 17.982 | 10.988 | 1.00 | 36.66 E | C |
| ATOM | 1509 | C6 | THY | E | 16 | 10.828 | 19.603 | 10.843 | 1.00 | 43.44 E | C |
| ATOM | 1510 | P | THY | E | 17 | 8.549 | 25.581 | 10.689 | 1.00 | 78.30 E | P |
| ATOM | 1511 | OP1 | THY | E | 17 | 7.626 | 26.522 | 10.012 | 1.00 | 60.38 E | O |
| ATOM | 1512 | OP2 | THY | E | 17 | 10.012 | 25.813 | 10.672 | 1.00 | 73.87 E | O |
| ATOM | 1513 | O5' | THY | E | 17 | 8.116 | 25.415 | 12.218 | 1.00 | 73.56 E | O |
| ATOM | 1514 | C5' | THY | E | 17 | 6.754 | 25.202 | 12.576 | 1.00 | 68.05 E | C |
| ATOM | 1515 | C4' | THY | E | 17 | 6.683 | 24.775 | 14.030 | 1.00 | 68.97 E | C |
| ATOM | 1516 | O4' | THY | E | 17 | 7.266 | 23.452 | 14.157 | 1.00 | 64.24 E | O |
| ATOM | 1517 | C3' | THY | E | 17 | 7.449 | 25.680 | 14.994 | 1.00 | 65.70 E | C |

TABLE 1-continued

| | | | | | | | | | | |
|---|---|---|---|---|---|---|---|---|---|---|
| ATOM | 1518 | O3' | THY | E | 17 | 6.707 | 25.874 | 16.192 | 1.00 | 71.08 E | O |
| ATOM | 1519 | C2' | THY | E | 17 | 8.741 | 24.910 | 15.254 | 1.00 | 65.84 E | C |
| ATOM | 1520 | C1' | THY | E | 17 | 8.250 | 23.470 | 15.169 | 1.00 | 71.79 E | C |
| ATOM | 1521 | N1 | THY | E | 17 | 9.320 | 22.512 | 14.802 | 1.00 | 62.90 E | N |
| ATOM | 1522 | C2 | THY | E | 17 | 9.211 | 21.191 | 15.192 | 1.00 | 55.41 E | C |
| ATOM | 1523 | O2 | THY | E | 17 | 8.264 | 20.754 | 15.830 | 1.00 | 43.12 E | O |
| ATOM | 1524 | N3 | THY | E | 17 | 10.263 | 20.397 | 14.798 | 1.00 | 44.40 E | N |
| ATOM | 1525 | C4 | THY | E | 17 | 11.380 | 20.789 | 14.081 | 1.00 | 46.62 E | C |
| ATOM | 1526 | O4 | THY | E | 17 | 12.273 | 20.005 | 13.779 | 1.00 | 49.59 E | O |
| ATOM | 1527 | C5 | THY | E | 17 | 11.425 | 22.183 | 13.711 | 1.00 | 62.54 E | C |
| ATOM | 1528 | C7 | THY | E | 17 | 12.591 | 22.718 | 12.930 | 1.00 | 69.77 E | C |
| ATOM | 1529 | C6 | THY | E | 17 | 10.407 | 22.970 | 14.086 | 1.00 | 59.82 E | C |
| TER | | | | | | | | | | | |
| ATOM | 1530 | O5' | THY | F | 1 | 15.151 | 15.405 | 19.847 | 1.00 | 35.44 F | O |
| ATOM | 1531 | C5' | THY | F | 1 | 15.320 | 14.944 | 21.178 | 1.00 | 28.60 F | C |
| ATOM | 1532 | C4' | THY | F | 1 | 13.978 | 14.889 | 21.887 | 1.00 | 27.43 F | C |
| ATOM | 1533 | O4' | THY | F | 1 | 13.339 | 16.188 | 21.818 | 1.00 | 29.22 F | O |
| ATOM | 1534 | C3' | THY | F | 1 | 12.977 | 13.892 | 21.316 | 1.00 | 28.97 F | C |
| ATOM | 1535 | O3' | THY | F | 1 | 12.248 | 13.304 | 22.386 | 1.00 | 29.78 F | O |
| ATOM | 1536 | C2' | THY | F | 1 | 12.095 | 14.750 | 20.407 | 1.00 | 32.74 F | C |
| ATOM | 1537 | C1' | THY | F | 1 | 12.142 | 16.129 | 21.065 | 1.00 | 29.02 F | C |
| ATOM | 1538 | N1 | THY | F | 1 | 12.145 | 17.296 | 20.117 | 1.00 | 27.55 F | N |
| ATOM | 1539 | C2 | THY | F | 1 | 11.029 | 18.102 | 20.029 | 1.00 | 26.62 F | C |
| ATOM | 1540 | O2 | THY | F | 1 | 10.018 | 17.923 | 20.677 | 1.00 | 32.29 F | O |
| ATOM | 1541 | N3 | THY | F | 1 | 11.126 | 19.142 | 19.148 | 1.00 | 24.47 F | N |
| ATOM | 1542 | C4 | THY | F | 1 | 12.206 | 19.455 | 18.356 | 1.00 | 27.28 F | C |
| ATOM | 1543 | O4 | THY | F | 1 | 12.186 | 20.415 | 17.595 | 1.00 | 32.91 F | O |
| ATOM | 1544 | C5 | THY | F | 1 | 13.344 | 18.577 | 18.487 | 1.00 | 26.29 F | C |
| ATOM | 1545 | C7 | THY | F | 1 | 14.575 | 18.823 | 17.668 | 1.00 | 33.04 F | C |
| ATOM | 1546 | C6 | THY | F | 1 | 13.265 | 17.553 | 19.348 | 1.00 | 27.16 F | C |
| ATOM | 1547 | P | ADE | F | 2 | 11.449 | 11.931 | 22.178 | 1.00 | 39.94 F | P |
| ATOM | 1548 | OP1 | ADE | F | 2 | 11.319 | 11.249 | 23.481 | 1.00 | 40.24 F | O |
| ATOM | 1549 | OP2 | ADE | F | 2 | 12.049 | 11.216 | 21.034 | 1.00 | 31.49 F | O |
| ATOM | 1550 | O5' | ADE | F | 2 | 10.007 | 12.422 | 21.708 | 1.00 | 39.09 F | O |
| ATOM | 1551 | C5' | ADE | F | 2 | 9.242 | 13.377 | 22.427 | 1.00 | 26.83 F | C |
| ATOM | 1552 | C4' | ADE | F | 2 | 8.068 | 13.787 | 21.551 | 1.00 | 33.76 F | C |
| ATOM | 1553 | O4' | ADE | F | 2 | 8.510 | 14.720 | 20.526 | 1.00 | 38.96 F | O |
| ATOM | 1554 | C3' | ADE | F | 2 | 7.419 | 12.650 | 20.766 | 1.00 | 35.68 F | C |
| ATOM | 1555 | O3' | ADE | F | 2 | 6.097 | 13.018 | 20.473 | 1.00 | 42.23 F | O |
| ATOM | 1556 | C2' | ADE | F | 2 | 8.221 | 12.663 | 19.471 | 1.00 | 30.26 F | C |
| ATOM | 1557 | C1' | ADE | F | 2 | 8.209 | 14.169 | 19.255 | 1.00 | 30.49 F | C |
| ATOM | 1558 | N9 | ADE | F | 2 | 9.163 | 14.657 | 18.268 | 1.00 | 26.53 F | N |
| ATOM | 1559 | C8 | ADE | F | 2 | 10.195 | 13.977 | 17.681 | 1.00 | 28.86 F | C |
| ATOM | 1560 | N7 | ADE | F | 2 | 10.879 | 14.698 | 16.815 | 1.00 | 28.94 F | N |
| ATOM | 1561 | C5 | ADE | F | 2 | 10.251 | 15.934 | 16.841 | 1.00 | 27.05 F | C |
| ATOM | 1562 | C6 | ADE | F | 2 | 10.482 | 17.144 | 16.157 | 1.00 | 25.84 F | C |
| ATOM | 1563 | N6 | ADE | F | 2 | 11.464 | 17.322 | 15.272 | 1.00 | 28.80 F | N |
| ATOM | 1564 | N1 | ADE | F | 2 | 9.662 | 18.179 | 16.421 | 1.00 | 25.80 F | N |
| ATOM | 1565 | C2 | ADE | F | 2 | 8.678 | 18.020 | 17.310 | 1.00 | 24.88 F | C |
| ATOM | 1566 | N3 | ADE | F | 2 | 8.363 | 16.936 | 18.012 | 1.00 | 26.79 F | N |
| ATOM | 1567 | C4 | ADE | F | 2 | 9.192 | 15.922 | 17.731 | 1.00 | 27.44 F | C |
| ATOM | 1568 | P | ADE | F | 3 | 4.853 | 12.162 | 20.988 | 1.00 | 39.47 F | P |
| ATOM | 1569 | OP1 | ADE | F | 3 | 4.873 | 12.164 | 22.468 | 1.00 | 40.90 F | O |
| ATOM | 1570 | OP2 | ADE | F | 3 | 4.808 | 10.885 | 20.235 | 1.00 | 38.47 F | O |
| ATOM | 1571 | O5' | ADE | F | 3 | 3.662 | 13.097 | 20.486 | 1.00 | 32.45 F | O |
| ATOM | 1572 | C5' | ADE | F | 3 | 3.672 | 14.458 | 20.891 | 1.00 | 32.40 F | C |
| ATOM | 1573 | C4' | ADE | F | 3 | 3.160 | 15.342 | 19.773 | 1.00 | 28.86 F | C |
| ATOM | 1574 | O4' | ADE | F | 3 | 4.231 | 15.629 | 18.842 | 1.00 | 28.94 F | O |
| ATOM | 1575 | C3' | ADE | F | 3 | 2.036 | 14.721 | 18.953 | 1.00 | 39.96 F | C |
| ATOM | 1576 | O3' | ADE | F | 3 | 0.991 | 15.679 | 18.813 | 1.00 | 36.97 F | O |
| ATOM | 1577 | C2' | ADE | F | 3 | 2.694 | 14.359 | 17.614 | 1.00 | 33.14 F | C |
| ATOM | 1578 | C1' | ADE | F | 3 | 3.792 | 15.414 | 17.514 | 1.00 | 36.24 F | C |
| ATOM | 1579 | N9 | ADE | F | 3 | 4.967 | 15.021 | 16.739 | 1.00 | 28.30 F | N |
| ATOM | 1580 | C8 | ADE | F | 3 | 5.621 | 13.819 | 16.767 | 1.00 | 29.94 F | C |
| ATOM | 1581 | N7 | ADE | F | 3 | 6.663 | 13.762 | 15.969 | 1.00 | 29.86 F | N |
| ATOM | 1582 | C5 | ADE | F | 3 | 6.697 | 15.018 | 15.379 | 1.00 | 29.66 F | C |
| ATOM | 1583 | C6 | ADE | F | 3 | 7.562 | 15.605 | 14.433 | 1.00 | 26.28 F | C |
| ATOM | 1584 | N6 | ADE | F | 3 | 8.605 | 14.972 | 13.892 | 1.00 | 30.60 F | N |
| ATOM | 1585 | N1 | ADE | F | 3 | 7.314 | 16.879 | 14.061 | 1.00 | 28.86 F | N |
| ATOM | 1586 | C2 | ADE | F | 3 | 6.267 | 17.520 | 14.600 | 1.00 | 28.38 F | C |
| ATOM | 1587 | N3 | ADE | F | 3 | 5.387 | 17.076 | 15.499 | 1.00 | 30.45 F | N |
| ATOM | 1588 | C4 | ADE | F | 3 | 5.660 | 15.807 | 15.848 | 1.00 | 30.12 F | C |
| ATOM | 1589 | P | GUA | F | 4 | −0.306 | 15.279 | 17.977 | 1.00 | 36.44 F | P |
| ATOM | 1590 | OP1 | GUA | F | 4 | −1.461 | 15.980 | 18.572 | 1.00 | 30.12 F | O |
| ATOM | 1591 | OP2 | GUA | F | 4 | −0.313 | 13.800 | 17.840 | 1.00 | 37.68 F | O |
| ATOM | 1592 | O5' | GUA | F | 4 | 0.019 | 15.913 | 16.539 | 1.00 | 38.14 F | O |
| ATOM | 1593 | C5' | GUA | F | 4 | 0.319 | 17.304 | 16.457 | 1.00 | 34.43 F | C |
| ATOM | 1594 | C4' | GUA | F | 4 | 0.845 | 17.689 | 15.083 | 1.00 | 37.40 F | C |
| ATOM | 1595 | O4' | GUA | F | 4 | 2.082 | 16.992 | 14.785 | 1.00 | 40.03 F | O |
| ATOM | 1596 | C3' | GUA | F | 4 | −0.082 | 17.399 | 13.905 | 1.00 | 48.37 F | C |

TABLE 1-continued

| ATOM | 1597 | O3' | GUA | F | 4 | −0.224 | 18.621 | 13.194 | 1.00 | 50.22 | F | O |
|---|---|---|---|---|---|---|---|---|---|---|---|---|
| ATOM | 1598 | C2' | GUA | F | 4 | 0.650 | 16.322 | 13.096 | 1.00 | 37.79 | F | C |
| ATOM | 1599 | C1' | GUA | F | 4 | 2.096 | 16.693 | 13.404 | 1.00 | 35.99 | F | C |
| ATOM | 1600 | N9 | GUA | F | 4 | 3.113 | 15.662 | 13.184 | 1.00 | 32.40 | F | N |
| ATOM | 1601 | C8 | GUA | F | 4 | 3.178 | 14.408 | 13.743 | 1.00 | 30.83 | F | C |
| ATOM | 1602 | N7 | GUA | F | 4 | 4.226 | 13.724 | 13.367 | 1.00 | 30.41 | F | N |
| ATOM | 1603 | C5 | GUA | F | 4 | 4.907 | 14.581 | 12.507 | 1.00 | 30.17 | F | C |
| ATOM | 1604 | C6 | GUA | F | 4 | 6.116 | 14.396 | 11.787 | 1.00 | 27.54 | F | C |
| ATOM | 1605 | O6 | GUA | F | 4 | 6.864 | 13.403 | 11.757 | 1.00 | 25.09 | F | O |
| ATOM | 1606 | N1 | GUA | F | 4 | 6.442 | 15.526 | 11.041 | 1.00 | 28.44 | F | N |
| ATOM | 1607 | C2 | GUA | F | 4 | 5.697 | 16.679 | 10.991 | 1.00 | 31.59 | F | C |
| ATOM | 1608 | N2 | GUA | F | 4 | 6.170 | 17.660 | 10.212 | 1.00 | 36.28 | F | N |
| ATOM | 1609 | N3 | GUA | F | 4 | 4.567 | 16.866 | 11.657 | 1.00 | 30.17 | F | N |
| ATOM | 1610 | C4 | GUA | F | 4 | 4.234 | 15.778 | 12.391 | 1.00 | 31.30 | F | C |
| ATOM | 1611 | P | CYT | F | 5 | −1.174 | 18.766 | 11.913 | 1.00 | 55.22 | F | P |
| ATOM | 1612 | OP1 | CYT | F | 5 | −1.967 | 20.000 | 12.116 | 1.00 | 35.41 | F | O |
| ATOM | 1613 | OP2 | CYT | F | 5 | −1.818 | 17.463 | 11.625 | 1.00 | 41.84 | F | O |
| ATOM | 1614 | O5' | CYT | F | 5 | −0.117 | 19.042 | 10.750 | 1.00 | 45.09 | F | O |
| ATOM | 1615 | C5' | CYT | F | 5 | 0.805 | 20.099 | 10.935 | 1.00 | 36.95 | F | C |
| ATOM | 1616 | C4' | CYT | F | 5 | 1.679 | 20.233 | 9.710 | 1.00 | 34.80 | F | C |
| ATOM | 1617 | O4' | CYT | F | 5 | 2.599 | 19.115 | 9.620 | 1.00 | 30.71 | F | O |
| ATOM | 1618 | C3' | CYT | F | 5 | 0.917 | 20.269 | 8.395 | 1.00 | 32.81 | F | C |
| ATOM | 1619 | O3' | CYT | F | 5 | 1.552 | 21.256 | 7.611 | 1.00 | 38.98 | F | O |
| ATOM | 1620 | C2' | CYT | F | 5 | 1.090 | 18.847 | 7.850 | 1.00 | 30.04 | F | C |
| ATOM | 1621 | C1' | CYT | F | 5 | 2.483 | 18.494 | 8.360 | 1.00 | 30.96 | F | C |
| ATOM | 1622 | N1 | CYT | F | 5 | 2.763 | 17.057 | 8.621 | 1.00 | 32.68 | F | N |
| ATOM | 1623 | C2 | CYT | F | 5 | 3.866 | 16.455 | 8.007 | 1.00 | 28.42 | F | C |
| ATOM | 1624 | O2 | CYT | F | 5 | 4.574 | 17.122 | 7.239 | 1.00 | 30.64 | F | O |
| ATOM | 1625 | N3 | CYT | F | 5 | 4.129 | 15.152 | 8.271 | 1.00 | 29.28 | F | N |
| ATOM | 1626 | C4 | CYT | F | 5 | 3.344 | 14.461 | 9.101 | 1.00 | 28.82 | F | C |
| ATOM | 1627 | N4 | CYT | F | 5 | 3.652 | 13.176 | 9.319 | 1.00 | 26.68 | F | N |
| ATOM | 1628 | C5 | CYT | F | 5 | 2.218 | 15.058 | 9.741 | 1.00 | 26.50 | F | C |
| ATOM | 1629 | C6 | CYT | F | 5 | 1.973 | 16.347 | 9.477 | 1.00 | 34.18 | F | C |
| ATOM | 1630 | P | THY | F | 6 | 0.911 | 21.797 | 6.257 | 1.00 | 45.82 | F | P |
| ATOM | 1631 | OP1 | THY | F | 6 | 1.340 | 23.204 | 6.087 | 1.00 | 50.17 | F | O |
| ATOM | 1632 | OP2 | THY | F | 6 | −0.527 | 21.445 | 6.242 | 1.00 | 48.70 | F | O |
| ATOM | 1633 | O5' | THY | F | 6 | 1.645 | 20.899 | 5.156 | 1.00 | 45.06 | F | O |
| ATOM | 1634 | C5' | THY | F | 6 | 2.993 | 21.162 | 4.785 | 1.00 | 41.65 | F | C |
| ATOM | 1635 | C4' | THY | F | 6 | 3.362 | 20.354 | 3.556 | 1.00 | 37.82 | F | C |
| ATOM | 1636 | O4' | THY | F | 6 | 3.682 | 18.997 | 3.962 | 1.00 | 40.57 | F | O |
| ATOM | 1637 | C3' | THY | F | 6 | 2.234 | 20.213 | 2.540 | 1.00 | 38.89 | F | C |
| ATOM | 1638 | O3' | THY | F | 6 | 2.758 | 19.997 | 1.240 | 1.00 | 45.07 | F | O |
| ATOM | 1639 | C2' | THY | F | 6 | 1.555 | 18.940 | 3.018 | 1.00 | 39.65 | F | C |
| ATOM | 1640 | C1' | THY | F | 6 | 2.810 | 18.118 | 3.277 | 1.00 | 40.46 | F | C |
| ATOM | 1641 | N1 | THY | F | 6 | 2.575 | 16.902 | 4.089 | 1.00 | 33.12 | F | N |
| ATOM | 1642 | C2 | THY | F | 6 | 3.531 | 15.917 | 4.063 | 1.00 | 33.34 | F | C |
| ATOM | 1643 | O2 | THY | F | 6 | 4.553 | 16.018 | 3.409 | 1.00 | 36.26 | F | O |
| ATOM | 1644 | N3 | THY | F | 6 | 3.244 | 14.819 | 4.836 | 1.00 | 29.65 | F | N |
| ATOM | 1645 | C4 | THY | F | 6 | 2.113 | 14.623 | 5.607 | 1.00 | 30.16 | F | C |
| ATOM | 1646 | O4 | THY | F | 6 | 1.944 | 13.601 | 6.265 | 1.00 | 28.94 | F | O |
| ATOM | 1647 | C5 | THY | F | 6 | 1.146 | 15.697 | 5.580 | 1.00 | 31.04 | F | C |
| ATOM | 1648 | C7 | THY | F | 6 | −0.125 | 15.596 | 6.376 | 1.00 | 27.30 | F | C |
| ATOM | 1649 | C6 | THY | F | 6 | 1.420 | 16.773 | 4.831 | 1.00 | 29.41 | F | C |
| ATOM | 1650 | P | ADE | F | 7 | 3.087 | 21.237 | 0.286 | 1.00 | 43.24 | F | P |
| ATOM | 1651 | OP1 | ADE | F | 7 | 3.511 | 22.361 | 1.152 | 1.00 | 39.52 | F | O |
| ATOM | 1652 | OP2 | ADE | F | 7 | 1.946 | 21.410 | −0.641 | 1.00 | 43.23 | F | O |
| ATOM | 1653 | O5' | ADE | F | 7 | 4.337 | 20.696 | −0.558 | 1.00 | 31.77 | F | O |
| ATOM | 1654 | C5' | ADE | F | 7 | 5.573 | 20.439 | 0.091 | 1.00 | 31.76 | F | C |
| ATOM | 1655 | C4' | ADE | F | 7 | 6.250 | 19.186 | −0.442 | 1.00 | 34.10 | F | C |
| ATOM | 1656 | O4' | ADE | F | 7 | 5.668 | 17.997 | 0.158 | 1.00 | 36.40 | F | O |
| ATOM | 1657 | C3' | ADE | F | 7 | 6.159 | 18.965 | −1.945 | 1.00 | 37.37 | F | C |
| ATOM | 1658 | O3' | ADE | F | 7 | 7.365 | 18.325 | −2.375 | 1.00 | 37.11 | F | O |
| ATOM | 1659 | C2' | ADE | F | 7 | 4.922 | 18.068 | −2.076 | 1.00 | 34.22 | F | C |
| ATOM | 1660 | C1' | ADE | F | 7 | 5.045 | 17.190 | −0.831 | 1.00 | 36.46 | F | C |
| ATOM | 1661 | N9 | ADE | F | 7 | 3.796 | 16.716 | −0.234 | 1.00 | 29.12 | F | N |
| ATOM | 1662 | C8 | ADE | F | 7 | 2.603 | 17.380 | −0.136 | 1.00 | 31.32 | F | C |
| ATOM | 1663 | N7 | ADE | F | 7 | 1.664 | 16.695 | 0.484 | 1.00 | 32.25 | F | N |
| ATOM | 1664 | C5 | ADE | F | 7 | 2.284 | 15.502 | 0.826 | 1.00 | 26.57 | F | C |
| ATOM | 1665 | C6 | ADE | F | 7 | 1.838 | 14.346 | 1.503 | 1.00 | 22.11 | F | C |
| ATOM | 1666 | N6 | ADE | F | 7 | 0.599 | 14.190 | 1.983 | 1.00 | 20.31 | F | N |
| ATOM | 1667 | N1 | ADE | F | 7 | 2.723 | 13.340 | 1.670 | 1.00 | 22.14 | F | N |
| ATOM | 1668 | C2 | ADE | F | 7 | 3.964 | 13.483 | 1.198 | 1.00 | 23.50 | F | C |
| ATOM | 1669 | N3 | ADE | F | 7 | 4.500 | 14.518 | 0.551 | 1.00 | 28.66 | F | N |
| ATOM | 1670 | C4 | ADE | F | 7 | 3.601 | 15.505 | 0.395 | 1.00 | 30.88 | F | C |
| ATOM | 1671 | P | ADE | F | 8 | 7.584 | 17.995 | −3.924 | 1.00 | 57.47 | F | P |
| ATOM | 1672 | OP1 | ADE | F | 8 | 9.025 | 18.154 | −4.225 | 1.00 | 44.64 | F | O |
| ATOM | 1673 | OP2 | ADE | F | 8 | 6.546 | 18.735 | −4.687 | 1.00 | 39.39 | F | O |
| ATOM | 1674 | O5' | ADE | F | 8 | 7.234 | 16.441 | −4.011 | 1.00 | 40.95 | F | O |
| ATOM | 1675 | C5' | ADE | F | 8 | 7.986 | 15.526 | −3.241 | 1.00 | 40.65 | F | C |
| ATOM | 1676 | C4' | ADE | F | 8 | 7.318 | 14.166 | −3.261 | 1.00 | 42.55 | F | C |

TABLE 1-continued

| ATOM | 1677 | O4' | ADE | F | 8 | 6.068 | 14.237 | −2.542 | 1.00 | 43.82 | F | O |
|---|---|---|---|---|---|---|---|---|---|---|---|---|
| ATOM | 1678 | C3' | ADE | F | 8 | 6.962 | 13.635 | −4.648 | 1.00 | 37.24 | F | C |
| ATOM | 1679 | O3' | ADE | F | 8 | 7.876 | 12.598 | −4.962 | 1.00 | 36.02 | F | O |
| ATOM | 1680 | C2' | ADE | F | 8 | 5.523 | 13.126 | −4.513 | 1.00 | 34.48 | F | C |
| ATOM | 1681 | C1' | ADE | F | 8 | 5.279 | 13.168 | −3.007 | 1.00 | 36.61 | F | C |
| ATOM | 1682 | N9 | ADE | F | 8 | 3.897 | 13.418 | −2.605 | 1.00 | 35.16 | F | N |
| ATOM | 1683 | C8 | ADE | F | 8 | 3.136 | 14.523 | −2.874 | 1.00 | 34.63 | F | C |
| ATOM | 1684 | N7 | ADE | F | 8 | 1.924 | 14.470 | −2.372 | 1.00 | 33.52 | F | N |
| ATOM | 1685 | C5 | ADE | F | 8 | 1.890 | 13.243 | −1.730 | 1.00 | 30.78 | F | C |
| ATOM | 1686 | C6 | ADE | F | 8 | 0.881 | 12.586 | −1.000 | 1.00 | 36.08 | F | C |
| ATOM | 1687 | N6 | ADE | F | 8 | −0.330 | 13.117 | −0.802 | 1.00 | 31.29 | F | N |
| ATOM | 1688 | N1 | ADE | F | 8 | 1.168 | 11.366 | −0.482 | 1.00 | 34.00 | F | N |
| ATOM | 1689 | C2 | ADE | F | 8 | 2.390 | 10.849 | −0.691 | 1.00 | 37.64 | F | C |
| ATOM | 1690 | N3 | ADE | F | 8 | 3.421 | 11.372 | −1.364 | 1.00 | 31.88 | F | N |
| ATOM | 1691 | C4 | ADE | F | 8 | 3.099 | 12.581 | −1.860 | 1.00 | 32.34 | F | C |
| ATOM | 1692 | P | THY | F | 9 | 7.678 | 11.637 | −6.223 | 1.00 | 38.24 | F | P |
| ATOM | 1693 | OP1 | THY | F | 9 | 9.021 | 11.281 | −6.729 | 1.00 | 31.02 | F | O |
| ATOM | 1694 | OP2 | THY | F | 9 | 6.669 | 12.226 | −7.135 | 1.00 | 36.79 | F | O |
| ATOM | 1695 | O5' | THY | F | 9 | 7.060 | 10.340 | −5.528 | 1.00 | 35.06 | F | O |
| ATOM | 1696 | C5' | THY | F | 9 | 7.848 | 9.687 | −4.551 | 1.00 | 35.57 | F | C |
| ATOM | 1697 | C4' | THY | F | 9 | 7.066 | 8.560 | −3.913 | 1.00 | 34.01 | F | C |
| ATOM | 1698 | O4' | THY | F | 9 | 5.808 | 9.079 | −3.419 | 1.00 | 27.93 | F | O |
| ATOM | 1699 | C3' | THY | F | 9 | 6.722 | 7.390 | −4.832 | 1.00 | 28.47 | F | C |
| ATOM | 1700 | O3' | THY | F | 9 | 6.955 | 6.202 | −4.082 | 1.00 | 28.04 | F | O |
| ATOM | 1701 | C2' | THY | F | 9 | 5.248 | 7.620 | −5.164 | 1.00 | 26.35 | F | C |
| ATOM | 1702 | C1' | THY | F | 9 | 4.753 | 8.259 | −3.869 | 1.00 | 27.34 | F | C |
| ATOM | 1703 | N1 | THY | F | 9 | 3.561 | 9.140 | −3.995 | 1.00 | 25.52 | F | N |
| ATOM | 1704 | C2 | THY | F | 9 | 2.512 | 8.921 | −3.143 | 1.00 | 27.45 | F | C |
| ATOM | 1705 | O2 | THY | F | 9 | 2.528 | 8.038 | −2.306 | 1.00 | 29.33 | F | O |
| ATOM | 1706 | N3 | THY | F | 9 | 1.451 | 9.776 | −3.308 | 1.00 | 28.84 | F | N |
| ATOM | 1707 | C4 | THY | F | 9 | 1.345 | 10.805 | −4.226 | 1.00 | 26.17 | F | C |
| ATOM | 1708 | O4 | THY | F | 9 | 0.357 | 11.526 | −4.310 | 1.00 | 27.50 | F | O |
| ATOM | 1709 | C5 | THY | F | 9 | 2.477 | 10.978 | −5.088 | 1.00 | 27.41 | F | C |
| ATOM | 1710 | C7 | THY | F | 9 | 2.450 | 12.071 | −6.119 | 1.00 | 26.72 | F | C |
| ATOM | 1711 | C6 | THY | F | 9 | 3.522 | 10.151 | −4.933 | 1.00 | 27.85 | F | C |
| ATOM | 1712 | P | ADE | F | 10 | 6.614 | 4.738 | −4.629 | 1.00 | 23.93 | F | P |
| ATOM | 1713 | OP1 | ADE | F | 10 | 7.397 | 3.770 | −3.830 | 1.00 | 23.75 | F | O |
| ATOM | 1714 | OP2 | ADE | F | 10 | 6.742 | 4.742 | −6.104 | 1.00 | 31.81 | F | O |
| ATOM | 1715 | O5' | ADE | F | 10 | 5.071 | 4.571 | −4.220 | 1.00 | 35.82 | F | O |
| ATOM | 1716 | C5' | ADE | F | 10 | 4.732 | 4.500 | −2.835 | 1.00 | 25.94 | F | C |
| ATOM | 1717 | C4' | ADE | F | 10 | 3.369 | 3.873 | −2.576 | 1.00 | 20.59 | F | C |
| ATOM | 1718 | O4' | ADE | F | 10 | 2.313 | 4.838 | −2.795 | 1.00 | 22.02 | F | O |
| ATOM | 1719 | C3' | ADE | F | 10 | 2.998 | 2.665 | −3.428 | 1.00 | 25.03 | F | C |
| ATOM | 1720 | O3' | ADE | F | 10 | 2.352 | 1.741 | −2.564 | 1.00 | 21.68 | F | O |
| ATOM | 1721 | C2' | ADE | F | 10 | 2.059 | 3.247 | −4.486 | 1.00 | 20.64 | F | C |
| ATOM | 1722 | C1' | ADE | F | 10 | 1.340 | 4.328 | −3.686 | 1.00 | 21.60 | F | C |
| ATOM | 1723 | N9 | ADE | F | 10 | 0.878 | 5.487 | −4.447 | 1.00 | 24.05 | F | N |
| ATOM | 1724 | C8 | ADE | F | 10 | 1.593 | 6.194 | −5.377 | 1.00 | 20.24 | F | C |
| ATOM | 1725 | N7 | ADE | F | 10 | 0.930 | 7.207 | −5.882 | 1.00 | 22.47 | F | N |
| ATOM | 1726 | C5 | ADE | F | 10 | −0.296 | 7.166 | −5.240 | 1.00 | 19.26 | F | C |
| ATOM | 1727 | C6 | ADE | F | 10 | −1.445 | 7.976 | −5.337 | 1.00 | 21.91 | F | C |
| ATOM | 1728 | N6 | ADE | F | 10 | −1.537 | 9.028 | −6.159 | 1.00 | 22.42 | F | N |
| ATOM | 1729 | N1 | ADE | F | 10 | −2.502 | 7.663 | −4.556 | 1.00 | 20.46 | F | N |
| ATOM | 1730 | C2 | ADE | F | 10 | −2.404 | 6.608 | −3.738 | 1.00 | 21.25 | F | C |
| ATOM | 1731 | N3 | ADE | F | 10 | −1.373 | 5.777 | −3.557 | 1.00 | 21.22 | F | N |
| ATOM | 1732 | C4 | ADE | F | 10 | −0.343 | 6.115 | −4.348 | 1.00 | 18.15 | F | C |
| ATOM | 1733 | P | ADE | F | 11 | 1.831 | 0.323 | −3.073 | 1.00 | 26.26 | F | P |
| ATOM | 1734 | OP1 | ADE | F | 11 | 2.148 | −0.677 | −2.034 | 1.00 | 33.89 | F | O |
| ATOM | 1735 | OP2 | ADE | F | 11 | 2.267 | 0.111 | −4.472 | 1.00 | 23.71 | F | O |
| ATOM | 1736 | O5' | ADE | F | 11 | 0.251 | 0.571 | −3.069 | 1.00 | 30.04 | F | O |
| ATOM | 1737 | C5' | ADE | F | 11 | −0.359 | 1.033 | −1.884 | 1.00 | 23.86 | F | C |
| ATOM | 1738 | C4' | ADE | F | 11 | −1.850 | 1.245 | −2.067 | 1.00 | 25.98 | F | C |
| ATOM | 1739 | O4' | ADE | F | 11 | −2.088 | 2.375 | −2.942 | 1.00 | 21.87 | F | O |
| ATOM | 1740 | C3' | ADE | F | 11 | −2.629 | 0.077 | −2.661 | 1.00 | 27.40 | F | C |
| ATOM | 1741 | O3' | ADE | F | 11 | −3.869 | 0.048 | −1.963 | 1.00 | 27.22 | F | O |
| ATOM | 1742 | C2' | ADE | F | 11 | −2.785 | 0.484 | −4.126 | 1.00 | 22.69 | F | C |
| ATOM | 1743 | C1' | ADE | F | 11 | −2.949 | 1.997 | −3.991 | 1.00 | 25.23 | F | C |
| ATOM | 1744 | N9 | ADE | F | 11 | −2.484 | 2.813 | −5.103 | 1.00 | 25.79 | F | N |
| ATOM | 1745 | C8 | ADE | F | 11 | −1.310 | 2.670 | −5.794 | 1.00 | 25.41 | F | C |
| ATOM | 1746 | N7 | ADE | F | 11 | −1.138 | 3.568 | −6.736 | 1.00 | 26.27 | F | N |
| ATOM | 1747 | C5 | ADE | F | 11 | −2.274 | 4.357 | −6.639 | 1.00 | 24.40 | F | C |
| ATOM | 1748 | C6 | ADE | F | 11 | −2.693 | 5.484 | −7.361 | 1.00 | 26.97 | F | C |
| ATOM | 1749 | N6 | ADE | F | 11 | −1.962 | 6.001 | −8.355 | 1.00 | 30.79 | F | N |
| ATOM | 1750 | N1 | ADE | F | 11 | −3.880 | 6.043 | −7.028 | 1.00 | 26.76 | F | N |
| ATOM | 1751 | C2 | ADE | F | 11 | −4.594 | 5.498 | −6.030 | 1.00 | 27.39 | F | C |
| ATOM | 1752 | N3 | ADE | F | 11 | −4.296 | 4.433 | −5.279 | 1.00 | 24.26 | F | N |
| ATOM | 1753 | C4 | ADE | F | 11 | −3.113 | 3.912 | −5.638 | 1.00 | 22.08 | F | C |
| ATOM | 1754 | P | THY | F | 12 | −4.857 | −1.211 | −1.981 | 1.00 | 26.75 | F | P |
| ATOM | 1755 | OP1 | THY | F | 12 | −5.433 | −1.311 | −0.619 | 1.00 | 27.03 | F | O |
| ATOM | 1756 | OP2 | THY | F | 12 | −4.163 | −2.383 | −2.556 | 1.00 | 22.77 | F | O |

TABLE 1-continued

| | | | | | | | | | | | |
|---|---|---|---|---|---|---|---|---|---|---|---|
| ATOM | 1757 | O5' | THY | F | 12 | −5.993 | −0.716 | −2.998 | 1.00 | 26.06 F | O |
| ATOM | 1758 | C5' | THY | F | 12 | −6.803 | 0.411 | −2.603 | 1.00 | 24.65 F | C |
| ATOM | 1759 | C4' | THY | F | 12 | −7.609 | 0.986 | −3.754 | 1.00 | 27.12 F | C |
| ATOM | 1760 | O4' | THY | F | 12 | −6.751 | 1.762 | −4.633 | 1.00 | 24.99 F | O |
| ATOM | 1761 | C3' | THY | F | 12 | −8.307 | −0.047 | −4.646 | 1.00 | 27.27 F | C |
| ATOM | 1762 | O3' | THY | F | 12 | −9.654 | 0.322 | −4.869 | 1.00 | 26.89 F | O |
| ATOM | 1763 | C2' | THY | F | 12 | −7.524 | 0.037 | −5.955 | 1.00 | 22.09 F | C |
| ATOM | 1764 | C1' | THY | F | 12 | −7.222 | 1.528 | −5.945 | 1.00 | 23.77 F | C |
| ATOM | 1765 | N1 | THY | F | 12 | −6.198 | 1.950 | −6.926 | 1.00 | 23.74 F | N |
| ATOM | 1766 | C2 | THY | F | 12 | −6.346 | 3.165 | −7.564 | 1.00 | 24.23 F | C |
| ATOM | 1767 | O2 | THY | F | 12 | −7.277 | 3.925 | −7.363 | 1.00 | 22.95 F | O |
| ATOM | 1768 | N3 | THY | F | 12 | −5.346 | 3.463 | −8.452 | 1.00 | 21.71 F | N |
| ATOM | 1769 | C4 | THY | F | 12 | −4.250 | 2.684 | −8.753 | 1.00 | 21.38 F | C |
| ATOM | 1770 | O4 | THY | F | 12 | −3.416 | 3.055 | −9.568 | 1.00 | 26.86 F | O |
| ATOM | 1771 | C5 | THY | F | 12 | −4.161 | 1.425 | −8.051 | 1.00 | 19.72 F | C |
| ATOM | 1772 | C7 | THY | F | 12 | −3.013 | 0.485 | −8.294 | 1.00 | 20.68 F | C |
| ATOM | 1773 | C6 | THY | F | 12 | −5.128 | 1.120 | −7.183 | 1.00 | 19.97 F | C |
| ATOM | 1774 | P | ADE | F | 13 | −10.808 | 0.035 | −3.799 | 1.00 | 37.17 F | P |
| ATOM | 1775 | OP1 | ADE | F | 13 | −10.428 | 0.709 | −2.533 | 1.00 | 31.49 F | O |
| ATOM | 1776 | OP2 | ADE | F | 13 | −11.117 | −1.414 | −3.821 | 1.00 | 25.92 F | O |
| ATOM | 1777 | O5' | ADE | F | 13 | −12.042 | 0.827 | −4.445 | 1.00 | 33.97 F | O |
| ATOM | 1778 | C5' | ADE | F | 13 | −12.010 | 2.251 | −4.451 | 1.00 | 31.66 F | C |
| ATOM | 1779 | C4' | ADE | F | 13 | −12.914 | 2.837 | −5.523 | 1.00 | 36.86 F | C |
| ATOM | 1780 | O4' | ADE | F | 13 | −12.183 | 3.096 | −6.750 | 1.00 | 31.85 F | O |
| ATOM | 1781 | C3' | ADE | F | 13 | −14.115 | 1.994 | −5.925 | 1.00 | 27.27 F | C |
| ATOM | 1782 | O3' | ADE | F | 13 | −15.155 | 2.910 | −6.228 | 1.00 | 29.73 F | O |
| ATOM | 1783 | C2' | ADE | F | 13 | −13.604 | 1.237 | −7.148 | 1.00 | 26.25 F | C |
| ATOM | 1784 | C1' | ADE | F | 13 | −12.558 | 2.173 | −7.754 | 1.00 | 29.08 F | C |
| ATOM | 1785 | N9 | ADE | F | 13 | −11.324 | 1.523 | −8.187 | 1.00 | 25.69 F | N |
| ATOM | 1786 | C8 | ADE | F | 13 | −10.877 | 0.272 | −7.861 | 1.00 | 22.17 F | C |
| ATOM | 1787 | N7 | ADE | F | 13 | −9.718 | −0.031 | −8.405 | 1.00 | 23.97 F | N |
| ATOM | 1788 | C5 | ADE | F | 13 | −9.372 | 1.106 | −9.123 | 1.00 | 22.53 F | C |
| ATOM | 1789 | C6 | ADE | F | 13 | −8.249 | 1.433 | −9.914 | 1.00 | 23.42 F | C |
| ATOM | 1790 | N6 | ADE | F | 13 | −7.222 | 0.600 | −10.129 | 1.00 | 20.47 F | N |
| ATOM | 1791 | N1 | ADE | F | 13 | −8.224 | 2.655 | −10.485 | 1.00 | 23.63 F | N |
| ATOM | 1792 | C2 | ADE | F | 13 | −9.251 | 3.487 | −10.274 | 1.00 | 24.20 F | C |
| ATOM | 1793 | N3 | ADE | F | 13 | −10.355 | 3.295 | −9.551 | 1.00 | 24.43 F | N |
| ATOM | 1794 | C4 | ADE | F | 13 | −10.352 | 2.074 | −8.994 | 1.00 | 23.99 F | C |
| ATOM | 1795 | P | GUA | F | 14 | −16.572 | 2.450 | −6.800 | 1.00 | 30.58 F | P |
| ATOM | 1796 | OP1 | GUA | F | 14 | −17.581 | 3.404 | −6.283 | 1.00 | 29.22 F | O |
| ATOM | 1797 | OP2 | GUA | F | 14 | −16.732 | 0.996 | −6.558 | 1.00 | 28.14 F | O |
| ATOM | 1798 | O5' | GUA | F | 14 | −16.417 | 2.710 | −8.369 | 1.00 | 21.73 F | O |
| ATOM | 1799 | C5' | GUA | F | 14 | −16.239 | 4.053 | −8.799 | 1.00 | 28.86 F | C |
| ATOM | 1800 | C4' | GUA | F | 14 | −15.866 | 4.106 | −10.267 | 1.00 | 35.27 F | C |
| ATOM | 1801 | O4' | GUA | F | 14 | −14.568 | 3.491 | −10.468 | 1.00 | 32.56 F | O |
| ATOM | 1802 | C3' | GUA | F | 14 | −16.849 | 3.401 | −11.197 | 1.00 | 41.42 F | C |
| ATOM | 1803 | O3' | GUA | F | 14 | −17.292 | 4.357 | −12.165 | 1.00 | 50.72 F | O |
| ATOM | 1804 | C2' | GUA | F | 14 | −16.046 | 2.239 | −11.786 | 1.00 | 35.19 F | C |
| ATOM | 1805 | C1' | GUA | F | 14 | −14.601 | 2.711 | −11.636 | 1.00 | 28.95 F | C |
| ATOM | 1806 | N9 | GUA | F | 14 | −13.629 | 1.628 | −11.502 | 1.00 | 28.65 F | N |
| ATOM | 1807 | C8 | GUA | F | 14 | −13.734 | 0.478 | −10.751 | 1.00 | 27.50 F | C |
| ATOM | 1808 | N7 | GUA | F | 14 | −12.690 | −0.305 | −10.845 | 1.00 | 25.21 F | N |
| ATOM | 1809 | C5 | GUA | F | 14 | −11.835 | 0.372 | −11.706 | 1.00 | 22.23 F | C |
| ATOM | 1810 | C6 | GUA | F | 14 | −10.554 | 0.025 | −12.185 | 1.00 | 23.99 F | C |
| ATOM | 1811 | O6 | GUA | F | 14 | −9.894 | −0.990 | −11.930 | 1.00 | 26.66 F | O |
| ATOM | 1812 | N1 | GUA | F | 14 | −10.039 | 0.991 | −13.050 | 1.00 | 23.15 F | N |
| ATOM | 1813 | C2 | GUA | F | 14 | −10.683 | 2.153 | −13.402 | 1.00 | 27.10 F | C |
| ATOM | 1814 | N2 | GUA | F | 14 | −10.040 | 2.977 | −14.244 | 1.00 | 27.62 F | N |
| ATOM | 1815 | N3 | GUA | F | 14 | −11.882 | 2.492 | −12.955 | 1.00 | 29.89 F | N |
| ATOM | 1816 | C4 | GUA | F | 14 | −12.397 | 1.559 | −12.118 | 1.00 | 28.73 F | C |
| ATOM | 1817 | P | CYT | F | 15 | −17.994 | 3.944 | −13.540 | 1.00 | 57.53 F | P |
| ATOM | 1818 | OP1 | CYT | F | 15 | −18.880 | 5.065 | −13.912 | 1.00 | 66.77 F | O |
| ATOM | 1819 | OP2 | CYT | F | 15 | −18.533 | 2.569 | −13.429 | 1.00 | 45.10 F | O |
| ATOM | 1820 | O5' | CYT | F | 15 | −16.765 | 3.919 | −14.561 | 1.00 | 61.13 F | O |
| ATOM | 1821 | C5' | CYT | F | 15 | −16.011 | 5.107 | −14.774 | 1.00 | 60.71 F | C |
| ATOM | 1822 | C4' | CYT | F | 15 | −14.957 | 4.886 | −15.844 | 1.00 | 63.70 F | C |
| ATOM | 1823 | O4' | CYT | F | 15 | −14.016 | 3.870 | −15.408 | 1.00 | 56.35 F | O |
| ATOM | 1824 | C3' | CYT | F | 15 | −15.507 | 4.415 | −17.186 | 1.00 | 63.78 F | C |
| ATOM | 1825 | O3' | CYT | F | 15 | −14.833 | 5.094 | −18.244 | 1.00 | 69.14 F | O |
| ATOM | 1826 | C2' | CYT | F | 15 | −15.220 | 2.915 | −17.180 | 1.00 | 54.75 F | C |
| ATOM | 1827 | C1' | CYT | F | 15 | −13.925 | 2.848 | −16.379 | 1.00 | 50.07 F | C |
| ATOM | 1828 | N1 | CYT | F | 15 | −13.730 | 1.550 | −15.671 | 1.00 | 42.12 F | N |
| ATOM | 1829 | C2 | CYT | F | 15 | −12.553 | 0.820 | −15.884 | 1.00 | 38.81 F | C |
| ATOM | 1830 | O2 | CYT | F | 15 | −11.691 | 1.262 | −16.660 | 1.00 | 38.49 F | O |
| ATOM | 1831 | N3 | CYT | F | 15 | −12.390 | −0.357 | −15.231 | 1.00 | 32.50 F | N |
| ATOM | 1832 | C4 | CYT | F | 15 | −13.338 | −0.803 | −14.404 | 1.00 | 36.68 F | C |
| ATOM | 1833 | N4 | CYT | F | 15 | −13.119 | −1.972 | −13.789 | 1.00 | 32.28 F | N |
| ATOM | 1834 | C5 | CYT | F | 15 | −14.546 | −0.071 | −14.174 | 1.00 | 36.00 F | C |
| ATOM | 1835 | C6 | CYT | F | 15 | −14.696 | 1.089 | −14.822 | 1.00 | 37.43 F | C |
| ATOM | 1836 | P | THY | F | 16 | −15.377 | 5.023 | −19.751 | 1.00 | 80.16 F | P |

TABLE 1-continued

| | | | | | | | | | | |
|---|---|---|---|---|---|---|---|---|---|---|
| ATOM | 1837 | OP1 | THY | F | 16 | −15.380 | 6.409 | −20.269 | 1.00 | 68.74 F | O |
| ATOM | 1838 | OP2 | THY | F | 16 | −16.614 | 4.202 | −19.786 | 1.00 | 59.17 F | O |
| ATOM | 1839 | O5' | THY | F | 16 | −14.242 | 4.186 | −20.504 | 1.00 | 74.20 F | O |
| ATOM | 1840 | C5' | THY | F | 16 | −12.868 | 4.527 | −20.356 | 1.00 | 64.50 F | C |
| ATOM | 1841 | C4' | THY | F | 16 | −12.005 | 3.433 | −20.959 | 1.00 | 61.48 F | C |
| ATOM | 1842 | O4' | THY | F | 16 | −11.933 | 2.288 | −20.071 | 1.00 | 56.08 F | O |
| ATOM | 1843 | C3' | THY | F | 16 | −12.522 | 2.903 | −22.292 | 1.00 | 64.84 F | C |
| ATOM | 1844 | O3' | THY | F | 16 | −11.448 | 2.856 | −23.218 | 1.00 | 65.11 F | O |
| ATOM | 1845 | C2' | THY | F | 16 | −13.065 | 1.514 | −21.959 | 1.00 | 58.52 F | C |
| ATOM | 1846 | C1' | THY | F | 16 | −12.146 | 1.106 | −20.816 | 1.00 | 48.55 F | C |
| ATOM | 1847 | N1 | THY | F | 16 | −12.712 | 0.088 | −19.887 | 1.00 | 44.56 F | N |
| ATOM | 1848 | C2 | THY | F | 16 | −11.930 | −0.987 | −19.523 | 1.00 | 41.93 F | C |
| ATOM | 1849 | O2 | THY | F | 16 | −10.789 | −1.154 | −19.928 | 1.00 | 36.72 F | O |
| ATOM | 1850 | N3 | THY | F | 16 | −12.540 | −1.862 | −18.658 | 1.00 | 37.33 F | N |
| ATOM | 1851 | C4 | THY | F | 16 | −13.817 | −1.771 | −18.138 | 1.00 | 38.23 F | C |
| ATOM | 1852 | O4 | THY | F | 16 | −14.279 | −2.606 | −17.367 | 1.00 | 38.67 F | O |
| ATOM | 1853 | C5 | THY | F | 16 | −14.576 | −0.625 | −18.564 | 1.00 | 39.50 F | C |
| ATOM | 1854 | C7 | THY | F | 16 | −15.975 | −0.438 | −18.059 | 1.00 | 37.21 F | C |
| ATOM | 1855 | C6 | THY | F | 16 | −13.998 | 0.241 | −19.406 | 1.00 | 43.36 F | C |
| ATOM | 1856 | P | THY | F | 17 | −11.767 | 2.951 | −24.778 | 1.00 | 81.71 F | P |
| ATOM | 1857 | OP1 | THY | F | 17 | −10.777 | 3.861 | −25.394 | 1.00 | 56.22 F | O |
| ATOM | 1858 | OP2 | THY | F | 17 | −13.218 | 3.216 | −24.919 | 1.00 | 75.03 F | O |
| ATOM | 1859 | O5' | THY | F | 17 | −11.493 | 1.459 | −25.283 | 1.00 | 76.85 F | O |
| ATOM | 1860 | C5' | THY | F | 17 | −10.171 | 0.932 | −25.289 | 1.00 | 71.22 F | C |
| ATOM | 1861 | C4' | THY | F | 17 | −10.213 | −0.575 | −25.471 | 1.00 | 71.63 F | C |
| ATOM | 1862 | O4' | THY | F | 17 | −10.789 | −1.183 | −24.287 | 1.00 | 63.05 F | O |
| ATOM | 1863 | C3' | THY | F | 17 | −11.042 | −1.060 | −26.661 | 1.00 | 64.78 F | C |
| ATOM | 1864 | O3' | THY | F | 17 | −10.284 | −1.985 | −27.435 | 1.00 | 63.87 F | O |
| ATOM | 1865 | C2' | THY | F | 17 | −12.265 | −1.721 | −26.025 | 1.00 | 64.01 F | C |
| ATOM | 1866 | C1' | THY | F | 17 | −11.714 | −2.172 | −24.678 | 1.00 | 67.24 F | C |
| ATOM | 1867 | N1 | THY | F | 17 | −12.743 | −2.246 | −23.624 | 1.00 | 64.24 F | N |
| ATOM | 1868 | C2 | THY | F | 17 | −12.611 | −3.176 | −22.614 | 1.00 | 58.85 F | C |
| ATOM | 1869 | O2 | THY | F | 17 | −11.674 | −3.955 | −22.540 | 1.00 | 48.20 F | O |
| ATOM | 1870 | N3 | THY | F | 17 | −13.627 | −3.153 | −21.689 | 1.00 | 46.71 F | N |
| ATOM | 1871 | C4 | THY | F | 17 | −14.726 | −2.314 | −21.681 | 1.00 | 48.10 F | C |
| ATOM | 1872 | O4 | THY | F | 17 | −15.585 | −2.370 | −20.808 | 1.00 | 54.41 F | O |
| ATOM | 1873 | C5 | THY | F | 17 | −14.795 | −1.367 | −22.768 | 1.00 | 57.18 F | C |
| ATOM | 1874 | C7 | THY | F | 17 | −15.944 | −0.406 | −22.864 | 1.00 | 61.07 F | C |
| ATOM | 1875 | C6 | THY | F | 17 | −13.813 | −1.379 | −23.678 | 1.00 | 62.83 F | C |
| TER | | | | | | | | | | | |
| ATOM | 1876 | N | GLY | C | 2 | 26.102 | −30.410 | −22.106 | 1.00 | 37.16 C | N |
| ATOM | 1877 | CA | GLY | C | 2 | 27.225 | −30.891 | −22.889 | 1.00 | 37.40 C | C |
| ATOM | 1878 | C | GLY | C | 2 | 27.997 | −31.989 | −22.183 | 1.00 | 41.01 C | C |
| ATOM | 1879 | O | GLY | C | 2 | 27.938 | −32.110 | −20.958 | 1.00 | 42.86 C | O |
| ATOM | 1880 | N | ARG | C | 3 | 28.721 | −32.793 | −22.956 | 1.00 | 39.84 C | N |
| ATOM | 1881 | CA | ARG | C | 3 | 29.520 | −33.876 | −22.393 | 1.00 | 40.18 C | C |
| ATOM | 1882 | C | ARG | C | 3 | 30.538 | −33.327 | −21.398 | 1.00 | 43.21 C | C |
| ATOM | 1883 | O | ARG | C | 3 | 30.820 | −33.945 | −20.369 | 1.00 | 45.60 C | O |
| ATOM | 1884 | CB | ARG | C | 3 | 30.219 | −34.661 | −23.504 | 1.00 | 39.06 C | C |
| ATOM | 1885 | CG | ARG | C | 3 | 29.272 | −35.479 | −24.372 | 1.00 | 38.76 C | C |
| ATOM | 1886 | CD | ARG | C | 3 | 28.414 | −36.403 | −23.522 | 1.00 | 43.44 C | C |
| ATOM | 1887 | NE | ARG | C | 3 | 27.577 | −37.286 | −24.330 | 1.00 | 39.28 C | N |
| ATOM | 1888 | CZ | ARG | C | 3 | 27.994 | −38.428 | −24.868 | 1.00 | 44.32 C | C |
| ATOM | 1889 | NH1 | ARG | C | 3 | 29.247 | −38.828 | −24.698 | 1.00 | 35.70 C | N |
| ATOM | 1890 | NH2 | ARG | C | 3 | 27.159 | −39.167 | −25.583 | 1.00 | 41.27 C | N |
| ATOM | 1891 | N | LYS | C | 4 | 31.082 | −32.159 | −21.716 | 1.00 | 38.21 C | N |
| ATOM | 1892 | CA | LYS | C | 4 | 31.986 | −31.455 | −20.817 | 1.00 | 40.07 C | C |
| ATOM | 1893 | C | LYS | C | 4 | 31.589 | −29.985 | −20.733 | 1.00 | 44.07 C | C |
| ATOM | 1894 | O | LYS | C | 4 | 31.123 | −29.404 | −21.713 | 1.00 | 36.32 C | O |
| ATOM | 1895 | CB | LYS | C | 4 | 33.437 | −31.575 | −21.299 | 1.00 | 41.27 C | C |
| ATOM | 1896 | CG | LYS | C | 4 | 34.023 | −32.977 | −21.180 | 1.00 | 43.87 C | C |
| ATOM | 1897 | CD | LYS | C | 4 | 33.886 | −33.497 | −19.754 | 1.00 | 44.62 C | C |
| ATOM | 1898 | CE | LYS | C | 4 | 33.899 | −35.016 | −19.705 | 1.00 | 58.07 C | C |
| ATOM | 1899 | NZ | LYS | C | 4 | 33.253 | −35.524 | −18.459 | 1.00 | 51.82 C | N |
| ATOM | 1900 | N | LYS | C | 5 | 31.768 | −29.387 | −19.561 | 1.00 | 44.47 C | N |
| ATOM | 1901 | CA | LYS | C | 5 | 31.606 | −27.947 | −19.433 | 1.00 | 41.82 C | C |
| ATOM | 1902 | C | LYS | C | 5 | 32.702 | −27.261 | −20.233 | 1.00 | 44.25 C | C |
| ATOM | 1903 | O | LYS | C | 5 | 33.806 | −27.791 | −20.359 | 1.00 | 49.21 C | O |
| ATOM | 1904 | CB | LYS | C | 5 | 31.682 | −27.513 | −17.971 | 1.00 | 39.15 C | C |
| ATOM | 1905 | CG | LYS | C | 5 | 31.691 | −26.002 | −17.792 | 1.00 | 46.63 C | C |
| ATOM | 1906 | CD | LYS | C | 5 | 31.374 | −25.594 | −16.363 | 1.00 | 42.50 C | C |
| ATOM | 1907 | CE | LYS | C | 5 | 31.225 | −24.090 | −16.258 | 1.00 | 46.51 C | C |
| ATOM | 1908 | NZ | LYS | C | 5 | 30.818 | −23.663 | −14.892 | 1.00 | 51.90 C | N |
| ATOM | 1909 | N | ILE | C | 6 | 32.398 | −26.089 | −20.782 | 1.00 | 37.05 C | N |
| ATOM | 1910 | CA | ILE | C | 6 | 33.394 | −25.321 | −21.521 | 1.00 | 35.04 C | C |
| ATOM | 1911 | C | ILE | C | 6 | 33.581 | −23.914 | −20.958 | 1.00 | 40.67 C | C |
| ATOM | 1912 | O | ILE | C | 6 | 32.791 | −23.446 | −20.136 | 1.00 | 41.66 C | O |
| ATOM | 1913 | CB | ILE | C | 6 | 33.041 | −25.223 | −23.013 | 1.00 | 38.26 C | C |
| ATOM | 1914 | CG1 | ILE | C | 6 | 31.877 | −24.255 | −23.235 | 1.00 | 33.65 C | C |
| ATOM | 1915 | CG2 | ILE | C | 6 | 32.721 | −26.603 | −23.569 | 1.00 | 41.12 C | C |

TABLE 1-continued

| | | | | | | | | | | |
|---|---|---|---|---|---|---|---|---|---|---|
| ATOM | 1916 | CD1 | ILE | C | 6 | 31.712 | −23.841 | −24.682 | 1.00 | 34.76 C | C |
| ATOM | 1917 | N | GLN | C | 7 | 34.644 | −23.249 | −21.396 | 1.00 | 46.96 C | N |
| ATOM | 1918 | CA | GLN | C | 7 | 34.892 | −21.873 | −20.999 | 1.00 | 46.22 C | C |
| ATOM | 1919 | C | GLN | C | 7 | 34.452 | −20.956 | −22.120 | 1.00 | 44.41 C | C |
| ATOM | 1920 | O | GLN | C | 7 | 34.662 | −21.257 | −23.296 | 1.00 | 43.97 C | O |
| ATOM | 1921 | CB | GLN | C | 7 | 36.374 | −21.649 | −20.687 | 1.00 | 54.97 C | C |
| ATOM | 1922 | CG | GLN | C | 7 | 36.843 | −22.323 | −19.409 | 1.00 | 57.18 C | C |
| ATOM | 1923 | CD | GLN | C | 7 | 35.980 | −21.963 | −18.213 | 1.00 | 73.60 C | C |
| ATOM | 1924 | OE1 | GLN | C | 7 | 35.636 | −20.797 | −18.008 | 1.00 | 77.65 C | O |
| ATOM | 1925 | NE2 | GLN | C | 7 | 35.629 | −22.966 | −17.413 | 1.00 | 72.99 C | N |
| ATOM | 1926 | N | ILE | C | 8 | 33.830 | −19.839 | −21.761 | 1.00 | 28.39 C | N |
| ATOM | 1927 | CA | ILE | C | 8 | 33.363 | −18.899 | −22.767 | 1.00 | 21.10 C | C |
| ATOM | 1928 | C | ILE | C | 8 | 34.548 | −18.138 | −23.353 | 1.00 | 24.35 C | C |
| ATOM | 1929 | O | ILE | C | 8 | 34.920 | −17.062 | −22.879 | 1.00 | 25.10 C | O |
| ATOM | 1930 | CB | ILE | C | 8 | 32.292 | −17.944 | −22.211 | 1.00 | 20.86 C | C |
| ATOM | 1931 | CG1 | ILE | C | 8 | 31.062 | −18.743 | −21.773 | 1.00 | 27.03 C | C |
| ATOM | 1932 | CG2 | ILE | C | 8 | 31.895 | −16.916 | −23.249 | 1.00 | 18.08 C | C |
| ATOM | 1933 | CD1 | ILE | C | 8 | 30.547 | −19.712 | −22.835 | 1.00 | 21.56 C | C |
| ATOM | 1934 | N | THR | C | 9 | 35.149 | −18.718 | −24.386 | 1.00 | 18.31 C | N |
| ATOM | 1935 | CA | THR | C | 9 | 36.265 | −18.074 | −25.064 | 1.00 | 18.73 C | C |
| ATOM | 1936 | C | THR | C | 9 | 36.330 | −18.510 | −26.528 | 1.00 | 16.20 C | C |
| ATOM | 1937 | O | THR | C | 9 | 35.998 | −19.652 | −26.865 | 1.00 | 19.80 C | O |
| ATOM | 1938 | CB | THR | C | 9 | 37.604 | −18.337 | −24.335 | 1.00 | 22.75 C | C |
| ATOM | 1939 | OG1 | THR | C | 9 | 38.643 | −17.538 | −24.920 | 1.00 | 29.46 C | O |
| ATOM | 1940 | CG2 | THR | C | 9 | 37.976 | −19.817 | −24.395 | 1.00 | 15.15 C | C |
| ATOM | 1941 | N | ARG | C | 10 | 36.736 | −17.577 | −27.385 | 1.00 | 22.69 C | N |
| ATOM | 1942 | CA | ARG | C | 10 | 36.805 | −17.797 | −28.828 | 1.00 | 28.13 C | C |
| ATOM | 1943 | C | ARG | C | 10 | 37.364 | −19.165 | −29.205 | 1.00 | 26.44 C | C |
| ATOM | 1944 | O | ARG | C | 10 | 38.497 | −19.501 | −28.866 | 1.00 | 27.25 C | O |
| ATOM | 1945 | CB | ARG | C | 10 | 37.635 | −16.698 | −29.496 | 1.00 | 25.83 C | C |
| ATOM | 1946 | CG | ARG | C | 10 | 37.636 | −16.769 | −31.009 | 1.00 | 25.49 C | C |
| ATOM | 1947 | CD | ARG | C | 10 | 38.512 | −15.688 | −31.619 | 1.00 | 26.19 C | C |
| ATOM | 1948 | NE | ARG | C | 10 | 38.533 | −15.776 | −33.077 | 1.00 | 42.34 C | N |
| ATOM | 1949 | CZ | ARG | C | 10 | 39.313 | −16.606 | −33.764 | 1.00 | 35.92 C | C |
| ATOM | 1950 | NH1 | ARG | C | 10 | 40.138 | −17.421 | −33.123 | 1.00 | 40.43 C | N |
| ATOM | 1951 | NH2 | ARG | C | 10 | 39.269 | −16.620 | −35.089 | 1.00 | 33.33 C | N |
| ATOM | 1952 | N | ILE | C | 11 | 36.546 | −19.948 | −29.898 | 1.00 | 13.48 C | N |
| ATOM | 1953 | CA | ILE | C | 11 | 36.954 | −21.246 | −30.411 | 1.00 | 16.65 C | C |
| ATOM | 1954 | C | ILE | C | 11 | 37.985 | −21.029 | −31.516 | 1.00 | 20.36 C | C |
| ATOM | 1955 | O | ILE | C | 11 | 37.745 | −20.268 | −32.458 | 1.00 | 21.24 C | O |
| ATOM | 1956 | CB | ILE | C | 11 | 35.741 | −22.022 | −30.952 | 1.00 | 21.38 C | C |
| ATOM | 1957 | CG1 | ILE | C | 11 | 34.750 | −22.296 | −29.816 | 1.00 | 14.80 C | C |
| ATOM | 1958 | CG2 | ILE | C | 11 | 36.177 | −23.320 | −31.635 | 1.00 | 14.57 C | C |
| ATOM | 1959 | CD1 | ILE | C | 11 | 33.463 | −22.954 | −30.264 | 1.00 | 16.69 C | C |
| ATOM | 1960 | N | MET | C | 12 | 39.138 | −21.678 | −31.382 | 1.00 | 22.82 C | N |
| ATOM | 1961 | CA | MET | C | 12 | 40.267 | −21.407 | −32.262 | 1.00 | 29.62 C | C |
| ATOM | 1962 | C | MET | C | 12 | 40.202 | −22.231 | −33.544 | 1.00 | 29.22 C | C |
| ATOM | 1963 | O | MET | C | 12 | 40.707 | −21.810 | −34.581 | 1.00 | 28.51 C | O |
| ATOM | 1964 | CB | MET | C | 12 | 41.594 | −21.653 | −31.533 | 1.00 | 24.77 C | C |
| ATOM | 1965 | CG | MET | C | 12 | 41.796 | −20.801 | −30.272 | 1.00 | 29.84 C | C |
| ATOM | 1966 | SD | MET | C | 12 | 41.935 | −19.026 | −30.587 | 1.00 | 31.80 C | S |
| ATOM | 1967 | CE | MET | C | 12 | 43.472 | −18.972 | −31.519 | 1.00 | 25.97 C | C |
| ATOM | 1968 | N | ASP | C | 13 | 39.577 | −23.401 | −33.461 | 1.00 | 47.38 C | N |
| ATOM | 1969 | CA | ASP | C | 13 | 39.448 | −24.301 | −34.604 | 1.00 | 49.89 C | C |
| ATOM | 1970 | C | ASP | C | 13 | 38.251 | −23.913 | −35.472 | 1.00 | 45.31 C | C |
| ATOM | 1971 | O | ASP | C | 13 | 37.102 | −24.017 | −35.041 | 1.00 | 43.32 C | O |
| ATOM | 1972 | CB | ASP | C | 13 | 39.301 | −25.745 | −34.114 | 1.00 | 49.98 C | C |
| ATOM | 1973 | CG | ASP | C | 13 | 38.903 | −26.707 | −35.223 | 1.00 | 66.17 C | C |
| ATOM | 1974 | OD1 | ASP | C | 13 | 39.467 | −26.610 | −36.335 | 1.00 | 72.90 C | O |
| ATOM | 1975 | OD2 | ASP | C | 13 | 38.030 | −27.571 | −34.979 | 1.00 | 61.32 C | O |
| ATOM | 1976 | N | GLU | C | 14 | 38.530 | −23.461 | −36.690 | 1.00 | 27.77 C | N |
| ATOM | 1977 | CA | GLU | C | 14 | 37.488 | −23.055 | −37.629 | 1.00 | 33.41 C | C |
| ATOM | 1978 | C | GLU | C | 14 | 36.413 | −24.122 | −37.807 | 1.00 | 38.75 C | C |
| ATOM | 1979 | O | GLU | C | 14 | 35.233 | −23.808 | −37.960 | 1.00 | 31.01 C | O |
| ATOM | 1980 | CB | GLU | C | 14 | 38.096 | −22.710 | −38.991 | 1.00 | 30.94 C | C |
| ATOM | 1981 | CG | GLU | C | 14 | 37.079 | −22.438 | −40.088 | 1.00 | 33.31 C | C |
| ATOM | 1982 | CD | GLU | C | 14 | 37.732 | −22.114 | −41.426 | 1.00 | 61.19 C | C |
| ATOM | 1983 | OE1 | GLU | C | 14 | 38.831 | −22.642 | −41.705 | 1.00 | 66.85 C | O |
| ATOM | 1984 | OE2 | GLU | C | 14 | 37.144 | −21.333 | −42.204 | 1.00 | 51.72 C | O |
| ATOM | 1985 | N | ARG | C | 15 | 36.816 | −25.386 | −37.785 | 1.00 | 49.66 C | N |
| ATOM | 1986 | CA | ARG | C | 15 | 35.856 | −26.464 | −37.972 | 1.00 | 42.37 C | C |
| ATOM | 1987 | C | ARG | C | 15 | 34.830 | −26.496 | −36.843 | 1.00 | 37.98 C | C |
| ATOM | 1988 | O | ARG | C | 15 | 33.637 | −26.352 | −37.088 | 1.00 | 34.22 C | O |
| ATOM | 1989 | CB | ARG | C | 15 | 36.562 | −27.814 | −38.111 | 1.00 | 51.26 C | C |
| ATOM | 1990 | CG | ARG | C | 15 | 35.704 | −28.875 | −38.771 | 1.00 | 56.80 C | C |
| ATOM | 1991 | CD | ARG | C | 15 | 36.503 | −29.690 | −39.775 | 1.00 | 67.79 C | C |
| ATOM | 1992 | NE | ARG | C | 15 | 35.708 | −29.979 | −40.966 | 1.00 | 74.25 C | N |
| ATOM | 1993 | CZ | ARG | C | 15 | 35.568 | −29.141 | −41.990 | 1.00 | 70.71 C | C |
| ATOM | 1994 | NH1 | ARG | C | 15 | 36.173 | −27.959 | −41.971 | 1.00 | 78.90 C | N |
| ATOM | 1995 | NH2 | ARG | C | 15 | 34.822 | −29.481 | −43.035 | 1.00 | 52.78 C | N |

TABLE 1-continued

| | | | | | | | | | | | |
|---|---|---|---|---|---|---|---|---|---|---|---|
| ATOM | 1996 | N | ASN | C | 16 | 35.292 | −26.677 | −35.608 | 1.00 | 39.27 C | N |
| ATOM | 1997 | CA | ASN | C | 16 | 34.381 | −26.706 | −34.469 | 1.00 | 35.73 C | C |
| ATOM | 1998 | C | ASN | C | 16 | 33.650 | −25.380 | −34.274 | 1.00 | 31.63 C | C |
| ATOM | 1999 | O | ASN | C | 16 | 32.565 | −25.346 | −33.705 | 1.00 | 30.78 C | O |
| ATOM | 2000 | CB | ASN | C | 16 | 35.103 | −27.106 | −33.173 | 1.00 | 41.02 C | C |
| ATOM | 2001 | CG | ASN | C | 16 | 34.151 | −27.172 | −31.964 | 1.00 | 49.30 C | C |
| ATOM | 2002 | OD1 | ASN | C | 16 | 33.053 | −27.730 | −32.049 | 1.00 | 39.61 C | O |
| ATOM | 2003 | ND2 | ASN | C | 16 | 34.576 | −26.601 | −30.838 | 1.00 | 35.86 C | N |
| ATOM | 2004 | N | ARG | C | 17 | 34.237 | −24.287 | −34.745 | 1.00 | 19.12 C | N |
| ATOM | 2005 | CA | ARG | C | 17 | 33.618 | −22.985 | −34.552 | 1.00 | 21.97 C | C |
| ATOM | 2006 | C | ARG | C | 17 | 32.409 | −22.833 | −35.466 | 1.00 | 23.23 C | C |
| ATOM | 2007 | O | ARG | C | 17 | 31.385 | −22.271 | −35.074 | 1.00 | 21.76 C | O |
| ATOM | 2008 | CB | ARG | C | 17 | 34.618 | −21.851 | −34.783 | 1.00 | 18.63 C | C |
| ATOM | 2009 | CG | ARG | C | 17 | 34.048 | −20.470 | −34.495 | 1.00 | 19.22 C | C |
| ATOM | 2010 | CD | ARG | C | 17 | 35.129 | −19.388 | −34.498 | 1.00 | 23.09 C | C |
| ATOM | 2011 | NE | ARG | C | 17 | 35.704 | −19.201 | −35.826 | 1.00 | 26.86 C | N |
| ATOM | 2012 | CZ | ARG | C | 17 | 36.947 | −19.533 | −36.164 | 1.00 | 30.01 C | C |
| ATOM | 2013 | NH1 | ARG | C | 17 | 37.775 | −20.055 | −35.261 | 1.00 | 22.90 C | N |
| ATOM | 2014 | NH2 | ARG | C | 17 | 37.366 | −19.328 | −37.409 | 1.00 | 30.60 C | N |
| ATOM | 2015 | N | GLN | C | 18 | 32.531 | −23.336 | −36.687 | 1.00 | 26.75 C | N |
| ATOM | 2016 | CA | GLN | C | 18 | 31.417 | −23.314 | −37.621 | 1.00 | 28.13 C | C |
| ATOM | 2017 | C | GLN | C | 18 | 30.264 | −24.158 | −37.079 | 1.00 | 24.45 C | C |
| ATOM | 2018 | O | GLN | C | 18 | 29.106 | −23.745 | −37.125 | 1.00 | 19.76 C | O |
| ATOM | 2019 | CB | GLN | C | 18 | 31.855 | −23.839 | −38.990 | 1.00 | 24.27 C | C |
| ATOM | 2020 | CG | GLN | C | 18 | 30.779 | −23.713 | −40.054 | 1.00 | 25.41 C | C |
| ATOM | 2021 | CD | GLN | C | 18 | 30.429 | −22.266 | −40.352 | 1.00 | 39.70 C | C |
| ATOM | 2022 | OE1 | GLN | C | 18 | 31.245 | −21.517 | −40.894 | 1.00 | 47.66 C | O |
| ATOM | 2023 | NE2 | GLN | C | 18 | 29.211 | −21.867 | −40.004 | 1.00 | 49.70 C | N |
| ATOM | 2024 | N | VAL | C | 19 | 30.603 | −25.338 | −36.566 | 1.00 | 29.15 C | N |
| ATOM | 2025 | CA | VAL | C | 19 | 29.631 | −26.274 | −36.016 | 1.00 | 28.04 C | C |
| ATOM | 2026 | C | VAL | C | 19 | 28.932 | −25.697 | −34.789 | 1.00 | 31.99 C | C |
| ATOM | 2027 | O | VAL | C | 19 | 27.708 | −25.733 | −34.679 | 1.00 | 31.77 C | O |
| ATOM | 2028 | CB | VAL | C | 19 | 30.314 | −27.597 | −35.621 | 1.00 | 30.57 C | C |
| ATOM | 2029 | CG1 | VAL | C | 19 | 29.381 | −28.459 | −34.788 | 1.00 | 28.68 C | C |
| ATOM | 2030 | CG2 | VAL | C | 19 | 30.767 | −28.337 | −36.856 | 1.00 | 28.38 C | C |
| ATOM | 2031 | N | THR | C | 20 | 29.718 | −25.167 | −33.863 | 1.00 | 23.43 C | N |
| ATOM | 2032 | CA | THR | C | 20 | 29.167 | −24.575 | −32.659 | 1.00 | 24.62 C | C |
| ATOM | 2033 | C | THR | C | 20 | 28.283 | −23.392 | −33.022 | 1.00 | 24.14 C | C |
| ATOM | 2034 | O | THR | C | 20 | 27.247 | −23.149 | −32.391 | 1.00 | 21.70 C | O |
| ATOM | 2035 | CB | THR | C | 20 | 30.279 | −24.114 | −31.717 | 1.00 | 26.92 C | C |
| ATOM | 2036 | OG1 | THR | C | 20 | 30.934 | −25.264 | −31.172 | 1.00 | 25.57 C | O |
| ATOM | 2037 | CG2 | THR | C | 20 | 29.705 | −23.271 | −30.584 | 1.00 | 22.17 C | C |
| ATOM | 2038 | N | PHE | C | 21 | 28.693 | −22.665 | −34.053 | 1.00 | 21.78 C | N |
| ATOM | 2039 | CA | PHE | C | 21 | 27.948 | −21.492 | −34.491 | 1.00 | 24.12 C | C |
| ATOM | 2040 | C | PHE | C | 21 | 26.587 | −21.851 | −35.081 | 1.00 | 23.04 C | C |
| ATOM | 2041 | O | PHE | C | 21 | 25.603 | −21.162 | −34.832 | 1.00 | 22.41 C | O |
| ATOM | 2042 | CB | PHE | C | 21 | 28.757 | −20.679 | −35.501 | 1.00 | 19.76 C | C |
| ATOM | 2043 | CG | PHE | C | 21 | 27.948 | −19.642 | −36.219 | 1.00 | 21.70 C | C |
| ATOM | 2044 | CD1 | PHE | C | 21 | 27.773 | −18.379 | −35.672 | 1.00 | 16.96 C | C |
| ATOM | 2045 | CD2 | PHE | C | 21 | 27.349 | −19.932 | −37.438 | 1.00 | 21.89 C | C |
| ATOM | 2046 | CE1 | PHE | C | 21 | 27.027 | −17.419 | −36.328 | 1.00 | 19.77 C | C |
| ATOM | 2047 | CE2 | PHE | C | 21 | 26.594 | −18.976 | −38.100 | 1.00 | 22.15 C | C |
| ATOM | 2048 | CZ | PHE | C | 21 | 26.434 | −17.719 | −37.549 | 1.00 | 26.78 C | C |
| ATOM | 2049 | N | THR | C | 22 | 26.531 | −22.919 | −35.869 | 1.00 | 17.14 C | N |
| ATOM | 2050 | CA | THR | C | 22 | 25.265 | −23.334 | −36.471 | 1.00 | 17.72 C | C |
| ATOM | 2051 | C | THR | C | 22 | 24.301 | −23.861 | −35.409 | 1.00 | 16.28 C | C |
| ATOM | 2052 | O | THR | C | 22 | 23.096 | −23.613 | −35.476 | 1.00 | 17.19 C | O |
| ATOM | 2053 | CB | THR | C | 22 | 25.455 | −24.402 | −37.590 | 1.00 | 18.91 C | C |
| ATOM | 2054 | OG1 | THR | C | 22 | 26.031 | −23.796 | −38.757 | 1.00 | 15.99 C | O |
| ATOM | 2055 | CG2 | THR | C | 22 | 24.121 | −25.011 | −37.968 | 1.00 | 12.54 C | C |
| ATOM | 2056 | N | LYS | C | 23 | 24.831 | −24.589 | −34.428 | 1.00 | 18.67 C | N |
| ATOM | 2057 | CA | LYS | C | 23 | 23.995 | −25.125 | −33.359 | 1.00 | 19.65 C | C |
| ATOM | 2058 | C | LYS | C | 23 | 23.422 | −24.010 | −32.493 | 1.00 | 19.04 C | C |
| ATOM | 2059 | O | LYS | C | 23 | 22.209 | −23.923 | −32.305 | 1.00 | 19.52 C | O |
| ATOM | 2060 | CB | LYS | C | 23 | 24.775 | −26.114 | −32.488 | 1.00 | 22.98 C | C |
| ATOM | 2061 | CG | LYS | C | 23 | 25.091 | −27.443 | −33.169 | 1.00 | 29.30 C | C |
| ATOM | 2062 | CD | LYS | C | 23 | 25.900 | −28.341 | −32.235 | 1.00 | 32.52 C | C |
| ATOM | 2063 | CE | LYS | C | 23 | 26.088 | −29.726 | −32.813 | 1.00 | 35.94 C | C |
| ATOM | 2064 | NZ | LYS | C | 23 | 27.012 | −30.536 | −31.973 | 1.00 | 33.98 C | N |
| ATOM | 2065 | N | ARG | C | 24 | 24.302 | −23.153 | −31.980 | 1.00 | 16.23 C | N |
| ATOM | 2066 | CA | ARG | C | 24 | 23.895 | −22.083 | −31.072 | 1.00 | 15.69 C | C |
| ATOM | 2067 | C | ARG | C | 24 | 23.079 | −20.973 | −31.746 | 1.00 | 17.54 C | C |
| ATOM | 2068 | O | ARG | C | 24 | 22.246 | −20.339 | −31.088 | 1.00 | 16.19 C | O |
| ATOM | 2069 | CB | ARG | C | 24 | 25.106 | −21.494 | −30.346 | 1.00 | 13.13 C | C |
| ATOM | 2070 | CG | ARG | C | 24 | 25.567 | −22.316 | −29.145 | 1.00 | 14.55 C | C |
| ATOM | 2071 | CD | ARG | C | 24 | 26.824 | −21.735 | −28.509 | 1.00 | 13.70 C | C |
| ATOM | 2072 | NE | ARG | C | 24 | 27.168 | −22.430 | −27.273 | 1.00 | 15.96 C | N |
| ATOM | 2073 | CZ | ARG | C | 24 | 26.860 | −21.988 | −26.055 | 1.00 | 17.74 C | C |
| ATOM | 2074 | NH1 | ARG | C | 24 | 26.203 | −20.842 | −25.901 | 1.00 | 17.55 C | N |
| ATOM | 2075 | NH2 | ARG | C | 24 | 27.209 | −22.690 | −24.990 | 1.00 | 13.06 C | N |

TABLE 1-continued

| | | | | | | | | | | |
|---|---|---|---|---|---|---|---|---|---|---|
| ATOM | 2076 | N | LYS | C | 25 | 23.313 | −20.732 | −33.040 | 1.00 | 20.57 C | N |
| ATOM | 2077 | CA | LYS | C | 25 | 22.542 | −19.711 | −33.763 | 1.00 | 21.27 C | C |
| ATOM | 2078 | C | LYS | C | 25 | 21.087 | −20.126 | −33.788 | 1.00 | 21.17 C | C |
| ATOM | 2079 | O | LYS | C | 25 | 20.188 | −19.314 | −33.581 | 1.00 | 21.37 C | O |
| ATOM | 2080 | CB | LYS | C | 25 | 23.040 | −19.522 | −35.196 | 1.00 | 27.14 C | C |
| ATOM | 2081 | CG | LYS | C | 25 | 22.094 | −18.694 | −36.068 | 1.00 | 23.36 C | C |
| ATOM | 2082 | CD | LYS | C | 25 | 22.799 | −18.097 | −37.285 | 1.00 | 29.03 C | C |
| ATOM | 2083 | CE | LYS | C | 25 | 23.198 | −19.165 | −38.317 | 1.00 | 25.05 C | C |
| ATOM | 2084 | NZ | LYS | C | 25 | 22.025 | −19.796 | −38.986 | 1.00 | 22.30 C | N |
| ATOM | 2085 | N | PHE | C | 26 | 20.870 | −21.407 | −34.050 | 1.00 | 16.86 C | N |
| ATOM | 2086 | CA | PHE | C | 26 | 19.541 | −21.989 | −33.996 | 1.00 | 19.25 C | C |
| ATOM | 2087 | C | PHE | C | 26 | 18.942 | −21.777 | −32.593 | 1.00 | 19.01 C | C |
| ATOM | 2088 | O | PHE | C | 26 | 17.915 | −21.115 | −32.435 | 1.00 | 20.38 C | O |
| ATOM | 2089 | CB | PHE | C | 26 | 19.629 | −23.478 | −34.344 | 1.00 | 16.09 C | C |
| ATOM | 2090 | CG | PHE | C | 26 | 18.300 | −24.149 | −34.472 | 1.00 | 20.27 C | C |
| ATOM | 2091 | CD1 | PHE | C | 26 | 17.753 | −24.395 | −35.723 | 1.00 | 22.76 C | C |
| ATOM | 2092 | CD2 | PHE | C | 26 | 17.595 | −24.539 | −33.343 | 1.00 | 18.57 C | C |
| ATOM | 2093 | CE1 | PHE | C | 26 | 16.525 | −25.014 | −35.846 | 1.00 | 23.64 C | C |
| ATOM | 2094 | CE2 | PHE | C | 26 | 16.369 | −25.160 | −33.458 | 1.00 | 21.64 C | C |
| ATOM | 2095 | CZ | PHE | C | 26 | 15.831 | −25.398 | −34.714 | 1.00 | 28.23 C | C |
| ATOM | 2096 | N | GLY | C | 27 | 19.606 | −22.329 | −31.579 | 1.00 | 21.08 C | N |
| ATOM | 2097 | CA | GLY | C | 27 | 19.207 | −22.147 | −30.196 | 1.00 | 19.30 C | C |
| ATOM | 2098 | C | GLY | C | 27 | 18.916 | −20.709 | −29.804 | 1.00 | 17.49 C | C |
| ATOM | 2099 | O | GLY | C | 27 | 18.010 | −20.459 | −29.013 | 1.00 | 19.26 C | O |
| ATOM | 2100 | N | LEU | C | 28 | 19.676 | −19.760 | −30.346 | 1.00 | 18.92 C | N |
| ATOM | 2101 | CA | LEU | C | 28 | 19.486 | −18.351 | −29.999 | 1.00 | 19.41 C | C |
| ATOM | 2102 | C | LEU | C | 28 | 18.215 | −17.781 | −30.627 | 1.00 | 18.47 C | C |
| ATOM | 2103 | O | LEU | C | 28 | 17.478 | −17.031 | −29.983 | 1.00 | 16.61 C | O |
| ATOM | 2104 | CB | LEU | C | 28 | 20.697 | −17.513 | −30.410 | 1.00 | 22.21 C | C |
| ATOM | 2105 | CG | LEU | C | 28 | 20.668 | −16.026 | −30.026 | 1.00 | 18.79 C | C |
| ATOM | 2106 | CD1 | LEU | C | 28 | 20.508 | −15.853 | −28.534 | 1.00 | 15.60 C | C |
| ATOM | 2107 | CD2 | LEU | C | 28 | 21.923 | −15.305 | −30.508 | 1.00 | 16.50 C | C |
| ATOM | 2108 | N | MET | C | 29 | 17.965 | −18.147 | −31.883 | 1.00 | 24.79 C | N |
| ATOM | 2109 | CA | MET | C | 29 | 16.753 | −17.736 | −32.583 | 1.00 | 21.90 C | C |
| ATOM | 2110 | C | MET | C | 29 | 15.530 | −18.403 | −31.971 | 1.00 | 20.00 C | C |
| ATOM | 2111 | O | MET | C | 29 | 14.478 | −17.790 | −31.847 | 1.00 | 18.56 C | O |
| ATOM | 2112 | CB | MET | C | 29 | 16.838 | −18.074 | −34.075 | 1.00 | 22.28 C | C |
| ATOM | 2113 | CG | MET | C | 29 | 17.931 | −17.326 | −34.839 | 1.00 | 21.94 C | C |
| ATOM | 2114 | SD | MET | C | 29 | 17.603 | −17.288 | −36.625 | 1.00 | 24.71 C | S |
| ATOM | 2115 | CE | MET | C | 29 | 19.065 | −16.419 | −37.197 | 1.00 | 27.04 C | C |
| ATOM | 2116 | N | LYS | C | 30 | 15.672 | −19.664 | −31.585 | 1.00 | 18.86 C | N |
| ATOM | 2117 | CA | LYS | C | 30 | 14.565 | −20.375 | −30.958 | 1.00 | 19.52 C | C |
| ATOM | 2118 | C | LYS | C | 30 | 14.080 | −19.641 | −29.701 | 1.00 | 19.23 C | C |
| ATOM | 2119 | O | LYS | C | 30 | 12.881 | −19.397 | −29.537 | 1.00 | 21.59 C | O |
| ATOM | 2120 | CB | LYS | C | 30 | 14.945 | −21.821 | −30.627 | 1.00 | 18.29 C | C |
| ATOM | 2121 | CG | LYS | C | 30 | 13.752 | −22.660 | −30.193 | 1.00 | 26.72 C | C |
| ATOM | 2122 | CD | LYS | C | 30 | 14.138 | −24.070 | −29.781 | 1.00 | 26.48 C | C |
| ATOM | 2123 | CE | LYS | C | 30 | 12.902 | −24.862 | −29.372 | 1.00 | 33.14 C | C |
| ATOM | 2124 | NZ | LYS | C | 30 | 13.230 | −26.088 | −28.587 | 1.00 | 28.25 C | N |
| ATOM | 2125 | N | LYS | C | 31 | 15.010 | −19.277 | −28.823 | 1.00 | 18.87 C | N |
| ATOM | 2126 | CA | LYS | C | 31 | 14.640 | −18.561 | −27.600 | 1.00 | 22.08 C | C |
| ATOM | 2127 | C | LYS | C | 31 | 14.141 | −17.141 | −27.870 | 1.00 | 17.64 C | C |
| ATOM | 2128 | O | LYS | C | 31 | 13.226 | −16.662 | −27.209 | 1.00 | 21.08 C | O |
| ATOM | 2129 | CB | LYS | C | 31 | 15.790 | −18.571 | −26.590 | 1.00 | 18.89 C | C |
| ATOM | 2130 | CG | LYS | C | 31 | 15.972 | −19.926 | −25.938 | 1.00 | 20.04 C | C |
| ATOM | 2131 | CD | LYS | C | 31 | 17.018 | −19.903 | −24.839 | 1.00 | 22.25 C | C |
| ATOM | 2132 | CE | LYS | C | 31 | 17.024 | −21.223 | −24.079 | 1.00 | 21.58 C | C |
| ATOM | 2133 | NZ | LYS | C | 31 | 15.661 | −21.584 | −23.593 | 1.00 | 21.26 C | N |
| ATOM | 2134 | N | ALA | C | 32 | 14.725 | −16.476 | −28.856 | 1.00 | 9.09 C | N |
| ATOM | 2135 | CA | ALA | C | 32 | 14.263 | −15.148 | −29.228 | 1.00 | 9.04 C | C |
| ATOM | 2136 | C | ALA | C | 32 | 12.793 | −15.201 | −29.651 | 1.00 | 13.34 C | C |
| ATOM | 2137 | O | ALA | C | 32 | 11.980 | −14.402 | −29.184 | 1.00 | 13.09 C | O |
| ATOM | 2138 | CB | ALA | C | 32 | 15.130 | −14.569 | −30.337 | 1.00 | 8.32 C | C |
| ATOM | 2139 | N | TYR | C | 33 | 12.464 | −16.154 | −30.524 | 1.00 | 19.25 C | N |
| ATOM | 2140 | CA | TYR | C | 33 | 11.089 | −16.391 | −30.975 | 1.00 | 18.96 C | C |
| ATOM | 2141 | C | TYR | C | 33 | 10.127 | −16.715 | −29.822 | 1.00 | 21.93 C | C |
| ATOM | 2142 | O | TYR | C | 33 | 9.026 | −16.162 | −29.745 | 1.00 | 22.45 C | O |
| ATOM | 2143 | CB | TYR | C | 33 | 11.062 | −17.513 | −32.026 | 1.00 | 23.50 C | C |
| ATOM | 2144 | CG | TYR | C | 33 | 9.731 | −18.234 | −32.146 | 1.00 | 21.82 C | C |
| ATOM | 2145 | CD1 | TYR | C | 33 | 8.658 | −17.646 | −32.804 | 1.00 | 26.15 C | C |
| ATOM | 2146 | CD2 | TYR | C | 33 | 9.551 | −19.500 | −31.599 | 1.00 | 23.49 C | C |
| ATOM | 2147 | CE1 | TYR | C | 33 | 7.439 | −18.297 | −32.916 | 1.00 | 27.75 C | C |
| ATOM | 2148 | CE2 | TYR | C | 33 | 8.331 | −20.163 | −31.700 | 1.00 | 23.15 C | C |
| ATOM | 2149 | CZ | TYR | C | 33 | 7.281 | −19.555 | −32.362 | 1.00 | 29.01 C | C |
| ATOM | 2150 | OH | TYR | C | 33 | 6.069 | −20.198 | −32.475 | 1.00 | 28.01 C | O |
| ATOM | 2151 | N | GLU | C | 34 | 10.546 | −17.613 | −28.934 | 1.00 | 21.34 C | N |
| ATOM | 2152 | CA | GLU | C | 34 | 9.741 | −17.988 | −27.772 | 1.00 | 20.10 C | C |
| ATOM | 2153 | C | GLU | C | 34 | 9.478 | −16.799 | −26.852 | 1.00 | 20.64 C | C |
| ATOM | 2154 | O | GLU | C | 34 | 8.376 | −16.653 | −26.312 | 1.00 | 20.34 C | O |
| ATOM | 2155 | CB | GLU | C | 34 | 10.410 | −19.120 | −26.989 | 1.00 | 19.30 C | C |

TABLE 1-continued

| ATOM | 2156 | CG  | GLU | C | 34 | 10.422 | −20.458 | −27.724 | 1.00 | 18.54 | C | C |
| ATOM | 2157 | CD  | GLU | C | 34 | 11.121 | −21.552 | −26.934 | 1.00 | 20.08 | C | C |
| ATOM | 2158 | OE1 | GLU | C | 34 | 11.829 | −21.227 | −25.954 | 1.00 | 21.18 | C | O |
| ATOM | 2159 | OE2 | GLU | C | 34 | 10.966 | −22.738 | −27.292 | 1.00 | 17.80 | C | O |
| ATOM | 2160 | N   | LEU | C | 35 | 10.485 | −15.947 | −26.673 | 1.00 | 18.35 | C | N |
| ATOM | 2161 | CA  | LEU | C | 35 | 10.300 | −14.753 | −25.852 | 1.00 | 18.79 | C | C |
| ATOM | 2162 | C   | LEU | C | 35 | 9.309  | −13.789 | −26.505 | 1.00 | 19.94 | C | C |
| ATOM | 2163 | O   | LEU | C | 35 | 8.488  | −13.171 | −25.824 | 1.00 | 21.37 | C | O |
| ATOM | 2164 | CB  | LEU | C | 35 | 11.627 | −14.050 | −25.582 | 1.00 | 15.90 | C | C |
| ATOM | 2165 | CG  | LEU | C | 35 | 11.519 | −12.771 | −24.750 | 1.00 | 18.38 | C | C |
| ATOM | 2166 | CD1 | LEU | C | 35 | 10.931 | −13.071 | −23.382 | 1.00 | 16.74 | C | C |
| ATOM | 2167 | CD2 | LEU | C | 35 | 12.871 | −12.089 | −24.618 | 1.00 | 17.45 | C | C |
| ATOM | 2168 | N   | SER | C | 36 | 9.385  | −13.661 | −27.823 | 1.00 | 25.87 | C | N |
| ATOM | 2169 | CA  | SER | C | 36 | 8.449  | −12.811 | −28.548 | 1.00 | 31.09 | C | C |
| ATOM | 2170 | C   | SER | C | 36 | 6.995  | −13.257 | −28.326 | 1.00 | 28.04 | C | C |
| ATOM | 2171 | O   | SER | C | 36 | 6.123  | −12.443 | −28.038 | 1.00 | 29.80 | C | O |
| ATOM | 2172 | CB  | SER | C | 36 | 8.778  | −12.805 | −30.043 | 1.00 | 32.46 | C | C |
| ATOM | 2173 | OG  | SER | C | 36 | 7.835  | −12.024 | −30.756 | 1.00 | 31.96 | C | O |
| ATOM | 2174 | N   | VAL | C | 37 | 6.749  | −14.557 | −28.450 | 1.00 | 20.90 | C | N |
| ATOM | 2175 | CA  | VAL | C | 37 | 5.406  | −15.109 | −28.320 | 1.00 | 20.27 | C | C |
| ATOM | 2176 | C   | VAL | C | 37 | 4.903  | −15.111 | −26.873 | 1.00 | 22.08 | C | C |
| ATOM | 2177 | O   | VAL | C | 37 | 3.773  | −14.706 | −26.602 | 1.00 | 21.87 | C | O |
| ATOM | 2178 | CB  | VAL | C | 37 | 5.332  | −16.546 | −28.876 | 1.00 | 21.06 | C | C |
| ATOM | 2179 | CG1 | VAL | C | 37 | 4.025  | −17.211 | −28.469 | 1.00 | 17.91 | C | C |
| ATOM | 2180 | CG2 | VAL | C | 37 | 5.488  | −16.541 | −30.392 | 1.00 | 22.26 | C | C |
| ATOM | 2181 | N   | LEU | C | 38 | 5.738  | −15.579 | −25.952 | 1.00 | 28.66 | C | N |
| ATOM | 2182 | CA  | LEU | C | 38 | 5.337  | −15.712 | −24.557 | 1.00 | 24.96 | C | C |
| ATOM | 2183 | C   | LEU | C | 38 | 4.994  | −14.367 | −23.933 | 1.00 | 26.61 | C | C |
| ATOM | 2184 | O   | LEU | C | 38 | 4.017  | −14.247 | −23.189 | 1.00 | 28.76 | C | O |
| ATOM | 2185 | CB  | LEU | C | 38 | 6.454  | −16.364 | −23.739 | 1.00 | 24.38 | C | C |
| ATOM | 2186 | CG  | LEU | C | 38 | 6.792  | −17.832 | −23.978 | 1.00 | 22.80 | C | C |
| ATOM | 2187 | CD1 | LEU | C | 38 | 8.138  | −18.157 | −23.352 | 1.00 | 20.95 | C | C |
| ATOM | 2188 | CD2 | LEU | C | 38 | 5.703  | −18.741 | −23.431 | 1.00 | 23.41 | C | C |
| ATOM | 2189 | N   | CYS | C | 39 | 5.807  | −13.359 | −24.231 | 1.00 | 22.88 | C | N |
| ATOM | 2190 | CA  | CYS | C | 39 | 5.695  | −12.077 | −23.543 | 1.00 | 24.78 | C | C |
| ATOM | 2191 | C   | CYS | C | 39 | 5.249  | −10.941 | −24.458 | 1.00 | 26.69 | C | C |
| ATOM | 2192 | O   | CYS | C | 39 | 5.319  | −9.770  | −24.089 | 1.00 | 30.51 | C | O |
| ATOM | 2193 | CB  | CYS | C | 39 | 7.020  | −11.733 | −22.861 | 1.00 | 20.36 | C | C |
| ATOM | 2194 | SG  | CYS | C | 39 | 7.564  | −13.026 | −21.730 | 1.00 | 20.08 | C | S |
| ATOM | 2195 | N   | ASP | C | 40 | 4.789  | −11.294 | −25.653 | 1.00 | 29.36 | C | N |
| ATOM | 2196 | CA  | ASP | C | 40 | 4.248  | −10.299 | −26.565 | 1.00 | 31.01 | C | C |
| ATOM | 2197 | C   | ASP | C | 40 | 5.191  | −9.102  | −26.685 | 1.00 | 31.73 | C | C |
| ATOM | 2198 | O   | ASP | C | 40 | 4.928  | −8.041  | −26.125 | 1.00 | 30.95 | C | O |
| ATOM | 2199 | CB  | ASP | C | 40 | 2.870  | −9.845  | −26.070 | 1.00 | 27.98 | C | C |
| ATOM | 2200 | CG  | ASP | C | 40 | 2.188  | −8.875  | −27.017 | 1.00 | 31.87 | C | C |
| ATOM | 2201 | OD1 | ASP | C | 40 | 2.552  | −8.826  | −28.211 | 1.00 | 33.57 | C | O |
| ATOM | 2202 | OD2 | ASP | C | 40 | 1.274  | −8.154  | −26.559 | 1.00 | 47.98 | C | O |
| ATOM | 2203 | N   | CYS | C | 41 | 6.298  | −9.276  | −27.402 | 1.00 | 26.23 | C | N |
| ATOM | 2204 | CA  | CYS | C | 41 | 7.198  | −8.153  | −27.658 | 1.00 | 31.67 | C | C |
| ATOM | 2205 | C   | CYS | C | 41 | 7.834  | −8.179  | −29.047 | 1.00 | 31.20 | C | C |
| ATOM | 2206 | O   | CYS | C | 41 | 7.889  | −9.224  | −29.700 | 1.00 | 29.57 | C | O |
| ATOM | 2207 | CB  | CYS | C | 41 | 8.264  | −8.029  | −26.561 | 1.00 | 32.05 | C | C |
| ATOM | 2208 | SG  | CYS | C | 41 | 8.786  | −9.569  | −25.798 | 1.00 | 39.94 | C | S |
| ATOM | 2209 | N   | GLU | C | 42 | 8.279  | −7.010  | −29.501 | 1.00 | 36.27 | C | N |
| ATOM | 2210 | CA  | GLU | C | 42 | 9.014  | −6.898  | −30.751 | 1.00 | 32.55 | C | C |
| ATOM | 2211 | C   | GLU | C | 42 | 10.475 | −7.202  | −30.488 | 1.00 | 32.26 | C | C |
| ATOM | 2212 | O   | GLU | C | 42 | 11.072 | −6.659  | −29.560 | 1.00 | 35.73 | C | O |
| ATOM | 2213 | CB  | GLU | C | 42 | 8.912  | −5.487  | −31.328 | 1.00 | 37.23 | C | C |
| ATOM | 2214 | CG  | GLU | C | 42 | 7.590  | −5.143  | −31.974 | 1.00 | 51.44 | C | C |
| ATOM | 2215 | CD  | GLU | C | 42 | 7.655  | −3.824  | −32.718 | 1.00 | 50.05 | C | C |
| ATOM | 2216 | OE1 | GLU | C | 42 | 6.711  | −3.016  | −32.585 | 1.00 | 70.85 | C | O |
| ATOM | 2217 | OE2 | GLU | C | 42 | 8.658  | −3.592  | −33.426 | 1.00 | 41.10 | C | O |
| ATOM | 2218 | N   | ILE | C | 43 | 11.058 | −8.056  | −31.316 | 1.00 | 23.83 | C | N |
| ATOM | 2219 | CA  | ILE | C | 43 | 12.456 | −8.416  | −31.144 | 1.00 | 20.13 | C | C |
| ATOM | 2220 | C   | ILE | C | 43 | 13.185 | −8.409  | −32.473 | 1.00 | 19.57 | C | C |
| ATOM | 2221 | O   | ILE | C | 43 | 12.628 | −8.793  | −33.498 | 1.00 | 20.64 | C | O |
| ATOM | 2222 | CB  | ILE | C | 43 | 12.597 | −9.788  | −30.461 | 1.00 | 20.12 | C | C |
| ATOM | 2223 | CG1 | ILE | C | 43 | 12.116 | −9.689  | −29.009 | 1.00 | 20.57 | C | C |
| ATOM | 2224 | CG2 | ILE | C | 43 | 14.038 | −10.284 | −30.546 | 1.00 | 16.02 | C | C |
| ATOM | 2225 | CD1 | ILE | C | 43 | 12.008 | −11.011 | −28.293 | 1.00 | 18.94 | C | C |
| ATOM | 2226 | N   | ALA | C | 44 | 14.428 | −7.949  | −32.454 | 1.00 | 23.50 | C | N |
| ATOM | 2227 | CA  | ALA | C | 44 | 15.268 | −7.984  | −33.639 | 1.00 | 25.31 | C | C |
| ATOM | 2228 | C   | ALA | C | 44 | 16.633 | −8.531  | −33.268 | 1.00 | 24.34 | C | C |
| ATOM | 2229 | O   | ALA | C | 44 | 17.238 | −8.106  | −32.286 | 1.00 | 27.29 | C | O |
| ATOM | 2230 | CB  | ALA | C | 44 | 15.393 | −6.593  | −34.259 | 1.00 | 22.98 | C | C |
| ATOM | 2231 | N   | LEU | C | 45 | 17.115 | −9.478  | −34.059 | 1.00 | 20.02 | C | N |
| ATOM | 2232 | CA  | LEU | C | 45 | 18.407 | −10.093 | −33.815 | 1.00 | 17.99 | C | C |
| ATOM | 2233 | C   | LEU | C | 45 | 19.197 | −10.106 | −35.112 | 1.00 | 21.52 | C | C |
| ATOM | 2234 | O   | LEU | C | 45 | 18.795 | −10.747 | −36.080 | 1.00 | 21.38 | C | O |
| ATOM | 2235 | CB  | LEU | C | 45 | 18.217 | −11.525 | −33.304 | 1.00 | 20.52 | C | C |

TABLE 1-continued

| | | | | | | | | | | |
|---|---|---|---|---|---|---|---|---|---|---|
| ATOM | 2236 | CG | LEU | C | 45 | 19.472 | −12.387 | −33.136 | 1.00 | 21.79 C | C |
| ATOM | 2237 | CD1 | LEU | C | 45 | 20.440 | −11.730 | −32.161 | 1.00 | 16.43 C | C |
| ATOM | 2238 | CD2 | LEU | C | 45 | 19.118 | −13.805 | −32.685 | 1.00 | 18.07 C | C |
| ATOM | 2239 | N | ILE | C | 46 | 20.315 | −9.389 | −35.133 | 1.00 | 23.15 C | N |
| ATOM | 2240 | CA | ILE | C | 46 | 21.194 | −9.369 | −36.300 | 1.00 | 25.46 C | C |
| ATOM | 2241 | C | ILE | C | 46 | 22.539 | −10.013 | −35.976 | 1.00 | 25.84 C | C |
| ATOM | 2242 | O | ILE | C | 46 | 23.200 | −9.636 | −35.007 | 1.00 | 23.37 C | O |
| ATOM | 2243 | CB | ILE | C | 46 | 21.422 | −7.932 | −36.808 | 1.00 | 28.04 C | C |
| ATOM | 2244 | CG1 | ILE | C | 46 | 20.168 | −7.419 | −37.522 | 1.00 | 26.67 C | C |
| ATOM | 2245 | CG2 | ILE | C | 46 | 22.621 | −7.884 | −37.733 | 1.00 | 24.29 C | C |
| ATOM | 2246 | CD1 | ILE | C | 46 | 20.059 | −5.907 | −37.569 | 1.00 | 26.13 C | C |
| ATOM | 2247 | N | ILE | C | 47 | 22.937 | −10.983 | −36.793 | 1.00 | 21.24 C | N |
| ATOM | 2248 | CA | ILE | C | 47 | 24.164 | −11.736 | −36.563 | 1.00 | 21.52 C | C |
| ATOM | 2249 | C | ILE | C | 47 | 25.027 | −11.833 | −37.816 | 1.00 | 21.63 C | C |
| ATOM | 2250 | O | ILE | C | 47 | 24.573 | −12.316 | −38.852 | 1.00 | 24.81 C | O |
| ATOM | 2251 | CB | ILE | C | 47 | 23.857 | −13.181 | −36.123 | 1.00 | 22.08 C | C |
| ATOM | 2252 | CG1 | ILE | C | 47 | 22.955 | −13.203 | −34.890 | 1.00 | 20.26 C | C |
| ATOM | 2253 | CG2 | ILE | C | 47 | 25.152 | −13.946 | −35.860 | 1.00 | 22.81 C | C |
| ATOM | 2254 | CD1 | ILE | C | 47 | 22.536 | −14.600 | −34.492 | 1.00 | 18.30 C | C |
| ATOM | 2255 | N | PHE | C | 48 | 26.272 | −11.384 | −37.717 | 1.00 | 20.46 C | N |
| ATOM | 2256 | CA | PHE | C | 48 | 27.259 | −11.603 | −38.767 | 1.00 | 20.03 C | C |
| ATOM | 2257 | C | PHE | C | 48 | 28.281 | −12.567 | −38.203 | 1.00 | 22.91 C | C |
| ATOM | 2258 | O | PHE | C | 48 | 28.837 | −12.306 | −37.143 | 1.00 | 26.79 C | O |
| ATOM | 2259 | CB | PHE | C | 48 | 27.979 | −10.300 | −39.133 | 1.00 | 22.81 C | C |
| ATOM | 2260 | CG | PHE | C | 48 | 27.063 | −9.188 | −39.565 | 1.00 | 21.27 C | C |
| ATOM | 2261 | CD1 | PHE | C | 48 | 26.574 | −8.277 | −38.643 | 1.00 | 20.26 C | C |
| ATOM | 2262 | CD2 | PHE | C | 48 | 26.711 | −9.040 | −40.899 | 1.00 | 25.06 C | C |
| ATOM | 2263 | CE1 | PHE | C | 48 | 25.737 | −7.245 | −39.041 | 1.00 | 21.07 C | C |
| ATOM | 2264 | CE2 | PHE | C | 48 | 25.878 | −8.009 | −41.301 | 1.00 | 26.74 C | C |
| ATOM | 2265 | CZ | PHE | C | 48 | 25.390 | −7.111 | −40.367 | 1.00 | 22.39 C | C |
| ATOM | 2266 | N | ASN | C | 49 | 28.541 | −13.671 | −38.893 | 1.00 | 26.25 C | N |
| ATOM | 2267 | CA | ASN | C | 49 | 29.561 | −14.607 | −38.428 | 1.00 | 25.67 C | C |
| ATOM | 2268 | C | ASN | C | 49 | 30.963 | −14.054 | −38.686 | 1.00 | 26.63 C | C |
| ATOM | 2269 | O | ASN | C | 49 | 31.107 | −12.932 | −39.174 | 1.00 | 26.67 C | O |
| ATOM | 2270 | CB | ASN | C | 49 | 29.384 | −15.987 | −39.070 | 1.00 | 23.30 C | C |
| ATOM | 2271 | CG | ASN | C | 49 | 29.646 | −15.976 | −40.566 | 1.00 | 29.56 C | C |
| ATOM | 2272 | OD1 | ASN | C | 49 | 30.164 | −14.999 | −41.118 | 1.00 | 29.12 C | O |
| ATOM | 2273 | ND2 | ASN | C | 49 | 29.288 | −17.071 | −41.234 | 1.00 | 26.62 C | N |
| ATOM | 2274 | N | SER | C | 50 | 31.989 | −14.834 | −38.359 | 1.00 | 28.75 C | N |
| ATOM | 2275 | CA | SER | C | 50 | 33.368 | −14.384 | −38.534 | 1.00 | 34.68 C | C |
| ATOM | 2276 | C | SER | C | 50 | 33.729 | −14.177 | −40.001 | 1.00 | 39.26 C | C |
| ATOM | 2277 | O | SER | C | 50 | 34.583 | −13.354 | −40.321 | 1.00 | 44.25 C | O |
| ATOM | 2278 | CB | SER | C | 50 | 34.354 | −15.354 | −37.872 | 1.00 | 34.53 C | C |
| ATOM | 2279 | OG | SER | C | 50 | 34.054 | −16.698 | −38.196 | 1.00 | 39.66 C | O |
| ATOM | 2280 | N | SER | C | 51 | 33.076 | −14.922 | −40.889 | 1.00 | 44.85 C | N |
| ATOM | 2281 | CA | SER | C | 51 | 33.291 | −14.765 | −42.326 | 1.00 | 45.04 C | C |
| ATOM | 2282 | C | SER | C | 51 | 32.420 | −13.647 | −42.888 | 1.00 | 48.33 C | C |
| ATOM | 2283 | O | SER | C | 51 | 32.322 | −13.478 | −44.103 | 1.00 | 41.62 C | O |
| ATOM | 2284 | CB | SER | C | 51 | 33.005 | −16.070 | −43.066 | 1.00 | 39.28 C | C |
| ATOM | 2285 | OG | SER | C | 51 | 33.839 | −17.113 | −42.593 | 1.00 | 46.61 C | O |
| ATOM | 2286 | N | ASN | C | 52 | 31.771 | −12.911 | −41.991 | 1.00 | 49.99 C | N |
| ATOM | 2287 | CA | ASN | C | 52 | 31.033 | −11.700 | −42.347 | 1.00 | 47.32 C | C |
| ATOM | 2288 | C | ASN | C | 52 | 29.686 | −11.923 | −43.042 | 1.00 | 47.24 C | C |
| ATOM | 2289 | O | ASN | C | 52 | 29.085 | −10.976 | −43.552 | 1.00 | 47.87 C | O |
| ATOM | 2290 | CB | ASN | C | 52 | 31.907 | −10.776 | −43.197 | 1.00 | 48.20 C | C |
| ATOM | 2291 | CG | ASN | C | 52 | 31.878 | −9.343 | −42.714 | 1.00 | 61.86 C | C |
| ATOM | 2292 | OD1 | ASN | C | 52 | 32.478 | −9.010 | −41.690 | 1.00 | 55.65 C | O |
| ATOM | 2293 | ND2 | ASN | C | 52 | 31.187 | −8.482 | −43.453 | 1.00 | 61.83 C | N |
| ATOM | 2294 | N | LYS | C | 53 | 29.210 | −13.165 | −43.066 | 1.00 | 29.68 C | N |
| ATOM | 2295 | CA | LYS | C | 53 | 27.879 | −13.440 | −43.605 | 1.00 | 33.37 C | C |
| ATOM | 2296 | C | LYS | C | 53 | 26.774 | −13.075 | −42.608 | 1.00 | 31.12 C | C |
| ATOM | 2297 | O | LYS | C | 53 | 26.885 | −13.342 | −41.412 | 1.00 | 25.99 C | O |
| ATOM | 2298 | CB | LYS | C | 53 | 27.735 | −14.901 | −44.037 | 1.00 | 30.60 C | C |
| ATOM | 2299 | CG | LYS | C | 53 | 26.328 | −15.237 | −44.537 | 1.00 | 38.39 C | C |
| ATOM | 2300 | CD | LYS | C | 53 | 26.237 | −16.650 | −45.112 | 1.00 | 34.12 C | C |
| ATOM | 2301 | CE | LYS | C | 53 | 24.811 | −16.980 | −45.534 | 1.00 | 37.02 C | C |
| ATOM | 2302 | NZ | LYS | C | 53 | 24.680 | −18.380 | −46.033 | 1.00 | 36.06 C | N |
| ATOM | 2303 | N | LEU | C | 54 | 25.704 | −12.475 | −43.122 | 1.00 | 30.45 C | N |
| ATOM | 2304 | CA | LEU | C | 54 | 24.601 | −11.989 | −42.301 | 1.00 | 25.57 C | C |
| ATOM | 2305 | C | LEU | C | 54 | 23.541 | −13.053 | −41.998 | 1.00 | 24.16 C | C |
| ATOM | 2306 | O | LEU | C | 54 | 23.134 | −13.807 | −42.875 | 1.00 | 32.16 C | O |
| ATOM | 2307 | CB | LEU | C | 54 | 23.945 | −10.794 | −42.995 | 1.00 | 29.61 C | C |
| ATOM | 2308 | CG | LEU | C | 54 | 22.636 | −10.252 | −42.418 | 1.00 | 32.79 C | C |
| ATOM | 2309 | CD1 | LEU | C | 54 | 22.840 | −9.712 | −41.006 | 1.00 | 23.27 C | C |
| ATOM | 2310 | CD2 | LEU | C | 54 | 22.049 | −9.182 | −43.336 | 1.00 | 28.41 C | C |
| ATOM | 2311 | N | PHE | C | 55 | 23.103 | −13.106 | −40.745 | 1.00 | 28.59 C | N |
| ATOM | 2312 | CA | PHE | C | 55 | 21.941 | −13.900 | −40.355 | 1.00 | 28.10 C | C |
| ATOM | 2313 | C | PHE | C | 55 | 21.018 | −13.020 | −39.526 | 1.00 | 26.52 C | C |
| ATOM | 2314 | O | PHE | C | 55 | 21.479 | −12.122 | −38.824 | 1.00 | 32.90 C | O |
| ATOM | 2315 | CB | PHE | C | 55 | 22.358 | −15.131 | −39.550 | 1.00 | 28.39 C | C |

TABLE 1-continued

| ATOM | 2316 | CG | PHE | C | 55 | 23.239 | −16.080 | −40.307 | 1.00 | 23.77 C | C |
|---|---|---|---|---|---|---|---|---|---|---|---|
| ATOM | 2317 | CD1 | PHE | C | 55 | 24.614 | −15.973 | −40.234 | 1.00 | 26.43 C | C |
| ATOM | 2318 | CD2 | PHE | C | 55 | 22.689 | −17.081 | −41.085 | 1.00 | 27.00 C | C |
| ATOM | 2319 | CE1 | PHE | C | 55 | 25.430 | −16.845 | −40.927 | 1.00 | 31.50 C | C |
| ATOM | 2320 | CE2 | PHE | C | 55 | 23.496 | −17.963 | −41.783 | 1.00 | 30.53 C | C |
| ATOM | 2321 | CZ | PHE | C | 55 | 24.869 | −17.845 | −41.705 | 1.00 | 34.41 C | C |
| ATOM | 2322 | N | GLN | C | 56 | 19.718 | −13.263 | −39.599 | 1.00 | 25.53 C | N |
| ATOM | 2323 | CA | GLN | C | 56 | 18.785 | −12.363 | −38.948 | 1.00 | 26.25 C | C |
| ATOM | 2324 | C | GLN | C | 56 | 17.465 | −13.010 | −38.553 | 1.00 | 28.25 C | C |
| ATOM | 2325 | O | GLN | C | 56 | 17.007 | −13.966 | −39.181 | 1.00 | 30.62 C | O |
| ATOM | 2326 | CB | GLN | C | 56 | 18.523 | −11.149 | −39.843 | 1.00 | 32.99 C | C |
| ATOM | 2327 | CG | GLN | C | 56 | 17.979 | −11.493 | −41.221 | 1.00 | 29.99 C | C |
| ATOM | 2328 | CD | GLN | C | 56 | 17.877 | −10.276 | −42.131 | 1.00 | 41.74 C | C |
| ATOM | 2329 | OE1 | GLN | C | 56 | 17.110 | −9.348 | −41.868 | 1.00 | 36.88 C | O |
| ATOM | 2330 | NE2 | GLN | C | 56 | 18.651 | −10.279 | −43.210 | 1.00 | 39.31 C | N |
| ATOM | 2331 | N | TYR | C | 57 | 16.874 | −12.472 | −37.491 | 1.00 | 20.89 C | N |
| ATOM | 2332 | CA | TYR | C | 57 | 15.526 | −12.814 | −37.068 | 1.00 | 20.63 C | C |
| ATOM | 2333 | C | TYR | C | 57 | 14.833 | −11.554 | −36.575 | 1.00 | 22.04 C | C |
| ATOM | 2334 | O | TYR | C | 57 | 15.459 | −10.704 | −35.940 | 1.00 | 25.74 C | O |
| ATOM | 2335 | CB | TYR | C | 57 | 15.533 | −13.839 | −35.929 | 1.00 | 25.07 C | C |
| ATOM | 2336 | CG | TYR | C | 57 | 14.213 | −13.867 | −35.181 | 1.00 | 22.71 C | C |
| ATOM | 2337 | CD1 | TYR | C | 57 | 13.146 | −14.623 | −35.644 | 1.00 | 21.68 C | C |
| ATOM | 2338 | CD2 | TYR | C | 57 | 14.020 | −13.099 | −34.041 | 1.00 | 18.82 C | C |
| ATOM | 2339 | CE1 | TYR | C | 57 | 11.930 | −14.635 | −34.983 | 1.00 | 20.31 C | C |
| ATOM | 2340 | CE2 | TYR | C | 57 | 12.807 | −13.102 | −33.369 | 1.00 | 18.33 C | C |
| ATOM | 2341 | CZ | TYR | C | 57 | 11.766 | −13.872 | −33.844 | 1.00 | 22.22 C | C |
| ATOM | 2342 | OH | TYR | C | 57 | 10.560 | −13.885 | −33.180 | 1.00 | 22.44 C | O |
| ATOM | 2343 | N | ALA | C | 58 | 13.537 | −11.441 | −36.852 | 1.00 | 20.58 C | N |
| ATOM | 2344 | CA | ALA | C | 58 | 12.730 | −10.359 | −36.304 | 1.00 | 25.73 C | C |
| ATOM | 2345 | C | ALA | C | 58 | 11.279 | −10.807 | −36.148 | 1.00 | 24.38 C | C |
| ATOM | 2346 | O | ALA | C | 58 | 10.775 | −11.565 | −36.971 | 1.00 | 25.44 C | O |
| ATOM | 2347 | CB | ALA | C | 58 | 12.826 | −9.129 | −37.178 | 1.00 | 26.42 C | C |
| ATOM | 2348 | N | SER | C | 59 | 10.615 | −10.340 | −35.091 | 1.00 | 22.34 C | N |
| ATOM | 2349 | CA | SER | C | 59 | 9.232 | −10.730 | −34.829 | 1.00 | 26.18 C | C |
| ATOM | 2350 | C | SER | C | 59 | 8.270 | −10.052 | −35.799 | 1.00 | 28.25 C | C |
| ATOM | 2351 | O | SER | C | 59 | 7.095 | −10.402 | −35.857 | 1.00 | 29.20 C | O |
| ATOM | 2352 | CB | SER | C | 59 | 8.833 | −10.444 | −33.377 | 1.00 | 23.68 C | C |
| ATOM | 2353 | OG | SER | C | 59 | 9.017 | −9.078 | −33.047 | 1.00 | 22.70 C | O |
| ATOM | 2354 | N | THR | C | 60 | 8.786 | −9.076 | −36.547 | 1.00 | 41.26 C | N |
| ATOM | 2355 | CA | THR | C | 60 | 8.072 | −8.461 | −37.666 | 1.00 | 41.75 C | C |
| ATOM | 2356 | C | THR | C | 60 | 9.098 | −8.045 | −38.707 | 1.00 | 44.36 C | C |
| ATOM | 2357 | O | THR | C | 60 | 10.258 | −8.453 | −38.633 | 1.00 | 44.49 C | O |
| ATOM | 2358 | CB | THR | C | 60 | 7.283 | −7.209 | −37.247 | 1.00 | 50.98 C | C |
| ATOM | 2359 | OG1 | THR | C | 60 | 8.143 | −6.318 | −36.524 | 1.00 | 55.36 C | O |
| ATOM | 2360 | CG2 | THR | C | 60 | 6.088 | −7.582 | −36.380 | 1.00 | 58.49 C | C |
| ATOM | 2361 | N | ASP | C | 61 | 8.677 | −7.235 | −39.674 | 1.00 | 33.65 C | N |
| ATOM | 2362 | CA | ASP | C | 61 | 9.611 | −6.694 | −40.657 | 1.00 | 37.81 C | C |
| ATOM | 2363 | C | ASP | C | 61 | 10.768 | −6.016 | −39.933 | 1.00 | 38.30 C | C |
| ATOM | 2364 | O | ASP | C | 61 | 10.559 | −5.141 | −39.082 | 1.00 | 35.38 C | O |
| ATOM | 2365 | CB | ASP | C | 61 | 8.922 | −5.688 | −41.585 | 1.00 | 39.92 C | C |
| ATOM | 2366 | CG | ASP | C | 61 | 8.070 | −6.356 | −42.654 | 1.00 | 43.00 C | C |
| ATOM | 2367 | OD1 | ASP | C | 61 | 7.600 | −7.491 | −42.434 | 1.00 | 44.55 C | O |
| ATOM | 2368 | OD2 | ASP | C | 61 | 7.865 | −5.735 | −43.718 | 1.00 | 50.00 C | O |
| ATOM | 2369 | N | MET | C | 62 | 11.987 | −6.429 | −40.269 | 1.00 | 47.81 C | N |
| ATOM | 2370 | CA | MET | C | 62 | 13.183 | −5.871 | −39.650 | 1.00 | 41.37 C | C |
| ATOM | 2371 | C | MET | C | 62 | 13.177 | −4.343 | −39.681 | 1.00 | 44.59 C | C |
| ATOM | 2372 | O | MET | C | 62 | 13.376 | −3.695 | −38.654 | 1.00 | 47.74 C | O |
| ATOM | 2373 | CB | MET | C | 62 | 14.443 | −6.406 | −40.332 | 1.00 | 33.72 C | C |
| ATOM | 2374 | CG | MET | C | 62 | 15.737 | −5.950 | −39.669 | 1.00 | 43.23 C | C |
| ATOM | 2375 | SD | MET | C | 62 | 15.850 | −6.454 | −37.936 | 1.00 | 35.55 C | S |
| ATOM | 2376 | CE | MET | C | 62 | 16.116 | −8.214 | −38.110 | 1.00 | 32.61 C | C |
| ATOM | 2377 | N | ASP | C | 63 | 12.938 | −3.777 | −40.861 | 1.00 | 57.74 C | N |
| ATOM | 2378 | CA | ASP | C | 63 | 12.975 | −2.328 | −41.044 | 1.00 | 58.33 C | C |
| ATOM | 2379 | C | ASP | C | 63 | 12.066 | −1.600 | −40.057 | 1.00 | 52.55 C | C |
| ATOM | 2380 | O | ASP | C | 63 | 12.293 | −0.434 | −39.738 | 1.00 | 59.74 C | O |
| ATOM | 2381 | CB | ASP | C | 63 | 12.592 | −1.952 | −42.480 | 1.00 | 63.84 C | C |
| ATOM | 2382 | CG | ASP | C | 63 | 11.092 | −2.020 | −42.723 | 1.00 | 75.02 C | C |
| ATOM | 2383 | OD1 | ASP | C | 63 | 10.476 | −0.956 | −42.961 | 1.00 | 68.03 C | O |
| ATOM | 2384 | OD2 | ASP | C | 63 | 10.526 | −3.134 | −42.664 | 1.00 | 75.33 C | O |
| ATOM | 2385 | N | LYS | C | 64 | 11.035 | −2.286 | −39.578 | 1.00 | 39.30 C | N |
| ATOM | 2386 | CA | LYS | C | 64 | 10.108 | −1.681 | −38.629 | 1.00 | 41.27 C | C |
| ATOM | 2387 | C | LYS | C | 64 | 10.700 | −1.602 | −37.220 | 1.00 | 43.64 C | C |
| ATOM | 2388 | O | LYS | C | 64 | 10.672 | −0.543 | −36.588 | 1.00 | 32.45 C | O |
| ATOM | 2389 | CB | LYS | C | 64 | 8.772 | −2.427 | −38.623 | 1.00 | 39.82 C | C |
| ATOM | 2390 | CG | LYS | C | 64 | 7.983 | −2.266 | −39.916 | 1.00 | 47.23 C | C |
| ATOM | 2391 | CD | LYS | C | 64 | 6.671 | −3.034 | −39.884 | 1.00 | 48.40 C | C |
| ATOM | 2392 | CE | LYS | C | 64 | 5.854 | −2.764 | −41.138 | 1.00 | 49.45 C | C |
| ATOM | 2393 | NZ | LYS | C | 64 | 4.682 | −3.676 | −41.241 | 1.00 | 56.67 C | N |
| ATOM | 2394 | N | VAL | C | 65 | 11.242 | −2.719 | −36.735 | 1.00 | 36.46 C | N |
| ATOM | 2395 | CA | VAL | C | 65 | 11.875 | −2.743 | −35.421 | 1.00 | 33.96 C | C |

TABLE 1-continued

| | | | | | | | | | | |
|---|---|---|---|---|---|---|---|---|---|---|
| ATOM | 2396 | C | VAL | C | 65 | 13.000 | −1.716 | −35.377 | 1.00 | 34.08 C | C |
| ATOM | 2397 | O | VAL | C | 65 | 13.153 | −0.983 | −34.398 | 1.00 | 31.90 C | O |
| ATOM | 2398 | CB | VAL | C | 65 | 12.461 | −4.127 | −35.083 | 1.00 | 32.40 C | C |
| ATOM | 2399 | CG1 | VAL | C | 65 | 12.862 | −4.181 | −33.616 | 1.00 | 24.46 C | C |
| ATOM | 2400 | CG2 | VAL | C | 65 | 11.463 | −5.226 | −35.406 | 1.00 | 30.21 C | C |
| ATOM | 2401 | N | LEU | C | 66 | 13.783 | −1.669 | −36.451 | 1.00 | 33.80 C | N |
| ATOM | 2402 | CA | LEU | C | 66 | 14.885 | −0.726 | −36.546 | 1.00 | 34.69 C | C |
| ATOM | 2403 | C | LEU | C | 66 | 14.385 | 0.714 | −36.476 | 1.00 | 43.32 C | C |
| ATOM | 2404 | O | LEU | C | 66 | 14.915 | 1.529 | −35.717 | 1.00 | 40.55 C | O |
| ATOM | 2405 | CB | LEU | C | 66 | 15.684 | −0.958 | −37.829 | 1.00 | 37.87 C | C |
| ATOM | 2406 | CG | LEU | C | 66 | 16.467 | −2.272 | −37.880 | 1.00 | 41.36 C | C |
| ATOM | 2407 | CD1 | LEU | C | 66 | 17.377 | −2.307 | −39.094 | 1.00 | 40.31 C | C |
| ATOM | 2408 | CD2 | LEU | C | 66 | 17.268 | −2.463 | −36.599 | 1.00 | 34.80 C | C |
| ATOM | 2409 | N | LEU | C | 67 | 13.358 | 1.023 | −37.258 | 1.00 | 41.33 C | N |
| ATOM | 2410 | CA | LEU | C | 67 | 12.827 | 2.379 | −37.292 | 1.00 | 42.27 C | C |
| ATOM | 2411 | C | LEU | C | 67 | 12.264 | 2.795 | −35.938 | 1.00 | 41.27 C | C |
| ATOM | 2412 | O | LEU | C | 67 | 12.381 | 3.950 | −35.542 | 1.00 | 42.99 C | O |
| ATOM | 2413 | CB | LEU | C | 67 | 11.780 | 2.530 | −38.397 | 1.00 | 46.70 C | C |
| ATOM | 2414 | CG | LEU | C | 67 | 12.391 | 2.585 | −39.802 | 1.00 | 55.15 C | C |
| ATOM | 2415 | CD1 | LEU | C | 67 | 11.316 | 2.649 | −40.878 | 1.00 | 59.19 C | C |
| ATOM | 2416 | CD2 | LEU | C | 67 | 13.357 | 3.762 | −39.926 | 1.00 | 49.10 C | C |
| ATOM | 2417 | N | LYS | C | 68 | 11.664 | 1.844 | −35.230 | 1.00 | 31.65 C | N |
| ATOM | 2418 | CA | LYS | C | 68 | 11.140 | 2.100 | −33.900 | 1.00 | 33.17 C | C |
| ATOM | 2419 | C | LYS | C | 68 | 12.294 | 2.425 | −32.959 | 1.00 | 36.81 C | C |
| ATOM | 2420 | O | LYS | C | 68 | 12.152 | 3.226 | −32.032 | 1.00 | 36.59 C | O |
| ATOM | 2421 | CB | LYS | C | 68 | 10.362 | 0.882 | −33.394 | 1.00 | 35.82 C | C |
| ATOM | 2422 | CG | LYS | C | 68 | 9.523 | 1.146 | −32.148 | 1.00 | 38.59 C | C |
| ATOM | 2423 | CD | LYS | C | 68 | 8.716 | −0.082 | −31.741 | 1.00 | 36.40 C | C |
| ATOM | 2424 | CE | LYS | C | 68 | 7.671 | 0.265 | −30.686 | 1.00 | 34.03 C | C |
| ATOM | 2425 | NZ | LYS | C | 68 | 6.999 | −0.939 | −30.118 | 1.00 | 38.36 C | N |
| ATOM | 2426 | N | TYR | C | 69 | 13.442 | 1.804 | −33.212 | 1.00 | 40.52 C | N |
| ATOM | 2427 | CA | TYR | C | 69 | 14.630 | 2.003 | −32.387 | 1.00 | 42.48 C | C |
| ATOM | 2428 | C | TYR | C | 69 | 15.267 | 3.372 | −32.615 | 1.00 | 43.40 C | C |
| ATOM | 2429 | O | TYR | C | 69 | 15.696 | 4.030 | −31.666 | 1.00 | 39.36 C | O |
| ATOM | 2430 | CB | TYR | C | 69 | 15.657 | 0.900 | −32.658 | 1.00 | 34.93 C | C |
| ATOM | 2431 | CG | TYR | C | 69 | 16.992 | 1.127 | −31.984 | 1.00 | 29.50 C | C |
| ATOM | 2432 | CD1 | TYR | C | 69 | 17.206 | 0.731 | −30.671 | 1.00 | 30.62 C | C |
| ATOM | 2433 | CD2 | TYR | C | 69 | 18.037 | 1.736 | −32.662 | 1.00 | 31.05 C | C |
| ATOM | 2434 | CE1 | TYR | C | 69 | 18.423 | 0.936 | −30.055 | 1.00 | 26.77 C | C |
| ATOM | 2435 | CE2 | TYR | C | 69 | 19.258 | 1.945 | −32.053 | 1.00 | 28.66 C | C |
| ATOM | 2436 | CZ | TYR | C | 69 | 19.446 | 1.543 | −30.752 | 1.00 | 29.65 C | C |
| ATOM | 2437 | OH | TYR | C | 69 | 20.664 | 1.754 | −30.143 | 1.00 | 31.04 C | O |
| ATOM | 2438 | N | THR | C | 70 | 15.336 | 3.791 | −33.876 | 1.00 | 34.09 C | N |
| ATOM | 2439 | CA | THR | C | 70 | 15.916 | 5.086 | −34.214 | 1.00 | 40.99 C | C |
| ATOM | 2440 | C | THR | C | 70 | 15.029 | 6.237 | −33.744 | 1.00 | 42.40 C | C |
| ATOM | 2441 | O | THR | C | 70 | 15.524 | 7.234 | −33.212 | 1.00 | 46.32 C | O |
| ATOM | 2442 | CB | THR | C | 70 | 16.226 | 5.215 | −35.726 | 1.00 | 38.56 C | C |
| ATOM | 2443 | OG1 | THR | C | 70 | 15.097 | 4.777 | −36.493 | 1.00 | 53.43 C | O |
| ATOM | 2444 | CG2 | THR | C | 70 | 17.437 | 4.362 | −36.097 | 1.00 | 38.86 C | C |
| ATOM | 2445 | N | GLU | C | 71 | 13.719 | 6.091 | −33.924 | 1.00 | 65.54 C | N |
| ATOM | 2446 | CA | GLU | C | 71 | 12.772 | 7.104 | −33.465 | 1.00 | 76.80 C | C |
| ATOM | 2447 | C | GLU | C | 71 | 12.743 | 7.167 | −31.940 | 1.00 | 70.78 C | C |
| ATOM | 2448 | O | GLU | C | 71 | 12.413 | 8.200 | −31.358 | 1.00 | 75.57 C | O |
| ATOM | 2449 | CB | GLU | C | 71 | 11.359 | 6.816 | −33.992 | 1.00 | 72.64 C | C |
| ATOM | 2450 | CG | GLU | C | 71 | 11.274 | 6.464 | −35.473 | 1.00 | 80.52 C | C |
| ATOM | 2451 | CD | GLU | C | 71 | 11.482 | 7.652 | −36.391 | 1.00 | 84.86 C | C |
| ATOM | 2452 | OE1 | GLU | C | 71 | 11.645 | 8.782 | −35.883 | 1.00 | 91.87 C | O |
| ATOM | 2453 | OE2 | GLU | C | 71 | 11.478 | 7.453 | −37.625 | 1.00 | 77.75 C | O |
| ATOM | 2454 | N | TYR | C | 72 | 13.090 | 6.054 | −31.301 | 1.00 | 47.88 C | N |
| ATOM | 2455 | CA | TYR | C | 72 | 12.996 | 5.936 | −29.849 | 1.00 | 46.60 C | C |
| ATOM | 2456 | C | TYR | C | 72 | 13.701 | 7.082 | −29.129 | 1.00 | 43.98 C | C |
| ATOM | 2457 | O | TYR | C | 72 | 13.248 | 7.533 | −28.074 | 1.00 | 41.36 C | O |
| ATOM | 2458 | CB | TYR | C | 72 | 13.559 | 4.591 | −29.384 | 1.00 | 42.97 C | C |
| ATOM | 2459 | CG | TYR | C | 72 | 13.130 | 4.183 | −27.989 | 1.00 | 39.81 C | C |
| ATOM | 2460 | CD1 | TYR | C | 72 | 11.898 | 3.577 | −27.769 | 1.00 | 34.15 C | C |
| ATOM | 2461 | CD2 | TYR | C | 72 | 13.960 | 4.398 | −26.892 | 1.00 | 42.58 C | C |
| ATOM | 2462 | CE1 | TYR | C | 72 | 11.500 | 3.195 | −26.496 | 1.00 | 33.00 C | C |
| ATOM | 2463 | CE2 | TYR | C | 72 | 13.574 | 4.019 | −25.614 | 1.00 | 37.42 C | C |
| ATOM | 2464 | CZ | TYR | C | 72 | 12.342 | 3.417 | −25.423 | 1.00 | 41.04 C | C |
| ATOM | 2465 | OH | TYR | C | 72 | 11.949 | 3.037 | −24.156 | 1.00 | 37.34 C | O |
| TER | | | | | | | | | | | |
| ATOM | 2466 | N | GLY | D | 2 | 11.562 | −26.613 | −16.682 | 1.00 | 44.76 D | N |
| ATOM | 2467 | CA | GLY | D | 2 | 10.788 | −26.142 | −15.547 | 1.00 | 50.33 D | C |
| ATOM | 2468 | C | GLY | D | 2 | 10.001 | −27.255 | −14.883 | 1.00 | 52.81 D | C |
| ATOM | 2469 | O | GLY | D | 2 | 10.106 | −28.416 | −15.283 | 1.00 | 48.43 D | O |
| ATOM | 2470 | N | ARG | D | 3 | 9.213 | −26.906 | −13.868 | 1.00 | 33.83 D | N |
| ATOM | 2471 | CA | ARG | D | 3 | 8.433 | −27.898 | −13.132 | 1.00 | 35.82 D | C |
| ATOM | 2472 | C | ARG | D | 3 | 7.466 | −28.629 | −14.056 | 1.00 | 38.35 D | C |
| ATOM | 2473 | O | ARG | D | 3 | 7.232 | −29.830 | −13.909 | 1.00 | 42.90 D | O |
| ATOM | 2474 | CB | ARG | D | 3 | 7.679 | −27.246 | −11.973 | 1.00 | 36.26 D | C |

TABLE 1-continued

| | | | | | | | | | | | |
|---|---|---|---|---|---|---|---|---|---|---|---|
| ATOM | 2475 | CG | ARG | D | 3 | 8.573 | −26.827 | −10.813 | 1.00 | 38.60 D | C |
| ATOM | 2476 | CD | ARG | D | 3 | 9.475 | −27.974 | −10.376 | 1.00 | 41.15 D | C |
| ATOM | 2477 | NE | ARG | D | 3 | 10.365 | −27.594 | −9.283 | 1.00 | 37.71 D | N |
| ATOM | 2478 | CZ | ARG | D | 3 | 10.010 | −27.581 | −8.002 | 1.00 | 43.27 D | C |
| ATOM | 2479 | NH1 | ARG | D | 3 | 8.777 | −27.919 | −7.647 | 1.00 | 32.47 D | N |
| ATOM | 2480 | NH2 | ARG | D | 3 | 10.890 | −27.223 | −7.076 | 1.00 | 42.72 D | N |
| ATOM | 2481 | N | LYS | D | 4 | 6.907 | −27.891 | −15.007 | 1.00 | 31.39 D | N |
| ATOM | 2482 | CA | LYS | D | 4 | 6.073 | −28.468 | −16.048 | 1.00 | 31.49 D | C |
| ATOM | 2483 | C | LYS | D | 4 | 6.503 | −27.912 | −17.394 | 1.00 | 35.40 D | C |
| ATOM | 2484 | O | LYS | D | 4 | 6.887 | −26.745 | −17.500 | 1.00 | 30.53 D | O |
| ATOM | 2485 | CB | LYS | D | 4 | 4.598 | −28.134 | −15.815 | 1.00 | 34.27 D | C |
| ATOM | 2486 | CG | LYS | D | 4 | 3.970 | −28.821 | −14.615 | 1.00 | 38.44 D | C |
| ATOM | 2487 | CD | LYS | D | 4 | 2.695 | −28.101 | −14.200 | 1.00 | 34.29 D | C |
| ATOM | 2488 | CE | LYS | D | 4 | 2.224 | −28.546 | −12.829 | 1.00 | 46.09 D | C |
| ATOM | 2489 | NZ | LYS | D | 4 | 1.259 | −27.570 | −12.237 | 1.00 | 50.05 D | N |
| ATOM | 2490 | N | LYS | D | 5 | 6.449 | −28.751 | −18.421 | 1.00 | 40.77 D | N |
| ATOM | 2491 | CA | LYS | D | 5 | 6.620 | −28.270 | −19.779 | 1.00 | 38.60 D | C |
| ATOM | 2492 | C | LYS | D | 5 | 5.462 | −27.339 | −20.087 | 1.00 | 40.52 D | C |
| ATOM | 2493 | O | LYS | D | 5 | 4.311 | −27.649 | −19.774 | 1.00 | 41.68 D | O |
| ATOM | 2494 | CB | LYS | D | 5 | 6.630 | −29.431 | −20.776 | 1.00 | 36.17 D | C |
| ATOM | 2495 | CG | LYS | D | 5 | 6.437 | −28.994 | −22.224 | 1.00 | 41.05 D | C |
| ATOM | 2496 | CD | LYS | D | 5 | 6.857 | −30.075 | −23.210 | 1.00 | 37.55 D | C |
| ATOM | 2497 | CE | LYS | D | 5 | 6.782 | −29.563 | −24.640 | 1.00 | 46.97 D | C |
| ATOM | 2498 | NZ | LYS | D | 5 | 7.086 | −30.620 | −25.646 | 1.00 | 53.39 D | N |
| ATOM | 2499 | N | ILE | D | 6 | 5.765 | −26.189 | −20.678 | 1.00 | 41.72 D | N |
| ATOM | 2500 | CA | ILE | D | 6 | 4.721 | −25.288 | −21.141 | 1.00 | 41.31 D | C |
| ATOM | 2501 | C | ILE | D | 6 | 4.618 | −25.333 | −22.655 | 1.00 | 47.16 D | C |
| ATOM | 2502 | O | ILE | D | 6 | 5.421 | −25.980 | −23.331 | 1.00 | 45.51 D | O |
| ATOM | 2503 | CB | ILE | D | 6 | 4.988 | −23.837 | −20.726 | 1.00 | 45.87 D | C |
| ATOM | 2504 | CG1 | ILE | D | 6 | 6.267 | −23.317 | −21.388 | 1.00 | 43.98 D | C |
| ATOM | 2505 | CG2 | ILE | D | 6 | 5.053 | −23.716 | −19.210 | 1.00 | 49.90 D | C |
| ATOM | 2506 | CD1 | ILE | D | 6 | 6.495 | −21.833 | −21.180 | 1.00 | 41.94 D | C |
| ATOM | 2507 | N | GLN | D | 7 | 3.617 | −24.645 | −23.184 | 1.00 | 39.50 D | N |
| ATOM | 2508 | CA | GLN | D | 7 | 3.496 | −24.480 | −24.619 | 1.00 | 40.81 D | C |
| ATOM | 2509 | C | GLN | D | 7 | 3.747 | −23.028 | −24.966 | 1.00 | 37.12 D | C |
| ATOM | 2510 | O | GLN | D | 7 | 3.531 | −22.138 | −24.145 | 1.00 | 37.06 D | O |
| ATOM | 2511 | CB | GLN | D | 7 | 2.122 | −24.930 | −25.117 | 1.00 | 50.71 D | C |
| ATOM | 2512 | CG | GLN | D | 7 | 2.064 | −26.395 | −25.528 | 1.00 | 48.43 D | C |
| ATOM | 2513 | CD | GLN | D | 7 | 2.945 | −26.703 | −26.734 | 1.00 | 65.84 D | C |
| ATOM | 2514 | OE1 | GLN | D | 7 | 3.680 | −25.840 | −27.223 | 1.00 | 69.18 D | O |
| ATOM | 2515 | NE2 | GLN | D | 7 | 2.870 | −27.940 | −27.220 | 1.00 | 68.00 D | N |
| ATOM | 2516 | N | ILE | D | 8 | 4.214 | −22.794 | −26.185 | 1.00 | 28.04 D | N |
| ATOM | 2517 | CA | ILE | D | 8 | 4.606 | −21.461 | −26.605 | 1.00 | 23.21 D | C |
| ATOM | 2518 | C | ILE | D | 8 | 3.411 | −20.664 | −27.112 | 1.00 | 26.07 D | C |
| ATOM | 2519 | O | ILE | D | 8 | 3.090 | −20.678 | −28.299 | 1.00 | 25.34 D | O |
| ATOM | 2520 | CB | ILE | D | 8 | 5.734 | −21.519 | −27.662 | 1.00 | 19.94 D | C |
| ATOM | 2521 | CG1 | ILE | D | 8 | 6.967 | −22.203 | −27.066 | 1.00 | 20.05 D | C |
| ATOM | 2522 | CG2 | ILE | D | 8 | 6.100 | −20.128 | −28.149 | 1.00 | 17.49 D | C |
| ATOM | 2523 | CD1 | ILE | D | 8 | 7.431 | −21.586 | −25.758 | 1.00 | 19.55 D | C |
| ATOM | 2524 | N | THR | D | 9 | 2.746 | −19.978 | −26.190 | 1.00 | 29.37 D | N |
| ATOM | 2525 | CA | THR | D | 9 | 1.671 | −19.059 | −26.540 | 1.00 | 29.79 D | C |
| ATOM | 2526 | C | THR | D | 9 | 1.665 | −17.890 | −25.555 | 1.00 | 26.00 D | C |
| ATOM | 2527 | O | THR | D | 9 | 2.156 | −18.019 | −24.433 | 1.00 | 29.33 D | O |
| ATOM | 2528 | CB | THR | D | 9 | 0.297 | −19.768 | −26.584 | 1.00 | 36.05 D | C |
| ATOM | 2529 | OG1 | THR | D | 9 | −0.702 | −18.862 | −27.077 | 1.00 | 37.90 D | O |
| ATOM | 2530 | CG2 | THR | D | 9 | −0.098 | −20.291 | −25.203 | 1.00 | 27.70 D | C |
| ATOM | 2531 | N | ARG | D | 10 | 1.130 | −16.751 | −25.991 | 1.00 | 23.06 D | N |
| ATOM | 2532 | CA | ARG | D | 10 | 1.156 | −15.516 | −25.206 | 1.00 | 27.80 D | C |
| ATOM | 2533 | C | ARG | D | 10 | 0.578 | −15.685 | −23.805 | 1.00 | 27.06 D | C |
| ATOM | 2534 | O | ARG | D | 10 | −0.579 | −16.057 | −23.644 | 1.00 | 29.74 D | O |
| ATOM | 2535 | CB | ARG | D | 10 | 0.411 | −14.401 | −25.943 | 1.00 | 26.90 D | C |
| ATOM | 2536 | CG | ARG | D | 10 | 0.455 | −13.045 | −25.259 | 1.00 | 27.50 D | C |
| ATOM | 2537 | CD | ARG | D | 10 | −0.540 | −12.091 | −25.907 | 1.00 | 30.44 D | C |
| ATOM | 2538 | NE | ARG | D | 10 | −0.591 | −10.785 | −25.255 | 1.00 | 44.07 D | N |
| ATOM | 2539 | CZ | ARG | D | 10 | −1.163 | −10.559 | −24.076 | 1.00 | 41.22 D | C |
| ATOM | 2540 | NH1 | ARG | D | 10 | −1.722 | −11.559 | −23.409 | 1.00 | 42.54 D | N |
| ATOM | 2541 | NH2 | ARG | D | 10 | −1.170 | −9.337 | −23.559 | 1.00 | 34.81 D | N |
| ATOM | 2542 | N | ILE | D | 11 | 1.400 | −15.412 | −22.799 | 1.00 | 19.71 D | N |
| ATOM | 2543 | CA | ILE | D | 11 | 0.982 | −15.491 | −21.405 | 1.00 | 20.19 D | C |
| ATOM | 2544 | C | ILE | D | 11 | −0.007 | −14.372 | −21.096 | 1.00 | 26.44 D | C |
| ATOM | 2545 | O | ILE | D | 11 | 0.301 | −13.192 | −21.265 | 1.00 | 24.69 D | O |
| ATOM | 2546 | CB | ILE | D | 11 | 2.192 | −15.388 | −20.463 | 1.00 | 21.36 D | C |
| ATOM | 2547 | CG1 | ILE | D | 11 | 3.143 | −16.564 | −20.704 | 1.00 | 16.61 D | C |
| ATOM | 2548 | CG2 | ILE | D | 11 | 1.740 | −15.337 | −19.013 | 1.00 | 19.56 D | C |
| ATOM | 2549 | CD1 | ILE | D | 11 | 4.479 | −16.424 | −20.027 | 1.00 | 18.65 D | C |
| ATOM | 2550 | N | MET | D | 12 | −1.198 | −14.753 | −20.651 | 1.00 | 27.99 D | N |
| ATOM | 2551 | CA | MET | D | 12 | −2.297 | −13.806 | −20.503 | 1.00 | 30.35 D | C |
| ATOM | 2552 | C | MET | D | 12 | −2.204 | −12.994 | −19.216 | 1.00 | 36.56 D | C |
| ATOM | 2553 | O | MET | D | 12 | −2.780 | −11.910 | −19.122 | 1.00 | 31.16 D | O |
| ATOM | 2554 | CB | MET | D | 12 | −3.644 | −14.535 | −20.576 | 1.00 | 30.86 D | C |

TABLE 1-continued

| | | | | | | | | | | |
|---|---|---|---|---|---|---|---|---|---|---|
| ATOM | 2555 | CG | MET | D | 12 | −3.858 | −15.321 | −21.870 | 1.00 | 35.87 D | C |
| ATOM | 2556 | SD | MET | D | 12 | −3.790 | −14.291 | −23.356 | 1.00 | 41.14 D | S |
| ATOM | 2557 | CE | MET | D | 12 | −5.282 | −13.311 | −23.140 | 1.00 | 28.21 D | C |
| ATOM | 2558 | N | ASP | D | 13 | −1.483 | −13.521 | −18.231 | 1.00 | 43.22 D | N |
| ATOM | 2559 | CA | ASP | D | 13 | −1.325 | −12.844 | −16.948 | 1.00 | 44.34 D | C |
| ATOM | 2560 | C | ASP | D | 13 | −0.190 | −11.830 | −17.006 | 1.00 | 46.62 D | C |
| ATOM | 2561 | O | ASP | D | 13 | 0.960 | −12.195 | −17.240 | 1.00 | 41.87 D | O |
| ATOM | 2562 | CB | ASP | D | 13 | −1.051 | −13.860 | −15.836 | 1.00 | 44.62 D | C |
| ATOM | 2563 | CG | ASP | D | 13 | −0.742 | −13.200 | −14.501 | 1.00 | 64.34 D | C |
| ATOM | 2564 | OD1 | ASP | D | 13 | −1.403 | −12.192 | −14.165 | 1.00 | 63.68 D | O |
| ATOM | 2565 | OD2 | ASP | D | 13 | 0.156 | −13.692 | −13.783 | 1.00 | 61.32 D | O |
| ATOM | 2566 | N | GLU | D | 14 | −0.517 | −10.560 | −16.793 | 1.00 | 25.49 D | N |
| ATOM | 2567 | CA | GLU | D | 14 | 0.485 | −9.499 | −16.775 | 1.00 | 27.06 D | C |
| ATOM | 2568 | C | GLU | D | 14 | 1.566 | −9.766 | −15.735 | 1.00 | 32.28 D | C |
| ATOM | 2569 | O | GLU | D | 14 | 2.706 | −9.342 | −15.893 | 1.00 | 28.83 D | O |
| ATOM | 2570 | CB | GLU | D | 14 | −0.163 | −8.142 | −16.485 | 1.00 | 25.86 D | C |
| ATOM | 2571 | CG | GLU | D | 14 | 0.825 | −6.995 | −16.330 | 1.00 | 32.28 D | C |
| ATOM | 2572 | CD | GLU | D | 14 | 0.144 | −5.671 | −16.005 | 1.00 | 57.66 D | C |
| ATOM | 2573 | OE1 | GLU | D | 14 | −0.716 | −5.641 | −15.094 | 1.00 | 62.11 D | O |
| ATOM | 2574 | OE2 | GLU | D | 14 | 0.475 | −4.657 | −16.659 | 1.00 | 50.25 D | O |
| ATOM | 2575 | N | ARG | D | 15 | 1.208 | −10.467 | −14.667 | 1.00 | 43.07 D | N |
| ATOM | 2576 | CA | ARG | D | 15 | 2.156 | −10.710 | −13.590 | 1.00 | 36.63 D | C |
| ATOM | 2577 | C | ARG | D | 15 | 3.201 | −11.745 | −13.987 | 1.00 | 31.76 D | C |
| ATOM | 2578 | O | ARG | D | 15 | 4.397 | −11.465 | −13.948 | 1.00 | 27.80 D | O |
| ATOM | 2579 | CB | ARG | D | 15 | 1.435 | −11.130 | −12.309 | 1.00 | 44.69 D | C |
| ATOM | 2580 | CG | ARG | D | 15 | 2.312 | −11.052 | −11.080 | 1.00 | 50.57 D | C |
| ATOM | 2581 | CD | ARG | D | 15 | 1.567 | −10.443 | −9.904 | 1.00 | 58.18 D | C |
| ATOM | 2582 | NE | ARG | D | 15 | 2.426 | −9.509 | −9.180 | 1.00 | 64.06 D | N |
| ATOM | 2583 | CZ | ARG | D | 15 | 2.457 | −8.198 | −9.402 | 1.00 | 66.22 D | C |
| ATOM | 2584 | NH1 | ARG | D | 15 | 1.665 | −7.659 | −10.322 | 1.00 | 71.07 D | N |
| ATOM | 2585 | NH2 | ARG | D | 15 | 3.277 | −7.422 | −8.702 | 1.00 | 44.62 D | N |
| ATOM | 2586 | N | ASN | D | 16 | 2.748 | −12.937 | −14.372 | 1.00 | 36.62 D | N |
| ATOM | 2587 | CA | ASN | D | 16 | 3.664 | −13.988 | −14.798 | 1.00 | 31.52 D | C |
| ATOM | 2588 | C | ASN | D | 16 | 4.335 | −13.633 | −16.120 | 1.00 | 28.43 D | C |
| ATOM | 2589 | O | ASN | D | 16 | 5.345 | −14.225 | −16.487 | 1.00 | 29.39 D | O |
| ATOM | 2590 | CB | ASN | D | 16 | 2.957 | −15.347 | −14.911 | 1.00 | 36.44 D | C |
| ATOM | 2591 | CG | ASN | D | 16 | 3.906 | −16.472 | −15.369 | 1.00 | 46.78 D | C |
| ATOM | 2592 | OD1 | ASN | D | 16 | 5.005 | −16.634 | −14.831 | 1.00 | 29.58 D | O |
| ATOM | 2593 | ND2 | ASN | D | 16 | 3.474 | −17.251 | −16.364 | 1.00 | 33.15 D | N |
| ATOM | 2594 | N | ARG | D | 17 | 3.777 | −12.666 | −16.838 | 1.00 | 20.99 D | N |
| ATOM | 2595 | CA | ARG | D | 17 | 4.361 | −12.290 | −18.114 | 1.00 | 24.96 D | C |
| ATOM | 2596 | C | ARG | D | 17 | 5.567 | −11.391 | −17.900 | 1.00 | 26.75 D | C |
| ATOM | 2597 | O | ARG | D | 17 | 6.542 | −11.461 | −18.648 | 1.00 | 27.52 D | O |
| ATOM | 2598 | CB | ARG | D | 17 | 3.344 | −11.615 | −19.034 | 1.00 | 23.69 D | C |
| ATOM | 2599 | CG | ARG | D | 17 | 3.897 | −11.348 | −20.427 | 1.00 | 23.50 D | C |
| ATOM | 2600 | CD | ARG | D | 17 | 2.832 | −10.841 | −21.394 | 1.00 | 25.68 D | C |
| ATOM | 2601 | NE | ARG | D | 17 | 2.242 | −9.593 | −20.931 | 1.00 | 32.21 D | N |
| ATOM | 2602 | CZ | ARG | D | 17 | 0.991 | −9.472 | −20.502 | 1.00 | 33.52 D | C |
| ATOM | 2603 | NH1 | ARG | D | 17 | 0.179 | −10.526 | −20.491 | 1.00 | 26.29 D | N |
| ATOM | 2604 | NH2 | ARG | D | 17 | 0.552 | −8.290 | −20.091 | 1.00 | 33.61 D | N |
| ATOM | 2605 | N | GLN | D | 18 | 5.501 | −10.545 | −16.878 | 1.00 | 32.30 D | N |
| ATOM | 2606 | CA | GLN | D | 18 | 6.627 | −9.685 | −16.549 | 1.00 | 33.39 D | C |
| ATOM | 2607 | C | GLN | D | 18 | 7.768 | −10.507 | −15.957 | 1.00 | 28.83 D | C |
| ATOM | 2608 | O | GLN | D | 18 | 8.935 | −10.301 | −16.298 | 1.00 | 26.19 D | O |
| ATOM | 2609 | CB | GLN | D | 18 | 6.205 | −8.574 | −15.583 | 1.00 | 32.25 D | C |
| ATOM | 2610 | CG | GLN | D | 18 | 7.356 | −7.676 | −15.135 | 1.00 | 32.58 D | C |
| ATOM | 2611 | CD | GLN | D | 18 | 8.132 | −7.084 | −16.303 | 1.00 | 36.60 D | C |
| ATOM | 2612 | OE1 | GLN | D | 18 | 7.694 | −7.142 | −17.453 | 1.00 | 41.80 D | O |
| ATOM | 2613 | NE2 | GLN | D | 18 | 9.291 | −6.504 | −16.008 | 1.00 | 46.29 D | N |
| ATOM | 2614 | N | VAL | D | 19 | 7.415 | −11.444 | −15.078 | 1.00 | 21.98 D | N |
| ATOM | 2615 | CA | VAL | D | 19 | 8.385 | −12.348 | −14.470 | 1.00 | 25.53 D | C |
| ATOM | 2616 | C | VAL | D | 19 | 9.081 | −13.228 | −15.514 | 1.00 | 26.27 D | C |
| ATOM | 2617 | O | VAL | D | 19 | 10.310 | −13.331 | −15.540 | 1.00 | 27.24 D | O |
| ATOM | 2618 | CB | VAL | D | 19 | 7.719 | −13.250 | −13.421 | 1.00 | 24.87 D | C |
| ATOM | 2619 | CG1 | VAL | D | 19 | 8.645 | −14.396 | −13.040 | 1.00 | 25.36 D | C |
| ATOM | 2620 | CG2 | VAL | D | 19 | 7.335 | −12.436 | −12.203 | 1.00 | 28.33 D | C |
| ATOM | 2621 | N | THR | D | 20 | 8.293 | −13.860 | −16.376 | 1.00 | 28.30 D | N |
| ATOM | 2622 | CA | THR | D | 20 | 8.858 | −14.702 | −17.421 | 1.00 | 25.46 D | C |
| ATOM | 2623 | C | THR | D | 20 | 9.730 | −13.875 | −18.356 | 1.00 | 27.14 D | C |
| ATOM | 2624 | O | THR | D | 20 | 10.819 | −14.298 | −18.740 | 1.00 | 23.40 D | O |
| ATOM | 2625 | CB | THR | D | 20 | 7.770 | −15.430 | −18.210 | 1.00 | 27.19 D | C |
| ATOM | 2626 | OG1 | THR | D | 20 | 7.211 | −16.461 | −17.388 | 1.00 | 29.35 D | O |
| ATOM | 2627 | CG2 | THR | D | 20 | 8.353 | −16.058 | −19.471 | 1.00 | 24.16 D | C |
| ATOM | 2628 | N | PHE | D | 21 | 9.260 | −12.684 | −18.703 | 1.00 | 21.66 D | N |
| ATOM | 2629 | CA | PHE | D | 21 | 10.046 | −11.782 | −19.539 | 1.00 | 21.40 D | C |
| ATOM | 2630 | C | PHE | D | 21 | 11.423 | −11.454 | −18.939 | 1.00 | 18.44 D | C |
| ATOM | 2631 | O | PHE | D | 21 | 12.421 | −11.444 | −19.654 | 1.00 | 19.17 D | O |
| ATOM | 2632 | CB | PHE | D | 21 | 9.274 | −10.492 | −19.831 | 1.00 | 18.91 D | C |
| ATOM | 2633 | CG | PHE | D | 21 | 10.107 | −9.427 | −20.486 | 1.00 | 19.09 D | C |
| ATOM | 2634 | CD1 | PHE | D | 21 | 10.249 | −9.389 | −21.862 | 1.00 | 16.77 D | C |

TABLE 1-continued

| | | | | | | | | | | | |
|---|---|---|---|---|---|---|---|---|---|---|---|
| ATOM | 2635 | CD2 | PHE | D | 21 | 10.753 | −8.466 | −19.724 | 1.00 | 19.35 D | C |
| ATOM | 2636 | CE1 | PHE | D | 21 | 11.016 | −8.413 | −22.474 | 1.00 | 19.96 D | C |
| ATOM | 2637 | CE2 | PHE | D | 21 | 11.525 | −7.482 | −20.327 | 1.00 | 21.51 D | C |
| ATOM | 2638 | CZ | PHE | D | 21 | 11.657 | −7.454 | −21.703 | 1.00 | 27.86 D | C |
| ATOM | 2639 | N | THR | D | 22 | 11.474 | −11.182 | −17.638 | 1.00 | 21.93 D | N |
| ATOM | 2640 | CA | THR | D | 22 | 12.739 | −10.847 | −16.984 | 1.00 | 20.58 D | C |
| ATOM | 2641 | C | THR | D | 22 | 13.703 | −12.041 | −16.949 | 1.00 | 19.47 D | C |
| ATOM | 2642 | O | THR | D | 22 | 14.895 | −11.893 | −17.229 | 1.00 | 20.26 D | O |
| ATOM | 2643 | CB | THR | D | 22 | 12.537 | −10.271 | −15.544 | 1.00 | 24.22 D | C |
| ATOM | 2644 | OG1 | THR | D | 22 | 11.881 | −8.995 | −15.610 | 1.00 | 23.73 D | O |
| ATOM | 2645 | CG2 | THR | D | 22 | 13.871 | −10.089 | −14.852 | 1.00 | 15.77 D | C |
| ATOM | 2646 | N | LYS | D | 23 | 13.194 | −13.220 | −16.607 | 1.00 | 17.92 D | N |
| ATOM | 2647 | CA | LYS | D | 23 | 14.027 | −14.418 | −16.621 | 1.00 | 19.68 D | C |
| ATOM | 2648 | C | LYS | D | 23 | 14.579 | −14.696 | −18.021 | 1.00 | 18.83 D | C |
| ATOM | 2649 | O | LYS | D | 23 | 15.793 | −14.760 | −18.214 | 1.00 | 18.51 D | O |
| ATOM | 2650 | CB | LYS | D | 23 | 13.256 | −15.639 | −16.108 | 1.00 | 21.03 D | C |
| ATOM | 2651 | CG | LYS | D | 23 | 12.993 | −15.645 | −14.606 | 1.00 | 27.11 D | C |
| ATOM | 2652 | CD | LYS | D | 23 | 12.078 | −16.812 | −14.227 | 1.00 | 29.06 D | C |
| ATOM | 2653 | CE | LYS | D | 23 | 11.843 | −16.871 | −12.728 | 1.00 | 28.46 D | C |
| ATOM | 2654 | NZ | LYS | D | 23 | 10.620 | −17.648 | −12.375 | 1.00 | 33.25 D | N |
| ATOM | 2655 | N | ARG | D | 24 | 13.685 | −14.848 | −18.994 | 1.00 | 17.07 D | N |
| ATOM | 2656 | CA | ARG | D | 24 | 14.081 | −15.213 | −20.359 | 1.00 | 17.05 D | C |
| ATOM | 2657 | C | ARG | D | 24 | 14.898 | −14.148 | −21.099 | 1.00 | 19.13 D | C |
| ATOM | 2658 | O | ARG | D | 24 | 15.738 | −14.494 | −21.936 | 1.00 | 16.57 D | O |
| ATOM | 2659 | CB | ARG | D | 24 | 12.868 | −15.641 | −21.190 | 1.00 | 14.08 D | C |
| ATOM | 2660 | CG | ARG | D | 24 | 12.442 | −17.094 | −20.962 | 1.00 | 15.74 D | C |
| ATOM | 2661 | CD | ARG | D | 24 | 11.183 | −17.438 | −21.750 | 1.00 | 15.25 D | C |
| ATOM | 2662 | NE | ARG | D | 24 | 10.793 | −18.841 | −21.593 | 1.00 | 16.71 D | N |
| ATOM | 2663 | CZ | ARG | D | 24 | 11.206 | −19.831 | −22.384 | 1.00 | 19.10 D | C |
| ATOM | 2664 | NH1 | ARG | D | 24 | 12.030 | −19.590 | −23.399 | 1.00 | 16.99 D | N |
| ATOM | 2665 | NH2 | ARG | D | 24 | 10.799 | −21.069 | −22.159 | 1.00 | 17.86 D | N |
| ATOM | 2666 | N | LYS | D | 25 | 14.673 | −12.867 | −20.794 | 1.00 | 22.27 D | N |
| ATOM | 2667 | CA | LYS | D | 25 | 15.468 | −11.798 | −21.413 | 1.00 | 22.31 D | C |
| ATOM | 2668 | C | LYS | D | 25 | 16.932 | −11.926 | −21.021 | 1.00 | 21.68 D | C |
| ATOM | 2669 | O | LYS | D | 25 | 17.822 | −11.822 | −21.854 | 1.00 | 22.43 D | O |
| ATOM | 2670 | CB | LYS | D | 25 | 14.962 | −10.409 | −21.021 | 1.00 | 26.53 D | C |
| ATOM | 2671 | CG | LYS | D | 25 | 15.930 | −9.285 | −21.404 | 1.00 | 22.70 D | C |
| ATOM | 2672 | CD | LYS | D | 25 | 15.244 | −7.918 | −21.425 | 1.00 | 26.14 D | C |
| ATOM | 2673 | CE | LYS | D | 25 | 14.832 | −7.453 | −20.022 | 1.00 | 29.54 D | C |
| ATOM | 2674 | NZ | LYS | D | 25 | 15.996 | −7.018 | −19.195 | 1.00 | 23.97 D | N |
| ATOM | 2675 | N | PHE | D | 26 | 17.164 | −12.143 | −19.735 | 1.00 | 18.14 D | N |
| ATOM | 2676 | CA | PHE | D | 26 | 18.496 | −12.396 | −19.217 | 1.00 | 18.95 D | C |
| ATOM | 2677 | C | PHE | D | 26 | 19.113 | −13.614 | −19.920 | 1.00 | 20.89 D | C |
| ATOM | 2678 | O | PHE | D | 26 | 20.260 | −13.576 | −20.362 | 1.00 | 22.41 D | O |
| ATOM | 2679 | CB | PHE | D | 26 | 18.418 | −12.620 | −17.704 | 1.00 | 19.28 D | C |
| ATOM | 2680 | CG | PHE | D | 26 | 19.745 | −12.842 | −17.052 | 1.00 | 23.11 D | C |
| ATOM | 2681 | CD1 | PHE | D | 26 | 20.424 | −11.786 | −16.458 | 1.00 | 27.39 D | C |
| ATOM | 2682 | CD2 | PHE | D | 26 | 20.310 | −14.106 | −17.015 | 1.00 | 20.31 D | C |
| ATOM | 2683 | CE1 | PHE | D | 26 | 21.653 | −11.985 | −15.845 | 1.00 | 27.22 D | C |
| ATOM | 2684 | CE2 | PHE | D | 26 | 21.540 | −14.313 | −16.404 | 1.00 | 27.35 D | C |
| ATOM | 2685 | CZ | PHE | D | 26 | 22.211 | −13.250 | −15.818 | 1.00 | 25.37 D | C |
| ATOM | 2686 | N | GLY | D | 27 | 18.338 | −14.688 | −20.029 | 1.00 | 26.49 D | N |
| ATOM | 2687 | CA | GLY | D | 27 | 18.785 | −15.895 | −20.699 | 1.00 | 25.22 D | C |
| ATOM | 2688 | C | GLY | D | 27 | 19.100 | −15.689 | −22.168 | 1.00 | 24.07 D | C |
| ATOM | 2689 | O | GLY | D | 27 | 20.000 | −16.328 | −22.710 | 1.00 | 22.92 D | O |
| ATOM | 2690 | N | LEU | D | 28 | 18.358 | −14.800 | −22.820 | 1.00 | 19.89 D | N |
| ATOM | 2691 | CA | LEU | D | 28 | 18.568 | −14.540 | −24.243 | 1.00 | 20.40 D | C |
| ATOM | 2692 | C | LEU | D | 28 | 19.843 | −13.731 | −24.480 | 1.00 | 20.08 D | C |
| ATOM | 2693 | O | LEU | D | 28 | 20.624 | −14.034 | −25.380 | 1.00 | 17.81 D | O |
| ATOM | 2694 | CB | LEU | D | 28 | 17.362 | −13.822 | −24.851 | 1.00 | 19.92 D | C |
| ATOM | 2695 | CG | LEU | D | 28 | 17.417 | −13.605 | −26.370 | 1.00 | 19.33 D | C |
| ATOM | 2696 | CD1 | LEU | D | 28 | 17.456 | −14.923 | −27.104 | 1.00 | 17.21 D | C |
| ATOM | 2697 | CD2 | LEU | D | 28 | 16.237 | −12.763 | −26.841 | 1.00 | 18.71 D | C |
| ATOM | 2698 | N | MET | D | 29 | 20.054 | −12.707 | −23.659 | 1.00 | 23.68 D | N |
| ATOM | 2699 | CA | MET | D | 29 | 21.264 | −11.897 | −23.748 | 1.00 | 23.30 D | C |
| ATOM | 2700 | C | MET | D | 29 | 22.492 | −12.725 | −23.396 | 1.00 | 21.30 D | C |
| ATOM | 2701 | O | MET | D | 29 | 23.542 | −12.574 | −24.001 | 1.00 | 21.35 D | O |
| ATOM | 2702 | CB | MET | D | 29 | 21.173 | −10.677 | −22.828 | 1.00 | 24.49 D | C |
| ATOM | 2703 | CG | MET | D | 29 | 20.074 | −9.685 | −23.197 | 1.00 | 24.02 D | C |
| ATOM | 2704 | SD | MET | D | 29 | 20.345 | −8.057 | −22.447 | 1.00 | 28.67 D | S |
| ATOM | 2705 | CE | MET | D | 29 | 18.943 | −7.151 | −23.109 | 1.00 | 29.13 D | C |
| ATOM | 2706 | N | LYS | D | 30 | 22.358 | −13.603 | −22.411 | 1.00 | 20.43 D | N |
| ATOM | 2707 | CA | LYS | D | 30 | 23.473 | −14.454 | −22.016 | 1.00 | 22.74 D | C |
| ATOM | 2708 | C | LYS | D | 30 | 23.931 | −15.339 | −23.180 | 1.00 | 21.49 D | C |
| ATOM | 2709 | O | LYS | D | 30 | 25.126 | −15.417 | −23.474 | 1.00 | 22.26 D | O |
| ATOM | 2710 | CB | LYS | D | 30 | 23.117 | −15.300 | −20.791 | 1.00 | 22.13 D | C |
| ATOM | 2711 | CG | LYS | D | 30 | 24.277 | −16.134 | −20.270 | 1.00 | 30.47 D | C |
| ATOM | 2712 | CD | LYS | D | 30 | 23.915 | −16.879 | −18.989 | 1.00 | 29.56 D | C |
| ATOM | 2713 | CE | LYS | D | 30 | 25.042 | −17.812 | −18.567 | 1.00 | 31.49 D | C |
| ATOM | 2714 | NZ | LYS | D | 30 | 24.611 | −18.830 | −17.568 | 1.00 | 32.20 D | N |

TABLE 1-continued

| ATOM | 2715 | N | LYS | D | 31 | 22.983 | −15.992 | −23.850 | 1.00 | 17.89 | D | N |
|---|---|---|---|---|---|---|---|---|---|---|---|---|
| ATOM | 2716 | CA | LYS | D | 31 | 23.327 | −16.821 | −25.010 | 1.00 | 19.32 | D | C |
| ATOM | 2717 | C | LYS | D | 31 | 23.835 | −16.001 | −26.200 | 1.00 | 16.48 | D | C |
| ATOM | 2718 | O | LYS | D | 31 | 24.718 | −16.442 | −26.927 | 1.00 | 18.91 | D | O |
| ATOM | 2719 | CB | LYS | D | 31 | 22.169 | −17.749 | −25.403 | 1.00 | 16.34 | D | C |
| ATOM | 2720 | CG | LYS | D | 31 | 22.072 | −18.956 | −24.485 | 1.00 | 15.46 | D | C |
| ATOM | 2721 | CD | LYS | D | 31 | 20.927 | −19.876 | −24.834 | 1.00 | 21.61 | D | C |
| ATOM | 2722 | CE | LYS | D | 31 | 20.909 | −21.083 | −23.899 | 1.00 | 21.65 | D | C |
| ATOM | 2723 | NZ | LYS | D | 31 | 22.219 | −21.804 | −23.873 | 1.00 | 22.50 | D | N |
| ATOM | 2724 | N | ALA | D | 32 | 23.294 | −14.801 | −26.380 | 1.00 | 12.86 | D | N |
| ATOM | 2725 | CA | ALA | D | 32 | 23.778 | −13.905 | −27.423 | 1.00 | 13.63 | D | C |
| ATOM | 2726 | C | ALA | D | 32 | 25.246 | −13.545 | −27.177 | 1.00 | 17.24 | D | C |
| ATOM | 2727 | O | ALA | D | 32 | 26.068 | −13.598 | −28.097 | 1.00 | 15.16 | D | O |
| ATOM | 2728 | CB | ALA | D | 32 | 22.917 | −12.649 | −27.494 | 1.00 | 13.33 | D | C |
| ATOM | 2729 | N | TYR | D | 33 | 25.567 | −13.189 | −25.931 | 1.00 | 20.78 | D | N |
| ATOM | 2730 | CA | TYR | D | 33 | 26.941 | −12.884 | −25.524 | 1.00 | 19.80 | D | C |
| ATOM | 2731 | C | TYR | D | 33 | 27.907 | −14.059 | −25.734 | 1.00 | 21.73 | D | C |
| ATOM | 2732 | O | TYR | D | 33 | 29.020 | −13.875 | −26.231 | 1.00 | 23.12 | D | O |
| ATOM | 2733 | CB | TYR | D | 33 | 26.982 | −12.430 | −24.053 | 1.00 | 25.20 | D | C |
| ATOM | 2734 | CG | TYR | D | 33 | 28.347 | −12.555 | −23.402 | 1.00 | 23.34 | D | C |
| ATOM | 2735 | CD1 | TYR | D | 33 | 29.333 | −11.604 | −23.627 | 1.00 | 25.67 | D | C |
| ATOM | 2736 | CD2 | TYR | D | 33 | 28.649 | −13.629 | −22.571 | 1.00 | 23.73 | D | C |
| ATOM | 2737 | CE1 | TYR | D | 33 | 30.585 | −11.713 | −23.044 | 1.00 | 27.58 | D | C |
| ATOM | 2738 | CE2 | TYR | D | 33 | 29.900 | −13.751 | −21.983 | 1.00 | 23.48 | D | C |
| ATOM | 2739 | CZ | TYR | D | 33 | 30.864 | −12.788 | −22.223 | 1.00 | 27.91 | D | C |
| ATOM | 2740 | OH | TYR | D | 33 | 32.112 | −12.893 | −21.643 | 1.00 | 31.14 | D | O |
| ATOM | 2741 | N | GLU | D | 34 | 27.485 | −15.259 | −25.344 | 1.00 | 16.30 | D | N |
| ATOM | 2742 | CA | GLU | D | 34 | 28.327 | −16.447 | −25.480 | 1.00 | 18.09 | D | C |
| ATOM | 2743 | C | GLU | D | 34 | 28.590 | −16.796 | −26.940 | 1.00 | 19.40 | D | C |
| ATOM | 2744 | O | GLU | D | 34 | 29.687 | −17.243 | −27.289 | 1.00 | 16.16 | D | O |
| ATOM | 2745 | CB | GLU | D | 34 | 27.713 | −17.647 | −24.749 | 1.00 | 16.91 | D | C |
| ATOM | 2746 | CG | GLU | D | 34 | 27.580 | −17.446 | −23.240 | 1.00 | 18.31 | D | C |
| ATOM | 2747 | CD | GLU | D | 34 | 27.022 | −18.665 | −22.526 | 1.00 | 24.07 | D | C |
| ATOM | 2748 | OE1 | GLU | D | 34 | 26.407 | −19.524 | −23.200 | 1.00 | 21.36 | D | O |
| ATOM | 2749 | OE2 | GLU | D | 34 | 27.194 | −18.763 | −21.291 | 1.00 | 19.79 | D | O |
| ATOM | 2750 | N | LEU | D | 35 | 27.594 | −16.583 | −27.796 | 1.00 | 20.14 | D | N |
| ATOM | 2751 | CA | LEU | D | 35 | 27.767 | −16.883 | −29.216 | 1.00 | 19.52 | D | C |
| ATOM | 2752 | C | LEU | D | 35 | 28.752 | −15.907 | −29.858 | 1.00 | 19.84 | D | C |
| ATOM | 2753 | O | LEU | D | 35 | 29.528 | −16.279 | −30.740 | 1.00 | 21.48 | D | O |
| ATOM | 2754 | CB | LEU | D | 35 | 26.432 | −16.881 | −29.965 | 1.00 | 16.57 | D | C |
| ATOM | 2755 | CG | LEU | D | 35 | 26.558 | −17.224 | −31.453 | 1.00 | 17.82 | D | C |
| ATOM | 2756 | CD1 | LEU | D | 35 | 26.909 | −18.687 | −31.634 | 1.00 | 18.16 | D | C |
| ATOM | 2757 | CD2 | LEU | D | 35 | 25.292 | −16.887 | −32.217 | 1.00 | 17.25 | D | C |
| ATOM | 2758 | N | SER | D | 36 | 28.724 | −14.660 | −29.409 | 1.00 | 21.09 | D | N |
| ATOM | 2759 | CA | SER | D | 36 | 29.663 | −13.664 | −29.913 | 1.00 | 30.15 | D | C |
| ATOM | 2760 | C | SER | D | 36 | 31.111 | −14.016 | −29.541 | 1.00 | 25.03 | D | C |
| ATOM | 2761 | O | SER | D | 36 | 32.021 | −13.892 | −30.356 | 1.00 | 27.24 | D | O |
| ATOM | 2762 | CB | SER | D | 36 | 29.302 | −12.273 | −29.389 | 1.00 | 26.99 | D | C |
| ATOM | 2763 | OG | SER | D | 36 | 30.134 | −11.289 | −29.975 | 1.00 | 30.97 | D | O |
| ATOM | 2764 | N | VAL | D | 37 | 31.312 | −14.466 | −28.308 | 1.00 | 20.84 | D | N |
| ATOM | 2765 | CA | VAL | D | 37 | 32.641 | −14.814 | −27.827 | 1.00 | 21.81 | D | C |
| ATOM | 2766 | C | VAL | D | 37 | 33.133 | −16.126 | −28.435 | 1.00 | 22.28 | D | C |
| ATOM | 2767 | O | VAL | D | 37 | 34.225 | −16.187 | −29.000 | 1.00 | 22.33 | D | O |
| ATOM | 2768 | CB | VAL | D | 37 | 32.672 | −14.916 | −26.286 | 1.00 | 21.65 | D | C |
| ATOM | 2769 | CG1 | VAL | D | 37 | 33.953 | −15.589 | −25.815 | 1.00 | 17.21 | D | C |
| ATOM | 2770 | CG2 | VAL | D | 37 | 32.524 | −13.535 | −25.661 | 1.00 | 22.60 | D | C |
| ATOM | 2771 | N | LEU | D | 38 | 32.324 | −17.174 | −28.313 | 1.00 | 26.55 | D | N |
| ATOM | 2772 | CA | LEU | D | 38 | 32.696 | −18.493 | −28.808 | 1.00 | 26.12 | D | C |
| ATOM | 2773 | C | LEU | D | 38 | 33.008 | −18.494 | −30.302 | 1.00 | 26.33 | D | C |
| ATOM | 2774 | O | LEU | D | 38 | 33.987 | −19.104 | −30.733 | 1.00 | 26.16 | D | O |
| ATOM | 2775 | CB | LEU | D | 38 | 31.584 | −19.508 | −28.529 | 1.00 | 24.58 | D | C |
| ATOM | 2776 | CG | LEU | D | 38 | 31.256 | −19.849 | −27.078 | 1.00 | 23.98 | D | C |
| ATOM | 2777 | CD1 | LEU | D | 38 | 29.929 | −20.597 | −27.006 | 1.00 | 20.12 | D | C |
| ATOM | 2778 | CD2 | LEU | D | 38 | 32.379 | −20.656 | −26.435 | 1.00 | 21.85 | D | C |
| ATOM | 2779 | N | CYS | D | 39 | 32.173 | −17.822 | −31.090 | 1.00 | 17.78 | D | N |
| ATOM | 2780 | CA | CYS | D | 39 | 32.296 | −17.907 | −32.544 | 1.00 | 22.24 | D | C |
| ATOM | 2781 | C | CYS | D | 39 | 32.771 | −16.616 | −33.215 | 1.00 | 21.51 | D | C |
| ATOM | 2782 | O | CYS | D | 39 | 32.801 | −16.523 | −34.442 | 1.00 | 24.66 | D | O |
| ATOM | 2783 | CB | CYS | D | 39 | 30.979 | −18.382 | −33.166 | 1.00 | 16.09 | D | C |
| ATOM | 2784 | SG | CYS | D | 39 | 30.384 | −19.924 | −32.459 | 1.00 | 19.92 | D | S |
| ATOM | 2785 | N | ASP | D | 40 | 33.142 | −15.623 | −32.418 | 1.00 | 28.98 | D | N |
| ATOM | 2786 | CA | ASP | D | 40 | 33.704 | −14.402 | −32.978 | 1.00 | 34.97 | D | C |
| ATOM | 2787 | C | ASP | D | 40 | 32.764 | −13.804 | −34.019 | 1.00 | 34.35 | D | C |
| ATOM | 2788 | O | ASP | D | 40 | 33.042 | −13.863 | −35.217 | 1.00 | 31.75 | D | O |
| ATOM | 2789 | CB | ASP | D | 40 | 35.063 | −14.706 | −33.620 | 1.00 | 30.63 | D | C |
| ATOM | 2790 | CG | ASP | D | 40 | 35.796 | −13.455 | −34.078 | 1.00 | 38.54 | D | C |
| ATOM | 2791 | OD1 | ASP | D | 40 | 35.416 | −12.338 | −33.662 | 1.00 | 41.19 | D | O |
| ATOM | 2792 | OD2 | ASP | D | 40 | 36.764 | −13.595 | −34.859 | 1.00 | 49.72 | D | O |
| ATOM | 2793 | N | CYS | D | 41 | 31.652 | −13.233 | −33.567 | 1.00 | 30.83 | D | N |
| ATOM | 2794 | CA | CYS | D | 41 | 30.724 | −12.582 | −34.485 | 1.00 | 35.32 | D | C |

TABLE 1-continued

| | | | | | | | | | | | |
|---|---|---|---|---|---|---|---|---|---|---|---|
| ATOM | 2795 | C | CYS | D | 41 | 30.102 | −11.300 | −33.926 | 1.00 | 33.52 D | C |
| ATOM | 2796 | O | CYS | D | 41 | 29.998 | −11.126 | −32.715 | 1.00 | 33.59 D | O |
| ATOM | 2797 | CB | CYS | D | 41 | 29.642 | −13.562 | −34.953 | 1.00 | 32.70 D | C |
| ATOM | 2798 | SG | CYS | D | 41 | 29.124 | −14.785 | −33.747 | 1.00 | 41.68 D | S |
| ATOM | 2799 | N | GLU | D | 42 | 29.723 | −10.394 | −34.824 | 1.00 | 38.03 D | N |
| ATOM | 2800 | CA | GLU | D | 42 | 29.026 | −9.173 | −34.443 | 1.00 | 39.78 D | C |
| ATOM | 2801 | C | GLU | D | 42 | 27.562 | −9.498 | −34.243 | 1.00 | 37.32 D | C |
| ATOM | 2802 | O | GLU | D | 42 | 26.922 | −10.070 | −35.125 | 1.00 | 38.07 D | O |
| ATOM | 2803 | CB | GLU | D | 42 | 29.129 | −8.117 | −35.540 | 1.00 | 41.70 D | C |
| ATOM | 2804 | CG | GLU | D | 42 | 30.421 | −7.341 | −35.586 | 1.00 | 51.65 D | C |
| ATOM | 2805 | CD | GLU | D | 42 | 30.296 | −6.100 | −36.446 | 1.00 | 52.72 D | C |
| ATOM | 2806 | OE1 | GLU | D | 42 | 31.182 | −5.870 | −37.294 | 1.00 | 69.52 D | O |
| ATOM | 2807 | OE2 | GLU | D | 42 | 29.301 | −5.362 | −36.279 | 1.00 | 42.59 D | O |
| ATOM | 2808 | N | ILE | D | 43 | 27.021 | −9.121 | −33.094 | 1.00 | 23.73 D | N |
| ATOM | 2809 | CA | ILE | D | 43 | 25.625 | −9.403 | −32.817 | 1.00 | 23.65 D | C |
| ATOM | 2810 | C | ILE | D | 43 | 24.911 | −8.176 | −32.283 | 1.00 | 22.94 D | C |
| ATOM | 2811 | O | ILE | D | 43 | 25.486 | −7.383 | −31.541 | 1.00 | 24.65 D | O |
| ATOM | 2812 | CB | ILE | D | 43 | 25.473 | −10.568 | −31.821 | 1.00 | 24.33 D | C |
| ATOM | 2813 | CG1 | ILE | D | 43 | 26.097 | −11.841 | −32.402 | 1.00 | 21.59 D | C |
| ATOM | 2814 | CG2 | ILE | D | 43 | 24.006 | −10.775 | −31.462 | 1.00 | 17.28 D | C |
| ATOM | 2815 | CD1 | ILE | D | 43 | 25.800 | −13.090 | −31.606 | 1.00 | 19.31 D | C |
| ATOM | 2816 | N | ALA | D | 44 | 23.657 | −8.015 | −32.686 | 1.00 | 19.28 D | N |
| ATOM | 2817 | CA | ALA | D | 44 | 22.804 | −6.973 | −32.132 | 1.00 | 19.51 D | C |
| ATOM | 2818 | C | ALA | D | 44 | 21.447 | −7.568 | −31.789 | 1.00 | 17.23 D | C |
| ATOM | 2819 | O | ALA | D | 44 | 20.908 | −8.386 | −32.530 | 1.00 | 19.16 D | O |
| ATOM | 2820 | CB | ALA | D | 44 | 22.657 | −5.807 | −33.109 | 1.00 | 17.11 D | C |
| ATOM | 2821 | N | LEU | D | 45 | 20.906 | −7.150 | −30.654 | 1.00 | 21.67 D | N |
| ATOM | 2822 | CA | LEU | D | 45 | 19.642 | −7.659 | −30.167 | 1.00 | 18.49 D | C |
| ATOM | 2823 | C | LEU | D | 45 | 18.854 | −6.492 | −29.594 | 1.00 | 22.56 D | C |
| ATOM | 2824 | O | LEU | D | 45 | 19.270 | −5.884 | −28.614 | 1.00 | 25.66 D | O |
| ATOM | 2825 | CB | LEU | D | 45 | 19.902 | −8.704 | −29.080 | 1.00 | 20.89 D | C |
| ATOM | 2826 | CG | LEU | D | 45 | 18.716 | −9.287 | −28.309 | 1.00 | 21.08 D | C |
| ATOM | 2827 | CD1 | LEU | D | 45 | 17.745 | −9.969 | −29.262 | 1.00 | 18.48 D | C |
| ATOM | 2828 | CD2 | LEU | D | 45 | 19.201 | −10.255 | −27.229 | 1.00 | 15.51 D | C |
| ATOM | 2829 | N | ILE | D | 46 | 17.724 | −6.174 | −30.215 | 1.00 | 30.84 D | N |
| ATOM | 2830 | CA | ILE | D | 46 | 16.851 | −5.107 | −29.735 | 1.00 | 30.74 D | C |
| ATOM | 2831 | C | ILE | D | 46 | 15.512 | −5.683 | −29.296 | 1.00 | 30.19 D | C |
| ATOM | 2832 | O | ILE | D | 46 | 14.876 | −6.425 | −30.045 | 1.00 | 30.65 D | O |
| ATOM | 2833 | CB | ILE | D | 46 | 16.599 | −4.058 | −30.832 | 1.00 | 32.03 D | C |
| ATOM | 2834 | CG1 | ILE | D | 46 | 17.889 | −3.301 | −31.152 | 1.00 | 30.14 D | C |
| ATOM | 2835 | CG2 | ILE | D | 46 | 15.507 | −3.098 | −30.408 | 1.00 | 31.39 D | C |
| ATOM | 2836 | CD1 | ILE | D | 46 | 17.883 | −2.633 | −32.510 | 1.00 | 33.03 D | C |
| ATOM | 2837 | N | ILE | D | 47 | 15.084 | −5.340 | −28.087 | 1.00 | 26.87 D | N |
| ATOM | 2838 | CA | ILE | D | 47 | 13.849 | −5.882 | −27.528 | 1.00 | 24.21 D | C |
| ATOM | 2839 | C | ILE | D | 47 | 12.950 | −4.803 | −26.930 | 1.00 | 27.15 D | C |
| ATOM | 2840 | O | ILE | D | 47 | 13.366 | −4.063 | −26.036 | 1.00 | 28.75 D | O |
| ATOM | 2841 | CB | ILE | D | 47 | 14.146 | −6.894 | −26.406 | 1.00 | 27.99 D | C |
| ATOM | 2842 | CG1 | ILE | D | 47 | 15.148 | −7.952 | −26.873 | 1.00 | 27.63 D | C |
| ATOM | 2843 | CG2 | ILE | D | 47 | 12.851 | −7.531 | −25.900 | 1.00 | 30.34 D | C |
| ATOM | 2844 | CD1 | ILE | D | 47 | 15.679 | −8.797 | −25.742 | 1.00 | 24.42 D | C |
| ATOM | 2845 | N | PHE | D | 48 | 11.716 | −4.726 | −27.413 | 1.00 | 25.17 D | N |
| ATOM | 2846 | CA | PHE | D | 48 | 10.718 | −3.837 | −26.829 | 1.00 | 26.76 D | C |
| ATOM | 2847 | C | PHE | D | 48 | 9.667 | −4.690 | −26.139 | 1.00 | 31.80 D | C |
| ATOM | 2848 | O | PHE | D | 48 | 8.925 | −5.404 | −26.806 | 1.00 | 30.22 D | O |
| ATOM | 2849 | CB | PHE | D | 48 | 10.033 | −2.993 | −27.908 | 1.00 | 26.58 D | C |
| ATOM | 2850 | CG | PHE | D | 48 | 10.962 | −2.079 | −28.659 | 1.00 | 27.99 D | C |
| ATOM | 2851 | CD1 | PHE | D | 48 | 11.469 | −2.448 | −29.895 | 1.00 | 25.86 D | C |
| ATOM | 2852 | CD2 | PHE | D | 48 | 11.315 | −0.845 | −28.136 | 1.00 | 29.84 D | C |
| ATOM | 2853 | CE1 | PHE | D | 48 | 12.320 | −1.603 | −30.591 | 1.00 | 25.17 D | C |
| ATOM | 2854 | CE2 | PHE | D | 48 | 12.161 | 0.001 | −28.828 | 1.00 | 29.95 D | C |
| ATOM | 2855 | CZ | PHE | D | 48 | 12.664 | −0.380 | −30.058 | 1.00 | 27.12 D | C |
| ATOM | 2856 | N | ASN | D | 49 | 9.595 | −4.619 | −24.814 | 1.00 | 25.16 D | N |
| ATOM | 2857 | CA | ASN | D | 49 | 8.601 | −5.402 | −24.084 | 1.00 | 29.35 D | C |
| ATOM | 2858 | C | ASN | D | 49 | 7.180 | −4.950 | −24.428 | 1.00 | 29.70 D | C |
| ATOM | 2859 | O | ASN | D | 49 | 6.995 | −4.009 | −25.201 | 1.00 | 30.49 D | O |
| ATOM | 2860 | CB | ASN | D | 49 | 8.855 | −5.348 | −22.574 | 1.00 | 24.72 D | C |
| ATOM | 2861 | CG | ASN | D | 49 | 8.473 | −4.016 | −21.961 | 1.00 | 34.53 D | C |
| ATOM | 2862 | OD1 | ASN | D | 49 | 7.997 | −3.108 | −22.647 | 1.00 | 32.64 D | O |
| ATOM | 2863 | ND2 | ASN | D | 49 | 8.680 | −3.893 | −20.654 | 1.00 | 26.98 D | N |
| ATOM | 2864 | N | SER | D | 50 | 6.180 | −5.621 | −23.866 | 1.00 | 32.64 D | N |
| ATOM | 2865 | CA | SER | D | 50 | 4.789 | −5.308 | −24.192 | 1.00 | 40.15 D | C |
| ATOM | 2866 | C | SER | D | 50 | 4.389 | −3.893 | −23.767 | 1.00 | 39.76 D | C |
| ATOM | 2867 | O | SER | D | 50 | 3.391 | −3.361 | −24.247 | 1.00 | 41.34 D | O |
| ATOM | 2868 | CB | SER | D | 50 | 3.834 | −6.344 | −23.589 | 1.00 | 38.04 D | C |
| ATOM | 2869 | OG | SER | D | 50 | 3.958 | −6.401 | −22.179 | 1.00 | 41.22 D | O |
| ATOM | 2870 | N | SER | D | 51 | 5.173 | −3.288 | −22.876 | 1.00 | 39.13 D | N |
| ATOM | 2871 | CA | SER | D | 51 | 4.925 | −1.918 | −22.422 | 1.00 | 37.74 D | C |
| ATOM | 2872 | C | SER | D | 51 | 5.769 | −0.912 | −23.198 | 1.00 | 37.71 D | C |
| ATOM | 2873 | O | SER | D | 51 | 5.913 | 0.236 | −22.777 | 1.00 | 28.82 D | O |
| ATOM | 2874 | CB | SER | D | 51 | 5.226 | −1.770 | −20.925 | 1.00 | 33.74 D | C |

TABLE 1-continued

| ATOM | 2875 | OG | SER | D | 51 | 4.546 | −2.747 | −20.155 | 1.00 | 44.43 | D | O |
|---|---|---|---|---|---|---|---|---|---|---|---|---|
| ATOM | 2876 | N | ASN | D | 52 | 6.339 | −1.356 | −24.316 | 1.00 | 43.05 | D | N |
| ATOM | 2877 | CA | ASN | D | 52 | 7.168 | −0.503 | −25.176 | 1.00 | 38.17 | D | C |
| ATOM | 2878 | C | ASN | D | 52 | 8.504 | −0.025 | −24.602 | 1.00 | 37.13 | D | C |
| ATOM | 2879 | O | ASN | D | 52 | 9.169 | 0.821 | −25.202 | 1.00 | 38.98 | D | O |
| ATOM | 2880 | CB | ASN | D | 52 | 6.375 | 0.695 | −25.699 | 1.00 | 45.39 | D | C |
| ATOM | 2881 | CG | ASN | D | 52 | 5.833 | 0.463 | −27.088 | 1.00 | 52.26 | D | C |
| ATOM | 2882 | OD1 | ASN | D | 52 | 5.356 | −0.625 | −27.404 | 1.00 | 42.19 | D | O |
| ATOM | 2883 | ND2 | ASN | D | 52 | 5.909 | 1.486 | −27.933 | 1.00 | 50.55 | D | N |
| ATOM | 2884 | N | LYS | D | 53 | 8.902 | −0.554 | −23.451 | 1.00 | 34.11 | D | N |
| ATOM | 2885 | CA | LYS | D | 53 | 10.225 | −0.239 | −22.920 | 1.00 | 35.69 | D | C |
| ATOM | 2886 | C | LYS | D | 53 | 11.318 | −0.965 | −23.713 | 1.00 | 35.71 | D | C |
| ATOM | 2887 | O | LYS | D | 53 | 11.209 | −2.158 | −23.997 | 1.00 | 29.83 | D | O |
| ATOM | 2888 | CB | LYS | D | 53 | 10.326 | −0.582 | −21.434 | 1.00 | 29.99 | D | C |
| ATOM | 2889 | CG | LYS | D | 53 | 11.644 | −0.149 | −20.803 | 1.00 | 38.94 | D | C |
| ATOM | 2890 | CD | LYS | D | 53 | 11.669 | −0.437 | −19.309 | 1.00 | 44.66 | D | C |
| ATOM | 2891 | CE | LYS | D | 53 | 12.963 | 0.052 | −18.674 | 1.00 | 37.57 | D | C |
| ATOM | 2892 | NZ | LYS | D | 53 | 13.105 | −0.439 | −17.277 | 1.00 | 38.18 | D | N |
| ATOM | 2893 | N | LEU | D | 54 | 12.368 | −0.232 | −24.065 | 1.00 | 35.22 | D | N |
| ATOM | 2894 | CA | LEU | D | 54 | 13.446 | −0.762 | −24.889 | 1.00 | 29.03 | D | C |
| ATOM | 2895 | C | LEU | D | 54 | 14.521 | −1.472 | −24.060 | 1.00 | 31.24 | D | C |
| ATOM | 2896 | O | LEU | D | 54 | 14.893 | −1.012 | −22.982 | 1.00 | 37.90 | D | O |
| ATOM | 2897 | CB | LEU | D | 54 | 14.073 | 0.372 | −25.704 | 1.00 | 33.09 | D | C |
| ATOM | 2898 | CG | LEU | D | 54 | 15.377 | 0.103 | −26.459 | 1.00 | 35.38 | D | C |
| ATOM | 2899 | CD1 | LEU | D | 54 | 15.202 | −1.013 | −27.480 | 1.00 | 29.21 | D | C |
| ATOM | 2900 | CD2 | LEU | D | 54 | 15.871 | 1.375 | −27.131 | 1.00 | 34.55 | D | C |
| ATOM | 2901 | N | PHE | D | 55 | 15.002 | −2.602 | −24.568 | 1.00 | 25.28 | D | N |
| ATOM | 2902 | CA | PHE | D | 55 | 16.134 | −3.308 | −23.978 | 1.00 | 24.03 | D | C |
| ATOM | 2903 | C | PHE | D | 55 | 17.035 | −3.742 | −25.115 | 1.00 | 22.40 | D | C |
| ATOM | 2904 | O | PHE | D | 55 | 16.551 | −4.179 | −26.151 | 1.00 | 28.76 | D | O |
| ATOM | 2905 | CB | PHE | D | 55 | 15.671 | −4.538 | −23.196 | 1.00 | 24.17 | D | C |
| ATOM | 2906 | CG | PHE | D | 55 | 14.784 | −4.220 | −22.030 | 1.00 | 19.47 | D | C |
| ATOM | 2907 | CD1 | PHE | D | 55 | 13.411 | −4.163 | −22.185 | 1.00 | 18.73 | D | C |
| ATOM | 2908 | CD2 | PHE | D | 55 | 15.325 | −3.986 | −20.775 | 1.00 | 24.11 | D | C |
| ATOM | 2909 | CE1 | PHE | D | 55 | 12.590 | −3.873 | −21.114 | 1.00 | 26.91 | D | C |
| ATOM | 2910 | CE2 | PHE | D | 55 | 14.511 | −3.693 | −19.691 | 1.00 | 22.97 | D | C |
| ATOM | 2911 | CZ | PHE | D | 55 | 13.139 | −3.638 | −19.861 | 1.00 | 29.43 | D | C |
| ATOM | 2912 | N | GLN | D | 56 | 18.343 | −3.631 | −24.936 | 1.00 | 24.35 | D | N |
| ATOM | 2913 | CA | GLN | D | 56 | 19.245 | −3.946 | −26.028 | 1.00 | 23.77 | D | C |
| ATOM | 2914 | C | GLN | D | 56 | 20.546 | −4.595 | −25.591 | 1.00 | 27.79 | D | C |
| ATOM | 2915 | O | GLN | D | 56 | 20.981 | −4.452 | −24.453 | 1.00 | 34.31 | D | O |
| ATOM | 2916 | CB | GLN | D | 56 | 19.540 | −2.686 | −26.843 | 1.00 | 29.59 | D | C |
| ATOM | 2917 | CG | GLN | D | 56 | 20.008 | −1.501 | −26.014 | 1.00 | 28.77 | D | C |
| ATOM | 2918 | CD | GLN | D | 56 | 20.233 | −0.254 | −26.855 | 1.00 | 37.59 | D | C |
| ATOM | 2919 | OE1 | GLN | D | 56 | 20.772 | −0.324 | −27.961 | 1.00 | 36.74 | D | O |
| ATOM | 2920 | NE2 | GLN | D | 56 | 19.821 | 0.893 | −26.332 | 1.00 | 35.89 | D | N |
| ATOM | 2921 | N | TYR | D | 57 | 21.151 | −5.325 | −26.521 | 1.00 | 22.60 | D | N |
| ATOM | 2922 | CA | TYR | D | 57 | 22.489 | −5.859 | −26.355 | 1.00 | 23.14 | D | C |
| ATOM | 2923 | C | TYR | D | 57 | 23.214 | −5.785 | −27.693 | 1.00 | 22.80 | D | C |
| ATOM | 2924 | O | TYR | D | 57 | 22.613 | −6.004 | −28.747 | 1.00 | 24.23 | D | O |
| ATOM | 2925 | CB | TYR | D | 57 | 22.468 | −7.320 | −25.880 | 1.00 | 25.34 | D | C |
| ATOM | 2926 | CG | TYR | D | 57 | 23.786 | −8.010 | −26.165 | 1.00 | 23.93 | D | C |
| ATOM | 2927 | CD1 | TYR | D | 57 | 24.880 | −7.833 | −25.325 | 1.00 | 24.98 | D | C |
| ATOM | 2928 | CD2 | TYR | D | 57 | 23.955 | −8.790 | −27.302 | 1.00 | 22.24 | D | C |
| ATOM | 2929 | CE1 | TYR | D | 57 | 26.099 | −8.431 | −25.594 | 1.00 | 23.10 | D | C |
| ATOM | 2930 | CE2 | TYR | D | 57 | 25.170 | −9.399 | −27.581 | 1.00 | 21.19 | D | C |
| ATOM | 2931 | CZ | TYR | D | 57 | 26.240 | −9.215 | −26.726 | 1.00 | 25.96 | D | C |
| ATOM | 2932 | OH | TYR | D | 57 | 27.456 | −9.814 | −26.997 | 1.00 | 20.95 | D | O |
| ATOM | 2933 | N | ALA | D | 58 | 24.508 | −5.500 | −27.654 | 1.00 | 23.20 | D | N |
| ATOM | 2934 | CA | ALA | D | 58 | 25.312 | −5.524 | −28.866 | 1.00 | 25.98 | D | C |
| ATOM | 2935 | C | ALA | D | 58 | 26.761 | −5.845 | −28.536 | 1.00 | 21.59 | D | C |
| ATOM | 2936 | O | ALA | D | 58 | 27.281 | −5.390 | −27.522 | 1.00 | 22.42 | D | O |
| ATOM | 2937 | CB | ALA | D | 58 | 25.204 | −4.198 | −29.595 | 1.00 | 28.83 | D | C |
| ATOM | 2938 | N | SER | D | 59 | 27.409 | −6.633 | −29.394 | 1.00 | 22.61 | D | N |
| ATOM | 2939 | CA | SER | D | 59 | 28.807 | −7.013 | −29.182 | 1.00 | 24.17 | D | C |
| ATOM | 2940 | C | SER | D | 59 | 29.756 | −5.829 | −29.371 | 1.00 | 27.66 | D | C |
| ATOM | 2941 | O | SER | D | 59 | 30.931 | −5.913 | −29.031 | 1.00 | 18.97 | D | O |
| ATOM | 2942 | CB | SER | D | 59 | 29.209 | −8.182 | −30.087 | 1.00 | 20.53 | D | C |
| ATOM | 2943 | OG | SER | D | 59 | 28.979 | −7.887 | −31.454 | 1.00 | 23.14 | D | O |
| ATOM | 2944 | N | THR | D | 60 | 29.237 | −4.739 | −29.932 | 1.00 | 37.48 | D | N |
| ATOM | 2945 | CA | THR | D | 60 | 29.942 | −3.461 | −29.992 | 1.00 | 35.18 | D | C |
| ATOM | 2946 | C | THR | D | 60 | 28.887 | −2.370 | −29.967 | 1.00 | 41.12 | D | C |
| ATOM | 2947 | O | THR | D | 60 | 27.719 | −2.643 | −29.695 | 1.00 | 38.33 | D | O |
| ATOM | 2948 | CB | THR | D | 60 | 30.758 | −3.289 | −31.282 | 1.00 | 43.32 | D | C |
| ATOM | 2949 | OG1 | THR | D | 60 | 29.872 | −3.275 | −32.409 | 1.00 | 45.89 | D | O |
| ATOM | 2950 | CG2 | THR | D | 60 | 31.776 | −4.410 | −31.444 | 1.00 | 53.89 | D | C |
| ATOM | 2951 | N | ASP | D | 61 | 29.287 | −1.139 | −30.267 | 1.00 | 32.58 | D | N |
| ATOM | 2952 | CA | ASP | D | 61 | 28.330 | −0.043 | −30.326 | 1.00 | 31.13 | D | C |
| ATOM | 2953 | C | ASP | D | 61 | 27.159 | −0.437 | −31.216 | 1.00 | 35.70 | D | C |
| ATOM | 2954 | O | ASP | D | 61 | 27.335 | −0.752 | −32.398 | 1.00 | 31.62 | D | O |

TABLE 1-continued

| | | | | | | | | | | | |
|---|---|---|---|---|---|---|---|---|---|---|---|
| ATOM | 2955 | CB | ASP | D | 61 | 28.983 | 1.240 | −30.845 | 1.00 | 36.78 D | C |
| ATOM | 2956 | CG | ASP | D | 61 | 30.123 | 1.712 | −29.963 | 1.00 | 44.94 D | C |
| ATOM | 2957 | OD1 | ASP | D | 61 | 31.217 | 1.107 | −30.021 | 1.00 | 48.90 D | O |
| ATOM | 2958 | OD2 | ASP | D | 61 | 29.928 | 2.695 | −29.220 | 1.00 | 39.72 D | O |
| ATOM | 2959 | N | MET | D | 62 | 25.967 | −0.432 | −30.629 | 1.00 | 43.29 D | N |
| ATOM | 2960 | CA | MET | D | 62 | 24.751 | −0.809 | −31.333 | 1.00 | 38.50 D | C |
| ATOM | 2961 | C | MET | D | 62 | 24.690 | −0.227 | −32.739 | 1.00 | 42.94 D | C |
| ATOM | 2962 | O | MET | D | 62 | 24.307 | −0.909 | −33.692 | 1.00 | 41.35 D | O |
| ATOM | 2963 | CB | MET | D | 62 | 23.525 | −0.356 | −30.545 | 1.00 | 31.73 D | C |
| ATOM | 2964 | CG | MET | D | 62 | 22.224 | −0.571 | −31.291 | 1.00 | 37.28 D | C |
| ATOM | 2965 | SD | MET | D | 62 | 22.020 | −2.280 | −31.823 | 1.00 | 31.31 D | S |
| ATOM | 2966 | CE | MET | D | 62 | 21.853 | −3.121 | −30.255 | 1.00 | 24.52 D | C |
| ATOM | 2967 | N | ASP | D | 63 | 25.074 | 1.038 | −32.861 | 1.00 | 46.37 D | N |
| ATOM | 2968 | CA | ASP | D | 63 | 24.940 | 1.758 | −34.120 | 1.00 | 44.58 D | C |
| ATOM | 2969 | C | ASP | D | 63 | 25.941 | 1.303 | −35.182 | 1.00 | 41.10 D | C |
| ATOM | 2970 | O | ASP | D | 63 | 25.705 | 1.471 | −36.377 | 1.00 | 43.44 D | O |
| ATOM | 2971 | CB | ASP | D | 63 | 25.030 | 3.263 | −33.877 | 1.00 | 56.07 D | C |
| ATOM | 2972 | CG | ASP | D | 63 | 23.875 | 3.781 | −33.033 | 1.00 | 63.85 D | C |
| ATOM | 2973 | OD1 | ASP | D | 63 | 22.752 | 3.914 | −33.570 | 1.00 | 56.52 D | O |
| ATOM | 2974 | OD2 | ASP | D | 63 | 24.089 | 4.051 | −31.830 | 1.00 | 64.52 D | O |
| ATOM | 2975 | N | LYS | D | 64 | 27.051 | 0.718 | −34.750 | 1.00 | 39.39 D | N |
| ATOM | 2976 | CA | LYS | D | 64 | 28.013 | 0.173 | −35.701 | 1.00 | 38.16 D | C |
| ATOM | 2977 | C | LYS | D | 64 | 27.443 | −1.065 | −36.399 | 1.00 | 38.15 D | C |
| ATOM | 2978 | O | LYS | D | 64 | 27.552 | −1.205 | −37.618 | 1.00 | 31.22 D | O |
| ATOM | 2979 | CB | LYS | D | 64 | 29.341 | −0.148 | −35.013 | 1.00 | 42.22 D | C |
| ATOM | 2980 | CG | LYS | D | 64 | 30.070 | 1.082 | −34.497 | 1.00 | 52.48 D | C |
| ATOM | 2981 | CD | LYS | D | 64 | 31.475 | 0.748 | −34.033 | 1.00 | 56.05 D | C |
| ATOM | 2982 | CE | LYS | D | 64 | 32.217 | 1.996 | −33.586 | 1.00 | 54.72 D | C |
| ATOM | 2983 | NZ | LYS | D | 64 | 33.614 | 1.680 | −33.185 | 1.00 | 55.86 D | N |
| ATOM | 2984 | N | VAL | D | 65 | 26.826 | −1.952 | −35.621 | 1.00 | 35.03 D | N |
| ATOM | 2985 | CA | VAL | D | 65 | 26.206 | −3.151 | −36.173 | 1.00 | 31.99 D | C |
| ATOM | 2986 | C | VAL | D | 65 | 25.102 | −2.778 | −37.157 | 1.00 | 32.00 D | C |
| ATOM | 2987 | O | VAL | D | 65 | 24.979 | −3.375 | −38.230 | 1.00 | 28.64 D | O |
| ATOM | 2988 | CB | VAL | D | 65 | 25.595 | −4.036 | −35.067 | 1.00 | 29.41 D | C |
| ATOM | 2989 | CG1 | VAL | D | 65 | 25.033 | −5.312 | −35.664 | 1.00 | 24.64 D | C |
| ATOM | 2990 | CG2 | VAL | D | 65 | 26.630 | −4.351 | −34.000 | 1.00 | 33.52 D | C |
| ATOM | 2991 | N | LEU | D | 66 | 24.304 | −1.782 | −36.785 | 1.00 | 30.13 D | N |
| ATOM | 2992 | CA | LEU | D | 66 | 23.175 | −1.357 | −37.598 | 1.00 | 34.53 D | C |
| ATOM | 2993 | C | LEU | D | 66 | 23.600 | −0.784 | −38.952 | 1.00 | 41.59 D | C |
| ATOM | 2994 | O | LEU | D | 66 | 23.020 | −1.125 | −39.985 | 1.00 | 39.34 D | O |
| ATOM | 2995 | CB | LEU | D | 66 | 22.309 | −0.363 | −36.825 | 1.00 | 35.86 D | C |
| ATOM | 2996 | CG | LEU | D | 66 | 21.616 | −0.997 | −35.616 | 1.00 | 36.70 D | C |
| ATOM | 2997 | CD1 | LEU | D | 66 | 20.698 | −0.009 | −34.920 | 1.00 | 32.04 D | C |
| ATOM | 2998 | CD2 | LEU | D | 66 | 20.844 | −2.239 | −36.046 | 1.00 | 31.94 D | C |
| ATOM | 2999 | N | LEU | D | 67 | 24.615 | 0.076 | −38.950 | 1.00 | 45.33 D | N |
| ATOM | 3000 | CA | LEU | D | 67 | 25.112 | 0.643 | −40.198 | 1.00 | 45.57 D | C |
| ATOM | 3001 | C | LEU | D | 67 | 25.707 | −0.442 | −41.082 | 1.00 | 45.23 D | C |
| ATOM | 3002 | O | LEU | D | 67 | 25.634 | −0.367 | −42.306 | 1.00 | 48.91 D | O |
| ATOM | 3003 | CB | LEU | D | 67 | 26.142 | 1.747 | −39.940 | 1.00 | 48.90 D | C |
| ATOM | 3004 | CG | LEU | D | 67 | 25.592 | 3.174 | −39.830 | 1.00 | 50.39 D | C |
| ATOM | 3005 | CD1 | LEU | D | 67 | 24.565 | 3.429 | −40.929 | 1.00 | 55.28 D | C |
| ATOM | 3006 | CD2 | LEU | D | 67 | 24.986 | 3.442 | −38.456 | 1.00 | 51.05 D | C |
| ATOM | 3007 | N | LYS | D | 68 | 26.298 | −1.452 | −40.455 | 1.00 | 30.19 D | N |
| ATOM | 3008 | CA | LYS | D | 68 | 26.851 | −2.574 | −41.195 | 1.00 | 28.53 D | C |
| ATOM | 3009 | C | LYS | D | 68 | 25.714 | −3.334 | −41.864 | 1.00 | 36.93 D | C |
| ATOM | 3010 | O | LYS | D | 68 | 25.860 | −3.848 | −42.974 | 1.00 | 38.76 D | O |
| ATOM | 3011 | CB | LYS | D | 68 | 27.650 | −3.494 | −40.269 | 1.00 | 31.26 D | C |
| ATOM | 3012 | CG | LYS | D | 68 | 28.446 | −4.569 | −41.002 | 1.00 | 36.31 D | C |
| ATOM | 3013 | CD | LYS | D | 68 | 29.462 | −5.248 | −40.092 | 1.00 | 41.17 D | C |
| ATOM | 3014 | CE | LYS | D | 68 | 30.185 | −6.366 | −40.824 | 1.00 | 38.47 D | C |
| ATOM | 3015 | NZ | LYS | D | 68 | 31.084 | −7.147 | −39.930 | 1.00 | 37.84 D | N |
| ATOM | 3016 | N | TYR | D | 69 | 24.574 | −3.384 | −41.182 | 1.00 | 36.80 D | N |
| ATOM | 3017 | CA | TYR | D | 69 | 23.388 | −4.048 | −41.711 | 1.00 | 38.58 D | C |
| ATOM | 3018 | C | TYR | D | 69 | 22.826 | −3.312 | −42.924 | 1.00 | 37.48 D | C |
| ATOM | 3019 | O | TYR | D | 69 | 22.574 | −3.916 | −43.969 | 1.00 | 36.91 D | O |
| ATOM | 3020 | CB | TYR | D | 69 | 22.312 | −4.154 | −40.628 | 1.00 | 33.48 D | C |
| ATOM | 3021 | CG | TYR | D | 69 | 20.993 | −4.704 | −41.125 | 1.00 | 28.61 D | C |
| ATOM | 3022 | CD1 | TYR | D | 69 | 20.791 | −6.071 | −41.248 | 1.00 | 25.44 D | C |
| ATOM | 3023 | CD2 | TYR | D | 69 | 19.949 | −3.856 | −41.466 | 1.00 | 29.91 D | C |
| ATOM | 3024 | CE1 | TYR | D | 69 | 19.594 | −6.577 | −41.694 | 1.00 | 23.48 D | C |
| ATOM | 3025 | CE2 | TYR | D | 69 | 18.743 | −4.356 | −41.915 | 1.00 | 23.47 D | C |
| ATOM | 3026 | CZ | TYR | D | 69 | 18.573 | −5.719 | −42.028 | 1.00 | 24.70 D | C |
| ATOM | 3027 | OH | TYR | D | 69 | 17.374 | −6.229 | −42.478 | 1.00 | 27.28 D | O |
| ATOM | 3028 | N | THR | D | 70 | 22.625 | −2.007 | −42.779 | 1.00 | 35.91 D | N |
| ATOM | 3029 | CA | THR | D | 70 | 22.044 | −1.209 | −43.851 | 1.00 | 41.72 D | C |
| ATOM | 3030 | C | THR | D | 70 | 22.985 | −1.143 | −45.048 | 1.00 | 45.23 D | C |
| ATOM | 3031 | O | THR | D | 70 | 22.556 | −1.280 | −46.195 | 1.00 | 54.00 D | O |
| ATOM | 3032 | CB | THR | D | 70 | 21.669 | 0.208 | −43.371 | 1.00 | 43.34 D | C |
| ATOM | 3033 | OG1 | THR | D | 70 | 22.794 | 0.812 | −42.723 | 1.00 | 52.52 D | O |
| ATOM | 3034 | CG2 | THR | D | 70 | 20.510 | 0.140 | −42.386 | 1.00 | 39.54 D | C |

TABLE 1-continued

| | | | | | | | | | | | |
|---|---|---|---|---|---|---|---|---|---|---|---|
| ATOM | 3035 | N | GLU | D | 71 | 24.270 | −0.950 | −44.775 | 1.00 | 37.17 D | N |
| ATOM | 3036 | CA | GLU | D | 71 | 25.285 | −0.959 | −45.822 | 1.00 | 45.08 D | C |
| ATOM | 3037 | C | GLU | D | 71 | 25.360 | −2.327 | −46.502 | 1.00 | 40.36 D | C |
| ATOM | 3038 | O | GLU | D | 71 | 25.728 | −2.431 | −47.671 | 1.00 | 44.26 D | O |
| ATOM | 3039 | CB | GLU | D | 71 | 26.656 | −0.580 | −45.247 | 1.00 | 34.24 D | C |
| ATOM | 3040 | N | TYR | D | 72 | 25.014 | −3.372 | −45.756 | 1.00 | 43.08 D | N |
| ATOM | 3041 | CA | TYR | D | 72 | 25.049 | −4.736 | −46.269 | 1.00 | 44.67 D | C |
| ATOM | 3042 | C | TYR | D | 72 | 24.000 | −4.905 | −47.359 | 1.00 | 53.17 D | C |
| ATOM | 3043 | O | TYR | D | 72 | 24.293 | −5.401 | −48.450 | 1.00 | 52.85 D | O |
| ATOM | 3044 | CB | TYR | D | 72 | 24.790 | −5.729 | −45.133 | 1.00 | 45.47 D | C |
| ATOM | 3045 | CG | TYR | D | 72 | 25.057 | −7.181 | −45.473 | 1.00 | 41.46 D | C |
| ATOM | 3046 | CD1 | TYR | D | 72 | 26.211 | −7.816 | −45.029 | 1.00 | 36.92 D | C |
| ATOM | 3047 | CD2 | TYR | D | 72 | 24.149 | −7.922 | −46.224 | 1.00 | 42.67 D | C |
| ATOM | 3048 | CE1 | TYR | D | 72 | 26.461 | −9.148 | −45.328 | 1.00 | 34.28 D | C |
| ATOM | 3049 | CE2 | TYR | D | 72 | 24.386 | −9.255 | −46.526 | 1.00 | 36.45 D | C |
| ATOM | 3050 | CZ | TYR | D | 72 | 25.542 | −9.863 | −46.075 | 1.00 | 41.64 D | C |
| ATOM | 3051 | OH | TYR | D | 72 | 25.786 | −11.187 | −46.372 | 1.00 | 43.36 D | O |
| ATOM | 3052 | N | ASN | D | 73 | 22.775 | −4.487 | −47.047 | 1.00 | 80.06 D | N |
| ATOM | 3053 | CA | ASN | D | 73 | 21.657 | −4.569 | −47.981 | 1.00 | 81.24 D | C |
| ATOM | 3054 | C | ASN | D | 73 | 21.840 | −3.626 | −49.166 | 1.00 | 89.74 D | C |
| ATOM | 3055 | O | ASN | D | 73 | 21.953 | −2.411 | −48.994 | 1.00 | 87.49 D | O |
| ATOM | 3056 | CB | ASN | D | 73 | 20.332 | −4.264 | −47.268 | 1.00 | 78.13 D | C |
| ATOM | 3057 | CG | ASN | D | 73 | 19.902 | −5.374 | −46.315 | 1.00 | 68.24 D | C |
| ATOM | 3058 | OD1 | ASN | D | 73 | 18.773 | −5.859 | −46.380 | 1.00 | 71.72 D | O |
| ATOM | 3059 | ND2 | ASN | D | 73 | 20.801 | −5.778 | −45.426 | 1.00 | 60.27 D | N |
| TER | | | | | | | | | | | |
| ATOM | 3060 | O5' | ADE | G | 1 | 2.089 | −11.162 | −3.297 | 1.00 | 30.09 G | O |
| ATOM | 3061 | C5' | ADE | G | 1 | 1.758 | −9.795 | −3.078 | 1.00 | 31.54 G | C |
| ATOM | 3062 | C4' | ADE | G | 1 | 2.994 | −8.975 | −2.748 | 1.00 | 32.18 G | C |
| ATOM | 3063 | O4' | ADE | G | 1 | 3.673 | −9.553 | −1.599 | 1.00 | 29.23 G | O |
| ATOM | 3064 | C3' | ADE | G | 1 | 4.047 | −8.913 | −3.851 | 1.00 | 36.39 G | C |
| ATOM | 3065 | O3' | ADE | G | 1 | 4.751 | −7.683 | −3.778 | 1.00 | 32.25 G | O |
| ATOM | 3066 | C2' | ADE | G | 1 | 4.963 | −10.064 | −3.462 | 1.00 | 36.96 G | C |
| ATOM | 3067 | C1' | ADE | G | 1 | 5.015 | −9.805 | −1.964 | 1.00 | 31.04 G | C |
| ATOM | 3068 | N9 | ADE | G | 1 | 5.528 | −10.926 | −1.189 | 1.00 | 30.97 G | N |
| ATOM | 3069 | C8 | ADE | G | 1 | 6.758 | −11.000 | −0.601 | 1.00 | 31.87 G | C |
| ATOM | 3070 | N7 | ADE | G | 1 | 6.970 | −12.124 | 0.035 | 1.00 | 29.74 G | N |
| ATOM | 3071 | C5 | ADE | G | 1 | 5.802 | −12.836 | −0.151 | 1.00 | 25.19 G | C |
| ATOM | 3072 | C6 | ADE | G | 1 | 5.409 | −14.110 | 0.280 | 1.00 | 27.04 G | C |
| ATOM | 3073 | N6 | ADE | G | 1 | 6.195 | −14.892 | 1.021 | 1.00 | 29.70 G | N |
| ATOM | 3074 | N1 | ADE | G | 1 | 4.179 | −14.536 | −0.076 | 1.00 | 33.56 G | N |
| ATOM | 3075 | C2 | ADE | G | 1 | 3.408 | −13.727 | −0.818 | 1.00 | 33.14 G | C |
| ATOM | 3076 | N3 | ADE | G | 1 | 3.673 | −12.505 | −1.284 | 1.00 | 29.79 G | N |
| ATOM | 3077 | C4 | ADE | G | 1 | 4.899 | −12.115 | −0.907 | 1.00 | 29.22 G | C |
| ATOM | 3078 | P | ADE | G | 2 | 5.814 | −7.300 | −4.906 | 1.00 | 38.84 G | P |
| ATOM | 3079 | OP1 | ADE | G | 2 | 6.230 | −5.901 | −4.689 | 1.00 | 40.00 G | O |
| ATOM | 3080 | OP2 | ADE | G | 2 | 5.266 | −7.699 | −6.218 | 1.00 | 34.10 G | O |
| ATOM | 3081 | O5' | ADE | G | 2 | 7.049 | −8.252 | −4.565 | 1.00 | 46.24 G | O |
| ATOM | 3082 | C5' | ADE | G | 2 | 8.141 | −7.809 | −3.759 | 1.00 | 34.96 G | C |
| ATOM | 3083 | C4' | ADE | G | 2 | 9.293 | −8.790 | −3.905 | 1.00 | 37.08 G | C |
| ATOM | 3084 | O4' | ADE | G | 2 | 8.859 | −10.100 | −3.448 | 1.00 | 40.16 G | O |
| ATOM | 3085 | C3' | ADE | G | 2 | 9.760 | −9.022 | −5.341 | 1.00 | 35.45 G | C |
| ATOM | 3086 | O3' | ADE | G | 2 | 11.106 | −9.463 | −5.356 | 1.00 | 43.32 G | O |
| ATOM | 3087 | C2' | ADE | G | 2 | 8.863 | −10.169 | −5.773 | 1.00 | 36.55 G | C |
| ATOM | 3088 | C1' | ADE | G | 2 | 9.019 | −11.013 | −4.517 | 1.00 | 31.98 G | C |
| ATOM | 3089 | N9 | ADE | G | 2 | 8.071 | −12.116 | −4.422 | 1.00 | 29.90 G | N |
| ATOM | 3090 | C8 | ADE | G | 2 | 7.016 | −12.377 | −5.252 | 1.00 | 32.71 G | C |
| ATOM | 3091 | N7 | ADE | G | 2 | 6.345 | −13.460 | −4.924 | 1.00 | 30.52 G | N |
| ATOM | 3092 | C5 | ADE | G | 2 | 7.008 | −13.937 | −3.804 | 1.00 | 29.99 G | C |
| ATOM | 3093 | C6 | ADE | G | 2 | 6.796 | −15.056 | −2.977 | 1.00 | 29.21 G | C |
| ATOM | 3094 | N6 | ADE | G | 2 | 5.803 | −15.932 | −3.158 | 1.00 | 29.86 G | N |
| ATOM | 3095 | N1 | ADE | G | 2 | 7.649 | −15.243 | −1.950 | 1.00 | 27.42 G | N |
| ATOM | 3096 | C2 | ADE | G | 2 | 8.642 | −14.369 | −1.759 | 1.00 | 26.74 G | C |
| ATOM | 3097 | N3 | ADE | G | 2 | 8.938 | −13.282 | −2.466 | 1.00 | 27.47 G | N |
| ATOM | 3098 | C4 | ADE | G | 2 | 8.076 | −13.122 | −3.483 | 1.00 | 29.22 G | C |
| ATOM | 3099 | P | ADE | G | 3 | 12.320 | −8.428 | −5.459 | 1.00 | 41.20 G | P |
| ATOM | 3100 | OP1 | ADE | G | 3 | 11.995 | −7.245 | −4.633 | 1.00 | 36.86 G | O |
| ATOM | 3101 | OP2 | ADE | G | 3 | 12.648 | −8.262 | −6.893 | 1.00 | 38.02 G | O |
| ATOM | 3102 | O5' | ADE | G | 3 | 13.507 | −9.254 | −4.767 | 1.00 | 33.94 G | O |
| ATOM | 3103 | C5' | ADE | G | 3 | 13.430 | −9.595 | −3.390 | 1.00 | 28.55 G | C |
| ATOM | 3104 | C4' | ADE | G | 3 | 14.057 | −10.954 | −3.120 | 1.00 | 32.01 G | C |
| ATOM | 3105 | O4' | ADE | G | 3 | 13.052 | −12.001 | −3.180 | 1.00 | 29.13 G | O |
| ATOM | 3106 | C3' | ADE | G | 3 | 15.169 | −11.380 | −4.075 | 1.00 | 39.18 G | C |
| ATOM | 3107 | O3' | ADE | G | 3 | 16.238 | −11.933 | −3.311 | 1.00 | 36.03 G | O |
| ATOM | 3108 | C2' | ADE | G | 3 | 14.504 | −12.438 | −4.960 | 1.00 | 33.01 G | C |
| ATOM | 3109 | C1' | ADE | G | 3 | 13.501 | −13.065 | −4.000 | 1.00 | 35.72 G | C |
| ATOM | 3110 | N9 | ADE | G | 3 | 12.333 | −13.631 | −4.667 | 1.00 | 30.02 G | N |
| ATOM | 3111 | C8 | ADE | G | 3 | 11.696 | −13.134 | −5.771 | 1.00 | 29.04 G | C |
| ATOM | 3112 | N7 | ADE | G | 3 | 10.663 | −13.842 | −6.159 | 1.00 | 29.82 G | N |
| ATOM | 3113 | C5 | ADE | G | 3 | 10.618 | −14.879 | −5.241 | 1.00 | 28.28 G | C |

TABLE 1-continued

| ATOM | 3114 | C6 | ADE | G | 3 | 9.747 | −15.976 | −5.095 | 1.00 | 26.79 | G | C |
|---|---|---|---|---|---|---|---|---|---|---|---|---|
| ATOM | 3115 | N6 | ADE | G | 3 | 8.719 | −16.211 | −5.916 | 1.00 | 30.72 | G | N |
| ATOM | 3116 | N1 | ADE | G | 3 | 9.980 | −16.825 | −4.071 | 1.00 | 30.91 | G | N |
| ATOM | 3117 | C2 | ADE | G | 3 | 11.013 | −16.589 | −3.248 | 1.00 | 28.20 | G | C |
| ATOM | 3118 | N3 | ADE | G | 3 | 11.893 | −15.589 | −3.285 | 1.00 | 28.13 | G | N |
| ATOM | 3119 | C4 | ADE | G | 3 | 11.639 | −14.764 | −4.314 | 1.00 | 26.77 | G | C |
| ATOM | 3120 | P | GUA | G | 4 | 17.525 | −12.572 | −4.017 | 1.00 | 44.94 | G | P |
| ATOM | 3121 | OP1 | GUA | G | 4 | 18.657 | −12.319 | −3.104 | 1.00 | 26.60 | G | O |
| ATOM | 3122 | OP2 | GUA | G | 4 | 17.569 | −12.119 | −5.430 | 1.00 | 43.10 | G | O |
| ATOM | 3123 | O5' | GUA | G | 4 | 17.206 | −14.141 | −4.011 | 1.00 | 41.67 | G | O |
| ATOM | 3124 | C5' | GUA | G | 4 | 17.066 | −14.783 | −2.751 | 1.00 | 41.51 | G | C |
| ATOM | 3125 | C4' | GUA | G | 4 | 16.533 | −16.199 | −2.887 | 1.00 | 40.62 | G | C |
| ATOM | 3126 | O4' | GUA | G | 4 | 15.266 | −16.214 | −3.593 | 1.00 | 41.42 | G | O |
| ATOM | 3127 | C3' | GUA | G | 4 | 17.429 | −17.186 | −3.627 | 1.00 | 49.83 | G | C |
| ATOM | 3128 | O3' | GUA | G | 4 | 17.570 | −18.307 | −2.768 | 1.00 | 51.67 | G | O |
| ATOM | 3129 | C2' | GUA | G | 4 | 16.656 | −17.515 | −4.908 | 1.00 | 40.85 | G | C |
| ATOM | 3130 | C1' | GUA | G | 4 | 15.220 | −17.355 | −4.420 | 1.00 | 36.12 | G | C |
| ATOM | 3131 | N9 | GUA | G | 4 | 14.207 | −17.099 | −5.442 | 1.00 | 35.49 | G | N |
| ATOM | 3132 | C8 | GUA | G | 4 | 14.154 | −16.049 | −6.329 | 1.00 | 31.33 | G | C |
| ATOM | 3133 | N7 | GUA | G | 4 | 13.109 | −16.088 | −7.115 | 1.00 | 30.40 | G | N |
| ATOM | 3134 | C5 | GUA | G | 4 | 12.422 | −17.235 | −6.723 | 1.00 | 31.20 | G | C |
| ATOM | 3135 | C6 | GUA | G | 4 | 11.212 | −17.799 | −7.209 | 1.00 | 29.78 | G | C |
| ATOM | 3136 | O6 | GUA | G | 4 | 10.467 | −17.389 | −8.120 | 1.00 | 26.03 | G | O |
| ATOM | 3137 | N1 | GUA | G | 4 | 10.882 | −18.965 | −6.518 | 1.00 | 27.82 | G | N |
| ATOM | 3138 | C2 | GUA | G | 4 | 11.619 | −19.516 | −5.497 | 1.00 | 32.35 | G | C |
| ATOM | 3139 | N2 | GUA | G | 4 | 11.140 | −20.647 | −4.957 | 1.00 | 36.86 | G | N |
| ATOM | 3140 | N3 | GUA | G | 4 | 12.750 | −18.998 | −5.034 | 1.00 | 30.81 | G | N |
| ATOM | 3141 | C4 | GUA | G | 4 | 13.087 | −17.863 | −5.691 | 1.00 | 32.84 | G | C |
| ATOM | 3142 | P | CYT | G | 5 | 18.538 | −19.531 | −3.110 | 1.00 | 55.72 | G | P |
| ATOM | 3143 | OP1 | CYT | G | 5 | 19.281 | −19.838 | −1.867 | 1.00 | 38.31 | G | O |
| ATOM | 3144 | OP2 | CYT | G | 5 | 19.231 | −19.265 | −4.393 | 1.00 | 40.25 | G | O |
| ATOM | 3145 | O5' | CYT | G | 5 | 17.491 | −20.711 | −3.363 | 1.00 | 37.47 | G | O |
| ATOM | 3146 | C5' | CYT | G | 5 | 16.519 | −20.951 | −2.356 | 1.00 | 33.10 | G | C |
| ATOM | 3147 | C4' | CYT | G | 5 | 15.692 | −22.166 | −2.706 | 1.00 | 33.20 | G | C |
| ATOM | 3148 | O4' | CYT | G | 5 | 14.748 | −21.822 | −3.746 | 1.00 | 30.86 | G | O |
| ATOM | 3149 | C3' | CYT | G | 5 | 16.490 | −23.358 | −3.215 | 1.00 | 34.33 | G | C |
| ATOM | 3150 | O3' | CYT | G | 5 | 15.942 | −24.508 | −2.587 | 1.00 | 39.29 | G | O |
| ATOM | 3151 | C2' | CYT | G | 5 | 16.264 | −23.310 | −4.729 | 1.00 | 31.29 | G | C |
| ATOM | 3152 | C1' | CYT | G | 5 | 14.868 | −22.703 | −4.835 | 1.00 | 28.72 | G | C |
| ATOM | 3153 | N1 | CYT | G | 5 | 14.580 | −21.859 | −6.034 | 1.00 | 29.55 | G | N |
| ATOM | 3154 | C2 | CYT | G | 5 | 13.502 | −22.187 | −6.861 | 1.00 | 26.17 | G | C |
| ATOM | 3155 | O2 | CYT | G | 5 | 12.818 | −23.189 | −6.597 | 1.00 | 28.47 | G | O |
| ATOM | 3156 | N3 | CYT | G | 5 | 13.239 | −21.397 | −7.932 | 1.00 | 26.81 | G | N |
| ATOM | 3157 | C4 | CYT | G | 5 | 13.999 | −20.328 | −8.189 | 1.00 | 25.37 | G | C |
| ATOM | 3158 | N4 | CYT | G | 5 | 13.695 | −19.590 | −9.264 | 1.00 | 22.67 | G | N |
| ATOM | 3159 | C5 | CYT | G | 5 | 15.098 | −19.973 | −7.353 | 1.00 | 25.47 | G | C |
| ATOM | 3160 | C6 | CYT | G | 5 | 15.344 | −20.758 | −6.297 | 1.00 | 30.74 | G | C |
| ATOM | 3161 | P | THY | G | 6 | 16.549 | −25.968 | −2.798 | 1.00 | 62.65 | G | P |
| ATOM | 3162 | OP1 | THY | G | 6 | 16.186 | −26.778 | −1.614 | 1.00 | 56.50 | G | O |
| ATOM | 3163 | OP2 | THY | G | 6 | 17.966 | −25.841 | −3.210 | 1.00 | 52.21 | G | O |
| ATOM | 3164 | O5' | THY | G | 6 | 15.727 | −26.497 | −4.064 | 1.00 | 49.96 | G | O |
| ATOM | 3165 | C5' | THY | G | 6 | 14.396 | −26.977 | −3.929 | 1.00 | 48.74 | G | C |
| ATOM | 3166 | C4' | THY | G | 6 | 14.019 | −27.782 | −5.157 | 1.00 | 40.65 | G | C |
| ATOM | 3167 | O4' | THY | G | 6 | 13.704 | −26.874 | −6.246 | 1.00 | 41.97 | G | O |
| ATOM | 3168 | C3' | THY | G | 6 | 15.131 | −28.676 | −5.695 | 1.00 | 45.61 | G | C |
| ATOM | 3169 | O3' | THY | G | 6 | 14.577 | −29.772 | −6.399 | 1.00 | 51.56 | G | O |
| ATOM | 3170 | C2' | THY | G | 6 | 15.817 | −27.746 | −6.684 | 1.00 | 42.12 | G | C |
| ATOM | 3171 | C1' | THY | G | 6 | 14.568 | −27.158 | −7.330 | 1.00 | 46.59 | G | C |
| ATOM | 3172 | N1 | THY | G | 6 | 14.811 | −25.913 | −8.108 | 1.00 | 38.83 | G | N |
| ATOM | 3173 | C2 | THY | G | 6 | 13.846 | −25.493 | −8.994 | 1.00 | 36.66 | G | C |
| ATOM | 3174 | O2 | THY | G | 6 | 12.799 | −26.093 | −9.164 | 1.00 | 35.66 | G | O |
| ATOM | 3175 | N3 | THY | G | 6 | 14.152 | −24.339 | −9.668 | 1.00 | 31.51 | G | N |
| ATOM | 3176 | C4 | THY | G | 6 | 15.308 | −23.590 | −9.545 | 1.00 | 33.13 | G | C |
| ATOM | 3177 | O4 | THY | G | 6 | 15.497 | −22.569 | −10.194 | 1.00 | 36.34 | G | O |
| ATOM | 3178 | C5 | THY | G | 6 | 16.280 | −24.092 | −8.604 | 1.00 | 35.08 | G | C |
| ATOM | 3179 | C7 | THY | G | 6 | 17.572 | −23.358 | −8.395 | 1.00 | 29.54 | G | C |
| ATOM | 3180 | C6 | THY | G | 6 | 15.990 | −25.217 | −7.938 | 1.00 | 33.15 | G | C |
| ATOM | 3181 | P | ADE | G | 7 | 14.158 | −31.112 | −5.635 | 1.00 | 45.98 | G | P |
| ATOM | 3182 | OP1 | ADE | G | 7 | 13.536 | −30.737 | −4.346 | 1.00 | 49.15 | G | O |
| ATOM | 3183 | OP2 | ADE | G | 7 | 15.320 | −32.024 | −5.661 | 1.00 | 50.69 | G | O |
| ATOM | 3184 | O5' | ADE | G | 7 | 13.029 | −31.710 | −6.594 | 1.00 | 37.82 | G | O |
| ATOM | 3185 | C5' | ADE | G | 7 | 11.731 | −31.143 | −6.586 | 1.00 | 40.93 | G | C |
| ATOM | 3186 | C4' | ADE | G | 7 | 11.136 | −31.093 | −7.982 | 1.00 | 41.28 | G | C |
| ATOM | 3187 | O4' | ADE | G | 7 | 11.745 | −30.022 | −8.750 | 1.00 | 42.69 | G | O |
| ATOM | 3188 | C3' | ADE | G | 7 | 11.307 | −32.355 | −8.812 | 1.00 | 44.26 | G | C |
| ATOM | 3189 | O3' | ADE | G | 7 | 10.102 | −32.546 | −9.548 | 1.00 | 46.58 | G | O |
| ATOM | 3190 | C2' | ADE | G | 7 | 12.522 | −32.032 | −9.691 | 1.00 | 39.03 | G | C |
| ATOM | 3191 | C1' | ADE | G | 7 | 12.369 | −30.527 | −9.915 | 1.00 | 40.77 | G | C |
| ATOM | 3192 | N9 | ADE | G | 7 | 13.605 | −29.761 | −10.075 | 1.00 | 35.79 | G | N |
| ATOM | 3193 | C8 | ADE | G | 7 | 14.800 | −29.956 | −9.437 | 1.00 | 38.83 | G | C |

TABLE 1-continued

| | | | | | | | | | | | |
|---|---|---|---|---|---|---|---|---|---|---|---|
| ATOM | 3194 | N7 | ADE | G | 7 | 15.733 | −29.090 | −9.772 | 1.00 | 39.23 G | N |
| ATOM | 3195 | C5 | ADE | G | 7 | 15.106 | −28.261 | −10.690 | 1.00 | 32.85 G | C |
| ATOM | 3196 | C6 | ADE | G | 7 | 15.548 | −27.137 | −11.423 | 1.00 | 28.85 G | C |
| ATOM | 3197 | N6 | ADE | G | 7 | 16.783 | −26.630 | −11.346 | 1.00 | 24.36 6 | N |
| ATOM | 3198 | N1 | ADE | G | 7 | 14.662 | −26.547 | −12.252 | 1.00 | 28.50 G | N |
| ATOM | 3199 | C2 | ADE | G | 7 | 13.422 | −27.042 | −12.340 | 1.00 | 28.65 G | C |
| ATOM | 3200 | N3 | ADE | G | 7 | 12.893 | −28.087 | −11.701 | 1.00 | 35.16 G | N |
| ATOM | 3201 | C4 | ADE | G | 7 | 13.794 | −28.659 | −10.883 | 1.00 | 35.41 G | C |
| ATOM | 3202 | P | THY | G | 8 | 9.904 | −33.839 | −10.469 | 1.00 | 58.11 G | P |
| ATOM | 3203 | OP1 | THY | G | 8 | 8.471 | −34.212 | −10.428 | 1.00 | 52.37 G | O |
| ATOM | 3204 | OP2 | THY | G | 8 | 10.968 | −34.817 | −10.125 | 1.00 | 42.98 G | O |
| ATOM | 3205 | O5' | THY | G | 8 | 10.202 | −33.255 | −11.925 | 1.00 | 39.07 G | O |
| ATOM | 3206 | C5' | THY | G | 8 | 9.502 | −32.094 | −12.335 | 1.00 | 39.40 G | C |
| ATOM | 3207 | C4' | THY | G | 8 | 10.160 | −31.489 | −13.559 | 1.00 | 40.04 G | C |
| ATOM | 3208 | O4' | THY | G | 8 | 11.414 | −30.863 | −13.208 | 1.00 | 41.59 G | O |
| ATOM | 3209 | C3' | THY | G | 8 | 10.517 | −32.477 | −14.664 | 1.00 | 32.24 G | C |
| ATOM | 3210 | O3' | THY | G | 8 | 9.467 | −32.466 | −15.624 | 1.00 | 32.65 G | O |
| ATOM | 3211 | C2' | THY | G | 8 | 11.839 | −31.938 | −15.220 | 1.00 | 30.22 G | C |
| ATOM | 3212 | C1' | THY | G | 8 | 12.062 | −30.645 | −14.439 | 1.00 | 33.04 G | C |
| ATOM | 3213 | N1 | THY | G | 8 | 13.493 | −30.260 | −14.190 | 1.00 | 32.43 G | N |
| ATOM | 3214 | C2 | THY | G | 8 | 14.016 | −29.165 | −14.847 | 1.00 | 30.93 G | C |
| ATOM | 3215 | O2 | THY | G | 8 | 13.380 | −28.485 | −15.636 | 1.00 | 29.88 G | O |
| ATOM | 3216 | N3 | THY | G | 8 | 15.327 | −28.890 | −14.551 | 1.00 | 26.98 G | N |
| ATOM | 3217 | C4 | THY | G | 8 | 16.154 | −29.577 | −13.683 | 1.00 | 29.88 G | C |
| ATOM | 3218 | O4 | THY | G | 8 | 17.326 | −29.246 | −13.490 | 1.00 | 25.74 G | O |
| ATOM | 3219 | C5 | THY | G | 8 | 15.541 | −30.708 | −13.027 | 1.00 | 30.10 G | C |
| ATOM | 3220 | C7 | THY | G | 8 | 16.337 | −31.538 | −12.060 | 1.00 | 38.26 G | C |
| ATOM | 3221 | C6 | THY | G | 8 | 14.263 | −30.992 | −13.307 | 1.00 | 28.43 G | C |
| ATOM | 3222 | P | THY | G | 9 | 9.616 | −33.145 | −17.068 | 1.00 | 40.40 G | P |
| ATOM | 3223 | OP1 | THY | G | 9 | 8.257 | −33.380 | −17.598 | 1.00 | 29.13 G | O |
| ATOM | 3224 | OP2 | THY | G | 9 | 10.591 | −34.251 | −16.958 | 1.00 | 33.30 G | O |
| ATOM | 3225 | O5' | THY | G | 9 | 10.257 | −31.979 | −17.948 | 1.00 | 35.54 G | O |
| ATOM | 3226 | C5' | THY | G | 9 | 9.490 | −30.803 | −18.126 | 1.00 | 33.56 G | C |
| ATOM | 3227 | C4' | THY | G | 9 | 10.278 | −29.781 | −18.911 | 1.00 | 31.82 G | C |
| ATOM | 3228 | O4' | THY | G | 9 | 11.559 | −29.580 | −18.269 | 1.00 | 27.85 G | O |
| ATOM | 3229 | C3' | THY | G | 9 | 10.574 | −30.170 | −20.355 | 1.00 | 26.02 G | C |
| ATOM | 3230 | O3' | THY | G | 9 | 10.419 | −28.984 | −21.121 | 1.00 | 29.19 G | O |
| ATOM | 3231 | C2' | THY | G | 9 | 12.015 | −30.683 | −20.291 | 1.00 | 25.44 G | C |
| ATOM | 3232 | C1' | THY | G | 9 | 12.588 | −29.753 | −19.223 | 1.00 | 29.00 G | C |
| ATOM | 3233 | N1 | THY | G | 9 | 13.781 | −30.239 | −18.474 | 1.00 | 26.11 G | N |
| ATOM | 3234 | C2 | THY | G | 9 | 14.842 | −29.387 | −18.366 | 1.00 | 23.17 G | C |
| ATOM | 3235 | O2 | THY | G | 9 | 14.839 | −28.276 | −18.867 | 1.00 | 24.88 G | O |
| ATOM | 3236 | N3 | THY | G | 9 | 15.901 | −29.890 | −17.652 | 1.00 | 24.78 G | N |
| ATOM | 3237 | C4 | THY | G | 9 | 16.000 | −31.129 | −17.047 | 1.00 | 22.42 G | C |
| ATOM | 3238 | O4 | THY | G | 9 | 16.996 | −31.492 | −16.427 | 1.00 | 25.07 G | O |
| ATOM | 3239 | C5 | THY | G | 9 | 14.851 | −31.971 | −17.199 | 1.00 | 24.19 G | C |
| ATOM | 3240 | C7 | THY | G | 9 | 14.855 | −33.340 | −16.582 | 1.00 | 24.67 G | C |
| ATOM | 3241 | C6 | THY | G | 9 | 13.807 | −31.492 | −17.895 | 1.00 | 28.98 G | C |
| ATOM | 3242 | P | ADE | G | 10 | 10.667 | −28.948 | −22.697 | 1.00 | 27.55 G | P |
| ATOM | 3243 | OP1 | ADE | G | 10 | 9.807 | −27.892 | −23.275 | 1.00 | 25.17 G | O |
| ATOM | 3244 | OP2 | ADE | G | 10 | 10.572 | −30.334 | −23.209 | 1.00 | 31.35 G | O |
| ATOM | 3245 | O5' | ADE | G | 10 | 12.182 | −28.437 | −22.773 | 1.00 | 37.21 G | O |
| ATOM | 3246 | C5' | ADE | G | 10 | 12.484 | −27.120 | −22.314 | 1.00 | 23.68 G | C |
| ATOM | 3247 | C4' | ADE | G | 10 | 13.858 | −26.640 | −22.756 | 1.00 | 22.58 G | C |
| ATOM | 3248 | O4' | ADE | G | 10 | 14.884 | −27.249 | −21.939 | 1.00 | 22.97 G | O |
| ATOM | 3249 | C3' | ADE | G | 10 | 14.259 | −26.935 | −24.196 | 1.00 | 25.44 G | C |
| ATOM | 3250 | O3' | ADE | G | 10 | 14.904 | −25.776 | −24.681 | 1.00 | 22.78 G | O |
| ATOM | 3251 | C2' | ADE | G | 10 | 15.215 | −28.121 | −24.073 | 1.00 | 18.98 G | C |
| ATOM | 3252 | C1' | ADE | G | 10 | 15.893 | −27.822 | −22.744 | 1.00 | 23.52 G | C |
| ATOM | 3253 | N9 | ADE | G | 10 | 16.359 | −28.998 | −22.015 | 1.00 | 23.49 G | N |
| ATOM | 3254 | C8 | ADE | G | 10 | 15.649 | −30.147 | −21.787 | 1.00 | 20.29 G | C |
| ATOM | 3255 | N7 | ADE | G | 10 | 16.309 | −31.040 | −21.086 | 1.00 | 21.42 G | N |
| ATOM | 3256 | C5 | ADE | G | 10 | 17.529 | −30.433 | −20.832 | 1.00 | 20.13 G | C |
| ATOM | 3257 | C6 | ADE | G | 10 | 18.673 | −30.865 | −20.131 | 1.00 | 23.13 G | C |
| ATOM | 3258 | N6 | ADE | G | 10 | 18.761 | −32.062 | −19.540 | 1.00 | 22.41 G | N |
| ATOM | 3259 | N1 | ADE | G | 10 | 19.723 | −30.018 | −20.065 | 1.00 | 21.54 G | N |
| ATOM | 3260 | C2 | ADE | G | 10 | 19.626 | −28.826 | −20.665 | 1.00 | 19.94 G | C |
| ATOM | 3261 | N3 | ADE | G | 10 | 18.602 | −28.309 | −21.347 | 1.00 | 21.70 G | N |
| ATOM | 3262 | C4 | ADE | G | 10 | 17.577 | −29.173 | −21.396 | 1.00 | 20.19 G | C |
| ATOM | 3263 | P | THY | G | 11 | 15.529 | −25.684 | −26.145 | 1.00 | 28.15 G | P |
| ATOM | 3264 | OP1 | THY | G | 11 | 15.315 | −24.302 | −26.619 | 1.00 | 28.86 G | O |
| ATOM | 3265 | OP2 | THY | G | 11 | 15.080 | −26.832 | −26.967 | 1.00 | 20.38 G | O |
| ATOM | 3266 | O5' | THY | G | 11 | 17.085 | −25.861 | −25.826 | 1.00 | 29.02 G | O |
| ATOM | 3267 | C5' | THY | G | 11 | 17.711 | −24.929 | −24.951 | 1.00 | 22.15 G | C |
| ATOM | 3268 | C4' | THY | G | 11 | 19.189 | −25.234 | −24.789 | 1.00 | 25.89 G | C |
| ATOM | 3269 | O4' | THY | G | 11 | 19.351 | −26.501 | −24.106 | 1.00 | 23.80 G | O |
| ATOM | 3270 | C3' | THY | G | 11 | 19.983 | −25.330 | −26.086 | 1.00 | 27.91 G | C |
| ATOM | 3271 | O3' | THY | G | 11 | 21.157 | −24.518 | −25.923 | 1.00 | 24.16 G | O |
| ATOM | 3272 | C2' | THY | G | 11 | 20.256 | −26.836 | −26.215 | 1.00 | 24.53 G | C |
| ATOM | 3273 | C1' | THY | G | 11 | 20.358 | −27.248 | −24.746 | 1.00 | 23.90 G | C |

TABLE 1-continued

| | | | | | | | | | | | |
|---|---|---|---|---|---|---|---|---|---|---|---|
| ATOM | 3274 | N1 | THY | G | 11 | 20.093 | −28.677 | −24.366 | 1.00 | 21.31 G | N |
| ATOM | 3275 | C2 | THY | G | 11 | 21.003 | −29.314 | −23.544 | 1.00 | 22.11 G | C |
| ATOM | 3276 | O2 | THY | G | 11 | 22.023 | −28.796 | −23.131 | 1.00 | 27.11 G | O |
| ATOM | 3277 | N3 | THY | G | 11 | 20.696 | −30.601 | −23.208 | 1.00 | 20.87 G | N |
| ATOM | 3278 | C4 | THY | G | 11 | 19.583 | −31.305 | −23.599 | 1.00 | 26.65 G | C |
| ATOM | 3279 | O4 | THY | G | 11 | 19.404 | −32.466 | −23.242 | 1.00 | 34.71 G | O |
| ATOM | 3280 | C5 | THY | G | 11 | 18.659 | −30.590 | −24.453 | 1.00 | 22.77 G | C |
| ATOM | 3281 | C7 | THY | G | 11 | 17.411 | −31.282 | −24.931 | 1.00 | 22.15 G | C |
| ATOM | 3282 | C6 | THY | G | 11 | 18.948 | −29.321 | −24.791 | 1.00 | 20.01 G | C |
| ATOM | 3283 | P | THY | G | 12 | 22.165 | −24.182 | −27.131 | 1.00 | 26.73 G | P |
| ATOM | 3284 | OP1 | THY | G | 12 | 22.786 | −22.874 | −26.830 | 1.00 | 25.84 G | O |
| ATOM | 3285 | OP2 | THY | G | 12 | 21.475 | −24.391 | −28.426 | 1.00 | 33.91 G | O |
| ATOM | 3286 | O5' | THY | G | 12 | 23.291 | −25.310 | −26.972 | 1.00 | 28.10 G | O |
| ATOM | 3287 | C5' | THY | G | 12 | 24.116 | −25.288 | −25.804 | 1.00 | 22.77 G | C |
| ATOM | 3288 | C4' | THY | G | 12 | 24.934 | −26.556 | −25.716 | 1.00 | 25.11 G | C |
| ATOM | 3289 | O4' | THY | G | 12 | 24.081 | −27.685 | −25.387 | 1.00 | 24.96 G | O |
| ATOM | 3290 | C3' | THY | G | 12 | 25.642 | −26.935 | −27.019 | 1.00 | 26.10 G | C |
| ATOM | 3291 | O3' | THY | G | 12 | 26.982 | −27.309 | −26.745 | 1.00 | 26.65 G | O |
| ATOM | 3292 | C2' | THY | G | 12 | 24.836 | −28.135 | −27.515 | 1.00 | 19.97 G | C |
| ATOM | 3293 | C1' | THY | G | 12 | 24.544 | −28.771 | −26.163 | 1.00 | 21.80 G | C |
| ATOM | 3294 | N1 | THY | G | 12 | 23.535 | −29.859 | −26.186 | 1.00 | 22.69 G | N |
| ATOM | 3295 | C2 | THY | G | 12 | 23.743 | −30.974 | −25.393 | 1.00 | 23.34 G | C |
| ATOM | 3296 | O2 | THY | G | 12 | 24.706 | −31.116 | −24.664 | 1.00 | 22.76 G | O |
| ATOM | 3297 | N3 | THY | G | 12 | 22.767 | −31.929 | −25.484 | 1.00 | 20.07 G | N |
| ATOM | 3298 | C4 | THY | G | 12 | 21.637 | −31.872 | −26.270 | 1.00 | 20.42 G | C |
| ATOM | 3299 | O4 | THY | G | 12 | 20.824 | −32.787 | −26.267 | 1.00 | 28.04 G | O |
| ATOM | 3300 | C5 | THY | G | 12 | 21.484 | −30.682 | −27.080 | 1.00 | 19.54 G | C |
| ATOM | 3301 | C7 | THY | G | 12 | 20.292 | −30.510 | −27.982 | 1.00 | 20.80 G | C |
| ATOM | 3302 | C6 | THY | G | 12 | 22.431 | −29.745 | −27.003 | 1.00 | 20.75 G | C |
| ATOM | 3303 | P | ADE | G | 13 | 28.151 | −26.224 | −26.639 | 1.00 | 29.02 G | P |
| ATOM | 3304 | OP1 | ADE | G | 13 | 27.795 | −25.263 | −25.568 | 1.00 | 26.54 G | O |
| ATOM | 3305 | OP2 | ADE | G | 13 | 28.443 | −25.746 | −28.011 | 1.00 | 21.47 G | O |
| ATOM | 3306 | O5' | ADE | G | 13 | 29.379 | −27.113 | −26.119 | 1.00 | 27.76 G | O |
| ATOM | 3307 | C5' | ADE | G | 13 | 29.266 | −27.784 | −24.858 | 1.00 | 24.82 G | C |
| ATOM | 3308 | C4' | ADE | G | 13 | 30.220 | −28.968 | −24.783 | 1.00 | 29.40 G | C |
| ATOM | 3309 | O4' | ADE | G | 13 | 29.546 | −30.226 | −25.060 | 1.00 | 24.95 G | O |
| ATOM | 3310 | C3' | ADE | G | 13 | 31.405 | −28.915 | −25.739 | 1.00 | 22.88 G | C |
| ATOM | 3311 | O3' | ADE | G | 13 | 32.510 | −29.502 | −25.053 | 1.00 | 23.06 G | O |
| ATOM | 3312 | C2' | ADE | G | 13 | 30.900 | −29.716 | −26.940 | 1.00 | 22.97 G | C |
| ATOM | 3313 | C1' | ADE | G | 13 | 29.905 | −30.707 | −26.338 | 1.00 | 26.35 G | C |
| ATOM | 3314 | N9 | ADE | G | 13 | 28.659 | −30.840 | −27.083 | 1.00 | 21.00 G | N |
| ATOM | 3315 | C8 | ADE | G | 13 | 28.200 | −30.019 | −28.074 | 1.00 | 18.52 G | C |
| ATOM | 3316 | N7 | ADE | G | 13 | 27.040 | −30.383 | −28.562 | 1.00 | 19.84 G | N |
| ATOM | 3317 | C5 | ADE | G | 13 | 26.706 | −31.513 | −27.834 | 1.00 | 17.67 G | C |
| ATOM | 3318 | C6 | ADE | G | 13 | 25.584 | −32.365 | −27.868 | 1.00 | 18.34 G | C |
| ATOM | 3319 | N6 | ADE | G | 13 | 24.554 | −32.194 | −28.711 | 1.00 | 17.04 G | N |
| ATOM | 3320 | N1 | ADE | G | 13 | 25.566 | −33.405 | −27.004 | 1.00 | 19.91 G | N |
| ATOM | 3321 | C2 | ADE | G | 13 | 26.602 | −33.570 | −26.170 | 1.00 | 19.44 G | C |
| ATOM | 3322 | N3 | ADE | G | 13 | 27.705 | −32.832 | −26.046 | 1.00 | 18.84 G | N |
| ATOM | 3323 | C4 | ADE | G | 13 | 27.694 | −31.809 | −26.915 | 1.00 | 19.36 G | C |
| ATOM | 3324 | P | GUA | G | 14 | 33.898 | −29.846 | −25.771 | 1.00 | 32.65 G | P |
| ATOM | 3325 | OP1 | GUA | G | 14 | 34.973 | −29.788 | −24.754 | 1.00 | 32.33 G | O |
| ATOM | 3326 | OP2 | GUA | G | 14 | 33.998 | −29.022 | −26.998 | 1.00 | 23.93 G | O |
| ATOM | 3327 | O5' | GUA | G | 14 | 33.703 | −31.383 | −26.160 | 1.00 | 26.41 G | O |
| ATOM | 3328 | C5' | GUA | G | 14 | 33.518 | −32.312 | −25.103 | 1.00 | 26.98 G | C |
| ATOM | 3329 | C4' | GUA | G | 14 | 33.190 | −33.695 | −25.629 | 1.00 | 35.30 G | C |
| ATOM | 3330 | O4' | GUA | G | 14 | 31.894 | −33.698 | −26.284 | 1.00 | 35.26 G | O |
| ATOM | 3331 | C3' | GUA | G | 14 | 34.194 | −34.247 | −26.636 | 1.00 | 38.49 G | C |
| ATOM | 3332 | O3' | GUA | G | 14 | 34.556 | −35.547 | −26.198 | 1.00 | 42.75 G | O |
| ATOM | 3333 | C2' | GUA | G | 14 | 33.433 | −34.245 | −27.963 | 1.00 | 35.46 G | C |
| ATOM | 3334 | C1' | GUA | G | 14 | 31.989 | −34.402 | −27.503 | 1.00 | 32.29 G | C |
| ATOM | 3335 | N9 | GUA | G | 14 | 31.010 | −33.838 | −28.426 | 1.00 | 30.90 G | N |
| ATOM | 3336 | C8 | GUA | G | 14 | 31.116 | −32.675 | −29.160 | 1.00 | 31.45 G | C |
| ATOM | 3337 | N7 | GUA | G | 14 | 30.067 | −32.428 | −29.899 | 1.00 | 29.52 G | N |
| ATOM | 3338 | C5 | GUA | G | 14 | 29.212 | −33.493 | −29.634 | 1.00 | 25.41 G | C |
| ATOM | 3339 | C6 | GUA | G | 14 | 27.926 | −33.776 | −30.139 | 1.00 | 25.42 G | C |
| ATOM | 3340 | O6 | GUA | G | 14 | 27.266 | −33.118 | −30.948 | 1.00 | 29.11 G | O |
| ATOM | 3341 | N1 | GUA | G | 14 | 27.403 | −34.958 | −29.623 | 1.00 | 25.64 G | N |
| ATOM | 3342 | C2 | GUA | G | 14 | 28.047 | −35.770 | −28.719 | 1.00 | 29.50 G | C |
| ATOM | 3343 | N2 | GUA | G | 14 | 27.381 | −36.867 | −28.331 | 1.00 | 29.82 G | N |
| ATOM | 3344 | N3 | GUA | G | 14 | 29.254 | −35.516 | −28.228 | 1.00 | 31.77 G | N |
| ATOM | 3345 | C4 | GUA | G | 14 | 29.774 | −34.368 | −28.731 | 1.00 | 30.52 G | C |
| ATOM | 3346 | P | CYT | G | 15 | 35.505 | −36.506 | −27.051 | 1.00 | 54.28 G | P |
| ATOM | 3347 | OP1 | CYT | G | 15 | 36.447 | −37.139 | −26.101 | 1.00 | 62.73 G | O |
| ATOM | 3348 | OP2 | CYT | G | 15 | 36.014 | −35.772 | −28.233 | 1.00 | 47.29 G | O |
| ATOM | 3349 | O5' | CYT | G | 15 | 34.460 | −37.607 | −27.548 | 1.00 | 52.63 G | O |
| ATOM | 3350 | C5' | CYT | G | 15 | 33.573 | −38.181 | −26.592 | 1.00 | 53.62 G | C |
| ATOM | 3351 | C4' | CYT | G | 15 | 32.470 | −38.966 | −27.277 | 1.00 | 58.86 G | C |
| ATOM | 3352 | O4' | CYT | G | 15 | 31.601 | −38.072 | −28.021 | 1.00 | 51.47 G | O |
| ATOM | 3353 | C3' | CYT | G | 15 | 32.956 | −40.011 | −28.277 | 1.00 | 61.10 G | C |

TABLE 1-continued

| | | | | | | | | | | |
|---|---|---|---|---|---|---|---|---|---|---|
| ATOM | 3354 | O3' | CYT | G | 15 | 32.168 | −41.184 | −28.119 | 1.00 | 67.43 G | O |
| ATOM | 3355 | C2' | CYT | G | 15 | 32.728 | −39.339 | −29.630 | 1.00 | 50.29 G | C |
| ATOM | 3356 | C1' | CYT | G | 15 | 31.450 | −38.562 | −29.339 | 1.00 | 46.79 G | C |
| ATOM | 3357 | N1 | CYT | G | 15 | 31.213 | −37.403 | −30.243 | 1.00 | 40.11 G | N |
| ATOM | 3358 | C2 | CYT | G | 15 | 30.017 | −37.344 | −30.967 | 1.00 | 34.63 G | C |
| ATOM | 3359 | O2 | CYT | G | 15 | 29.188 | −38.259 | −30.840 | 1.00 | 36.27 G | O |
| ATOM | 3360 | N3 | CYT | G | 15 | 29.803 | −36.280 | −31.785 | 1.00 | 29.35 G | N |
| ATOM | 3361 | C4 | CYT | G | 15 | 30.722 | −35.316 | −31.891 | 1.00 | 33.10 G | C |
| ATOM | 3362 | N4 | CYT | G | 15 | 30.454 | −34.295 | −32.714 | 1.00 | 30.61 G | N |
| ATOM | 3363 | C5 | CYT | G | 15 | 31.949 | −35.363 | −31.159 | 1.00 | 34.90 G | C |
| ATOM | 3364 | C6 | CYT | G | 15 | 32.148 | −36.413 | −30.354 | 1.00 | 36.04 G | C |
| ATOM | 3365 | P | THY | G | 16 | 32.672 | −42.606 | −28.657 | 1.00 | 78.68 G | P |
| ATOM | 3366 | OP1 | THY | G | 16 | 32.518 | −43.562 | −27.536 | 1.00 | 50.64 G | O |
| ATOM | 3367 | OP2 | THY | G | 16 | 33.979 | −42.435 | −29.342 | 1.00 | 63.43 G | O |
| ATOM | 3368 | O5' | THY | G | 16 | 31.590 | −42.950 | −29.783 | 1.00 | 70.30 G | O |
| ATOM | 3369 | C5' | THY | G | 16 | 30.199 | −42.830 | −29.506 | 1.00 | 65.85 G | C |
| ATOM | 3370 | C4' | THY | G | 16 | 29.414 | −43.044 | −30.786 | 1.00 | 64.65 G | C |
| ATOM | 3371 | O4' | THY | G | 16 | 29.315 | −41.810 | −31.544 | 1.00 | 56.89 G | O |
| ATOM | 3372 | C3' | THY | G | 16 | 30.042 | −44.062 | −31.730 | 1.00 | 65.14 G | C |
| ATOM | 3373 | O3' | THY | G | 16 | 29.007 | −44.854 | −32.288 | 1.00 | 70.25 G | O |
| ATOM | 3374 | C2' | THY | G | 16 | 30.740 | −43.188 | −32.771 | 1.00 | 55.68 G | C |
| ATOM | 3375 | C1' | THY | G | 16 | 29.732 | −42.051 | −32.873 | 1.00 | 50.22 G | C |
| ATOM | 3376 | N1 | THY | G | 16 | 30.256 | −40.770 | −33.414 | 1.00 | 47.13 G | N |
| ATOM | 3377 | C2 | THY | G | 16 | 29.417 | −40.015 | −34.201 | 1.00 | 41.96 G | C |
| ATOM | 3378 | O2 | THY | G | 16 | 28.279 | −40.363 | −34.473 | 1.00 | 36.49 G | O |
| ATOM | 3379 | N3 | THY | G | 16 | 29.965 | −38.839 | −34.656 | 1.00 | 36.69 G | N |
| ATOM | 3380 | C4 | THY | G | 16 | 31.240 | −38.363 | −34.403 | 1.00 | 38.39 G | C |
| ATOM | 3381 | O4 | THY | G | 16 | 31.654 | −37.296 | −34.849 | 1.00 | 36.45 G | O |
| ATOM | 3382 | C5 | THY | G | 16 | 32.061 | −39.205 | −33.574 | 1.00 | 39.77 G | C |
| ATOM | 3383 | C7 | THY | G | 16 | 33.458 | −38.768 | −33.250 | 1.00 | 36.90 G | C |
| ATOM | 3384 | C6 | THY | G | 16 | 31.541 | −40.355 | −33.119 | 1.00 | 43.68 G | C |
| ATOM | 3385 | P | THY | G | 17 | 29.304 | −46.363 | −32.712 | 1.00 | 77.32 G | P |
| ATOM | 3386 | OP1 | THY | G | 17 | 28.327 | −47.238 | −32.024 | 1.00 | 59.40 G | O |
| ATOM | 3387 | OP2 | THY | G | 17 | 30.758 | −46.597 | −32.559 | 1.00 | 72.89 G | O |
| ATOM | 3388 | O5' | THY | G | 17 | 28.986 | −46.342 | −34.277 | 1.00 | 72.58 G | O |
| ATOM | 3389 | C5' | THY | G | 17 | 27.648 | −46.174 | −34.735 | 1.00 | 67.07 G | C |
| ATOM | 3390 | C4' | THY | G | 17 | 27.670 | −45.705 | −36.178 | 1.00 | 67.99 G | C |
| ATOM | 3391 | O4' | THY | G | 17 | 28.227 | −44.366 | −36.227 | 1.00 | 63.26 G | O |
| ATOM | 3392 | C3' | THY | G | 17 | 28.524 | −46.566 | −37.110 | 1.00 | 64.72 G | C |
| ATOM | 3393 | O3' | THY | G | 17 | 27.805 | −46.864 | −38.302 | 1.00 | 70.10 G | O |
| ATOM | 3394 | C2' | THY | G | 17 | 29.749 | −45.700 | −37.392 | 1.00 | 64.86 G | C |
| ATOM | 3395 | C1' | THY | G | 17 | 29.155 | −44.302 | −37.283 | 1.00 | 70.81 G | C |
| ATOM | 3396 | N1 | THY | G | 17 | 30.165 | −43.280 | −36.948 | 1.00 | 61.92 G | N |
| ATOM | 3397 | C2 | THY | G | 17 | 29.971 | −41.973 | −37.348 | 1.00 | 54.43 G | C |
| ATOM | 3398 | O2 | THY | G | 17 | 28.988 | −41.597 | −37.970 | 1.00 | 42.14 G | O |
| ATOM | 3399 | N3 | THY | G | 17 | 30.982 | −41.118 | −36.981 | 1.00 | 43.42 G | N |
| ATOM | 3400 | C4 | THY | G | 17 | 32.130 | −41.437 | −36.279 | 1.00 | 45.64 G | C |
| ATOM | 3401 | O4 | THY | G | 17 | 32.978 | −40.598 | −36.002 | 1.00 | 48.61 G | O |
| ATOM | 3402 | C5 | THY | G | 17 | 32.264 | −42.821 | −35.897 | 1.00 | 61.56 G | C |
| ATOM | 3403 | C7 | THY | G | 17 | 33.471 | −43.283 | −35.133 | 1.00 | 68.79 G | C |
| ATOM | 3404 | C6 | THY | G | 17 | 31.288 | −43.667 | −36.248 | 1.00 | 58.84 G | C |
| TER | | | | | | | | | | | |
| ATOM | 3405 | O5' | THY | H | 1 | 35.925 | −36.030 | −41.955 | 1.00 | 32.94 H | O |
| ATOM | 3406 | C5' | THY | H | 1 | 36.090 | −35.750 | −43.338 | 1.00 | 26.10 H | C |
| ATOM | 3407 | C4' | THY | H | 1 | 34.748 | −35.736 | −44.051 | 1.00 | 24.93 H | C |
| ATOM | 3408 | O4' | THY | H | 1 | 34.124 | −37.044 | −43.969 | 1.00 | 26.72 H | O |
| ATOM | 3409 | C3' | THY | H | 1 | 33.737 | −34.740 | −43.496 | 1.00 | 26.47 H | C |
| ATOM | 3410 | O3' | THY | H | 1 | 33.035 | −34.134 | −44.575 | 1.00 | 27.28 H | O |
| ATOM | 3411 | C2' | THY | H | 1 | 32.837 | −35.598 | −42.606 | 1.00 | 30.24 H | C |
| ATOM | 3412 | C1' | THY | H | 1 | 32.898 | −36.976 | −43.266 | 1.00 | 26.52 H | C |
| ATOM | 3413 | N1 | THY | H | 1 | 32.836 | −38.138 | −42.310 | 1.00 | 25.05 H | N |
| ATOM | 3414 | C2 | THY | H | 1 | 31.673 | −38.878 | −42.229 | 1.00 | 24.12 H | C |
| ATOM | 3415 | O2 | THY | H | 1 | 30.678 | −38.651 | −42.891 | 1.00 | 29.79 H | O |
| ATOM | 3416 | N3 | THY | H | 1 | 31.702 | −39.913 | −41.338 | 1.00 | 21.97 H | N |
| ATOM | 3417 | C4 | THY | H | 1 | 32.752 | −40.277 | −40.528 | 1.00 | 24.78 H | C |
| ATOM | 3418 | O4 | THY | H | 1 | 32.673 | −41.229 | −39.761 | 1.00 | 30.41 H | O |
| ATOM | 3419 | C5 | THY | H | 1 | 33.938 | −39.466 | −40.649 | 1.00 | 23.79 H | C |
| ATOM | 3420 | C7 | THY | H | 1 | 35.133 | −39.787 | −39.804 | 1.00 | 30.54 H | C |
| ATOM | 3421 | C6 | THY | H | 1 | 33.930 | −38.445 | −41.520 | 1.00 | 24.66 H | C |
| ATOM | 3422 | P | ADE | H | 2 | 32.281 | −32.738 | −44.373 | 1.00 | 39.81 H | P |
| ATOM | 3423 | OP1 | ADE | H | 2 | 32.238 | −32.023 | −45.662 | 1.00 | 40.11 H | O |
| ATOM | 3424 | OP2 | ADE | H | 2 | 32.845 | −32.071 | −43.182 | 1.00 | 31.36 H | O |
| ATOM | 3425 | O5' | ADE | H | 2 | 30.800 | −33.199 | −44.012 | 1.00 | 38.96 H | O |
| ATOM | 3426 | C5' | ADE | H | 2 | 30.137 | −34.174 | −44.793 | 1.00 | 26.70 H | C |
| ATOM | 3427 | C4' | ADE | H | 2 | 28.912 | −34.646 | −44.031 | 1.00 | 33.63 H | C |
| ATOM | 3428 | O4' | ADE | H | 2 | 29.305 | −35.527 | −42.943 | 1.00 | 38.83 H | O |
| ATOM | 3429 | C3' | ADE | H | 2 | 28.096 | −33.540 | −43.370 | 1.00 | 35.55 H | C |
| ATOM | 3430 | O3' | ADE | H | 2 | 26.752 | −33.943 | −43.445 | 1.00 | 42.10 H | O |
| ATOM | 3431 | C2' | ADE | H | 2 | 28.613 | −33.534 | −41.931 | 1.00 | 30.13 H | C |
| ATOM | 3432 | C1' | ADE | H | 2 | 28.809 | −35.029 | −41.713 | 1.00 | 30.36 H | C |

TABLE 1-continued

| | | | | | | | | | | |
|---|---|---|---|---|---|---|---|---|---|---|
| ATOM | 3433 | N9 | ADE | H | 2 | 29.756 | −35.402 | −40.663 | 1.00 | 26.40 H | N |
| ATOM | 3434 | C8 | ADE | H | 2 | 30.726 | −34.630 | −40.086 | 1.00 | 28.73 H | C |
| ATOM | 3435 | N7 | ADE | H | 2 | 31.427 | −35.260 | −39.165 | 1.00 | 28.81 H | N |
| ATOM | 3436 | C5 | ADE | H | 2 | 30.880 | −36.532 | −39.142 | 1.00 | 26.92 H | C |
| ATOM | 3437 | C6 | ADE | H | 2 | 31.167 | −37.686 | −38.387 | 1.00 | 25.71 H | C |
| ATOM | 3438 | N6 | ADE | H | 2 | 32.131 | −37.739 | −37.469 | 1.00 | 28.67 H | N |
| ATOM | 3439 | N1 | ADE | H | 2 | 30.426 | −38.793 | −38.610 | 1.00 | 25.67 H | N |
| ATOM | 3440 | C2 | ADE | H | 2 | 29.461 | −38.747 | −39.531 | 1.00 | 24.75 H | C |
| ATOM | 3441 | N3 | ADE | H | 2 | 29.102 | −37.723 | −40.302 | 1.00 | 26.66 H | N |
| ATOM | 3442 | C4 | ADE | H | 2 | 29.853 | −36.636 | −40.060 | 1.00 | 27.31 H | C |
| ATOM | 3443 | P | ADE | H | 3 | 25.537 | −32.924 | −43.269 | 1.00 | 37.68 H | P |
| ATOM | 3444 | OP1 | ADE | H | 3 | 25.052 | −32.573 | −44.625 | 1.00 | 39.11 H | O |
| ATOM | 3445 | OP2 | ADE | H | 3 | 25.908 | −31.868 | −42.298 | 1.00 | 36.68 H | O |
| ATOM | 3446 | O5' | ADE | H | 3 | 24.475 | −33.891 | −42.568 | 1.00 | 30.66 H | O |
| ATOM | 3447 | C5' | ADE | H | 3 | 24.342 | −35.214 | −43.063 | 1.00 | 30.61 H | C |
| ATOM | 3448 | C4' | ADE | H | 3 | 23.861 | −36.132 | −41.960 | 1.00 | 27.07 H | C |
| ATOM | 3449 | O4' | ADE | H | 3 | 24.945 | −36.425 | −41.041 | 1.00 | 27.15 H | O |
| ATOM | 3450 | C3' | ADE | H | 3 | 22.734 | −35.546 | −41.114 | 1.00 | 38.17 H | C |
| ATOM | 3451 | O3' | ADE | H | 3 | 21.727 | −36.533 | −40.943 | 1.00 | 35.18 H | O |
| ATOM | 3452 | C2' | ADE | H | 3 | 23.406 | −35.175 | −39.787 | 1.00 | 31.35 H | C |
| ATOM | 3453 | C1' | ADE | H | 3 | 24.503 | −36.233 | −39.709 | 1.00 | 34.45 H | C |
| ATOM | 3454 | N9 | ADE | H | 3 | 25.666 | −35.869 | −38.903 | 1.00 | 26.51 H | N |
| ATOM | 3455 | C8 | ADE | H | 3 | 26.333 | −34.673 | −38.872 | 1.00 | 28.15 H | C |
| ATOM | 3456 | N7 | ADE | H | 3 | 27.358 | −34.655 | −38.047 | 1.00 | 28.07 H | N |
| ATOM | 3457 | C5 | ADE | H | 3 | 27.364 | −35.933 | −37.502 | 1.00 | 27.87 H | C |
| ATOM | 3458 | C6 | ADE | H | 3 | 28.197 | −36.572 | −36.559 | 1.00 | 24.49 H | C |
| ATOM | 3459 | N6 | ADE | H | 3 | 29.238 | −35.984 | −35.964 | 1.00 | 28.81 H | N |
| ATOM | 3460 | N1 | ADE | H | 3 | 27.912 | −37.853 | −36.241 | 1.00 | 27.07 H | N |
| ATOM | 3461 | C2 | ADE | H | 3 | 26.869 | −38.458 | −36.826 | 1.00 | 26.59 H | C |
| ATOM | 3462 | N3 | ADE | H | 3 | 26.022 | −37.964 | −37.727 | 1.00 | 28.66 H | N |
| ATOM | 3463 | C4 | ADE | H | 3 | 26.325 | −36.690 | −38.022 | 1.00 | 28.33 H | C |
| ATOM | 3464 | P | GUA | H | 4 | 20.373 | −36.128 | −40.204 | 1.00 | 38.36 H | P |
| ATOM | 3465 | OP1 | GUA | H | 4 | 19.287 | −36.963 | −40.758 | 1.00 | 32.04 H | O |
| ATOM | 3466 | OP2 | GUA | H | 4 | 20.290 | −34.647 | −40.237 | 1.00 | 39.60 H | O |
| ATOM | 3467 | O5' | GUA | H | 4 | 20.659 | −36.603 | −38.696 | 1.00 | 40.06 H | O |
| ATOM | 3468 | C5' | GUA | H | 4 | 20.817 | −38.005 | −38.466 | 1.00 | 36.35 H | C |
| ATOM | 3469 | C4' | GUA | H | 4 | 21.469 | −38.332 | −37.131 | 1.00 | 39.32 H | C |
| ATOM | 3470 | O4' | GUA | H | 4 | 22.664 | −37.542 | −36.913 | 1.00 | 41.95 H | O |
| ATOM | 3471 | C3' | GUA | H | 4 | 20.607 | −38.121 | −35.888 | 1.00 | 50.29 H | C |
| ATOM | 3472 | O3' | GUA | H | 4 | 20.415 | −39.409 | −35.314 | 1.00 | 52.14 H | O |
| ATOM | 3473 | C2' | GUA | H | 4 | 21.433 | −37.180 | −35.000 | 1.00 | 39.71 H | C |
| ATOM | 3474 | C1' | GUA | H | 4 | 22.845 | −37.449 | −35.516 | 1.00 | 37.91 H | C |
| ATOM | 3475 | N9 | GUA | H | 4 | 23.873 | −36.430 | −35.285 | 1.00 | 34.32 H | N |
| ATOM | 3476 | C8 | GUA | H | 4 | 23.917 | −35.163 | −35.816 | 1.00 | 32.75 H | C |
| ATOM | 3477 | N7 | GUA | H | 4 | 24.967 | −34.480 | −35.455 | 1.00 | 32.33 H | N |
| ATOM | 3478 | C5 | GUA | H | 4 | 25.678 | −35.349 | −34.635 | 1.00 | 32.09 H | C |
| ATOM | 3479 | C6 | GUA | H | 4 | 26.908 | −35.161 | −33.949 | 1.00 | 29.46 H | C |
| ATOM | 3480 | O6 | GUA | H | 4 | 27.644 | −34.161 | −33.920 | 1.00 | 27.01 H | O |
| ATOM | 3481 | N1 | GUA | H | 4 | 27.269 | −36.298 | −33.234 | 1.00 | 30.36 H | N |
| ATOM | 3482 | C2 | GUA | H | 4 | 26.540 | −37.459 | −33.182 | 1.00 | 33.51 H | C |
| ATOM | 3483 | N2 | GUA | H | 4 | 27.060 | −38.439 | −32.431 | 1.00 | 38.20 H | N |
| ATOM | 3484 | N3 | GUA | H | 4 | 25.387 | −37.649 | −33.815 | 1.00 | 32.09 H | N |
| ATOM | 3485 | C4 | GUA | H | 4 | 25.018 | −36.555 | −34.524 | 1.00 | 33.22 H | C |
| ATOM | 3486 | P | CYT | H | 5 | 19.453 | −39.649 | −34.057 | 1.00 | 55.11 H | P |
| ATOM | 3487 | OP1 | CYT | H | 5 | 18.684 | −40.887 | −34.324 | 1.00 | 35.30 H | O |
| ATOM | 3488 | OP2 | CYT | H | 5 | 18.767 | −38.374 | −33.738 | 1.00 | 41.73 H | O |
| ATOM | 3489 | O5' | CYT | H | 5 | 20.505 | −39.951 | −32.890 | 1.00 | 44.98 H | O |
| ATOM | 3490 | C5' | CYT | H | 5 | 21.501 | −40.935 | −33.116 | 1.00 | 36.84 H | C |
| ATOM | 3491 | C4' | CYT | H | 5 | 22.377 | −41.096 | −31.890 | 1.00 | 34.69 H | C |
| ATOM | 3492 | O4' | CYT | H | 5 | 23.328 | −40.005 | −31.777 | 1.00 | 30.60 H | O |
| ATOM | 3493 | C3' | CYT | H | 5 | 21.623 | −41.133 | −30.569 | 1.00 | 32.70 H | C |
| ATOM | 3494 | O3' | CYT | H | 5 | 22.280 | −42.089 | −29.765 | 1.00 | 38.87 H | O |
| ATOM | 3495 | C2' | CYT | H | 5 | 21.779 | −39.706 | −30.040 | 1.00 | 29.93 H | C |
| ATOM | 3496 | C1' | CYT | H | 5 | 23.178 | −39.355 | −30.530 | 1.00 | 30.85 H | C |
| ATOM | 3497 | N1 | CYT | H | 5 | 23.446 | −37.923 | −30.818 | 1.00 | 32.57 H | N |
| ATOM | 3498 | C2 | CYT | H | 5 | 24.513 | −37.289 | −30.181 | 1.00 | 28.31 H | C |
| ATOM | 3499 | O2 | CYT | H | 5 | 25.194 | −37.930 | −29.371 | 1.00 | 30.53 H | O |
| ATOM | 3500 | N3 | CYT | H | 5 | 24.771 | −35.990 | −30.466 | 1.00 | 29.17 H | N |
| ATOM | 3501 | C4 | CYT | H | 5 | 24.015 | −35.331 | −31.345 | 1.00 | 28.71 H | C |
| ATOM | 3502 | N4 | CYT | H | 5 | 24.319 | −34.049 | −31.580 | 1.00 | 26.57 H | N |
| ATOM | 3503 | C5 | CYT | H | 5 | 22.920 | −35.958 | −32.012 | 1.00 | 26.39 H | C |
| ATOM | 3504 | C6 | CYT | H | 5 | 22.679 | −37.244 | −31.724 | 1.00 | 34.07 H | C |
| ATOM | 3505 | P | THY | H | 6 | 21.626 | −42.654 | −28.425 | 1.00 | 47.41 H | P |
| ATOM | 3506 | OP1 | THY | H | 6 | 22.066 | −44.059 | −28.267 | 1.00 | 51.76 H | O |
| ATOM | 3507 | OP2 | THY | H | 6 | 20.184 | −42.310 | −28.415 | 1.00 | 50.29 H | O |
| ATOM | 3508 | O5' | THY | H | 6 | 22.348 | −41.762 | −27.313 | 1.00 | 46.65 H | O |
| ATOM | 3509 | C5' | THY | H | 6 | 23.725 | −41.957 | −27.019 | 1.00 | 43.24 H | C |
| ATOM | 3510 | C4' | THY | H | 6 | 24.116 | −41.139 | −25.804 | 1.00 | 39.41 H | C |
| ATOM | 3511 | O4' | THY | H | 6 | 24.396 | −39.776 | −26.215 | 1.00 | 42.16 H | O |
| ATOM | 3512 | C3' | THY | H | 6 | 23.026 | −41.017 | −24.750 | 1.00 | 40.48 H | C |

TABLE 1-continued

| | | | | | | | | | | | |
|---|---|---|---|---|---|---|---|---|---|---|---|
| ATOM | 3513 | O3' | THY | H | 6 | 23.617 | −40.802 | −23.485 | 1.00 | 46.66 H | O |
| ATOM | 3514 | C2' | THY | H | 6 | 22.315 | −39.745 | −25.192 | 1.00 | 41.24 H | C |
| ATOM | 3515 | C1' | THY | H | 6 | 23.550 | −38.906 | −25.486 | 1.00 | 42.05 H | C |
| ATOM | 3516 | N1 | THY | H | 6 | 23.298 | −37.688 | −26.293 | 1.00 | 34.71 H | N |
| ATOM | 3517 | C2 | THY | H | 6 | 24.259 | −36.704 | −26.309 | 1.00 | 34.93 H | C |
| ATOM | 3518 | O2 | THY | H | 6 | 25.305 | −36.793 | −25.692 | 1.00 | 37.85 H | O |
| ATOM | 3519 | N3 | THY | H | 6 | 23.951 | −35.612 | −27.080 | 1.00 | 31.24 H | N |
| ATOM | 3520 | C4 | THY | H | 6 | 22.797 | −35.421 | −27.816 | 1.00 | 31.75 H | C |
| ATOM | 3521 | O4 | THY | H | 6 | 22.607 | −34.408 | −28.479 | 1.00 | 30.53 H | O |
| ATOM | 3522 | C5 | THY | H | 6 | 21.830 | −36.489 | −27.749 | 1.00 | 32.63 H | C |
| ATOM | 3523 | C7 | THY | H | 6 | 20.538 | −36.385 | −28.507 | 1.00 | 28.89 H | C |
| ATOM | 3524 | C6 | THY | H | 6 | 22.122 | −37.560 | −27.000 | 1.00 | 31.00 H | C |
| ATOM | 3525 | P | ADE | H | 7 | 23.900 | −42.022 | −22.497 | 1.00 | 44.28 H | P |
| ATOM | 3526 | OP1 | ADE | H | 7 | 24.428 | −43.144 | −23.303 | 1.00 | 40.56 H | O |
| ATOM | 3527 | OP2 | ADE | H | 7 | 22.691 | −42.211 | −21.665 | 1.00 | 44.27 H | O |
| ATOM | 3528 | O5' | ADE | H | 7 | 25.065 | −41.436 | −21.569 | 1.00 | 32.81 H | O |
| ATOM | 3529 | C5' | ADE | H | 7 | 26.365 | −41.293 | −22.115 | 1.00 | 32.80 H | C |
| ATOM | 3530 | C4' | ADE | H | 7 | 27.031 | −40.015 | −21.640 | 1.00 | 35.14 H | C |
| ATOM | 3531 | O4' | ADE | H | 7 | 26.448 | −38.855 | −22.294 | 1.00 | 37.44 H | O |
| ATOM | 3532 | C3' | ADE | H | 7 | 26.918 | −39.744 | −20.149 | 1.00 | 38.41 H | C |
| ATOM | 3533 | O3' | ADE | H | 7 | 28.144 | −39.153 | −19.715 | 1.00 | 38.15 H | O |
| ATOM | 3534 | C2' | ADE | H | 7 | 25.717 | −38.794 | −20.060 | 1.00 | 35.26 H | C |
| ATOM | 3535 | C1' | ADE | H | 7 | 25.863 | −37.980 | −21.345 | 1.00 | 37.50 H | C |
| ATOM | 3536 | N9 | ADE | H | 7 | 24.621 | −37.499 | −21.953 | 1.00 | 30.16 H | N |
| ATOM | 3537 | C8 | ADE | H | 7 | 23.424 | −38.156 | −22.049 | 1.00 | 32.36 H | C |
| ATOM | 3538 | N7 | ADE | H | 7 | 22.490 | −37.470 | −22.674 | 1.00 | 33.29 H | N |
| ATOM | 3539 | C5 | ADE | H | 7 | 23.119 | −36.283 | −23.023 | 1.00 | 27.61 H | C |
| ATOM | 3540 | C6 | ADE | H | 7 | 22.680 | −35.129 | −23.709 | 1.00 | 23.15 H | C |
| ATOM | 3541 | N6 | ADE | H | 7 | 21.441 | −34.976 | −24.190 | 1.00 | 21.35 H | N |
| ATOM | 3542 | N1 | ADE | H | 7 | 23.570 | −34.127 | −23.879 | 1.00 | 23.18 H | N |
| ATOM | 3543 | C2 | ADE | H | 7 | 24.810 | −34.274 | −23.404 | 1.00 | 24.54 H | C |
| ATOM | 3544 | N3 | ADE | H | 7 | 25.341 | −35.308 | −22.749 | 1.00 | 29.70 H | N |
| ATOM | 3545 | C4 | ADE | H | 7 | 24.435 | −36.289 | −22.588 | 1.00 | 31.92 H | C |
| ATOM | 3546 | P | ADE | H | 8 | 28.347 | −38.809 | −18.169 | 1.00 | 58.35 H | P |
| ATOM | 3547 | OP1 | ADE | H | 8 | 29.786 | −38.970 | −17.855 | 1.00 | 45.52 H | O |
| ATOM | 3548 | OP2 | ADE | H | 8 | 27.304 | −39.547 | −17.411 | 1.00 | 40.27 H | O |
| ATOM | 3549 | O5' | ADE | H | 8 | 27.993 | −37.253 | −18.109 | 1.00 | 41.83 H | O |
| ATOM | 3550 | C5' | ADE | H | 8 | 28.734 | −36.350 | −18.906 | 1.00 | 41.53 H | C |
| ATOM | 3551 | C4' | ADE | H | 8 | 28.065 | −34.991 | −18.913 | 1.00 | 43.43 H | C |
| ATOM | 3552 | O4' | ADE | H | 8 | 26.830 | −35.073 | −19.655 | 1.00 | 44.70 H | O |
| ATOM | 3553 | C3' | ADE | H | 8 | 27.682 | −34.434 | −17.544 | 1.00 | 38.12 H | C |
| ATOM | 3554 | O3' | ADE | H | 8 | 28.599 | −33.402 | −17.223 | 1.00 | 36.90 H | O |
| ATOM | 3555 | C2' | ADE | H | 8 | 26.262 | −33.896 | −17.724 | 1.00 | 35.36 H | C |
| ATOM | 3556 | C1' | ADE | H | 8 | 26.032 | −33.996 | −19.228 | 1.00 | 37.49 H | C |
| ATOM | 3557 | N9 | ADE | H | 8 | 24.652 | −34.286 | −19.603 | 1.00 | 36.04 H | N |
| ATOM | 3558 | C8 | ADE | H | 8 | 23.938 | −35.416 | −19.312 | 1.00 | 35.51 H | C |
| ATOM | 3559 | N7 | ADE | H | 8 | 22.715 | −35.408 | −19.784 | 1.00 | 34.40 H | N |
| ATOM | 3560 | C5 | ADE | H | 8 | 22.625 | −34.186 | −20.427 | 1.00 | 31.66 H | C |
| ATOM | 3561 | C6 | ADE | H | 8 | 21.576 | −33.572 | −21.130 | 1.00 | 36.96 H | C |
| ATOM | 3562 | N6 | ADE | H | 8 | 20.385 | −34.157 | −21.290 | 1.00 | 32.17 H | N |
| ATOM | 3563 | N1 | ADE | H | 8 | 21.802 | −32.347 | −21.657 | 1.00 | 34.88 H | N |
| ATOM | 3564 | C2 | ADE | H | 8 | 23.006 | −31.781 | −21.483 | 1.00 | 38.52 H | C |
| ATOM | 3565 | N3 | ADE | H | 8 | 24.074 | −32.262 | −20.837 | 1.00 | 32.76 H | N |
| ATOM | 3566 | C4 | ADE | H | 8 | 23.809 | −33.480 | −20.330 | 1.00 | 33.22 H | C |
| ATOM | 3567 | P | THY | H | 9 | 28.397 | −32.411 | −15.982 | 1.00 | 36.15 H | P |
| ATOM | 3568 | OP1 | THY | H | 9 | 29.753 | −32.044 | −15.512 | 1.00 | 28.93 H | O |
| ATOM | 3569 | OP2 | THY | H | 9 | 27.402 | −32.984 | −15.044 | 1.00 | 34.70 H | O |
| ATOM | 3570 | O5' | THY | H | 9 | 27.768 | −31.124 | −16.688 | 1.00 | 32.97 H | O |
| ATOM | 3571 | C5' | THY | H | 9 | 28.548 | −30.497 | −17.690 | 1.00 | 33.48 H | C |
| ATOM | 3572 | C4' | THY | H | 9 | 27.801 | −29.333 | −18.307 | 1.00 | 31.92 H | C |
| ATOM | 3573 | O4' | THY | H | 9 | 26.530 | −29.798 | −18.818 | 1.00 | 25.84 H | O |
| ATOM | 3574 | C3' | THY | H | 9 | 27.493 | −28.172 | −17.365 | 1.00 | 26.38 H | C |
| ATOM | 3575 | O3' | THY | H | 9 | 27.716 | −26.976 | −18.100 | 1.00 | 25.95 H | O |
| ATOM | 3576 | C2' | THY | H | 9 | 26.025 | −28.395 | −16.999 | 1.00 | 24.26 H | C |
| ATOM | 3577 | C1' | THY | H | 9 | 25.491 | −29.001 | −18.293 | 1.00 | 25.25 H | C |
| ATOM | 3578 | N1 | THY | H | 9 | 24.315 | −29.902 | −18.168 | 1.00 | 23.43 H | N |
| ATOM | 3579 | C2 | THY | H | 9 | 23.279 | −29.705 | −19.043 | 1.00 | 25.36 H | C |
| ATOM | 3580 | O2 | THY | H | 9 | 23.298 | −28.825 | −19.883 | 1.00 | 27.24 H | O |
| ATOM | 3581 | N3 | THY | H | 9 | 22.230 | −30.577 | −18.888 | 1.00 | 26.75 H | N |
| ATOM | 3582 | C4 | THY | H | 9 | 22.123 | −31.604 | −17.968 | 1.00 | 24.08 H | C |
| ATOM | 3583 | O4 | THY | H | 9 | 21.143 | −32.337 | −17.900 | 1.00 | 25.41 H | O |
| ATOM | 3584 | C5 | THY | H | 9 | 23.243 | −31.757 | −17.084 | 1.00 | 25.32 H | C |
| ATOM | 3585 | C7 | THY | H | 9 | 23.213 | −32.843 | −16.047 | 1.00 | 24.63 H | C |
| ATOM | 3586 | C6 | THY | H | 9 | 24.278 | −30.911 | −17.223 | 1.00 | 25.76 H | C |
| ATOM | 3587 | P | ADE | H | 10 | 27.345 | −25.528 | −17.528 | 1.00 | 25.05 H | P |
| ATOM | 3588 | OP1 | ADE | H | 10 | 28.142 | −24.542 | −18.294 | 1.00 | 24.87 H | O |
| ATOM | 3589 | OP2 | ADE | H | 10 | 27.446 | −25.572 | −16.053 | 1.00 | 32.93 H | O |
| ATOM | 3590 | O5' | ADE | H | 10 | 25.801 | −25.365 | −17.942 | 1.00 | 36.94 H | O |
| ATOM | 3591 | C5' | ADE | H | 10 | 25.438 | −25.334 | −19.320 | 1.00 | 27.06 H | C |
| ATOM | 3592 | C4' | ADE | H | 10 | 24.104 | −24.641 | −19.578 | 1.00 | 21.71 H | C |

TABLE 1-continued

| | | | | | | | | | | | |
|---|---|---|---|---|---|---|---|---|---|---|---|
| ATOM | 3593 | O4' | ADE | H | 10 | 22.992 | −25.552 | −19.403 | 1.00 | 23.14 H | O |
| ATOM | 3594 | C3' | ADE | H | 10 | 23.766 | −23.430 | −18.718 | 1.00 | 26.15 H | C |
| ATOM | 3595 | O3' | ADE | H | 10 | 23.199 | −22.479 | −19.609 | 1.00 | 22.80 H | O |
| ATOM | 3596 | C2' | ADE | H | 10 | 22.770 | −23.973 | −17.689 | 1.00 | 21.76 H | C |
| ATOM | 3597 | C1' | ADE | H | 10 | 22.042 | −25.053 | −18.482 | 1.00 | 22.72 H | C |
| ATOM | 3598 | N9 | ADE | H | 10 | 21.627 | −26.239 | −17.736 | 1.00 | 25.17 H | N |
| ATOM | 3599 | C8 | ADE | H | 10 | 22.386 | −26.936 | −16.836 | 1.00 | 21.36 H | C |
| ATOM | 3600 | N7 | ADE | H | 10 | 21.773 | −27.981 | −16.336 | 1.00 | 23.59 H | N |
| ATOM | 3601 | C5 | ADE | H | 10 | 20.529 | −27.975 | −16.953 | 1.00 | 20.38 H | C |
| ATOM | 3602 | C6 | ADE | H | 10 | 19.407 | −28.827 | −16.848 | 1.00 | 23.03 H | C |
| ATOM | 3603 | N6 | ADE | H | 10 | 19.372 | −29.896 | −16.046 | 1.00 | 23.54 H | N |
| ATOM | 3604 | N1 | ADE | H | 10 | 18.319 | −28.541 | −17.599 | 1.00 | 21.58 H | N |
| ATOM | 3605 | C2 | ADE | H | 10 | 18.362 | −27.467 | −18.396 | 1.00 | 22.37 H | C |
| ATOM | 3606 | N3 | ADE | H | 10 | 19.360 | −26.599 | −18.579 | 1.00 | 22.34 H | N |
| ATOM | 3607 | C4 | ADE | H | 10 | 20.426 | −26.909 | −17.824 | 1.00 | 19.27 H | C |
| ATOM | 3608 | P | ADE | H | 11 | 22.583 | −21.095 | −19.118 | 1.00 | 26.29 H | P |
| ATOM | 3609 | OP1 | ADE | H | 11 | 22.825 | −20.107 | −20.187 | 1.00 | 33.92 H | O |
| ATOM | 3610 | OP2 | ADE | H | 11 | 23.049 | −20.823 | −17.739 | 1.00 | 23.74 H | O |
| ATOM | 3611 | O5' | ADE | H | 11 | 21.019 | −21.433 | −19.082 | 1.00 | 30.07 H | O |
| ATOM | 3612 | C5' | ADE | H | 11 | 20.386 | −21.868 | −20.271 | 1.00 | 23.89 H | C |
| ATOM | 3613 | C4' | ADE | H | 11 | 18.893 | −22.085 | −20.087 | 1.00 | 26.01 H | C |
| ATOM | 3614 | O4' | ADE | H | 11 | 18.646 | −23.201 | −19.196 | 1.00 | 21.90 H | O |
| ATOM | 3615 | C3' | ADE | H | 11 | 18.092 | −20.920 | −19.519 | 1.00 | 27.43 H | C |
| ATOM | 3616 | O3' | ADE | H | 11 | 16.835 | −20.955 | −20.172 | 1.00 | 27.25 H | O |
| ATOM | 3617 | C2' | ADE | H | 11 | 17.979 | −21.286 | −18.042 | 1.00 | 22.72 H | C |
| ATOM | 3618 | C1' | ADE | H | 11 | 17.810 | −22.801 | −18.134 | 1.00 | 25.26 H | C |
| ATOM | 3619 | N9 | ADE | H | 11 | 18.307 | −23.581 | −17.012 | 1.00 | 25.82 H | N |
| ATOM | 3620 | C8 | ADE | H | 11 | 19.473 | −23.388 | −16.320 | 1.00 | 25.44 H | C |
| ATOM | 3621 | N7 | ADE | H | 11 | 19.678 | −24.271 | −15.368 | 1.00 | 26.30 H | N |
| ATOM | 3622 | C5 | ADE | H | 11 | 18.573 | −25.103 | −15.458 | 1.00 | 24.43 H | C |
| ATOM | 3623 | C6 | ADE | H | 11 | 18.193 | −26.240 | −14.727 | 1.00 | 27.00 H | C |
| ATOM | 3624 | N6 | ADE | H | 11 | 18.934 | −26.728 | −13.724 | 1.00 | 30.82 H | N |
| ATOM | 3625 | N1 | ADE | H | 11 | 17.027 | −26.842 | −15.058 | 1.00 | 26.79 H | N |
| ATOM | 3626 | C2 | ADE | H | 11 | 16.298 | −26.332 | −16.063 | 1.00 | 27.42 H | C |
| ATOM | 3627 | N3 | ADE | H | 11 | 16.557 | −25.265 | −16.826 | 1.00 | 24.29 H | N |
| ATOM | 3628 | C4 | ADE | H | 11 | 17.720 | −24.697 | −16.468 | 1.00 | 22.11 H | C |
| ATOM | 3629 | P | THY | H | 12 | 15.843 | −19.698 | −20.193 | 1.00 | 25.52 H | P |
| ATOM | 3630 | OP1 | THY | H | 12 | 15.307 | −19.601 | −21.571 | 1.00 | 25.80 H | O |
| ATOM | 3631 | OP2 | THY | H | 12 | 16.525 | −18.534 | −19.586 | 1.00 | 21.54 H | O |
| ATOM | 3632 | O5' | THY | H | 12 | 14.679 | −20.166 | −19.189 | 1.00 | 24.83 H | O |
| ATOM | 3633 | C5' | THY | H | 12 | 13.875 | −21.310 | −19.552 | 1.00 | 23.42 H | C |
| ATOM | 3634 | C4' | THY | H | 12 | 13.066 | −21.839 | −18.381 | 1.00 | 25.89 H | C |
| ATOM | 3635 | O4' | THY | H | 12 | 13.908 | −22.629 | −17.499 | 1.00 | 23.76 H | O |
| ATOM | 3636 | C3' | THY | H | 12 | 12.424 | −20.761 | −17.504 | 1.00 | 26.04 H | C |
| ATOM | 3637 | O3' | THY | H | 12 | 11.060 | −21.064 | −17.263 | 1.00 | 25.66 H | O |
| ATOM | 3638 | C2' | THY | H | 12 | 13.230 | −20.844 | −16.208 | 1.00 | 20.86 H | C |
| ATOM | 3639 | C1' | THY | H | 12 | 13.490 | −22.343 | −16.179 | 1.00 | 22.54 H | C |
| ATOM | 3640 | N1 | THY | H | 12 | 14.533 | −22.765 | −15.212 | 1.00 | 22.51 H | N |
| ATOM | 3641 | C2 | THY | H | 12 | 14.403 | −23.972 | −14.554 | 1.00 | 23.00 H | C |
| ATOM | 3642 | O2 | THY | H | 12 | 13.472 | −24.737 | −14.721 | 1.00 | 21.72 H | O |
| ATOM | 3643 | N3 | THY | H | 12 | 15.419 | −24.266 | −13.684 | 1.00 | 20.48 H | N |
| ATOM | 3644 | C4 | THY | H | 12 | 16.523 | −23.486 | −13.419 | 1.00 | 20.15 H | C |
| ATOM | 3645 | O4 | THY | H | 12 | 17.373 | −23.849 | −12.617 | 1.00 | 25.63 H | O |
| ATOM | 3646 | C5 | THY | H | 12 | 16.597 | −22.234 | −14.136 | 1.00 | 18.49 H | C |
| ATOM | 3647 | C7 | THY | H | 12 | 17.746 | −21.289 | −13.933 | 1.00 | 19.45 H | C |
| ATOM | 3648 | C6 | THY | H | 12 | 15.613 | −21.936 | −14.987 | 1.00 | 18.74 H | C |
| ATOM | 3649 | P | ADE | H | 13 | 9.921 | −20.818 | −18.362 | 1.00 | 34.68 H | P |
| ATOM | 3650 | OP1 | ADE | H | 13 | 10.331 | −21.523 | −19.601 | 1.00 | 29.00 H | O |
| ATOM | 3651 | OP2 | ADE | H | 13 | 9.602 | −19.371 | −18.385 | 1.00 | 23.43 H | O |
| ATOM | 3652 | O5' | ADE | H | 13 | 8.680 | −21.612 | −17.735 | 1.00 | 31.48 H | O |
| ATOM | 3653 | C5' | ADE | H | 13 | 8.703 | −23.042 | −17.751 | 1.00 | 29.17 H | C |
| ATOM | 3654 | C4' | ADE | H | 13 | 7.813 | −23.633 | −16.668 | 1.00 | 34.37 H | C |
| ATOM | 3655 | O4' | ADE | H | 13 | 8.562 | −23.903 | −15.452 | 1.00 | 29.36 H | O |
| ATOM | 3656 | C3' | ADE | H | 13 | 6.624 | −22.779 | −16.250 | 1.00 | 24.78 H | C |
| ATOM | 3657 | O3' | ADE | H | 13 | 5.562 | −23.684 | −15.966 | 1.00 | 27.24 H | O |
| ATOM | 3658 | C2' | ADE | H | 13 | 7.157 | −22.038 | −15.022 | 1.00 | 23.76 H | C |
| ATOM | 3659 | C1' | ADE | H | 13 | 8.208 | −22.983 | −14.437 | 1.00 | 26.59 H | C |
| ATOM | 3660 | N9 | ADE | H | 13 | 9.444 | −22.331 | −14.012 | 1.00 | 23.20 H | N |
| ATOM | 3661 | C8 | ADE | H | 13 | 9.886 | −21.086 | −14.361 | 1.00 | 19.68 H | C |
| ATOM | 3662 | N7 | ADE | H | 13 | 11.043 | −20.769 | −13.826 | 1.00 | 21.48 H | N |
| ATOM | 3663 | C5 | ADE | H | 13 | 11.394 | −21.887 | −13.084 | 1.00 | 20.04 H | C |
| ATOM | 3664 | C6 | ADE | H | 13 | 12.518 | −22.191 | −12.283 | 1.00 | 20.93 H | C |
| ATOM | 3665 | N6 | ADE | H | 13 | 13.542 | −21.349 | −12.085 | 1.00 | 17.98 H | N |
| ATOM | 3666 | N1 | ADE | H | 13 | 12.548 | −23.401 | −11.684 | 1.00 | 21.14 H | N |
| ATOM | 3667 | C2 | ADE | H | 13 | 11.525 | −24.241 | −11.878 | 1.00 | 21.71 H | C |
| ATOM | 3668 | N3 | ADE | H | 13 | 10.422 | −24.069 | −12.608 | 1.00 | 21.94 H | N |
| ATOM | 3669 | C4 | ADE | H | 13 | 10.417 | −22.860 | −13.191 | 1.00 | 21.50 H | C |
| ATOM | 3670 | P | GUA | H | 14 | 4.132 | −23.212 | −15.419 | 1.00 | 31.73 H | P |
| ATOM | 3671 | OP1 | GUA | H | 14 | 3.121 | −24.184 | −15.895 | 1.00 | 30.37 H | O |
| ATOM | 3672 | OP2 | GUA | H | 14 | 3.978 | −21.769 | −15.712 | 1.00 | 29.29 H | O |

TABLE 1-continued

| | | | | | | | | | | |
|---|---|---|---|---|---|---|---|---|---|---|
| ATOM | 3673 | O5' | GUA | H | 14 | 4.287 | −23.434 | −13.842 | 1.00 | 22.88 H | O |
| ATOM | 3674 | C5' | GUA | H | 14 | 4.449 | −24.775 | −13.402 | 1.00 | 30.01 H | C |
| ATOM | 3675 | C4' | GUA | H | 14 | 4.825 | −24.840 | −11.937 | 1.00 | 36.42 H | C |
| ATOM | 3676 | O4' | GUA | H | 14 | 6.132 | −24.244 | −11.745 | 1.00 | 33.71 H | O |
| ATOM | 3677 | C3' | GUA | H | 14 | 3.857 | −24.124 | −11.000 | 1.00 | 42.57 H | C |
| ATOM | 3678 | O3' | GUA | H | 14 | 3.409 | −25.076 | −10.033 | 1.00 | 51.87 H | O |
| ATOM | 3679 | C2' | GUA | H | 14 | 4.680 | −22.978 | −10.410 | 1.00 | 36.34 H | C |
| ATOM | 3680 | C1' | GUA | H | 14 | 6.119 | −23.462 | −10.575 | 1.00 | 30.10 H | C |
| ATOM | 3681 | N9 | GUA | H | 14 | 7.096 | −22.389 | −10.734 | 1.00 | 29.80 H | N |
| ATOM | 3682 | C8 | GUA | H | 14 | 6.985 | −21.257 | −11.508 | 1.00 | 28.65 H | C |
| ATOM | 3683 | N7 | GUA | H | 14 | 8.033 | −20.476 | −11.442 | 1.00 | 26.36 H | N |
| ATOM | 3684 | C5 | GUA | H | 14 | 8.890 | −21.137 | −10.574 | 1.00 | 23.38 H | C |
| ATOM | 3685 | C6 | GUA | H | 14 | 10.174 | −20.779 | −10.118 | 1.00 | 25.14 H | C |
| ATOM | 3686 | O6 | GUA | H | 14 | 10.832 | −19.768 | −10.404 | 1.00 | 27.81 H | O |
| ATOM | 3687 | N1 | GUA | H | 14 | 10.694 | −21.728 | −9.239 | 1.00 | 24.30 H | N |
| ATOM | 3688 | C2 | GUA | H | 14 | 10.052 | −22.880 | −8.854 | 1.00 | 28.25 H | C |
| ATOM | 3689 | N2 | GUA | H | 14 | 10.706 | −23.682 | −8.003 | 1.00 | 28.77 H | N |
| ATOM | 3690 | N3 | GUA | H | 14 | 8.849 | −23.227 | −9.279 | 1.00 | 31.04 H | N |
| ATOM | 3691 | C4 | GUA | H | 14 | 8.330 | −22.312 | −10.131 | 1.00 | 29.88 H | C |
| ATOM | 3692 | P | CYT | H | 15 | 2.723 | −24.657 | −8.650 | 1.00 | 56.18 H | P |
| ATOM | 3693 | OP1 | CYT | H | 15 | 1.801 | −25.752 | −8.276 | 1.00 | 65.42 H | O |
| ATOM | 3694 | OP2 | CYT | H | 15 | 2.225 | −23.265 | −8.747 | 1.00 | 43.75 H | O |
| ATOM | 3695 | O5' | CYT | H | 15 | 3.957 | −24.676 | −7.638 | 1.00 | 59.78 H | O |
| ATOM | 3696 | C5' | CYT | H | 15 | 4.712 | −25.868 | −7.488 | 1.00 | 59.36 H | C |
| ATOM | 3697 | C4' | CYT | H | 15 | 5.779 | −25.661 | −6.431 | 1.00 | 62.35 H | C |
| ATOM | 3698 | O4' | CYT | H | 15 | 6.708 | −24.634 | −6.865 | 1.00 | 55.00 H | O |
| ATOM | 3699 | C3' | CYT | H | 15 | 5.233 | −25.203 | −5.085 | 1.00 | 62.43 H | C |
| ATOM | 3700 | O3' | CYT | H | 15 | 5.961 | −25.845 | −4.045 | 1.00 | 67.79 H | O |
| ATOM | 3701 | C2' | CYT | H | 15 | 5.457 | −23.692 | −5.113 | 1.00 | 53.40 H | C |
| ATOM | 3702 | C1' | CYT | H | 15 | 6.753 | −23.591 | −5.910 | 1.00 | 48.72 H | C |
| ATOM | 3703 | N1 | CYT | H | 15 | 6.917 | −22.294 | −6.633 | 1.00 | 40.77 H | N |
| ATOM | 3704 | C2 | CYT | H | 15 | 8.077 | −21.547 | −6.422 | 1.00 | 37.46 H | C |
| ATOM | 3705 | O2 | CYT | H | 15 | 8.931 | −21.987 | −5.643 | 1.00 | 37.14 H | O |
| ATOM | 3706 | N3 | CYT | H | 15 | 8.232 | −20.370 | −7.075 | 1.00 | 31.15 H | N |
| ATOM | 3707 | C4 | CYT | H | 15 | 7.280 | −19.941 | −7.906 | 1.00 | 35.33 H | C |
| ATOM | 3708 | N4 | CYT | H | 15 | 7.478 | −18.772 | −8.528 | 1.00 | 30.93 H | N |
| ATOM | 3709 | C5 | CYT | H | 15 | 6.084 | −20.690 | −8.137 | 1.00 | 34.65 H | C |
| ATOM | 3710 | C6 | CYT | H | 15 | 5.946 | −21.850 | −7.485 | 1.00 | 36.08 H | C |
| ATOM | 3711 | P | THY | H | 16 | 5.394 | −25.882 | −2.548 | 1.00 | 79.66 H | P |
| ATOM | 3712 | OP1 | THY | H | 16 | 5.429 | −27.295 | −2.109 | 1.00 | 68.24 H | O |
| ATOM | 3713 | OP2 | THY | H | 16 | 4.135 | −25.097 | −2.487 | 1.00 | 58.67 H | O |
| ATOM | 3714 | O5' | THY | H | 16 | 6.493 | −25.054 | −1.734 | 1.00 | 73.70 H | O |
| ATOM | 3715 | C5' | THY | H | 16 | 7.875 | −25.332 | −1.897 | 1.00 | 64.00 H | C |
| ATOM | 3716 | C4' | THY | H | 16 | 8.688 | −24.210 | −1.280 | 1.00 | 60.98 H | C |
| ATOM | 3717 | O4' | THY | H | 16 | 8.737 | −23.062 | −2.166 | 1.00 | 55.58 H | O |
| ATOM | 3718 | C3' | THY | H | 16 | 8.136 | −23.697 | 0.047 | 1.00 | 64.34 H | C |
| ATOM | 3719 | O3' | THY | H | 16 | 9.212 | −23.604 | 0.971 | 1.00 | 64.61 H | O |
| ATOM | 3720 | C2' | THY | H | 16 | 7.538 | −22.334 | −0.308 | 1.00 | 58.02 H | C |
| ATOM | 3721 | C1' | THY | H | 16 | 8.491 | −21.892 | −1.412 | 1.00 | 48.05 H | C |
| ATOM | 3722 | N1 | THY | H | 16 | 7.964 | −20.856 | −2.347 | 1.00 | 44.06 H | N |
| ATOM | 3723 | C2 | THY | H | 16 | 8.769 | −19.783 | −2.664 | 1.00 | 41.43 H | C |
| ATOM | 3724 | O2 | THY | H | 16 | 9.893 | −19.629 | −2.209 | 1.00 | 36.22 H | O |
| ATOM | 3725 | N3 | THY | H | 16 | 8.205 | −18.887 | −3.539 | 1.00 | 36.83 H | N |
| ATOM | 3726 | C4 | THY | H | 16 | 6.950 | −18.959 | −4.114 | 1.00 | 37.73 H | C |
| ATOM | 3727 | O4 | THY | H | 16 | 6.531 | −18.106 | −4.890 | 1.00 | 38.17 H | O |
| ATOM | 3728 | C5 | THY | H | 16 | 6.164 | −20.105 | −3.738 | 1.00 | 39.00 H | C |
| ATOM | 3729 | C7 | THY | H | 16 | 4.787 | −20.274 | −4.306 | 1.00 | 36.71 H | C |
| ATOM | 3730 | C6 | THY | H | 16 | 6.700 | −20.990 | −2.886 | 1.00 | 42.86 H | C |
| ATOM | 3731 | P | THY | H | 17 | 8.919 | −23.580 | 2.540 | 1.00 | 80.14 H | P |
| ATOM | 3732 | OP1 | THY | H | 17 | 9.864 | −24.510 | 3.199 | 1.00 | 54.65 H | O |
| ATOM | 3733 | OP2 | THY | H | 17 | 7.458 | −23.738 | 2.723 | 1.00 | 73.46 H | O |
| ATOM | 3734 | O5' | THY | H | 17 | 9.297 | −22.079 | 2.943 | 1.00 | 75.28 H | O |
| ATOM | 3735 | C5' | THY | H | 17 | 10.651 | −21.640 | 2.934 | 1.00 | 69.65 H | C |
| ATOM | 3736 | C4' | THY | H | 17 | 10.703 | −20.132 | 3.111 | 1.00 | 70.06 H | C |
| ATOM | 3737 | O4' | THY | H | 17 | 10.081 | −19.502 | 1.961 | 1.00 | 61.48 H | O |
| ATOM | 3738 | C3' | THY | H | 17 | 9.974 | −19.599 | 4.346 | 1.00 | 63.21 H | C |
| ATOM | 3739 | O3' | THY | H | 17 | 10.758 | −18.600 | 4.997 | 1.00 | 62.30 H | O |
| ATOM | 3740 | C2' | THY | H | 17 | 8.674 | −19.028 | 3.783 | 1.00 | 62.44 H | C |
| ATOM | 3741 | C1' | THY | H | 17 | 9.119 | −18.566 | 2.400 | 1.00 | 65.67 H | C |
| ATOM | 3742 | N1 | THY | H | 17 | 8.020 | −18.547 | 1.409 | 1.00 | 62.67 H | N |
| ATOM | 3743 | C2 | THY | H | 17 | 8.090 | −17.678 | 0.342 | 1.00 | 57.28 H | C |
| ATOM | 3744 | O2 | THY | H | 17 | 9.023 | −16.913 | 0.165 | 1.00 | 46.63 H | O |
| ATOM | 3745 | N3 | THY | H | 17 | 7.019 | −17.741 | −0.515 | 1.00 | 45.14 H | N |
| ATOM | 3746 | C4 | THY | H | 17 | 5.915 | −18.568 | −0.407 | 1.00 | 46.53 H | C |
| ATOM | 3747 | O4 | THY | H | 17 | 5.002 | −18.549 | −1.227 | 1.00 | 52.84 H | O |
| ATOM | 3748 | C5 | THY | H | 17 | 5.910 | −19.451 | 0.738 | 1.00 | 55.61 H | C |
| ATOM | 3749 | C7 | THY | H | 17 | 4.766 | −20.397 | 0.969 | 1.00 | 59.50 H | C |
| ATOM | 3750 | C6 | THY | H | 17 | 6.950 | −19.398 | 1.581 | 1.00 | 61.26 H | C |
| ATOM | 1 | C1 | BML | | 100 | 1.351 | −22.636 | 17.329 | 1.00 | 20.00 | C |
| ATOM | 2 | N1 | BML | | 100 | −2.345 | −22.477 | 17.385 | 1.00 | 20.00 | N |

TABLE 1-continued

| | | | | | | | | | |
|---|---|---|---|---|---|---|---|---|---|
| ATOM | 3 | O1 | BML | 100 | -2.760 | -23.946 | 19.172 | 1.00 | 20.00 | O |
| ATOM | 4 | C10 | BML | 100 | -4.869 | -20.497 | 19.319 | 1.00 | 20.00 | C |
| ATOM | 5 | C11 | BML | 100 | -5.507 | -19.741 | 20.482 | 1.00 | 20.00 | C |
| ATOM | 6 | C12 | BML | 100 | -5.137 | -18.259 | 20.457 | 1.00 | 20.00 | C |
| ATOM | 7 | C13 | BML | 100 | -5.895 | -17.473 | 21.526 | 1.00 | 20.00 | C |
| ATOM | 8 | C14 | BML | 100 | -5.909 | -15.978 | 21.264 | 1.00 | 20.00 | C |
| ATOM | 9 | C15 | BML | 100 | -7.826 | -14.603 | 22.201 | 1.00 | 20.00 | C |
| ATOM | 10 | C16 | BML | 100 | -7.966 | -13.378 | 21.524 | 1.00 | 20.00 | C |
| ATOM | 11 | C17 | BML | 100 | -9.198 | -12.742 | 21.447 | 1.00 | 20.00 | C |
| ATOM | 12 | C18 | BML | 100 | -10.316 | -13.314 | 22.038 | 1.00 | 20.00 | C |
| ATOM | 13 | C19 | BML | 100 | -10.196 | -14.520 | 22.715 | 1.00 | 20.00 | C |
| ATOM | 14 | C2 | BML | 100 | 1.603 | -23.425 | 16.212 | 1.00 | 20.00 | C |
| ATOM | 15 | O2 | BML | 100 | -5.383 | -15.494 | 20.271 | 1.00 | 20.00 | O |
| ATOM | 16 | N2 | BML | 100 | -6.582 | -15.302 | 22.279 | 1.00 | 20.00 | N |
| ATOM | 17 | C20 | BML | 100 | -8.959 | -15.167 | 22.831 | 1.00 | 20.00 | C |
| ATOM | 18 | C3 | BML | 100 | 0.544 | -23.917 | 15.459 | 1.00 | 20.00 | C |
| ATOM | 19 | N3 | BML | 100 | -8.917 | -16.414 | 23.490 | 1.00 | 20.00 | N |
| ATOM | 20 | C4 | BML | 100 | -0.770 | -23.623 | 15.816 | 1.00 | 20.00 | C |
| ATOM | 21 | C5 | BML | 100 | -1.039 | -22.828 | 16.942 | 1.00 | 20.00 | C |
| ATOM | 22 | C6 | BML | 100 | 0.039 | -22.340 | 17.692 | 1.00 | 20.00 | C |
| ATOM | 23 | C7 | BML | 100 | -3.131 | -23.145 | 18.322 | 1.00 | 20.00 | C |
| ATOM | 24 | C8 | BML | 100 | -4.596 | -22.775 | 18.212 | 1.00 | 20.00 | C |
| ATOM | 25 | C9 | BML | 100 | -5.105 | -22.006 | 19.432 | 1.00 | 20.00 | C |
| ATOM | 1 | C1 | BML | 200 | 22.035 | 3.898 | -37.176 | 1.00 | 20.00 | C |
| ATOM | 2 | N1 | BML | 200 | 19.679 | 2.774 | -39.797 | 1.00 | 20.00 | N |
| ATOM | 3 | O1 | BML | 200 | 17.888 | 2.589 | -38.298 | 1.00 | 20.00 | O |
| ATOM | 4 | C10 | BML | 200 | 16.884 | 0.264 | -42.287 | 1.00 | 20.00 | C |
| ATOM | 5 | C11 | BML | 200 | 16.812 | -1.252 | -42.480 | 1.00 | 20.00 | C |
| ATOM | 6 | C12 | BML | 200 | 15.887 | -1.617 | -43.642 | 1.00 | 20.00 | C |
| ATOM | 7 | C13 | BML | 200 | 15.592 | -3.118 | -43.719 | 1.00 | 20.00 | C |
| ATOM | 8 | C14 | BML | 200 | 14.527 | -3.479 | -44.739 | 1.00 | 20.00 | C |
| ATOM | 9 | C15 | BML | 200 | 13.205 | -5.621 | -44.418 | 1.00 | 20.00 | C |
| ATOM | 10 | C16 | BML | 200 | 12.291 | -6.196 | -45.320 | 1.00 | 20.00 | C |
| ATOM | 11 | C17 | BML | 200 | 11.237 | -6.979 | -44.865 | 1.00 | 20.00 | C |
| ATOM | 12 | C18 | BML | 200 | 11.075 | -7.203 | -43.507 | 1.00 | 20.00 | C |
| ATOM | 13 | C19 | BML | 200 | 11.958 | -6.631 | -42.603 | 1.00 | 20.00 | C |
| ATOM | 14 | C2 | BML | 200 | 23.026 | 2.924 | -37.221 | 1.00 | 20.00 | C |
| ATOM | 15 | O2 | BML | 200 | 13.953 | -2.593 | -45.361 | 1.00 | 20.00 | O |
| ATOM | 16 | N2 | BML | 200 | 14.331 | -4.854 | -44.847 | 1.00 | 20.00 | N |
| ATOM | 17 | C20 | BML | 200 | 13.008 | -5.810 | -43.032 | 1.00 | 20.00 | C |
| ATOM | 18 | C3 | BML | 200 | 22.921 | 1.873 | -38.124 | 1.00 | 20.00 | C |
| ATOM | 19 | N3 | BML | 200 | 13.896 | -5.297 | -42.064 | 1.00 | 20.00 | N |
| ATOM | 20 | C4 | BML | 200 | 21.833 | 1.792 | -38.990 | 1.00 | 20.00 | C |
| ATOM | 21 | C5 | BML | 200 | 20.828 | 2.772 | -38.956 | 1.00 | 20.00 | C |
| ATOM | 22 | C6 | BML | 200 | 20.940 | 3.819 | -38.033 | 1.00 | 20.00 | C |
| ATOM | 23 | C7 | BML | 200 | 18.359 | 2.534 | -39.426 | 1.00 | 20.00 | C |
| ATOM | 24 | C8 | BML | 200 | 17.500 | 2.146 | -40.618 | 1.00 | 20.00 | C |
| ATOM | 25 | C9 | BML | 200 | 17.731 | 0.706 | -41.088 | 1.00 | 20.00 | C |
| END | | | | | | | | | | |

REFERENCES

All publications cited herein are incorporated by reference in their entirety.

Bennett, C. L., Christie, J., Ramsdell, F., Brunkow, M. E., Ferguson, P. J., Whitesell, L., Kelly, T. E., Saulsbury, F. T., Chance, P. F., and Ochs, H. D. (2001). The immune dysregulation, polyendocrinopathy, enteropathy, X-linked syndrome (IPEX) is caused by mutations of FOXP3. Nature genetics 27, 20-21.

Chan, J. K., Sun, L., Yang, X. J., Zhu, G., and Wu, Z. (2003). Functional characterization of an amino-terminal region of HDAC4 that possesses MEF2 binding and transcriptional repressive activity. The Journal of biological chemistry 278, 23515-23521.

Chen, B., and Cepko, C. L. (2009). HDAC4 regulates neuronal survival in normal and diseased retinas. Science (New York, N.Y. 323, 256-259.

Chou, C. J., Herman, D., and Gottesfeld, J. M. (2008). Pimelic diphenylamide 106 is a slow, tight-binding inhibitor of class I histone deacetylases. The Journal of biological chemistry 283, 35402-35409.

de Ruijter, A. J., van Gennip, A. H., Caron, H. N., Kemp, S., and van Kuilenburg, A. B. (2003). Histone deacetylases (HDACs): characterization of the classical HDAC family. The Biochemical journal 370, 737-749.

Fischer, A., Sananbenesi, F., Wang, X., Dobbin, M., and Tsai, L. H. (2007). Recovery of learning and memory is associated with chromatin remodelling. Nature 447, 178-182.

Flavell, S. W., Cowan, C. W., Kim, T. K., Greer, P. L., Lin, Y., Paradis, S., Griffith, E. C., Hu, L. S., Chen, C., and Greenberg, M. E. (2006). Activity-dependent regulation of MEF2 transcription factors suppresses excitatory synapse number. Science (New York, N.Y. 311, 1008-1012.

Flavell, S. W., and Greenberg, M. E. (2008). Signaling mechanisms linking neuronal activity to gene expression and plasticity of the nervous system. Annual review of neuroscience 31, 563-590.

Flavell, S. W., Kim, T. K., Gray, J. M., Harmin, D. A., Hemberg, M., Hong, E. J., Markenscoff-Papadimitriou, E., Bear, D. M., and Greenberg, M. E. (2008). Genome-wide analysis of MEF2 transcriptional program reveals synaptic target genes and neuronal activity-dependent polyadenylation site selection. Neuron 60, 1022-1038.

Fontenot, J. D., Gavin, M. A., and Rudensky, A. Y. (2003). Foxp3 programs the development and function of CD4+ CD25+ regulatory T cells. Nature immunology 4, 330-336.

Gregoire, S., Tremblay, A. M., Xiao, L., Yang, Q., Ma, K., Nie, J., Mao, Z., Wu, Z., Giguere, V., and Yang, X. J. (2006). Control of MEF2 transcriptional activity by coordinated phosphorylation and sumoylation. The Journal of biological chemistry 281, 4423-4433.

Gregoire, S., and Yang, X. J. (2005). Association with class IIa histone deacetylases upregulates the sumoylation of MEF2 transcription factors. Molecular and cellular biology 25, 2273-2287.

Guo, L., Han, A., Bates, D. L., Cao, J., and Chen, L. (2007). Crystal structure of a conserved N-terminal domain of histone deacetylase 4 reveals functional insights into glutamine-rich domains. Proceedings of the National Academy of Sciences of the United States of America 104, 4297-4302.

Han, A., He, J., Wu, Y., Liu, J. O., and Chen, L. (2005). Mechanism of recruitment of class II histone deacetylases by myocyte enhancer factor-2. Journal of molecular biology 345, 91-102.

Han, A., Pan, F., Stroud, J. C., Youn, H. D., Liu, J. O., and Chen, L. (2003). Sequence-specific recruitment of transcriptional co-repressor Cabin1 by myocyte enhancer factor-2. Nature 422, 730-734.

Herman, D., Jenssen, K., Burnett, R., Soragni, E., Perlman, S. L., and Gottesfeld, J. M. (2006). Histone deacetylase inhibitors reverse gene silencing in Friedreich's ataxia. Nature chemical biology 2, 551-558.

Hori, S., Nomura, T., and Sakaguchi, S. (2003). Control of regulatory T cell development by the transcription factor Foxp3. Science (New York, N.Y. 299, 1057-1061.

Kim, Y., Phan, D., van Rooij, E., Wang, D. Z., McAnally, J., Qi, X., Richardson, J. A., Hill, J. A., Bassel-Duby, R., and Olson, E. N. (2008). The MEF2D transcription factor mediates stress-dependent cardiac remodeling in mice. J Clin Invest 118, 124-132.

Li, B., Samanta, A., Song, X., Iacono, K. T., Brennan, P., Chatila, T. A., Roncador, G., Banham, A. H., Riley, J. L., Wang, Q., et al. (2007). FOXP3 is a homo-oligomer and a component of a supramolecular regulatory complex disabled in the human XLAAD/IPEX autoimmune disease. International immunology 19, 825-835.

Mao, Z., Bonni, A., Xia, F., Nadal-Vicens, M., and Greenberg, M. E. (1999). Neuronal activity-dependent cell survival mediated by transcription factor MEF2. Science (New York, N.Y. 286, 785-790.

McKinsey, T. A., Zhang, C. L., and Olson, E. N. (2001). Control of muscle development by dueling HATs and HDACs. Current opinion in genetics & development 11, 497-504.

McKinsey, T. A., Zhang, C. L., and Olson, E. N. (2002). MEF2: a calcium-dependent regulator of cell division, differentiation and death. Trends Biochem Sci 27, 40-47.

Miska, E. A., Karlsson, C., Langley, E., Nielsen, S. J., Pines, J., and Kouzarides, T. (1999). HDAC4 deacetylase associates with and represses the MEF2 transcription factor. The EMBO journal 18, 5099-5107.

Molkentin, J. D., and Olson, E. N. (1996). Combinatorial control of muscle development by basic helix-loop-helix and MADS-box transcription factors. Proceedings of the National Academy of Sciences of the United States of America 93, 9366-9373.

Morrison, B. E., Majdzadeh, N., and D'Mello, S. R. (2007). Histone deacetylases: focus on the nervous system. Cell Mol Life Sci 64, 2258-2269.

Morrow, E. M., Yoo, S. Y., Flavell, S. W., Kim, T. K., Lin, Y., Hill, R. S., Mukaddes, N. M., Balkhy, S., Gascon, G., Hashmi, A., et al. (2008). Identifying autism loci and genes by tracing recent shared ancestry. Science (New York, N.Y. 321, 218-223.

Pan, F., Ye, Z., Cheng, L., and Liu, J. O. (2004). Myocyte enhancer factor 2 mediates calcium-dependent transcription of the interleukin-2 gene in T lymphocytes: a calcium signaling module that is distinct from but collaborates with the nuclear factor of activated T cells (NFAT). The Journal of biological chemistry 279, 14477-14480.

Paris, M., Porcelloni, M., Binaschi, M., and Fattori, D. (2008). Histone deacetylase inhibitors: from bench to clinic. Journal of medicinal chemistry 51, 1505-1529.

Potthoff, M. J., and Olson, E. N. (2007). MEF2: a central regulator of diverse developmental programs. Development (Cambridge, England) 134, 4131-4140.

Rai, M., Soragni, E., Jenssen, K., Burnett, R., Herman, D., Coppola, G., Geschwind, D. H., Gottesfeld, J. M., and Pandolfo, M. (2008). HDAC inhibitors correct frataxin deficiency in a Friedreich ataxia mouse model. PloS one 3, e1958.

Santelli, E., and Richmond, T. J. (2000). Crystal structure of MEF2A core bound to DNA at 1.5 A resolution. Journal of molecular biology 297, 437-449.

Sartorelli, V., Huang, J., Hamamori, Y., and Kedes, L. (1997). Molecular mechanisms of myogenic coactivation by p300: direct interaction with the activation domain of MyoD and with the MADS box of MEF2C. Molecular and cellular biology 17, 1010-1026.

Shalizi, A., Gaudilliere, B., Yuan, Z., Stegmuller, J., Shirogane, T., Ge, Q., Tan, Y., Schulman, B., Harper, J. W., and Bonni, A. (2006). A calcium-regulated MEF2 sumoylation switch controls postsynaptic differentiation. Science (New York, N.Y. 311, 1012-1017.

Shalizi, A. K., and Bonni, A. (2005). Brawn for Brains: The Role of MEF2 Proteins in the Developing Nervous System. Current topics in developmental biology 69, 239-266.

Shore, P., and Sharrocks, A. D. (1995). The MADS-box family of transcription factors. Eur J Biochem 229, 1-13.

Slepak, T. I., Webster, K. A., Zang, J., Prentice, H., O'Dowd, A., Hicks, M. N., and Bishopric, N. H. (2001). Control of cardiac-specific transcription by p300 through myocyte enhancer factor-2D. The Journal of biological chemistry 276, 7575-7585.

Somoza, J. R., Skene, R. J., Katz, B. A., Mol, C., Ho, J. D., Jennings, A. J., Luang, C., Arvai, A., Buggy, J. J., Chi, E., et al. (2004). Structural snapshots of human HDAC8 provide insights into the class I histone deacetylases. Structure 12, 1325-1334.

Sparrow, D. B., Miska, E. A., Langley, E., Reynaud-Deonauth, S., Kotecha, S., Towers, N., Spohr, G., Kouzarides, T., and Mohun, T. J. (1999). MEF-2 function is modified by a novel co-repressor, MITR. The EMBO journal 18, 5085-5098.

Stefanko, D. P., Barrett, R. M., Ly, A. R., Reolon, G. K., and Wood, M. A. (2009). Modulation of long-term memory for object recognition via HDAC inhibition. Proceedings of the National Academy of Sciences of the United States of America 106, 9447-9452.

Thomas, E. A., Coppola, G., Desplats, P. A., Tang, B., Soragni, E., Burnett, R., Gao, F., Fitzgerald, K. M., Borok, J. F., Herman, D., et al. (2008). The HDAC inhibitor 4b ameliorates the disease phenotype and transcriptional abnormalities in Huntington's disease transgenic mice. Proceedings of the National Academy of Sciences of the United States of America 105, 15564-15569.

Wang, L., Fan, C., Topol, S. E., Topol, E. J., and Wang, Q. (2003). Mutation of MEF2A in an inherited disorder with features of coronary artery disease. Science (New York, N.Y. 302, 1578-1581.

Wei, J. Q., Shehadeh, L. A., Mitrani, J. M., Pessanha, M., Slepak, T. I., Webster, K. A., and Bishopric, N. H. (2008). Quantitative control of adaptive cardiac hypertrophy by acetyltransferase p300. Circulation 118, 934-946.

Wong, J. C., Hong, R., and Schreiber, S. L. (2003). Structural biasing elements for in-cell histone deacetylase paralog selectivity. Journal of the American Chemical Society 125, 5586-5587.

Wu, Y., Borde, M., Heissmeyer, V., Feuerer, M., Lapan, A. D., Stroud, J. C., Bates, D. L., Guo, L., Han, A., Ziegler, S. F., et al. (2006). FOXP3 controls regulatory T cell function through cooperation with NFAT. Cell 126, 375-387.

Yang, Q., She, H., Gearing, M., Colla, E., Lee, M., Shacka, J. J., and Mao, Z. (2009). Regulation of neuronal survival factor MEF2D by chaperone-mediated autophagy. Science (New York, N.Y. 323, 124-127.

Youn, H. D., and Liu, J. O. (2000). Cabin1 represses MEF2-dependent Nur77 expression and T cell apoptosis by controlling association of histone deacetylases and acetylases with MEF2. Immunity 13, 85-94.

Youn, H. D., Sun, L., Prywes, R., and Liu, J. O. (1999). Apoptosis of T cells mediated by Ca2+-induced release of the transcription factor MEF2. Science (New York, N.Y. 286, 790-793.

Zhang, C. L., McKinsey, T. A., Chang, S., Antos, C. L., Hill, J. A., and Olson, E. N. (2002). Class II histone deacetylases act as signal-responsive repressors of cardiac hypertrophy. Cell 110, 479-488.

Zheng, Y., and Rudensky, A. Y. (2007). Foxp3 in control of the regulatory T cell lineage. Nature immunology 8, 457-462.

Zuo, T., Liu, R., Zhang, H., Chang, X., Liu, Y., Wang, L., Zheng, P., and Liu, Y. (2007a). FOXP3 is a novel transcriptional repressor for the breast cancer oncogene SKP2. J Clin Invest.

Zuo, T., Wang, L., Morrison, C., Chang, X., Zhang, H., Li, W., Liu, Y., Wang, Y., Liu, X., Chan, M. W., et al. (2007b). FOXP3 is an X-linked breast cancer suppressor gene and an important repressor of the HER-2/ErbB2 oncogene. Cell 129, 1275-1286.

What is claimed is:

1. A method of selectively modulating a myocyte enhancer factor-2 (MEF2) and its functions, said method comprising:
   contacting the MEF2 with a small molecule interfacial inhibitor,
   wherein said interfacial inhibitor is a compound having a formula of

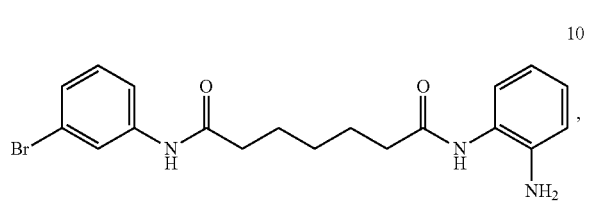 [SMILES: Nc1ccccc1NC(=O)CCCCCC(=O)Nc1cccc(Br)c1]

and
   whereby said interfacial inhibitor modulates the MEF2's function by disrupting the interactions between the MEF2 and a functional binding partner at the MEF2 binding site.

2. The method of claim 1, wherein said MEF2 is MEF2A.
3. The method of claim 1, wherein said MEF2 is MEF2B.
4. The method of claim 1, wherein said MEF2 is MEF2C.
5. The method of claim 1, wherein said MEF2 is MEF2D.
6. A method of modulating myocyte enhancer factor-2 functions in a subject suffering from a disease related to transcription factor dysregulation, comprising:
   administering an interfacial inhibitor to said subject,
   wherein said transcription factor dysregulation is a dysregulation of a transcription factor selected from a group consisting of MEF2A, MEF2B, MEF2C, and MEF2D, or combinations thereof, and,
   wherein said interfacial inhibitor is a compound having a formula of

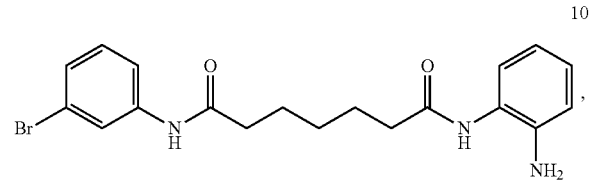 [SMILES: Nc1ccccc1NC(=O)CCCCCC(=O)Nc1cccc(Br)c1]

7. The method of claim 6, wherein said transcription factor dysregulation is a dysregulation of MEF2A.
8. The method of claim 6, wherein said transcription factor dysregulation is a dysregulation of MEF2B.
9. The method of claim 6, wherein said disease is one selected from transplant rejection, inflammation, autoimmune diseases, neurodegenerative diseases, cancer, and cardiovascular disease.
10. The method of claim 6, wherein said transcription factor dysregulation is a dysregulation of MEF2C.
11. The method of claim 6, wherein said transcription factor dysregulation is a dysregulation of MEF2D.

* * * * *